United States Patent
Moinet et al.

(10) Patent No.: US 7,816,397 B2
(45) Date of Patent: Oct. 19, 2010

(54) PHENYLCARBOXYLIC ACID DERIVATIVES AND USE THEREOF FOR THE TREATMENT OF DIABETES

(75) Inventors: Gérard Moinet, Orsay (FR); Gérard Botton, Buc (FR); Micheline Kergoat, Bures-sur-Yvette (FR)

(73) Assignee: Merck Patent GmbH, Darmstadt (DE)

( * ) Notice: Subject to any disclaimer, the term of this patent is extended or adjusted under 35 U.S.C. 154(b) by 16 days.

(21) Appl. No.: 11/630,892

(22) PCT Filed: Jun. 1, 2005

(86) PCT No.: PCT/EP2005/005868

§ 371 (c)(1),
(2), (4) Date: Dec. 27, 2006

(87) PCT Pub. No.: WO2006/000288

PCT Pub. Date: Jan. 5, 2006

(65) Prior Publication Data

US 2008/0045483 A1   Feb. 21, 2008

(30) Foreign Application Priority Data

Jun. 28, 2004   (FR) .................................. 04 07076

(51) Int. Cl.
| | |
|---|---|
| C07C 311/21 | (2006.01) |
| C07C 311/46 | (2006.01) |
| C07C 311/08 | (2006.01) |
| C07C 311/29 | (2006.01) |
| C07C 311/13 | (2006.01) |
| C07C 311/44 | (2006.01) |
| C07C 311/10 | (2006.01) |
| C07D 333/34 | (2006.01) |
| A61P 3/04 | (2006.01) |
| A61P 3/10 | (2006.01) |

(52) U.S. Cl. ................. 514/445; 514/602; 549/65; 562/430; 562/457; 564/92; 564/84

(58) Field of Classification Search ................ None
See application file for complete search history.

(56) References Cited

U.S. PATENT DOCUMENTS 3,296,252 A   1/1967   Frey et al.

(Continued)

FOREIGN PATENT DOCUMENTS

EP   0 292 202 A   11/1988

(Continued)

OTHER PUBLICATIONS

Labaudiniere et al. J.Med.Chem.1992, 35, 3156-3169.*

(Continued)

*Primary Examiner*—Sharmila Gollamudi Landau
*Assistant Examiner*—Kortney L Klinkel
(74) *Attorney, Agent, or Firm*—Millen, White, Zelano, Branigan, P.C

(57) ABSTRACT

The invention relates to compounds of general formula (1): in which R1, R2, R3, R4, R5, A, B, D and E are as defined in Claim 1, and also to the preparation process therefor and the therapeutic use thereof. These compounds can be used in the treatment of pathologies associated with hyperglycaemia.

21 Claims, 1 Drawing Sheet

Glucose tolerance, after oral glucose tolerance test (2 g/kg$_{body\ weight}$)

* $p<0.05$ vs diabetic controls

U.S. PATENT DOCUMENTS

| | | | |
|---|---|---|---|
| 4,922,022 | A | 5/1990 | Dixon et al. |
| 5,811,459 | A | 9/1998 | Breault et al. |
| 6,258,850 | B1 | 7/2001 | Andersson |
| 6,790,866 | B2 | 9/2004 | Ohuchida et al. |

FOREIGN PATENT DOCUMENTS

| | | |
|---|---|---|
| EP | 0 947 500 A | 10/1999 |
| WO | WO 96/11902 A | 4/1996 |
| WO | WO 99/62871 A | 12/1999 |

OTHER PUBLICATIONS

A. Kluge et al., J. Med. Chem, vol. 21, No. 6, 1978, pp. 529-536.

Patani G A et al., Bioisosterism : A Rational Approach in Drug Design, 1996, Chemical Reviews, American Chemical Society Easton, US pates 3147-3176.

Asfari, et al. "Establishment of 2-Mercaptoethanol-Dependent Differentiated Insulin-Secreting Cell Lines*" Endocrinology, 130(1):167-178 (1992).

* cited by examiner

* p<0.05 vs diabetic controls

PHENYLCARBOXYLIC ACID DERIVATIVES AND USE THEREOF FOR THE TREATMENT OF DIABETES

The present invention relates to aryl carboxylic acid derivatives of the formula (1), which are useful in the treatment of pathologies associated with insulin resistance syndrome.

Insulin resistance is characterised by a reduction in the action of insulin (cf. Presse Médicale, 1997, 26 (No. 14), 671-677) and is involved in a large number of pathological conditions, such as diabetes and more particularly non-insulin-dependent diabetes (type II diabetes or NIDDM), dyslipidaemia, obesity and also certain microvascular and macrovascular complications, for instance arterial hypertension, atherosclerosis, inflammatory processes, macroangiopathy, microangiopathy, retinopathy and neuropathy.

In this respect, reference may be made, for example, to Diabetes, Vol. 37, 1988, 1595-1607; *Journal of Diabetes And Its Complications,* 1998, 12, 110-119 or Horm. Res., 1992, 38, 28-32.

According to the present invention, the compounds of the formula (1) have hypoglycaemiant activity. They can reduce hyperglycaemia and more particularly the hyperglycaemia of non-insulin-dependent diabetes. The compounds of the invention especially have anti-hyperglycaemic activity.

Patent application EP 0 947 500 discloses two compounds similar in structure to the general formula (1), but do not, however, describe any antidiabetic activity.

The compounds of the invention are of the general formula (1) below:

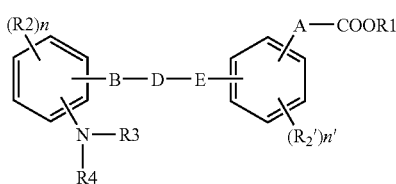

in which:

B and E each represent a —$CH_2$— group or an oxygen atom;

R1 is chosen without preference from the following groups:

H $(C_1-C_8)$alkyl, optionally substituted by one or more groups chosen independently from halogen, $(C_1-C_5)$alkyl, $(C_1-C_5)$alkoxy, $(C_3-C_8)$cycloalkyl and $(C_6-C_{14})$aryl $(C_2-C_{20})$alkene optionally substituted by one or more groups chosen independently from halogen, $(C_1-C_5)$alkyl, $(C_1-C_5)$alkoxy, $(C_3-C_8)$cycloalkyl and $(C_6-C_{14})$aryl $(C_2-C_{20})$alkyne optionally substituted by one or more groups chosen independently from halogen, $(C_1-C_5)$alkyl, $(C_1-C_5)$alkoxy, $(C_3-C_8)$cycloalkyl and $(C_6-C_{14})$aryl $(C_3-C_8)$cycloalkyl optionally substituted by one or more groups chosen independently from $(C_1-C_5)$alkyl and $(C_1-C_5)$alkoxy $(C_3-C_8)$heterocycle comprising one or more hetero atoms chosen from N, O and S and optionally substituted by one or more groups chosen independently from $(C_1-C_5)$alkyl and $(C_1-C_5)$alkoxy, $(C_6-C_{14})$aryl$(C_1-C_{20})$alkyl optionally substituted by one or more groups chosen independently from amino, hydroxyl, thio, halogen, $(C_1-C_5)$alkyl, $(C_1-C_5)$alkoxy, $(C_1-C_5)$alkylthio, $(C_1-C_5)$alkylamino, $(C_6-C_{14})$aryl, $(C_6-C_{14})$-aryloxy and $(C_6-C_{14})$aryl$(C_1-C_5)$alkoxy;

Preferably, R1 represents a hydrogen atom;

X represents a group chosen without preference from:

amino, hydroxyl, thio, halogen, cyano, nitro, trifluoromethoxy, trifluoromethyl, carboxyl, carboxymethyl or carboxyethyl, $(C_1-C_8)$alkyl, $(C_1-C_8)$-alkoxy, $(C_1-C_8)$alkylthio, $(C_1-C_8)$alkylamino, $(C_6-C_{14})$aryl, $(C_6-C_{14})$aryl-$(C_1-C_8)$sulfonylalkyl, $(C_6-C_{14})$aryloxy, $(C_6-C_{14})$aryl$(C_1-C_8)$alkoxy, —NHCO—$(C_1-C_8)$alkyl, —N—$(C_1-C_8)$alkylCO$(C_1-C_8)$alkyl, —CO$(C_1-C_8)$alkyl, —$SO_2$—$(C_6-C_{14})$aryl, di$(C_1-C_8)$alkylamino, $(C_3-C_8)$cycloalkyl or a ketone function;

Preferably, X represents hydroxyl, halogen, cyano, nitro, trifluoromethoxy, trifluoromethyl, carboxyl, $(C_1-C_8)$alkyl, —$SO_2(C_6-C_{14})$aryl, $(C_1-C_8)$alkoxy, di-$(C_1-C_8)$alkylamino, —NHCO$(C_1-C_8)$alkyl, —N—$(C_1-C_8)$alkylCO$(C_1-C_8)$alkyl, —CO$(C_1-C_8)$alkyl, $(C_6-C_{14})$aryl$(C_1-C_8)$alkoxy or a ketone function;

Z represents a group chosen without preference from:

$(C_1-C_{20})$alkyl optionally substituted by one or more groups chosen without preference from X;

$(C_2-C_{20})$alkene optionally substituted by one or more groups chosen without preference from X;

$(C_2-C_{20})$alkyne optionally substituted by one or more groups chosen without preference from X;

$(C_6-C_{14})$aryl, $(C_6-C_{14})$aryl$(C_1-C_5)$alkoxy, $(C_6-C_{14})$aryloxy and $(C_6-C_{14})$aryloxy$(C_1-C_5)$alkoxy, the aryl group of each of these groups itself possibly being substituted by one or more groups chosen without preference from X; preferably, aryl represents phenyl or naphthyl;

$(C_3-C_8)$cycloalkyl optionally substituted by one or more groups chosen without preference from X, preferably cyclohexyl or cyclopentyl;

$(C_3-C_8)$heterocycle comprising one or more hetero atoms chosen from N, O and S and X substituted by one or more groups chosen without preference from X;

$(C_6-C_{14})$aryl$(C_1-C_{20})$alkyl, $(C_6-C_{14})$aryl$(C_2-C_{20})$alkene and $(C_6-C_{14})$aryl-$(C_2-C_{20})$alkyne, the aryl group of each of these groups itself possibly being substituted by one or more groups chosen without preference from X;

$(C_5-C_{13})$heteroaryl and $(C_5-C_{13})$heteroaryl$(C_1-C_{20})$alkyl comprising one or more hetero atoms chosen from N, O and S, the heteroaryl group of each of these groups itself possibly being substituted by one or more groups chosen without preference from X; preferably, heteroaryl represents quinolyl, thiazolyl, thienyl, benzothienyl, quinoxalinyl or furyl;

$(C_3-C_8)$cycloalkyl$(C_1-C_{20})$alkyl, $(C_3-C_8)$cycloalkyl$(C_2-C_{20})$alkene or $(C_3-C_8)$cycloalkyl$(C_2-C_{20})$alkyne, the cycloalkyl group of each of these groups itself possibly being substituted by one or more groups chosen without preference from X;

Preferably, Z represents $(C_1-C_{20})$alkyl, $(C_6-C_{14})$aryl, $(C_3-C_8)$cycloalkyl, $(C_6-C_{14})$aryl$(C_1-C_{20})$alkyl or $(C_5-C_{13})$heteroaryl, each optionally substituted by one or more groups chosen without preference from X, in which X is defined as above;

R2 and R2' are chosen without preference from the following groups:

H

X,

Z;

Preferably, R2 and R2' represent H;

R3 is chosen without preference from the following groups:
H,
Z;

Preferably, R3 represents H or $(C_1-C_8)$alkyl;

R4 represents a group chosen from:

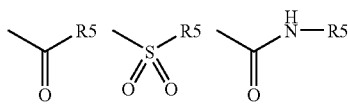

Preferably, R4 represents

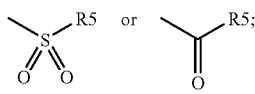

R5 is chosen without preference from Z;

Preferably, R5 represents $(C_1-C_{20})$alkyl, $(C_6-C_{14})$aryl, $(C_3-C_8)$cycloalkyl, $(C_3-C_8)$cycloalkyl$(C_1-C_{20})$alkyl, $(C_6-C_{14})$aryl$(C_1-C_{20})$alkyl or $(C_5-C_{13})$heteroaryl, each optionally substituted by one or more groups chosen without preference from X, in which X is defined as above;

D represents a single bond or a $(C_1-C_6)$alkyl group optionally substituted by one or more groups X or Z;

Preferably, D represents a single bond or an unsubstituted $(C_1-C_6)$alkyl group;

A represents a single bond or a $(C_1-C_6)$alkyl group optionally substituted by one or more groups X or Z;

Preferably, A represents a single bond;

n and n' represent an integer chosen independently from 1, 2 and 3, and also the tautomeric forms, enantiomers, diastereoisomers and epimers, and the pharmaceutically acceptable salts, with the exception of the compounds for which:

-ACOOR$_1$, and —NR3R4 are respectively ortho and para relative to the chain B-D-E, R1=H, A represents a single bond, B=E=CH$_2$, D=single bond, and 1) R3=H, R4=SO$_2$-Phenyl-Cl(4'), R2=Cl in a meta position relative to the chain B-D-E, or 2) R3=—CH(CH$_3$)$_2$, R4=SO$_2$-Phenyl, R2=CF$_3$ in a meta position relative to the chain B-D-E.

One particular group of compounds of the formula (1) is the group in which the compounds have a general formula (2) or (2') below in which the group -A-COOR1 is in an ortho or meta position on the ring relative to E.

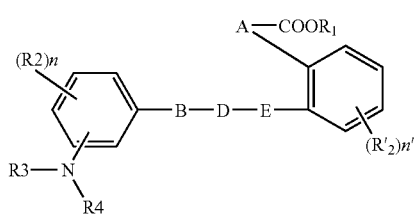

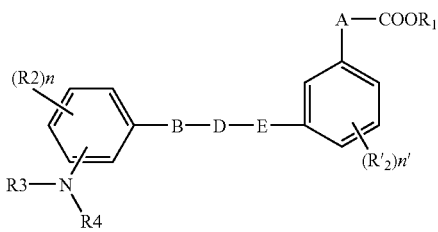

in which:

R$_1$, R$_2$, R$_3$, R$_4$, A, B, D and E are as defined above.

In the formula (1), if -ACOOR$_1$ is in the para position, preferably —NR3R4 is in the para or meta position relative to the chain B-D-E.

In the formula (1), if -ACOOR$_1$ is in the para position, —NR3R4 is in an ortho position relative to the chain B-D-E, preferably, R2=H and/or In the formula (1), if -ACOOR1 is in the para position, —NR3R4 is in an ortho position relative to the chain B-D-E, preferably, B-D-E represents an at least 5-membered chain and/or In the formula (1), if -ACOOR$_1$ is in the para position, —NR3R4 is in an ortho position relative to the chain B-D-E, preferably B and E each represent an oxygen atom.

In the formula (1), if -ACOOR$_1$ is in the para position, —NR3R4 is in an ortho position relative to the chain B-D-E, preferably R4 represents

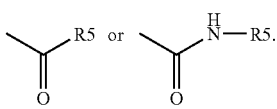

A particular group of compounds of the formula (1) is the group in which the compounds have a general formula (3) below in which the function NR3R4 is in a meta position on the ring relative to B.

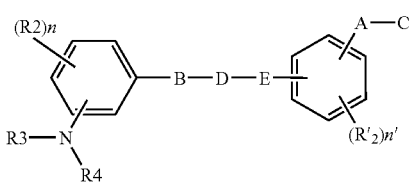

in which R$_1$, R$_2$, R$_3$, R$_4$, A, B, D and E are as defined above.

A particular group of compounds of the formula (1) is the group in which the compounds have a general formula (4) below in which the function NR3R4 is in the para position on the ring relative to B.

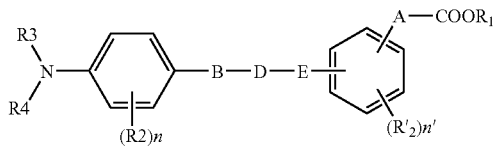

(4)

in which $R_1$, $R_2$, $R_3$, $R_4$, A, B, D and E are as defined above.

According to one preferred aspect of the invention, the compounds of the formula (1) are those for which B and E both represent a —CH$_2$— group and D represents a single bond or a —CH$_2$ group.

According to one preferred aspect of the invention, the compounds of the formula (1) are those for which B and E both represent an oxygen atom and D represents a —C$_2$H$_4$ group.

According to another preferred aspect of the invention, the compounds of the formula (1) are those for which B and E both represent a —CH$_2$— group, D representing a chain containing 3 carbon atoms.

A particular group of compounds of the formula (1) is the group for which the groups B, D and E taken together constitute an alkylene chain containing at least 5 carbon atoms.

The compounds of the formula (1) may be chosen from:
4-{2-[2-(4-chlorobenzenesulfonylamino)phenyl]ethyl}benzoic acid
4-[2-(2-methanesulfonylaminophenyl)ethyl]benzoic acid
4-{2-[2-(4-methoxybenzenesulfonylamino)phenyl]ethyl}benzoic acid
4-[2-(2-phenylmethanesulfonylaminophenyl)ethyl]benzoic acid
4-{2-[2-(butane-1-sulfonylamino)phenyl]ethyl}benzoic acid
4-[2-(2-benzenesulfonylaminophenyl)ethyl]benzoic acid
4-{2-[2-(4-acetylaminobenzenesulfonylamino)phenyl]ethyl}benzoic acid
4-{2-[2-(2-nitrobenzenesulfonylamino)phenyl]ethyl}benzoic acid
4-{2-[2-(4-methylbenzenesulfonylamino)phenyl]ethyl}benzoic acid
4-{2-[2-(3-trifluoromethylbenzenesulfonylamino)phenyl]ethyl}benzoic acid
4-{2-[2-(naphthalene-1-sulfonylamino)phenyl]ethyl}benzoic acid
4-{2-[2-(2,5-dimethoxybenzenesulfonylamino)phenyl]ethyl}benzoic acid
4-{2-[2-(2,4-dimethylbenzenesulfonylamino)phenyl]ethyl}benzoic acid
4-{2-[2-(2-fluorobenzenesulfonylamino)phenyl]ethyl}benzoic acid
4-{2-[2-(2,4-difluorobenzenesulfonylamino)phenyl]ethyl}benzoic acid
4-{2-[2-(2-trifluoromethylbenzenesulfonylamino)phenyl]ethyl}benzoic acid
4-{2-[2-(4-fluoromethylbenzenesulfonylamino)phenyl]ethyl}benzoic acid
4-{2-[2-(5-chloro-3-methylbenzo[b]thiophene-2-sulfonylamino)phenyl]ethyl}-benzoic acid
4-{2-[2-(4-acetylbenzenesulfonylamino)phenyl]ethyl}benzoic acid
4-{2-[2-(4-methoxy-2,5,6-trimethylbenzenesulfonylamino)phenyl]ethyl}benzoic acid
4-{2-[2-(naphthalene-2-sulfonylamino)phenyl]ethyl}benzoic acid
4-{2-[2-(2,5-dichlorobenzenesulfonylamino)phenyl]ethyl}benzoic acid
4-{2-[2-(2,4,6-triisopropylbenzenesulfonylamino)phenyl]ethyl}benzoic acid
4-{2-[2-(2,4,6-trimethylbenzenesulfonylamino)phenyl]ethyl}benzoic acid
4-{2-[2-(4-isopropylbenzenesulfonylamino)phenyl]ethyl}benzoic acid
4-{2-[2-(2-phenylethenesulfonylamino)phenyl]ethyl}benzoic acid
4-{2-[2-(3,4-dimethoxybenzenesulfonylamino)phenyl]ethyl}benzoic acid
4-{2-[2-(4-trifluoromethoxybenzenesulfonylamino)phenyl]ethyl}benzoic acid
4-{2-[2-(thiophene-2-sulfonylamino)phenyl]ethyl}benzoic acid
4-{2-[2-(propane-2-sulfonylamino)phenyl]ethyl}benzoic acid
4-{2-[2-(hexadecane-1-sulfonylamino)phenyl]ethyl}benzoic acid
4-{2-[2-(5-benzenesulfonylthiophene-2-sulfonylamino)phenyl]ethyl}benzoic acid
4-{2-[2-(2-trifluoromethoxybenzenesulfonylamino)phenyl]ethyl}benzoic acid
4-{2-[2-(4-butoxybenzenesulfonylamino)phenyl]ethyl}benzoic acid
4-{2-[2-(3-fluoro-6-methylbenzenesulfonylamino)phenyl]ethyl}benzoic acid
4-{2-[2-(2,6-difluorobenzenesulfonylamino)phenyl]ethyl}benzoic acid
4-{2-[2-(4-butylbenzenesulfonylamino)phenyl]ethyl}benzoic acid
4-{2-[2-(3-methoxybenzenesulfonylamino)phenyl]ethyl}benzoic acid
4-{2-[2-(2,3,4,5,6-pentamethylbenzenesulfonylamino)phenyl]ethyl}benzoic acid
4-{2-[2-(3,5-bis-trifluoromethylbenzenesulfonylamino)phenyl]ethyl}benzoic acid
4-{2-[2-(4-propylbenzenesulfonylamino)phenyl]ethyl}benzoic acid
4-{2-[2-(4-isopropylbenzenesulfonylamino)phenyl]ethyl}benzoic acid
4-{2-[2-(3-fluorobenzenesulfonylamino)phenyl]ethyl}benzoic acid
4-{2-[2-(3-methylbenzenesulfonylamino)phenyl]ethyl}benzoic acid
4-{2-[2-(4-benzenesulfonylthiophene-2-sulfonylamino)phenyl]ethyl}benzoic acid
4-(2-{2-[4-(1,1-dimethylpropyl)benzenesulfonylamino]phenyl}ethyl)benzoic acid
4-{2-[2-(4-ethylbenzenesulfonylamino)phenyl]ethyl}benzoic acid
4-{2-[2-(4-trifluoromethylbenzenesulfonylamino)phenyl]ethyl}benzoic acid
4-{2-[2-(5-dimethylaminonaphthalene-1-sulfonylamino)phenyl]ethyl}benzoic acid
4-{2-[2-(2-acetylamino-4-methylthiazole-5-sulfonylamino)phenyl]ethyl}benzoic acid
4-{2-[2-(2-cyanobenzenesulfonylamino)phenyl]ethyl}benzoic acid
4-{2-[2-(7,7-dimethyl-2-oxobicyclo[2.2.1]hept-1-yl-methanesulfonylamino)-phenyl]ethyl}benzoic acid
4-(2-{2-[(4-acetylaminobenzenesulfonyl)butylamino]phenyl}ethyl)benzoic acid
4-(2-{2-[butyl(4-chlorobenzenesulfonyl)amino]phenyl}ethyl)benzoic acid 4-(2-{2-[butyl(4-methoxybenzenesulfonyl)amino]
phenyl}ethyl)benzoic acid
4-(2-{2-[butyl(2-nitrobenzenesulfonyl)amino]phenyl}ethyl)
benzoic acid
4-(2-{2-[butyl(toluene-4-sulfonyl)amino]phenyl}ethyl)ben-
zoic acid
4-(2-{2-[butyl(3-trifluoromethylbenzenesulfonyl)amino]
phenyl}ethyl)benzoic acid
4-(2-{2-[butyl(naphthalene-1-sulfonyl)amino]phenyl}ethyl)
benzoic acid
4-(2-{2-[butyl(2,5-dimethoxybenzenesulfonyl)amino]
phenyl}ethyl)benzoic acid
4-(2-{2-[butyl(2,4-dimethylbenzenesulfonyl)amino]
phenyl}ethyl)benzoic acid
4-(2-{2-[butyl(2-fluorobenzenesulfonyl)amino]
phenyl}ethyl)benzoic acid
4-(2-{2-[butyl(2,4-difluorobenzenesulfonyl)amino]
phenyl}ethyl)benzoic acid
4-(2-{2-[(4-acetylbenzenesulfonyl)butylamino]
phenyl}ethyl)benzoic acid
4-(2-{2-[butyl(4-methoxy-2,3,6-trimethylbenzenesulfonyl)
amino]phenyl}ethyl)-benzoic acid
4-(2-{2-[butyl(5-dimethylaminonaphthalene-1-sulfonyl)
amino]phenyl}ethyl)-benzoic acid
4-(2-{2-[butyl(naphthalene-2-sulfonyl)amino]phenyl}ethyl)
benzoic acid
4-(2-{2-[(2-acetylamino-4-methylthiazole-5-sulfonyl)buty-
lamino]phenyl}ethyl)-benzoic acid
4-{2-[2-(benzenesulfonylbutylamino)phenyl]ethyl}benzoic
acid
4-(2-{2-[butyl(2,5-dichlorobenzenesulfonyl)amino]
phenyl}ethyl)benzoic acid
4-(2-{2-[butyl(2,4,6-trimethylbenzenesulfonyl)amino]
phenyl}ethyl)benzoic acid
4-(2-{2-[butyl(4-tert-butylbenzenesulfonyl)amino]
phenyl}ethyl)benzoic acid
4-(2-{2-[butyl((E)-2-phenylethenesulfonyl)amino]
phenyl}ethyl)benzoic acid
4-(2-{2-[butyl(3,4-dimethoxybenzenesulfonyl)amino]
phenyl}ethyl)benzoic acid
4-(2-{2-[butyl(4-trifluoromethoxybenzenesulfonyl)amino]
phenyl}ethyl)benzoic acid
4-(2-{2-[butyl(thiophene-2-sulfonyl)amino]phenyl}ethyl)
benzoic acid
4-(2-{2-[(5-benzenesulfonylthiophene-2-sulfonyl)buty-
lamino]phenyl}ethyl)-benzoic acid
4-(2-{2-[butyl(2-trifluoromethoxybenzenesulfonyl)amino]
phenyl}ethyl)benzoic acid
4-(2-{2-[(4-butoxybenzenesulfonyl)butylamino]
phenyl}ethyl)benzoic acid
4-(2-{2-[butyl(5-fluoro-2-methylbenzenesulfonyl)amino]
phenyl}ethyl)benzoic acid
4-(2-{2-[butyl(2,6-difluorobenzenesulfonyl)amino]
phenyl}ethyl)benzoic acid
4-(2-{2-[butyl(4-butylbenzenesulfonyl)amino]
phenyl}ethyl)benzoic acid
4-(2-{2-[butyl(3-methoxybenzenesulfonyl)amino]
phenyl}ethyl)benzoic acid
4-{2-[2-(butylpentamethylbenzenesulfonylamino)phenyl]
ethyl}benzoic acid
4-(2-{2-[(3,5-bis-trifluoromethylbenzenesulfonyl)buty-
lamino]phenyl}ethyl)benzoic acid
4-(2-{2-[butyl(4-propylbenzenesulfonyl)amino]
phenyl}ethyl)benzoic acid
4-(2-{2-[butyl(4-isopropylbenzenesulfonyl)amino]
phenyl}ethyl)benzoic acid
4-(2-{2-[butyl(3-fluorobenzenesulfonyl)amino]
phenyl}ethyl)benzoic acid
4-(2-{2-[butyl(toluene-3-sulfonyl)amino]phenyl}ethyl)ben-
zoic acid
4-[2-(2-{butyl-[4-(1,1-dimethylpropyl)benzenesulfonyl]
amino}phenyl)ethyl]-benzoic acid
4-(2-{2-[butyl(2-cyanobenzenesulfonyl)amino]
phenyl}ethyl)benzoic acid
4-(2-{2-[butyl(4-ethylbenzenesulfonyl)amino]
phenyl}ethyl)benzoic acid
4-(2-{2-[butyl(4-trifluoromethylbenzenesulfonyl)amino]
phenyl}ethyl)benzoic acid
4-(2-{2-[(4-chlorobenzenesulfonyl)heptylamino]
phenyl}ethyl)benzoic acid
4-(2-{2-[heptyl(toluene-4-sulfonyl)amino]phenyl}ethyl)
benzoic acid
4-(2-{2-[heptyl(3-trifluoromethylbenzenesulfonyl)amino]
phenyl}ethyl)benzoic acid
4-(2-{2-[heptyl(naphthalene-1-sulfonyl)amino]
phenyl}ethyl)benzoic acid
4-(2-{2-[(2,5-dimethoxybenzenesulfonyl)heptylamino]
phenyl}ethyl)benzoic acid
4-(2-{2-[(2,4-dimethylbenzenesulfonyl)heptylamino]
phenyl}ethyl)benzoic acid
4-(2-{2-[(2-fluorobenzenesulfonyl)heptylamino]
phenyl}ethyl)benzoic acid
4-(2-{2-[(2,4-difluorobenzenesulfonyl)heptylamino]
phenyl}ethyl)benzoic acid
4-(2-{2-[heptyl(2-trifluoromethylbenzenesulfonyl)amino]
phenyl}ethyl)benzoic acid
4-(2-{2-[(4-fluorobenzenesulfonyl)heptylamino]
phenyl}ethyl)benzoic acid
4-(2-{2-[(4-acetylbenzenesulfonyl)heptylamino]
phenyl}ethyl)benzoic acid
4-(2-{2-[heptyl(4-methoxy-2,3,6-trimethylbenzenesulfo-
nyl)amino]phenyl}ethyl)-benzoic acid
4-(2-{2-[heptyl(naphthalene-2-sulfonyl)amino]
phenyl}ethyl)benzoic acid
4-(2-{2-[(2-acetylamino-4-methylthiazole-5-sulfonyl)hep-
tylamino]phenyl}ethyl)-benzoic acid
4-{2-[2-(benzenesulfonylheptylamino)phenyl]
ethyl}benzoic acid
4-(2-{2-[heptyl((E)-2-phenylethenesulfonyl)amino]
phenyl}ethyl)benzoic acid
4-(2-{2-[(3,4-dimethoxybenzenesulfonyl)heptylamino]
phenyl}ethyl)benzoic acid
4-(2-{2-[heptyl(4-trifluoromethoxybenzenesulfonyl)amino]
phenyl}ethyl)benzoic acid
4-(2-{2-[heptyl(quinoline-8-sulfonyl)amino]phenyl}ethyl)
benzoic acid
4-(2-{2-[(5-fluoro-2-methylbenzenesulfonyl)heptylamino]
phenyl}ethyl)benzoic acid
4-(2-{2-[(2,6-difluorobenzenesulfonyl)heptylamino]
phenyl}ethyl)benzoic acid
4-(2-{2-[(4-butylbenzenesulfonyl)heptylamino]
phenyl}ethyl)benzoic acid
4-(2-{2-[heptyl(3-methoxybenzenesulfonyl)amino]
phenyl}ethyl)benzoic acid
4-(2-{2-[heptyl(4-propylbenzenesulfonyl)amino]
phenyl}ethyl)benzoic acid
4-(2-{2-[heptyl(4-isopropylbenzenesulfonyl)amino]
phenyl}ethyl)benzoic acid
4-(2-{2-[(3-fluorobenzenesulfonyl)heptylamino]
phenyl}ethyl)benzoic acid
4-(2-{2-[heptyl(toluene-3-sulfonyl)amino]phenyl}ethyl)
benzoic acid 4-[2-(2-{[4-(1,1-dimethylpropyl)benzenesulfonyl]-heptylamino}phenyl)ethyl]-benzoic acid
4-(2-{2-[(2-cyanobenzenesulfonyl)heptylamino]phenyl}ethyl)benzoic acid
4-(2-{2-[heptyl(4-trifluoromethylbenzenesulfonyl)amino]phenyl}ethyl)benzoic acid
4-{2-[3-(4-chlorobenzenesulfonylamino)phenyl]ethyl}benzoic acid
4-[2-(3-methanesulfonylaminophenyl)ethyl]benzoic acid
4-{2-[3-(4-methoxybenzenesulfonylamino)phenyl]ethyl}benzoic acid
4-[2-(3-phenylmethanesulfonylaminophenyl)ethyl]benzoic acid
4-{2-[3-(butane-1-sulfonylamino)phenyl]ethyl}benzoic acid
4-[2-(3-benzenesulfonylaminophenyl)ethyl]benzoic acid
4-{2-[3-(4-acetylaminobenzenesulfonylamino)phenyl]ethyl}benzoic acid
4-{2-[3-(2-nitrobenzenesulfonylamino)phenyl]ethyl}benzoic acid
4-{2-[3-(4-methylbenzenesulfonylamino)phenyl]ethyl}benzoic acid
4-{2-[3-(2-fluorobenzenesulfonylamino)phenyl]ethyl}benzoic acid
4-{2-[3-(2,4-difluorobenzenesulfonylamino)phenyl]ethyl}benzoic acid
4-{2-[3-(2-trifluoro-methylbenzenesulfonylamino)phenyl]ethyl}benzoic acid
4-{2-[3-(4-fluorobenzenesulfonylamino)phenyl]ethyl}benzoic acid
4-{2-[3-(4-acetylbenzenesulfonylamino)phenyl]ethyl}benzoic acid
4-{2-[3-(ethanesulfonylamino)phenyl]ethyl}benzoic acid
4-{2-[3-(naphthalene-2-sulfonylamino)phenyl]ethyl}benzoic acid
4-(2-{3-[4-(1,1-dimethylethyl)benzenesulfonylamino]phenyl}ethyl)benzoic acid
4-{2-[3-(thiophene-2-sulfonylamino)phenyl]ethyl}benzoic acid
4-{2-[3-(2-trifluoromethoxybenzenesulfonylamino)phenyl]ethyl}benzoic acid
4-{2-[3-(2,6-difluorobenzenesulfonylamino)phenyl]ethyl}benzoic acid
4-{2-[3-(4-butylbenzenesulfonylamino)phenyl]ethyl}benzoic acid
4-{2-[3-(4-trifluoromethoxybenzenesulfonylamino)phenyl]ethyl}benzoic acid
4-{2-[3-(3-trifluoromethylbenzenesulfonylamino)phenyl]ethyl}benzoic acid
4-{2-[3-(naphthalene-1-sulfonylamino)phenyl]ethyl}benzoic acid
4-{2-[3-(2,5-dimethoxybenzenesulfonylamino)phenyl]ethyl}benzoic acid
4-{2-[3-(2,4-dimethylbenzenesulfonylamino)phenyl]ethyl}benzoic acid
4-{2-[3-(biphenyl-4-sulfonylamino)phenyl]ethyl}benzoic acid
4-{2-[3-(4-methoxy-2,3,6-trimethylbenzenesulfonylamino)phenyl]ethyl}benzoic acid
4-{2-[3-(5-dimethylaminonaphthalene-1-sulfonylamino)phenyl]ethyl}benzoic acid
4-{2-[3-(2-acetylamino-4-methylthiazole-5-sulfonylamino)phenyl]ethyl}benzoic acid
4-{2-[3-(2,5-dichlorobenzenesulfonylamino)phenyl]ethyl}benzoic acid
4-{2-[3-(2,4,6-triisopropylbenzenesulfonylamino)phenyl]ethyl}benzoic acid
4-{2-[3-(2,4,6-trimethylbenzenesulfonylamino)phenyl]ethyl}benzoic acid
4-{2-[3-((E)-2-phenylethenesulfonylamino)phenyl]ethyl}benzoic acid
4-{2-[3-(3,4-dimethoxybenzenesulfonylamino)phenyl]ethyl}benzoic acid
4-{2-[3-(4-trifluoromethoxybenzenesulfonylamino)phenyl]ethyl}benzoic acid
4-{2-[3-(4-carboxybenzenesulfonylamino)phenyl]ethyl}benzoic acid
4-{2-[3-(propane-2-sulfonylamino)phenyl]ethyl}benzoic acid
4-{2-[3-(5-benzenesulfonylthiophene-2-sulfonylamino)phenyl]ethyl}benzoic acid
4-{2-[3-(4-butoxybenzenesulfonylamino)phenyl]ethyl}benzoic acid
4-{2-[3-(5-fluoro-2-methylbenzenesulfonylamino)phenyl]ethyl}benzoic acid
4-{2-[3-(3-methoxybenzenesulfonylamino)phenyl]ethyl}benzoic acid
4-[2-(3-pentamethylbenzenesulfonylaminophenyl)ethyl]benzoic acid
4-{2-[3-(3,5-bis-trifluoromethylbenzenesulfonylamino)phenyl]ethyl}benzoic acid
4-{2-[3-(4-isopropylbenzenesulfonylamino)phenyl]ethyl}benzoic acid
4-{2-[3-(3-fluorobenzenesulfonylamino)phenyl]ethyl}benzoic acid
4-{2-[3-(toluene-3-sulfonylamino)phenyl]ethyl}benzoic acid
4-{2-[3-(4-benzenesulfonylthiophene-2-sulfonylamino)phenyl]ethyl}benzoic acid
4-(2-{3-[4-(1,1-dimethylpropyl)benzenesulfonylamino]phenyl}ethyl)benzoic acid
4-{2-[3-(2-cyanobenzenesulfonylamino)phenyl]ethyl}benzoic acid
4-{2-[3-(4-ethylbenzenesulfonylamino)phenyl]ethyl}benzoic acid
4-{2-[3-(7,7-dimethyl-2-oxobicyclo[2.2.1]hept-1-yl-methanesulfonylamino)-phenyl]ethyl}benzoic acid
4-{2-[4-(4-chlorobenzenesulfonylamino)phenyl]ethyl}benzoic acid
4-[2-(4-methanesulfonylaminophenyl)ethyl]benzoic acid
4-{2-[4-(4-methoxybenzenesulfonylamino)phenyl]ethyl}benzoic acid
4-[2-(4-phenylmethanesulfonylaminophenyl)ethyl]benzoic acid
4-{2-[4-(butane-1-sulfonylamino)phenyl]ethyl}benzoic acid
4-[2-(4-benzenesulfonylaminophenyl)ethyl]benzoic acid
4-{2-[4-(4-acetylaminobenzenesulfonylamino)phenyl]ethyl}benzoic acid
4-{2-[4-(7,7-dimethyl-2-oxobicyclo[2.2.1]hept-1-yl-methanesulfonylamino)-phenyl]ethyl}benzoic acid
4-{2-[4-(4-methylbenzenesulfonylamino)phenyl]ethyl}benzoic acid
4-{2-[4-(3-trifluoromethylbenzenesulfonylamino)phenyl]ethyl}benzoic acid
4-{2-[4-(naphthalene-1-sulfonylamino)phenyl]ethyl}benzoic acid
4-{2-[4-(2,5-dimethoxybenzenesulfonylamino)phenyl]ethyl}benzoic acid
4-{2-[4-(2,4-dimethylbenzenesulfonylamino)phenyl]ethyl}benzoic acid
4-{2-[4-(2,4-difluorobenzenesulfonylamino)phenyl]ethyl}benzoic acid
4-{2-[4-(2-trifluoromethylbenzenesulfonylamino)phenyl]ethyl}benzoic acid 4-{2-[4-(4-fluorobenzenesulfonylamino)phenyl]ethyl}benzoic acid
4-{2-[4-(4-acetylbenzenesulfonylamino)phenyl]ethyl}benzoic acid
4-{2-[4-(ethanesulfonylamino)phenyl]ethyl}benzoic acid
4-{2-[4-(5-dimethylaminonaphthalene-1-sulfonylamino)phenyl]ethyl}benzoic acid
4-{2-[4-(2,5-dichlorobenzenesulfonylamino)phenyl]ethyl}benzoic acid
4-{2-[4-(2-phenylethenesulfonylamino)phenyl]ethyl}benzoic acid
4-{2-[4-(4-trifluoromethoxybenzenesulfonylamino)phenyl]ethyl}benzoic acid
4-{2-[4-(2-trifluoromethoxybenzenesulfonylamino)phenyl]ethyl}benzoic acid
4-{2-[4-(5-fluoro-2-methylbenzenesulfonylamino)phenyl]ethyl}benzoic acid 200
4-{2-[4-(4-butylbenzenesulfonylamino)phenyl]ethyl}benzoic acid
4-{2-[4-(2,3,4,5,6-pentamethylbenzenesulfonylamino)phenyl]ethyl}benzoic acid
4-{2-[4-(3,5-bis-trifluoromethylbenzenesulfonylamino)phenyl]ethyl}benzoic acid
4-{2-[4-(4-propylbenzenesulfonylamino)phenyl]ethyl}benzoic acid
4-{2-[4-(4-isopropylbenzenesulfonylamino)phenyl]ethyl}benzoic acid
4-{2-[4-(3-methylbenzenesulfonylamino)phenyl]ethyl}benzoic acid
4-{2-[4-(2-fluorobenzenesulfonylamino)phenyl]ethyl}benzoic acid
4-{2-[4-(naphthalene-2-sulfonylamino)phenyl]ethyl}benzoic acid
4-{2-[4-(2-acetylamino-4-methylthiazole-5-sulfonylamino)phenyl]ethyl}benzoic acid
4-{2-[4-(2,4,6-triisopropylbenzenesulfonylamino)phenyl]ethyl}benzoic acid
4-{2-[4-(2,4,6-trimethylbenzenesulfonylamino)phenyl]ethyl}benzoic acid
4-{2-[4-(4-tert-butylbenzenesulfonylamino)phenyl]ethyl}benzoic acid
4-{2-[4-(3,4-dimethoxybenzenesulfonylamino)phenyl]ethyl}benzoic acid
4-{2-[4-(thiophene-2-sulfonylamino)phenyl]ethyl}benzoic acid
4-{2-[4-(propane-2-sulfonylamino)phenyl]ethyl}benzoic acid
4-{2-[4-(5-benzenesulfonylthiophene-2-sulfonylamino)phenyl]ethyl}benzoic acid
4-{2-[4-(4-butoxybenzenesulfonylamino)phenyl]ethyl}benzoic acid
4-{2-[4-(2,6-difluorobenzenesulfonylamino)phenyl]ethyl}benzoic acid
4-{2-[4-(3-methoxybenzenesulfonylamino)phenyl]ethyl}benzoic acid
4-{2-[4-(3-fluorobenzenesulfonylamino)phenyl]ethyl}benzoic acid
4-{2-[4-(4-benzenesulfonylthiophene-2-sulfonylamino)phenyl]ethyl}benzoic acid
4-(2-{4-[4-(1,1-dimethylpropyl)benzenesulfonylamino]phenyl}ethyl)benzoic acid
4-{2-[4-(2-cyanobenzenesulfonylamino)phenyl]ethyl}benzoic acid
4-{2-[4-(4-trifluoromethylbenzenesulfonylamino)phenyl]ethyl}benzoic acid
3-{2-[2-(4-chlorobenzenesulfonylamino)phenyl]ethyl}benzoic acid
3-[2-(2-methanesulfonylaminophenyl)ethyl]benzoic acid
3-{2-[2-(4-methoxybenzenesulfonylamino)phenyl]ethyl}benzoic acid
3-[2-(2-phenylmethanesulfonylaminophenyl)ethyl]benzoic acid
3-{2-[2-(butane-1-sulfonylamino)phenyl]ethyl}benzoic acid
3-[2-(2-benzenesulfonylaminophenyl)ethyl]benzoic acid
3-{2-[2-(4-acetylaminobenzenesulfonylamino)phenyl]ethyl}benzoic acid
3-{2-[2-(2-nitrobenzenesulfonylamino)phenyl]ethyl}benzoic acid
3-{2-[2-(toluene-4-sulfonylamino)phenyl]ethyl}benzoic acid
3-{2-[2-(3-trifluoromethylbenzenesulfonylamino)phenyl]ethyl}benzoic acid
3-{2-[2-(naphthalene-1-sulfonylamino)phenyl]ethyl}benzoic acid
3-{2-[2-(2,5-dimethoxybenzenesulfonylamino)phenyl]ethyl}benzoic acid
3-{2-[2-(2,4-dimethylbenzenesulfonylamino)phenyl]ethyl}benzoic acid
3-{2-[2-(2,4-difluorobenzenesulfonylamino)phenyl]ethyl}benzoic acid
3-{2-[2-(2-trifluoromethylbenzenesulfonylamino)phenyl]ethyl}benzoic acid
3-{2-[2-(4-fluorobenzenesulfonylamino)phenyl]ethyl}benzoic acid
3-{2-[2-(5-chloro-3-methylbenzo[b]thiophene-2-sulfonylamino)phenyl]ethyl}-benzoic acid
3-{2-[2-(biphenyl-4-sulfonylamino)phenyl]ethyl}benzoic acid
3-{2-[2-(4-acetylbenzenesulfonylamino)phenyl]ethyl}benzoic acid
3-[2-(2-ethanesulfonylaminophenyl)ethyl]benzoic acid
3-{2-[2-(5-dimethylaminonaphthalene-1-sulfonylamino)phenyl]ethyl}benzoic acid
3-{2-[2-(naphthalene-2-sulfonylamino)phenyl]ethyl}benzoic acid
3-{2-[2-(2-acetylamino-4-methylthiazole-5-sulfonylamino)phenyl]ethyl}benzoic acid
3-{2-[2-(2,5-dichlorobenzenesulfonylamino)phenyl]ethyl}benzoic acid
3-{2-[2-(2,4,6-trimethylbenzenesulfonylamino)phenyl]ethyl}benzoic acid
3-{2-[2-(4-tert-butylbenzenesulfonylamino)phenyl]ethyl}benzoic acid
3-{2-[2-((E)-2-phenylethenesulfonylamino)phenyl]ethyl}benzoic acid
3-{2-[2-(3,4-dimethoxybenzenesulfonylamino)phenyl]ethyl}benzoic acid
3-{2-[2-(4-trifluoromethoxybenzenesulfonylamino)phenyl]ethyl}benzoic acid
3-{2-[2-(thiophene-2-sulfonylamino)phenyl]ethyl}benzoic acid
3-{2-[2-(4-carboxybenzenesulfonylamino)phenyl]ethyl}benzoic acid
3-{2-[2-(propane-2-sulfonylamino)phenyl]ethyl}benzoic acid
3-{2-[2-(hexadecane-1-sulfonylamino)phenyl]ethyl}benzoic acid
3-{2-[2-(quinoline-8-sulfonylamino)phenyl]ethyl}benzoic acid
3-{2-[2-(5-benzenesulfonylthiophene-2-sulfonylamino)phenyl]ethyl}benzoic acid
3-{2-[2-(2-trifluoromethoxybenzenesulfonylamino)phenyl]ethyl}benzoic acid 3-{2-[2-(4-butoxybenzenesulfonylamino)phenyl]
ethyl}benzoic acid
3-{2-[2-(5-fluoro-2-methylbenzenesulfonylamino)phenyl]
ethyl}benzoic acid
3-{2-[2-(2,6-difluorobenzenesulfonylamino)phenyl]
ethyl}benzoic acid
3-{2-[2-(4-butylbenzenesulfonylamino)phenyl]
ethyl}benzoic acid
3-{2-[2-(3-methoxybenzenesulfonylamino)phenyl]
ethyl}benzoic acid
3-[2-(2-pentamethylbenzenesulfonylaminophenyl)ethyl]
benzoic acid
3-{2-[2-(3,5-bis-trifluoromethylbenzenesulfonylamino)phenyl]ethyl}benzoic acid
3-{2-[2-(3-fluorobenzenesulfonylamino)phenyl]
ethyl}benzoic acid
3-{2-[2-(toluene-3-sulfonylamino)phenyl]ethyl}benzoic
acid
3-{2-[2-(4-benzenesulfonylthiophene-2-sulfonylamino)phenyl]ethyl}benzoic acid
3-(2-{2-[4-(1,1-dimethylpropyl)benzenesulfonylamino]
phenyl}ethyl)benzoic acid
3-{2-[2-(4-ethylbenzenesulfonylamino)phenyl]
ethyl}benzoic acid
3-{2-[2-(4-trifluoromethylbenzenesulfonylamino)phenyl]
ethyl}benzoic acid
3-{2-[2-(7,7-dimethyl-2-oxobicyclo[2.2.1]hept-1-yl-
methanesulfonylamino)-phenyl]ethyl}benzoic acid
3-{2-[2-(2-fluorobenzenesulfonylamino)phenyl]
ethyl}benzoic acid
3-{2-[2-(4-propylbenzenesulfonylamino)phenyl]
ethyl}benzoic acid
3-{2-[2-(4-isopropylbenzenesulfonylamino)phenyl]
ethyl}benzoic acid
3-{2-[2-(2-cyanobenzenesulfonylamino)phenyl]
ethyl}benzoic acid
3-{2-[3-(4-chlorobenzenesulfonylamino)phenyl]
ethyl}benzoic acid
3-[2-(3-methanesulfonylaminophenyl)ethyl]benzoic acid
3-{2-[3-(4-methoxybenzenesulfonylamino)phenyl]
ethyl}benzoic acid
3-[2-(3-phenylmethanesulfonylaminophenyl)ethyl]benzoic
acid
3-{2-[3-(butane-1-sulfonylamino)phenyl]ethyl}benzoic acid
3-[2-(3-benzenesulfonylaminophenyl)ethyl]benzoic acid
3-{2-[3-(4-acetylaminobenzenesulfonylamino)phenyl]
ethyl}benzoic acid
3-{2-[3-(2-nitrobenzenesulfonylamino)phenyl]
ethyl}benzoic acid
3-{2-[3-(toluene-4-sulfonylamino)phenyl]ethyl}benzoic
acid
3-{2-[3-(3-trifluoromethylbenzenesulfonylamino)phenyl]
ethyl}benzoic acid
3-{2-[3-(naphthalene-1-sulfonylamino)phenyl]
ethyl}benzoic acid
3-{2-[3-(2,5-dimethoxybenzenesulfonylamino)phenyl]
ethyl}benzoic acid
3-{2-[3-(2,4-dimethylbenzenesulfonylamino)phenyl]
ethyl}benzoic acid
3-{2-[3-(2-fluorobenzenesulfonylamino)phenyl]
ethyl}benzoic acid
3-{2-[3-(2,4-difluorobenzenesulfonylamino)phenyl]
ethyl}benzoic acid
3-{2-[3-(2-trifluoromethylbenzenesulfonylamino)phenyl]
ethyl}benzoic acid
3-{2-[3-(4-fluorobenzenesulfonylamino)phenyl]
ethyl}benzoic acid
3-{2-[3-(5-chloro-3-methylbenzo[b]thiophene-2-sulfonylamino)phenyl]ethyl}-benzoic acid
3-{2-[3-(biphenyl-4-sulfonylamino)phenyl]ethyl}benzoic
acid
3-{2-[3-(4-acetylbenzenesulfonylamino)phenyl]
ethyl}benzoic acid
3-[2-(3-ethanesulfonylaminophenyl)ethyl]benzoic acid
3-{2-[3-(5-dimethylaminonaphthalene-1-sulfonylamino)
phenyl]ethyl}benzoic acid
3-{2-[3-(naphthalene-2-sulfonylamino)phenyl]
ethyl}benzoic acid
3-{2-[3-(2-acetylamino-4-methylthiazole-5-sulfonylamino)
phenyl]ethyl}benzoic acid
3-{2-[3-(2,5-dichlorobenzenesulfonylamino)phenyl]
ethyl}benzoic acid
3-{2-[3-(2,4,6-triisopropylbenzenesulfonylamino)phenyl]
ethyl}benzoic acid
3-{2-[3-(2,4,6-trimethylbenzenesulfonylamino)phenyl]
ethyl}benzoic acid
3-{2-[3-(4-tert-butylbenzenesulfonylamino)phenyl]
ethyl}benzoic acid
3-{2-[3-((E)-2-phenylethenesulfonylamino)phenyl]
ethyl}benzoic acid
3-{2-[3-(3,4-dimethoxybenzenesulfonylamino)phenyl]
ethyl}benzoic acid
3-{2-[3-(4-trifluoromethoxybenzenesulfonylamino)phenyl]
ethyl}benzoic acid
3-{2-[3-(thiophene-2-sulfonylamino)phenyl]ethyl}benzoic
acid
3-{2-[3-(4-carboxybenzenesulfonylamino)phenyl]
ethyl}benzoic acid
3-{2-[3-(propane-2-sulfonylamino)phenyl]ethyl}benzoic
acid
3-{2-[3-(2,2,2-trifluoroethanesulfonylamino)phenyl]
ethyl}benzoic acid
3-{2-[3-(quinoline-8-sulfonylamino)phenyl]ethyl}benzoic
acid
3-{2-[3-(5-benzenesulfonylthiophene-2-sulfonylamino)phenyl]ethyl}benzoic acid
3-{2-[3-(2-trifluoromethoxybenzenesulfonylamino)phenyl]
ethyl}benzoic acid
3-{2-[3-(4-butoxybenzenesulfonylamino)phenyl]
ethyl}benzoic acid
3-{2-[3-(5-fluoro-2-methylbenzenesulfonylamino)phenyl]
ethyl}benzoic acid
3-{2-[3-(2,6-difluorobenzenesulfonylamino)phenyl]
ethyl}benzoic acid
3-{2-[3-(4-butylbenzenesulfonylamino)phenyl]
ethyl}benzoic acid
3-{2-[3-(3-methoxybenzenesulfonylamino)phenyl]
ethyl}benzoic acid
3-[2-(3-pentamethylbenzenesulfonylaminophenyl)ethyl]
benzoic acid
3-{2-[3-(3,5-bis-trifluoromethylbenzenesulfonylamino)phenyl]ethyl}benzoic acid
3-{2-[3-(3-fluorobenzenesulfonylamino)phenyl]
ethyl}benzoic acid
3-{2-[3-(toluene-3-sulfonylamino)phenyl]ethyl}benzoic
acid
3-{2-[3-(4-benzenesulfonylthiophene-2-sulfonylamino)phenyl]ethyl}benzoic acid
3-(2-{3-[4-(1,1-dimethylpropyl)benzenesulfonylamino]
phenyl}ethyl)benzoic acid
3-{2-[3-(2-cyanobenzenesulfonylamino)phenyl]
ethyl}benzoic acid
3-{2-[3-(4-ethylbenzenesulfonylamino)phenyl]
ethyl}benzoic acid 3-{2-[3-(4-trifluoromethylbenzenesulfonylamino)phenyl]ethyl}benzoic acid
3-{2-[3-(7,7-dimethyl-2-oxobicyclo[2,2,1]hept-1-yl-methanesulfonylamino)-phenyl]ethyl}benzoic acid
3-{2-[4-(4-chlorobenzenesulfonylamino)phenyl]ethyl}benzoic acid
3-[2-(4-methanesulfonylaminophenyl)ethyl]benzoic acid
3-{2-[4-(4-methoxybenzenesulfonylamino)phenyl]ethyl}benzoic acid
3-[2-(4-phenylmethanesulfonylaminophenyl)ethyl]benzoic acid
3-{2-[4-(butane-1-sulfonylamino)phenyl]ethyl}benzoic acid
3-[2-(4-benzenesulfonylaminophenyl)ethyl]benzoic acid
3-{2-[4-(4-acetylaminobenzenesulfonylamino)phenyl]ethyl}benzoic acid
3-{2-[4-(2-nitrobenzenesulfonylamino)phenyl]ethyl}benzoic acid
3-{2-[4-(toluene-4-sulfonylamino)phenyl]ethyl}benzoic acid
3-{2-[4-(3-trifluoromethylbenzenesulfonylamino)phenyl]ethyl}benzoic acid
3-{2-[4-(2,5-dimethoxybenzenesulfonylamino)phenyl]ethyl}benzoic acid
3-{2-[4-(2,4-dimethylbenzenesulfonylamino)phenyl]ethyl}benzoic acid
3-{2-[4-(2-fluorobenzenesulfonylamino)phenyl]ethyl}benzoic acid
3-{2-[4-(2,4-difluorobenzenesulfonylamino)phenyl]ethyl}benzoic acid
3-{2-[4-(2-trifluoromethylbenzenesulfonylamino)phenyl]ethyl}benzoic acid
3-{2-[4-(4-fluorobenzenesulfonylamino)phenyl]ethyl}benzoic acid
3-{2-[4-(5-chloro-3-methylbenzo[b]thiophene-2-sulfonylamino)phenyl]ethyl}-benzoic acid
3-{2-[4-(4-acetylbenzenesulfonylamino)phenyl]ethyl}benzoic acid
3-[2-(4-ethanesulfonylaminophenyl)ethyl]benzoic acid
3-{2-[4-(5-dimethylaminonaphthalene-1-sulfonylamino)phenyl]ethyl}benzoic acid
3-{2-[4-(naphthalene-2-sulfonylamino)phenyl]ethyl}benzoic acid
3-{2-[4-(2-acetylamino-4-methylthiazole-5-sulfonylamino)phenyl]ethyl}benzoic acid
3-{2-[4-(2,5-dichlorobenzenesulfonylamino)phenyl]ethyl}benzoic acid
3-{2-[4-(2,4,6-trimethylbenzenesulfonylamino)phenyl]ethyl}benzoic acid
3-{2-[4-(4-tert-butylbenzenesulfonylamino)phenyl]ethyl}benzoic acid
3-{2-[4-((E)-2-phenylethenesulfonylamino)phenyl]ethyl}benzoic acid
3-{2-[4-(3,4-dimethoxybenzenesulfonylamino)phenyl]ethyl}benzoic acid
3-{2-[4-(4-trifluoromethoxybenzenesulfonylamino)phenyl]ethyl}benzoic acid
3-{2-[4-(thiophene-2-sulfonylamino)phenyl]ethyl}benzoic acid
3-{2-[4-(4-carboxybenzenesulfonylamino)phenyl]ethyl}benzoic acid
3-{2-[4-(propane-2-sulfonylamino)phenyl]ethyl}benzoic acid
3-{2-[4-(quinoline-8-sulfonylamino)phenyl]ethyl}benzoic acid
3-{2-[4-(5-benzenesulfonylthiophene-2-sulfonylamino)phenyl]ethyl}benzoic acid
3-{2-[4-(2-trifluoromethoxybenzenesulfonylamino)phenyl]ethyl}benzoic acid
3-{2-[4-(4-butoxybenzenesulfonylamino)phenyl]ethyl}benzoic acid
3-{2-[4-(5-fluoro-2-methylbenzenesulfonylamino)phenyl]ethyl}benzoic acid
3-{2-[4-(2,6-difluorobenzenesulfonylamino)phenyl]ethyl}benzoic acid
3-{2-[4-(4-butylbenzenesulfonylamino)phenyl]ethyl}benzoic acid
3-{2-[4-(3-methoxybenzenesulfonylamino)phenyl]ethyl}benzoic acid
3-{2-[4-(3,5-bis-trifluoromethylbenzenesulfonylamino)phenyl]ethyl}benzoic acid
3-{2-[4-(3-fluorobenzenesulfonylamino)phenyl]ethyl}benzoic acid
3-{2-[4-(toluene-3-sulfonylamino)phenyl]ethyl}benzoic acid
3-{2-[4-(4-benzenesulfonylthiophene-2-sulfonylamino)phenyl]ethyl}benzoic acid
3-(2-{4-[4-(1,1-dimethylpropyl)benzenesulfonylamino]phenyl}ethyl)benzoic acid
3-{2-[4-(2-cyanobenzenesulfonylamino)phenyl]ethyl}benzoic acid
3-{2-[4-(4-ethylbenzenesulfonylamino)phenyl]ethyl}benzoic acid
3-{2-[4-(4-trifluoromethylbenzenesulfonylamino)phenyl]ethyl}benzoic acid
3-{2-[4-(7,7-dimethyl-2-oxobicyclo[2.2.1]hept-1-yl-methanesulfonylamino)-phenyl]ethyl}benzoic acid
3-{2-[4-(naphthalene-1-sulfonylamino)phenyl]ethyl}benzoic acid
3-[2-(4-pentamethylbenzenesulfonylaminophenyl)ethyl]benzoic acid
3-{2-[4-(4-propylbenzenesulfonylamino)phenyl]ethyl}benzoic acid
3-{2-[4-(4-isopropylbenzenesulfonylamino)phenyl]ethyl}benzoic acid
2-{2-[2-(2-nitrobenzenesulfonylamino)phenyl]ethyl}benzoic acid
2-{2-[2-(2,5-dimethoxybenzenesulfonylamino)phenyl]ethyl}benzoic acid
2-{2-[2-(2-fluorobenzenesulfonylamino)phenyl]ethyl}benzoic acid
2-{2-[2-(4-fluorobenzenesulfonylamino)phenyl]ethyl}benzoic acid
2-{2-[2-(5-chloro-3-methylbenzo[b]thiophene-2-sulfonylamino)phenyl]ethyl}-benzoic acid
2-{2-[2-(biphenyl-4-sulfonylamino)phenyl]ethyl}benzoic acid
2-{2-[2-(4-acetylbenzenesulfonylamino)phenyl]ethyl}benzoic acid
2-[2-(2-ethanesulfonylaminophenyl)ethyl]benzoic acid
2-{2-[2-(2,4,6-trimethylbenzenesulfonylamino)phenyl]ethyl}benzoic acid
2-{2-[2-(4-tert-butylbenzenesulfonylamino)phenyl]ethyl}benzoic acid
2-{2-[2-((E)-2-phenylethenesulfonylamino)phenyl]ethyl}benzoic acid
2-{2-[2-(3,4-dimethoxybenzenesulfonylamino)phenyl]ethyl}benzoic acid
2-{2-[2-(4-trifluoromethoxybenzenesulfonylamino)phenyl]ethyl}benzoic acid
2-{2-[2-(thiophene-2-sulfonylamino)phenyl]ethyl}benzoic acid
2-{2-[2-(4-carboxybenzenesulfonylamino)phenyl]ethyl}benzoic acid 2-{2-[2-(propane-2-sulfonylamino)phenyl]ethyl}benzoic acid
2-{2-[2-(quinoline-8-sulfonylamino)phenyl]ethyl}benzoic acid
2-{2-[2-(5-benzenesulfonylthiophene-2-sulfonylamino)phenyl]ethyl}benzoic acid
2-{2-[2-(2-trifluoromethoxybenzenesulfonylamino)phenyl]ethyl}benzoic acid
2-{2-[2-(4-butoxybenzenesulfonylamino)phenyl]ethyl}benzoic acid
2-{2-[2-(5-fluoro-2-methylbenzenesulfonylamino)phenyl]ethyl}benzoic acid
2-{2-[2-(2,6-difluorobenzenesulfonylamino)phenyl]ethyl}benzoic acid
2-{2-[2-(4-butylbenzenesulfonylamino)phenyl]ethyl}benzoic acid
2-{2-[2-(3-methoxybenzenesulfonylamino)phenyl]ethyl}benzoic acid
2-[2-(2-pentamethylbenzenesulfonylaminophenyl)ethyl]benzoic acid
2-{2-[2-(3,5-bis-trifluoromethylbenzenesulfonylamino)phenyl]ethyl}benzoic acid
2-{2-[2-(3-fluorobenzenesulfonylamino)phenyl]ethyl}benzoic acid
2-{2-[2-(toluene-3-sulfonylamino)phenyl]ethyl}benzoic acid
2-{2-[2-(4-benzenesulfonylthiophene-2-sulfonylamino)phenyl]ethyl}benzoic acid
2-(2-{2-[4-(1,1-dimethylpropyl)benzenesulfonylamino]phenyl}ethyl)benzoic acid
2-{2-[2-(2-cyanobenzenesulfonylamino)phenyl]ethyl}benzoic acid
2-{2-[2-(4-ethylbenzenesulfonylamino)phenyl]ethyl}benzoic acid
2-{2-[2-(4-trifluoromethylbenzenesulfonylamino)phenyl]ethyl}benzoic acid
2-{2-[2-(4-chlorobenzenesulfonylamino)phenyl]ethyl}benzoic acid
2-[2-(2-methanesulfonylaminophenyl)ethyl]benzoic acid
2-{2-[2-(4-methoxybenzenesulfonylamino)phenyl]ethyl}benzoic acid
2-[2-(2-phenylmethanesulfonylaminophenyl)ethyl]benzoic acid
2-{2-[2-(butane-1-sulfonylamino)phenyl]ethyl}benzoic acid
2-[2-(2-benzenesulfonylaminophenyl)ethyl]benzoic acid
2-{2-[2-(4-acetylaminobenzenesulfonylamino)phenyl]ethyl}benzoic acid
2-{2-[2-(2,4-difluorobenzenesulfonylamino)phenyl]ethyl}benzoic acid
2-{2-[2-(toluene-4-sulfonylamino)phenyl]ethyl}benzoic acid
2-{2-[2-(naphthalene-1-sulfonylamino)phenyl]ethyl}benzoic acid
2-{2-[2-(2-trifluoromethylbenzenesulfonylamino)phenyl]ethyl}benzoic acid
2-{2-[2-(5-dimethylaminonaphthalene-1-sulfonylamino)phenyl]ethyl}benzoic acid
2-{2-[2-(naphthalene-2-sulfonylamino)phenyl]ethyl}benzoic acid
2-{2-[2-(2-acetylamino-4-methylthiazole-5-sulfonylamino)phenyl]ethyl}benzoic acid
2-{2-[2-(2,5-dichlorobenzenesulfonylamino)phenyl]ethyl}benzoic acid
2-{2-[2-(2,4,6-triisopropylbenzenesulfonylamino)phenyl]ethyl}benzoic acid
2-{2-[2-(4-propylbenzenesulfonylamino)phenyl]ethyl}benzoic acid
2-{2-[2-(4-isopropylbenzenesulfonylamino)phenyl]ethyl}benzoic acid
2-{2-[2-(7,7-dimethyl-2-oxobicyclo[2.2.1]hept-1-yl-methanesulfonylamino)-phenyl]ethyl}benzoic acid
2-{2-[3-(4-acetylaminobenzenesulfonylamino)phenyl]ethyl}benzoic acid
2-{2-[3-(toluene-4-sulfonylamino)phenyl]ethyl}benzoic acid
2-{2-[3-(naphthalene-1-sulfonylamino)phenyl]ethyl}benzoic acid
2-{2-[3-(2,5-dimethoxybenzenesulfonylamino)phenyl]ethyl}benzoic acid
2-{2-[3-(2,4-dimethylbenzenesulfonylamino)phenyl]ethyl}benzoic acid
2-{2-[3-(2-trifluoromethylbenzenesulfonylamino)phenyl]ethyl}benzoic acid
2-{2-[3-(5-chloro-3-methylbenzo[b]thiophene-2-sulfonylamino)phenyl]ethyl}-benzoic acid
2-{2-[3-(naphthalene-2-sulfonylamino)phenyl]ethyl}benzoic acid
2-{2-[3-(2,5-dichlorobenzenesulfonylamino)phenyl]ethyl}benzoic acid
2-{2-[3-(2,4,6-trimethylbenzenesulfonylamino)phenyl]ethyl}benzoic acid
2-{2-[3-(4-tert-butylbenzenesulfonylamino)phenyl]ethyl}benzoic acid
2-{2-[3-((E)-2-phenylethenesulfonylamino)phenyl]ethyl}benzoic acid
2-{2-[3-(3,4-dimethoxybenzenesulfonylamino)phenyl]ethyl}benzoic acid
2-{2-[3-(4-trifluoromethoxybenzenesulfonylamino)phenyl]ethyl}benzoic acid
2-{2-[3-(thiophene-2-sulfonylamino)phenyl]ethyl}benzoic acid
2-{2-[3-(4-carboxybenzenesulfonylamino)phenyl]ethyl}benzoic acid
2-{2-[3-(propane-2-sulfonylamino)phenyl]ethyl}benzoic acid
2-{2-[3-(5-benzenesulfonylthiophene-2-sulfonylamino)phenyl]ethyl}benzoic acid
2-{2-[3-(2-trifluoromethoxybenzenesulfonylamino)phenyl]ethyl}benzoic acid
2-{2-[3-(4-butoxybenzenesulfonylamino)phenyl]ethyl}benzoic acid
2-{2-[3-(5-fluoro-2-methylbenzenesulfonylamino)phenyl]ethyl}benzoic acid
2-{2-[3-(2,6-difluorobenzenesulfonylamino)phenyl]ethyl}benzoic acid
2-{2-[3-(4-butylbenzenesulfonylamino)phenyl]ethyl}benzoic acid
2-{2-[3-(3-methoxybenzenesulfonylamino)phenyl]ethyl}benzoic acid
2-[2-(3-pentamethylbenzenesulfonylaminophenyl)ethyl]benzoic acid
2-{2-[3-(3,5-bis-trifluoromethylbenzenesulfonylamino)phenyl]ethyl}benzoic acid
2-{2-[3-(3-fluorobenzenesulfonylamino)phenyl]ethyl}benzoic acid
2-{2-[3-(toluene-3-sulfonylamino)phenyl]ethyl}benzoic acid
2-{2-[3-(4-benzenesulfonylthiophene-2-sulfonylamino)phenyl]ethyl}benzoic acid
2-(2-{3-[4-(1,1-dimethylpropyl)benzenesulfonylamino]phenyl}ethyl)benzoic acid
2-{2-[3-(4-ethylbenzenesulfonylamino)phenyl]ethyl}benzoic acid 2-{2-[3-(4-trifluoromethylbenzenesulfonylamino)phenyl]
ethyl}benzoic acid
2-{2-[3-(4-chlorobenzenesulfonylamino)phenyl]
ethyl}benzoic acid
2-[2-(3-methanesulfonylaminophenyl)ethyl]benzoic acid
2-{2-[3-(4-methoxybenzenesulfonylamino)phenyl]
ethyl}benzoic acid
2-[2-(3-phenylmethanesulfonylaminophenyl)ethyl]benzoic
acid
2-{2-[3-(butane-1-sulfonylamino)phenyl]ethyl}benzoic acid
2-[2-(3-benzenesulfonylaminophenyl)ethyl]benzoic acid
2-{2-[3-(2-nitrobenzenesulfonylamino)phenyl]
ethyl}benzoic acid
2-{2-[3-(2-fluorobenzenesulfonylamino)phenyl]
ethyl}benzoic acid
2-{2-[3-(2,4-difluorobenzenesulfonylamino)phenyl]
ethyl}benzoic acid
2-{2-[3-(4-fluorobenzenesulfonylamino)phenyl]
ethyl}benzoic acid
2-{2-[3-(4-acetylbenzenesulfonylamino)phenyl]
ethyl}benzoic acid
2-{2-[3-(2-acetylamino-4-methylthiazole-5-sulfonylamino)
phenyl]ethyl}benzoic acid
2-{2-[3-(2,4,6-triisopropylbenzenesulfonylamino)phenyl]
ethyl}benzoic acid
2-{2-[3-(4-propylbenzenesulfonylamino)phenyl]
ethyl}benzoic acid
2-{2-[3-(4-isopropylbenzenesulfonylamino)phenyl]
ethyl}benzoic acid
2-{2-[3-(2-cyanobenzenesulfonylamino)phenyl]
ethyl}benzoic acid
2-{2-[3-(7,7-dimethyl-2-oxobicyclo[2.2.1]hept-1-yl-
methanesulfonylamino)-phenyl]ethyl}benzoic acid
2-{2-[4-(4-acetylaminobenzenesulfonylamino)phenyl]
ethyl}benzoic acid
2-{2-[4-(toluene-4-sulfonylamino)phenyl]ethyl}benzoic
acid
2-{2-[4-(3-trifluoromethylbenzenesulfonylamino)phenyl]
ethyl}benzoic acid
2-{2-[4-(naphthalene-1-sulfonylamino)phenyl]
ethyl}benzoic acid
2-{2-[4-(2,5-dimethoxybenzenesulfonylamino)phenyl]
ethyl}benzoic acid
2-{2-[4-(2,4-dimethylbenzenesulfonylamino)phenyl]
ethyl}benzoic acid
2-{2-[4-(2-fluorobenzenesulfonylamino)phenyl]
ethyl}benzoic acid
2-{2-[4-(2,4-difluorobenzenesulfonylamino)phenyl]
ethyl}benzoic acid
2-{2-[4-(2-trifluoromethylbenzenesulfonylamino)phenyl]
ethyl}benzoic acid
2-{2-[4-(4-fluorobenzenesulfonylamino)phenyl]
ethyl}benzoic acid
2-{2-[4-(5-chloro-3-methylbenzo[b]thiophene-2-sulfony-
lamino)phenyl]ethyl}-benzoic acid
2-{2-[4-(biphenyl-4-sulfonylamino)phenyl]ethyl}benzoic
acid
2-{2-[4-(4-acetylbenzenesulfonylamino)phenyl]
ethyl}benzoic acid
2-[2-(4-ethanesulfonylaminophenyl)ethyl]benzoic acid
2-{2-[4-(naphthalene-2-sulfonylamino)phenyl]
ethyl}benzoic acid
2-{2-[4-(2-acetylamino-4-methylthiazole-5-sulfonylamino)
phenyl]ethyl}benzoic acid
2-{2-[4-(2,5-dichlorobenzenesulfonylamino)phenyl]
ethyl}benzoic acid 2-{2-[4-(2,4,6-trimethylbenzenesulfonylamino)phenyl]
ethyl}benzoic acid
2-{2-[4-(4-tert-butylbenzenesulfonylamino)phenyl]
ethyl}benzoic acid
2-{2-[4-((E)-2-phenylethenesulfonylamino)phenyl]
ethyl}benzoic acid
2-{2-[4-(3,4-dimethoxybenzenesulfonylamino)phenyl]
ethyl}benzoic acid
2-{2-[4-(4-trifluoromethoxybenzenesulfonylamino)phenyl]
ethyl}benzoic acid
2-{2-[4-(thiophene-2-sulfonylamino)phenyl]ethyl}benzoic
acid
2-{2-[4-(4-carboxybenzenesulfonylamino)phenyl]
ethyl}benzoic acid
2-{2-[4-(propane-2-sulfonylamino)phenyl]ethyl}benzoic
acid
2-{2-[4-(5-benzenesulfonylthiophene-2-sulfonylamino)phe-
nyl]ethyl}benzoic acid
2-{2-[4-(2-trifluoromethoxybenzenesulfonylamino)phenyl]
ethyl}benzoic acid
2-{2-[4-(4-butoxybenzenesulfonylamino)phenyl]
ethyl}benzoic acid
2-{2-[4-(5-fluoro-2-methylbenzenesulfonylamino)phenyl]
ethyl}benzoic acid
2-{2-[4-(2,6-difluorobenzenesulfonylamino)phenyl]
ethyl}benzoic acid
2-{2-[4-(4-butylbenzenesulfonylamino)phenyl]
ethyl}benzoic acid
2-{2-[4-(3-methoxybenzenesulfonylamino)phenyl]
ethyl}benzoic acid
2-[2-(4-pentamethylbenzenesulfonylaminophenyl)ethyl]
benzoic acid
2-{2-[4-(3,5-bis-trifluoromethylbenzenesulfonylamino)phe-
nyl]ethyl}benzoic acid
2-{2-[4-(3-fluorobenzenesulfonylamino)phenyl]
ethyl}benzoic acid
2-{2-[4-(toluene-3-sulfonylamino)phenyl]ethyl}benzoic
acid
2-{2-[4-(4-benzenesulfonylthiophene-2-sulfonylamino)phe-
nyl]ethyl}benzoic acid
2-(2-{4-[4-(1,1-dimethylpropyl)benzenesulfonylamino]
phenyl}ethyl)benzoic acid
2-{2-[4-(2-cyanobenzenesulfonylamino)phenyl]
ethyl}benzoic acid
2-{2-[4-(4-ethylbenzenesulfonylamino)phenyl]
ethyl}benzoic acid
2-{2-[4-(4-trifluoromethylbenzenesulfonylamino)phenyl]
ethyl}benzoic acid
2-{2-[4-(4-chlorobenzenesulfonylamino)phenyl]
ethyl}benzoic acid
2-[2-(4-methanesulfonylaminophenyl)ethyl]benzoic acid
2-{2-[4-(4-methoxybenzenesulfonylamino)phenyl]
ethyl}benzoic acid
2-[2-(4-phenylmethanesulfonylaminophenyl)ethyl]benzoic
acid
2-{2-[4-(butane-1-sulfonylamino)phenyl]ethyl}benzoic acid
2-[2-(4-benzenesulfonylaminophenyl)ethyl]benzoic acid
2-{2-[4-(2-nitrobenzenesulfonylamino)phenyl]
ethyl}benzoic acid
2-{2-[4-(2,4,6-triisopropylbenzenesulfonylamino)phenyl]
ethyl}benzoic acid
2-{2-[4-(4-propylbenzenesulfonylamino)phenyl]
ethyl}benzoic acid
2-{2-[4-(4-isopropylbenzenesulfonylamino)phenyl]
ethyl}benzoic acid
2-{2-[4-(7,7-dimethyl-2-oxobicyclo[2.2.1]hept-1-yl-
methanesulfonylamino)-phenyl]ethyl}benzoic acid 2-{3-[2-(4-acetylaminobenzenesulfonylamino)phenyl] propyl}benzoic acid
2-{3-[2-(4-chlorobenzenesulfonylamino)phenyl] propyl}benzoic acid
2-{3-[2-(4-methoxybenzenesulfonylamino)phenyl] propyl}benzoic acid
2-{3-[2-(2-nitrobenzenesulfonylamino)phenyl] propyl}benzoic acid
2-{3-[2-(toluene-4-sulfonylamino)phenyl]propyl}benzoic acid
2-{3-[2-(3-trifluoromethylbenzenesulfonylamino)phenyl] propyl}benzoic acid
2-{3-[2-(naphthalene-1-sulfonylamino)phenyl] propyl}benzoic acid
2-{3-[2-(2,5-dimethoxybenzenesulfonylamino)phenyl] propyl}benzoic acid
2-{3-[2-(2,4-dimethylbenzenesulfonylamino)phenyl] propyl}benzoic acid
2-{3-[2-(2-fluorobenzenesulfonylamino)phenyl] propyl}benzoic acid
2-{3-[2-(2,4-difluorobenzenesulfonylamino)phenyl] propyl}benzoic acid
2-{3-[2-(2-trifluoromethylbenzenesulfonylamino)phenyl] propyl}benzoic acid
2-{3-[2-(4-fluorobenzenesulfonylamino)phenyl] propyl}benzoic acid
2-{3-[2-(5-chloro-3-methylbenzo[b]thiophene-2-sulfonylamino)phenyl]propyl}-benzoic acid
2-{3-[2-(biphenyl-4-sulfonylamino)phenyl]propyl}benzoic acid
2-{3-[2-(4-acetylbenzenesulfonylamino)phenyl] propyl}benzoic acid
2-{3-[2-(5-dimethylaminonaphthalene-1-sulfonylamino) phenyl]propyl}benzoic acid
2-{3-[2-(naphthalene-2-sulfonylamino)phenyl] propyl}benzoic acid
2-{3-[2-(2-acetylamino-4-methylthiazole-5-sulfonylamino) phenyl]propyl}benzoic acid
2-[3-(2-benzenesulfonylaminophenyl)propyl]benzoic acid
2-{3-[2-(2,5-dichlorobenzenesulfonylamino)phenyl] propyl}benzoic acid
2-{3-[2-(2,4,6-trimethylbenzenesulfonylamino)phenyl] propyl}benzoic acid
2-{3-[2-(4-isopropylbenzenesulfonylamino)phenyl] propyl}benzoic acid
2-{3-[2-((E)-2-phenylethenesulfonylamino)phenyl] propyl}benzoic acid
2-{3-[2-(3,4-dimethoxybenzenesulfonylamino)phenyl] propyl}benzoic acid
2-{3-[2-(4-trifluoromethoxybenzenesulfonylamino)phenyl] propyl}benzoic acid
2-{3-[2-(4-carboxybenzenesulfonylamino)phenyl] propyl}benzoic acid
2-{3-[2-(5-benzenesulfonylthiophene-2-sulfonylamino)phenyl]propyl}benzoic acid
2-{3-[2-(2-trifluoromethoxybenzenesulfonylamino)phenyl] propyl}benzoic acid
2-{3-[2-(4-butoxybenzenesulfonylamino)phenyl] propyl}benzoic acid
2-{3-[2-(5-fluoro-2-methylbenzenesulfonylamino)phenyl] propyl}benzoic acid
2-{3-[2-(2,6-difluorobenzenesulfonylamino)phenyl] propyl}benzoic acid
2-{3-[2-(4-butylbenzenesulfonylamino)phenyl] propyl}benzoic acid
2-{3-[2-(3-methoxybenzenesulfonylamino)phenyl] propyl}benzoic acid
2-[3-(2,3,4,5,6-pentamethylbenzenesulfonylaminophenyl) propyl]benzoic acid
2-{3-[2-(4-propylbenzenesulfonylamino)phenyl] propyl}benzoic acid
2-{3-[2-(4-isopropylbenzenesulfonylamino)phenyl] propyl}benzoic acid
2-{3-[2-(3-fluorobenzenesulfonylamino)phenyl] propyl}benzoic acid
2-{3-[2-(toluene-3-sulfonylamino)phenyl]propyl}benzoic acid
2-{3-[2-(4-benzenesulfonylthiophene-2-sulfonylamino)phenyl]propyl}benzoic acid
3-{3-[2-(4-acetylaminobenzenesulfonylamino)phenyl] propyl}benzoic acid
3-{3-[2-(4-chlorobenzenesulfonylamino)phenyl] propyl}benzoic acid
3-[3-(2-methanesulfonylaminophenyl)propyl]benzoic acid
3-{3-[2-(4-methoxybenzenesulfonylamino)phenyl] propyl}benzoic acid
3-{3-[2-(2-nitrobenzenesulfonylamino)phenyl] propyl}benzoic acid
3-{3-[2-(toluene-4-sulfonylamino)phenyl]propyl}benzoic acid
3-{3-[2-(3-trifluoromethylbenzenesulfonylamino)phenyl] propyl}benzoic acid
3-{3-[2-(naphthalene-1-sulfonylamino)phenyl] propyl}benzoic acid
3-[3-(2-phenylmethanesulfonylaminophenyl)propyl]benzoic acid
3-{3-[2-(2,5-dimethoxybenzenesulfonylamino)phenyl] propyl}benzoic acid
3-{3-[2-(2,4-dimethylbenzenesulfonylamino)phenyl] propyl}benzoic acid
3-{3-[2-(2-fluorobenzenesulfonylamino)phenyl] propyl}benzoic acid
3-{3-[2-(2,4-difluorobenzenesulfonylamino)phenyl] propyl}benzoic acid
3-{3-[2-(2-trifluoromethylbenzenesulfonylamino)phenyl] propyl}benzoic acid
3-{3-[2-(4-fluorobenzenesulfonylamino)phenyl] propyl}benzoic acid
3-{3-[2-(biphenyl-4-sulfonylamino)phenyl]propyl}benzoic acid
3-{3-[2-(4-acetylbenzenesulfonylamino)phenyl] propyl}benzoic acid
3-[3-(2-ethanesulfonylaminophenyl)propyl]benzoic acid
3-{3-[2-(butane-1-sulfonylamino)phenyl]propyl}benzoic acid
3-{3-[2-(4-methoxy-2,3,6-trimethylbenzenesulfonylamino) phenyl]propyl}benzoic acid
3-{3-[2-(5-dimethylaminonaphthalene-1-sulfonylamino) phenyl]propyl}benzoic acid
3-{3-[2-(naphthalene-2-sulfonylamino)phenyl] propyl}benzoic acid
3-{3-[2-(2-acetylamino-4-methylthiazole-5-sulfonylamino) phenyl]propyl}benzoic acid
3-[3-(2-benzenesulfonylaminophenyl)propyl]benzoic acid
3-{3-[2-(2,5-dichlorobenzenesulfonylamino)phenyl] propyl}benzoic acid
3-{3-[2-(2,4,6-triisopropylbenzenesulfonylamino)phenyl] propyl}benzoic acid
3-{3-[2-(2,4,6-trimethylbenzenesulfonylamino)phenyl] propyl}benzoic acid
3-{3-[2-(4-tert-butylbenzenesulfonylamino)phenyl] propyl}benzoic acid
3-[3-(2-trifluoromethanesulfonylaminophenyl)propyl]benzoic acid 3-{3-[2-((E)-2-phenylethenesulfonylamino)phenyl]propyl}benzoic acid
3-{3-[2-(3,4-dimethoxybenzenesulfonylamino)phenyl]propyl}benzoic acid
3-{3-[2-(thiophene-2-sulfonylamino)phenyl]propyl}benzoic acid
3-{3-[2-(propane-2-sulfonylamino)phenyl]propyl}benzoic acid
3-{3-[2-(5-benzenesulfonylthiophene-2-sulfonylamino)phenyl]propyl}benzoic acid
3-{3-[2-(2-trifluoromethoxybenzenesulfonylamino)phenyl]propyl}benzoic acid
3-{3-[2-(4-butoxybenzenesulfonylamino)phenyl]propyl}benzoic acid
3-{3-[2-(5-fluoro-2-methylbenzenesulfonylamino)phenyl]propyl}benzoic acid
3-{3-[2-(2,6-difluorobenzenesulfonylamino)phenyl]propyl}benzoic acid
3-{3-[2-(4-butylbenzenesulfonylamino)phenyl]propyl}benzoic acid
3-{3-[2-(3-methoxybenzenesulfonylamino)phenyl]propyl}benzoic acid
3-[3-(2-pentamethylbenzenesulfonylaminophenyl)propyl]benzoic acid
3-{3-[2-(3,5-bis-trifluoromethylbenzenesulfonylamino)phenyl]propyl}benzoic acid
3-{3-[2-(4-propylbenzenesulfonylamino)phenyl]propyl}benzoic acid
3-{3-[2-(4-isopropylbenzenesulfonylamino)phenyl]propyl}benzoic acid
3-{3-[2-(3-fluorobenzenesulfonylamino)phenyl]propyl}benzoic acid
3-{3-[2-(toluene-3-sulfonylamino)phenyl]propyl}benzoic acid
3-{3-[2-(4-benzenesulfonylthiophene-2-sulfonylamino)phenyl]propyl}benzoic acid
3-(3-{2-[4-(1,1-dimethylpropyl)benzenesulfonylamino]phenyl}propyl)benzoic acid
3-{3-[2-(2-cyanobenzenesulfonylamino)phenyl]propyl}benzoic acid
3-{3-[2-(4-ethylbenzenesulfonylamino)phenyl]propyl}benzoic acid
3-{3-[2-(4-trifluoromethylbenzenesulfonylamino)phenyl]propyl}benzoic acid
3-{3-[2-(7,7-dimethyl-2-oxobicyclo[2.2.1]hept-1-yl-methanesulfonylamino)-phenyl]propyl}benzoic acid
4-{3-[2-(4-acetylaminobenzenesulfonylamino)phenyl]propyl}benzoic acid
4-{3-[2-(4-chlorobenzenesulfonylamino)phenyl]propyl}benzoic acid
4-[3-(2-methanesulfonylaminophenyl)propyl]benzoic acid
4-{3-[2-(4-methoxybenzenesulfonylamino)phenyl]propyl}benzoic acid
4-{3-[2-(2-nitrobenzenesulfonylamino)phenyl]propyl}benzoic acid
4-{3-[2-(toluene-4-sulfonylamino)phenyl]propyl}benzoic acid
4-{3-[2-(3-trifluoromethylbenzenesulfonylamino)phenyl]propyl}benzoic acid
4-{3-[2-(naphthalene-1-sulfonylamino)phenyl]propyl}benzoic acid
4-[3-(2-phenylmethanesulfonylaminophenyl)propyl]benzoic acid
4-{3-[2-(2,5-dimethoxybenzenesulfonylamino)phenyl]propyl}benzoic acid
4-{3-[2-(2,4-dimethylbenzenesulfonylamino)phenyl]propyl}benzoic acid
4-{3-[2-(2-fluorobenzenesulfonylamino)phenyl]propyl}benzoic acid
4-{3-[2-(2,4-difluorobenzenesulfonylamino)phenyl]propyl}benzoic acid
4-{3-[2-(2-trifluoromethylbenzenesulfonylamino)phenyl]propyl}benzoic acid
4-{3-[2-(4-fluorobenzenesulfonylamino)phenyl]propyl}benzoic acid
4-{3-[2-(biphenyl-4-sulfonylamino)phenyl]propyl}benzoic acid
4-{3-[2-(4-acetylbenzenesulfonylamino)phenyl]propyl}benzoic acid
4-[3-(2-ethanesulfonylaminophenyl)propyl]benzoic acid
4-{3-[2-(butane-1-sulfonylamino)phenyl]propyl}benzoic acid
4-{3-[2-(4-methoxy-2,3,6-trimethylbenzenesulfonylamino)phenyl]propyl}benzoic acid
4-{3-[2-(5-dimethylaminonaphthalene-1-sulfonylamino)phenyl]propyl}benzoic acid
4-{3-[2-(naphthalene-2-sulfonylamino)phenyl]propyl}benzoic acid
4-{3-[2-(2-acetylamino-4-methylthiazole-5-sulfonylamino)phenyl]propyl}benzoic acid
4-[3-(2-benzenesulfonylaminophenyl)propyl]benzoic acid
4-{3-[2-(2,5-dichlorobenzenesulfonylamino)phenyl]propyl}benzoic acid
4-{3-[2-(2,4,6-trimethylbenzenesulfonylamino)phenyl]propyl}benzoic acid
4-{3-[2-(4-tert-butylbenzenesulfonylamino)phenyl]propyl}benzoic acid
4-{3-[2-((E)-2-phenylethenesulfonylamino)phenyl]propyl}benzoic acid
4-{3-[2-(3,4-dimethoxybenzenesulfonylamino)phenyl]propyl}benzoic acid
4-{3-[2-(4-trifluoromethoxybenzenesulfonylamino)phenyl]propyl}benzoic acid
4-{3-[2-(thiophene-2-sulfonylamino)phenyl]propyl}benzoic acid
4-{3-[2-(propane-2-sulfonylamino)phenyl]propyl}benzoic acid
4-{3-[2-(5-benzenesulfonylthiophene-2-sulfonylamino)phenyl]propyl}benzoic acid
4-{3-[2-(2-trifluoromethoxybenzenesulfonylamino)phenyl]propyl}benzoic acid
4-{3-[2-(4-butoxybenzenesulfonylamino)phenyl]propyl}benzoic acid
4-{3-[2-(5-fluoro-2-methylbenzenesulfonylamino)phenyl]propyl}benzoic acid
4-{3-[2-(2,6-difluorobenzenesulfonylamino)phenyl]propyl}benzoic acid
4-{3-[2-(4-butylbenzenesulfonylamino)phenyl]propyl}benzoic acid
4-{3-[2-(3-methoxybenzenesulfonylamino)phenyl]propyl}benzoic acid
4-[3-(2,3,4,5,6-pentamethylbenzenesulfonylaminophenyl)propyl]benzoic acid
4-{3-[2-(3,5-bis-trifluoromethylbenzenesulfonylamino)phenyl]propyl}benzoic acid
4-{3-[2-(4-propylbenzenesulfonylamino)phenyl]propyl}benzoic acid
4-{3-[2-(4-isopropylbenzenesulfonylamino)phenyl]propyl}benzoic acid
4-{3-[2-(3-fluorobenzenesulfonylamino)phenyl]propyl}benzoic acid
4-{3-[2-(toluene-3-sulfonylamino)phenyl]propyl}benzoic acid 4-{3-[2-(4-benzenesulfonylthiophene-2-sulfonylamino)phenyl]propyl}benzoic acid
4-(3-{2-[4-(1,1-dimethylpropyl)benzenesulfonylamino]phenyl}propyl)benzoic acid
4-{3-[2-(2-cyanobenzenesulfonylamino)phenyl]propyl}benzoic acid
4-{3-[2-(4-ethylbenzenesulfonylamino)phenyl]propyl}benzoic acid
4-{3-[2-(4-trifluoromethylbenzenesulfonylamino)phenyl]propyl}benzoic acid
2-{5-[2-(4-acetylaminobenzenesulfonylamino)phenyl]pentyl}benzoic acid
2-{5-[2-(4-chlorobenzenesulfonylamino)phenyl]pentyl}benzoic acid
2-[5-(2-methanesulfonylaminophenyl)pentyl]benzoic acid
2-{5-[2-(4-methoxybenzenesulfonylamino)phenyl]pentyl}benzoic acid
2-{5-[2-(2-nitrobenzenesulfonylamino)phenyl]pentyl}benzoic acid
2-{5-[2-(toluene-4-sulfonylamino)phenyl]pentyl}benzoic acid
2-{5-[2-(3-trifluoromethylbenzenesulfonylamino)phenyl]pentyl}benzoic acid
2-{5-[2-(naphthalene-1-sulfonylamino)phenyl]pentyl}benzoic acid
2-[5-(2-phenylmethanesulfonylaminophenyl)pentyl]benzoic acid
2-{5-[2-(2,5-dimethoxybenzenesulfonylamino)phenyl]pentyl}benzoic acid
2-{5-[2-(2,4-dimethylbenzenesulfonylamino)phenyl]pentyl}benzoic acid
2-{5-[2-(2-fluorobenzenesulfonylamino)phenyl]pentyl}benzoic acid
2-{5-[2-(2,4-difluorobenzenesulfonylamino)phenyl]pentyl}benzoic acid
2-{5-[2-(2-trifluoromethylbenzenesulfonylamino)phenyl]pentyl}benzoic acid
2-{5-[2-(4-fluorobenzenesulfonylamino)phenyl]pentyl}benzoic acid
2-{5-[2-(4-acetylbenzenesulfonylamino)phenyl]pentyl}benzoic acid
2-[5-(2-ethanesulfonylaminophenyl)pentyl]benzoic acid
2-{5-[2-(4-methoxy-2,3,6-trimethylbenzenesulfonylamino)phenyl]pentyl}benzoic acid
2-{5-[2-(5-dimethylaminonaphthalene-1-sulfonylamino)phenyl]pentyl}benzoic acid
2-{5-[2-(naphthalene-2-sulfonylamino)phenyl]pentyl}benzoic acid
2-[5-(2-benzenesulfonylaminophenyl)pentyl]benzoic acid
2-{5-[2-(2,5-dichlorobenzenesulfonylamino)phenyl]pentyl}benzoic acid
2-{5-[2-(2,4,6-triisopropylbenzenesulfonylamino)phenyl]pentyl}benzoic acid
2-{5-[2-(2,4,6-trimethylbenzenesulfonylamino)phenyl]pentyl}benzoic acid
2-{5-[2-(4-tert-butylbenzenesulfonylamino)phenyl]pentyl}benzoic acid
2-{5-[2-(3,4-dimethoxybenzenesulfonylamino)phenyl]pentyl}benzoic acid
2-{5-[2-(4-trifluoromethoxybenzenesulfonylamino)phenyl]pentyl}benzoic acid
2-{5-[2-(thiophene-2-sulfonylamino)phenyl]pentyl}benzoic acid
2-{5-[2-(quinoline-8-sulfonylamino)phenyl]pentyl}benzoic acid
2-{5-[2-(2-trifluoromethoxybenzenesulfonylamino)phenyl]pentyl}benzoic acid
2-{5-[2-(4-butoxybenzenesulfonylamino)phenyl]pentyl}benzoic acid
2-{5-[2-(2,6-difluorobenzenesulfonylamino)phenyl]pentyl}benzoic acid
2-{5-[2-(3-methoxybenzenesulfonylamino)phenyl]pentyl}benzoic acid
2-[5-(2-pentamethylbenzenesulfonylaminophenyl)pentyl]benzoic acid
2-{5-[2-(4-propylbenzenesulfonylamino)phenyl]pentyl}benzoic acid
2-{5-[2-(4-isopropylbenzenesulfonylamino)phenyl]pentyl}benzoic acid
2-{5-[2-(toluene-3-sulfonylamino)phenyl]pentyl}benzoic acid
2-{5-[2-(4-benzenesulfonylthiophene-2-sulfonylamino)phenyl]pentyl}benzoic acid
2-(5-{2-[4-(1,1-dimethylpropyl)benzenesulfonylamino]phenyl}pentyl)benzoic acid
2-{5-[2-(2-carboxybenzenesulfonylamino)phenyl]pentyl}benzoic acid
2-{5-[2-(4-ethylbenzenesulfonylamino)phenyl]pentyl}benzoic acid
2-{5-[2-(4-trifluoromethylbenzenesulfonylamino)phenyl]pentyl}benzoic acid
2-{5-[2-(3-methoxybenzoylamino)phenyl]pentyl}benzoic acid
2-{5-[2-(4-tert-butylbenzoylamino)phenyl]pentyl}benzoic acid
2-{5-[2-(3-carboxypropionylamino)phenyl]pentyl}benzoic acid
2-{5-[2-(4-carboxybutyrylamino)phenyl]pentyl}benzoic acid
2-(5-{2-[2-(4-chlorophenyl)acetylamino]phenyl}pentyl)benzoic acid
2-{5-[2-(4-chlorobenzoylamino)phenyl]pentyl}benzoic acid
2-{5-[2-(3,4-dichlorobenzoylamino)phenyl]pentyl}benzoic acid
2-{5-[2-(2,6-dichlorobenzoylamino)phenyl]pentyl}benzoic acid
2-{5-[2-(2-carboxyacetylamino)phenyl]pentyl}benzoic acid
2-{5-[2-(2-fluorobenzoylamino)phenyl]pentyl}benzoic acid
2-{5-[2-(3-phenylpropionylamino)phenyl]pentyl}benzoic acid
2-{5-[2-(3-methylbutyrylamino)phenyl]pentyl}benzoic acid
2-{5-[2-(2-phenoxyacetylamino)phenyl]pentyl}benzoic acid
2-[5-(2-phenylacetylaminophenyl)pentyl]benzoic acid
2-{5-[2-(2,2-dimeithylpropionylamino)phenyl]pentyl}benzoic acid
2-{5-[2-(2-methylbenzoylamino)phenyl]pentyl}benzoic acid
2-{5-[2-(4-methylbenzoylamino)phenyl]pentyl}benzoic acid
2-{5-[2-(3,5-difluorobenzoylamino)phenyl]pentyl}benzoic acid
2-(5-{2-[((1R,2R)-2-phenylcyclopropanecarbonyl)amino]phenyl}pentyl)benzoic acid
2-{5-[2-(2-ethylhexanoylamino)phenyl]pentyl}benzoic acid
2-{5-[2-(4-ethylbenzoylamino)phenyl]pentyl}benzoic acid
2-{5-[2-(3,5-dichlorobenzoylamino)phenyl]pentyl}benzoic acid
2-(5-{2-[(naphthalene-2-carbonyl)amino]phenyl}pentyl)benzoic acid
2-{5-[2-(2-benzyloxyacetylamino)phenyl]pentyl}benzoic acid
2-{5-[2-(2-methoxyacetylamino)phenyl]pentyl}benzoic acid 2-{5-[2-(cyclohexanecarbonylamino)phenyl]pentyl}benzoic acid
2-[5-(2-butyrylaminophenyl)pentyl]benzoic acid
2-{5-[2-(cyclopentanecarbonylamino)phenyl]pentyl}benzoic acid
2-[5-(2-isobutyrylaminophenyl)pentyl]benzoic acid
2-{5-[2-(2-hydroxyacetylamino)phenyl]pentyl}benzoic acid
2-{5-[2-(2-phenylbutyrylamino)phenyl]pentyl}benzoic acid
2-[5-(2-propionylaminophenyl)pentyl]benzoic acid
2-(5-{2-[2-(4-fluorophenyl)acetylamino]phenyl}pentyl)benzoic acid
2-{5-[2-((S)-2-hydroxypropionylamino)phenyl]pentyl}benzoic acid
2-(5-{2-[2-(4-methoxyphenyl)acetylamino]phenyl}pentyl)benzoic acid
2-{5-[2-(2-ethylbutyrylamino)phenyl]pentyl}benzoic acid
2-{5-[2-(2-methylpentanoylamino)phenyl]pentyl}benzoic acid
2-{5-[2-(3-cyclopentylpropionylamino)phenyl]pentyl}benzoic acid
2-{5-[2-(2-methylbutyrylamino)phenyl]pentyl}benzoic acid
2-(5-{2-[(quinoxaline-2-carbonyl)amino]phenyl}pentyl)benzoic acid
2-{5-[2-(2,3-difluorobenzoylamino)phenyl]pentyl}benzoic acid
2-{5-[2-(2-fluoro-4-trifluoromethylbenzoylamino)phenyl]pentyl}benzoic acid
2-{5-[2-(3-chlorobenzoylamino)phenyl]pentyl}benzoic acid
2-{5-[2-(4-methoxybenzoylamino)phenyl]pentyl}benzoic acid
2-[5-(2-benzoylaminophenyl)pentyl]benzoic acid
2-{5-[2-(3,3-dimethylbutyrylamino)phenyl]pentyl}benzoic acid
2-{5-[2-(2-chlorobenzoylamino)phenyl]pentyl}benzoic acid
2-{5-[2-(4-fluorobenzoylamino)phenyl]pentyl}benzoic acid
2-(5-{2-[(naphthalene-1-carbonyl)amino]phenyl}pentyl)benzoic acid
4-{2-[2-(4-acetylaminobenzenesulfonylamino)phenoxy]ethoxy}benzoic acid
4-{2-[2-(4-chlorobenzenesulfonylamino)phenoxy]ethoxy}benzoic acid
4-[2-(2-methanesulfonylaminophenoxy)ethoxy]benzoic acid
4-{2-[2-(4-methoxybenzenesulfonylamino)phenoxy]ethoxy}benzoic acid
4-{2-[2-(2-nitrobenzenesulfonylamino)phenoxy]ethoxy}benzoic acid
4-{2-[2-(toluene-4-sulfonylamino)phenoxy]ethoxy}benzoic acid
4-{2-[2-(3-trifluoromethylbenzenesulfonylamino)phenoxy]ethoxy}benzoic acid
4-{2-[2-(naphthalene-1-sulfonylamino)phenoxy]ethoxy}benzoic acid
4-[2-(2-phenylmethanesulfonylaminophenoxy)ethoxy]benzoic acid
4-{2-[2-(2,5-dimethoxybenzenesulfonylamino)phenoxy]ethoxy}benzoic acid
4-{2-[2-(2,4-dimethylbenzenesulfonylamino)phenoxy]ethoxy}benzoic acid
4-{2-[2-(2-fluorobenzenesulfonylamino)phenoxy]ethoxy}benzoic acid
4-{2-[2-(2,4-difluorobenzenesulfonylamino)phenoxy]ethoxy}benzoic acid
4-{2-[2-(2-trifluoromethylbenzenesulfonylamino)phenoxy]ethoxy}benzoic acid
4-{2-[2-(4-fluorobenzenesulfonylamino)phenoxy]ethoxy}benzoic acid
4-{2-[2-(biphenyl-4-sulfonylamino)phenoxy]ethoxy}benzoic acid
4-{2-[2-(4-acetylbenzenesulfonylamino)phenoxy]ethoxy}benzoic acid
4-[2-(2-ethanesulfonylaminophenoxy)ethoxy]benzoic acid
4-{2-[2-(butane-1-sulfonylamino)phenoxy]ethoxy}benzoic acid
4-{2-[2-(4-methoxy-2,3,6-trimethylbenzenesulfonylamino)phenoxy]ethoxy}-benzoic acid
4-{2-[2-(5-dimethylaminonaphthalene-1-sulfonylamino)phenoxy]ethoxy}benzoic acid
4-{2-[2-(naphthalene-2-sulfonylamino)phenoxy]ethoxy}benzoic acid
4-{2-[2-(2-acetylamino-4-methylthiazole-5-sulfonylamino)phenoxy]ethoxy}-benzoic acid
4-[2-(2-benzenesulfonylaminophenoxy)ethoxy]benzoic acid
4-{2-[2-(2,5-dichlorobenzenesulfonylamino)phenoxy]ethoxy}benzoic acid
4-{2-[2-(2,4,6-triisopropylbenzenesulfonylamino)phenoxy]ethoxy}benzoic acid
4-{2-[2-(2,4,6-trimethylbenzenesulfonylamino)phenoxy]ethoxy}benzoic acid
4-{2-[2-(4-tert-butylbenzenesulfonylamino)phenoxy]ethoxy}benzoic acid
4-{2-[2-((E)-2-phenylethenesulfonylamino)phenoxy]ethoxy}benzoic acid
4-{2-[2-(3,4-dimethoxybenzenesulfonylamino)phenoxy]ethoxy}benzoic acid
4-{2-[2-(4-trifluoromethoxybenzenesulfonylamino)phenoxy]ethoxy}benzoic acid
4-{2-[2-(thiophene-2-sulfonylamino)phenoxy]ethoxy}benzoic acid
4-{2-[2-(4-carboxybenzenesulfonylamino)phenoxy]ethoxy}benzoic acid
4-{2-[2-(quinoline-8-sulfonylamino)phenoxy]ethoxy}benzoic acid
4-{2-[2-(5-benzenesulfonylthiophene-2-sulfonylamino)phenoxy]ethoxy}benzoic acid
4-{2-[2-(2-trifluoromethoxybenzenesulfonylamino)phenoxy]ethoxy}benzoic acid
4-{2-[2-(4-butoxybenzenesulfonylamino)phenoxy]ethoxy}benzoic acid
4-{2-[2-(5-fluoro-2-methylbenzenesulfonylamino)phenoxy]ethoxy}benzoic acid
4-{2-[2-(2,6-difluorobenzenesulfonylamino)phenoxy]ethoxy}benzoic acid
4-{2-[2-(4-butylbenzenesulfonylamino)phenoxy]ethoxy}benzoic acid
4-{2-[2-(3-methoxybenzenesulfonylamino)phenoxy]ethoxy}benzoic acid
4-[2-(2-pentamethylbenzenesulfonylaminophenoxy)ethoxy]benzoic acid
4-{2-[2-(3,5-bis-trifluoromethylbenzenesulfonylamino)phenoxy]ethoxy}benzoic acid
4-{2-[2-(4-propylbenzenesulfonylamino)phenoxy]ethoxy}benzoic acid
4-{2-[2-(4-isopropylbenzenesulfonylamino)phenoxy]ethoxy}benzoic acid
4-{2-[2-(3-fluorobenzenesulfonylamino)phenoxy]ethoxy}benzoic acid
4-{2-[2-(toluene-3-sulfonylamino)phenoxy]ethoxy}benzoic acid
4-{2-[2-(4-benzenesulfonylthiophene-2-sulfonylamino)phenoxy]ethoxy}benzoic acid
4-(2-{2-[4-(1,1-dimethylpropyl)benzenesulfonylamino]phenoxy}ethoxy)benzoic acid 4-{2-[2-(2-carboxybenzenesulfonylamino)phenoxy]ethoxy}benzoic acid
4-{2-[2-(2-cyanobenzenesulfonylamino)phenoxy]ethoxy}benzoic acid
4-{2-[2-(4-ethylbenzenesulfonylamino)phenoxy]ethoxy}benzoic acid
4-{2-[2-(4-trifluoromethylbenzenesulfonylamino)phenoxy]ethoxy}benzoic acid
4-{2-[2-(7,7-dimethyl-2-oxobicyclo[2.2.1]hept-1-yl-methanesulfonylamino)-phenoxy]ethoxy}benzoic acid
2-{2-[4-(4-chlorobenzenesulfonylamino)phenoxy]ethoxy}benzoic acid
2-[2-(4-methanesulfonylaminophenoxy)ethoxy]benzoic acid
2-{2-[4-(4-methoxybenzenesulfonylamino)phenoxy]ethoxy}benzoic acid
2-{2-[4-(2-nitrobenzenesulfonylamino)phenoxy]ethoxy}benzoic acid
2-{2-[4-(toluene-4-sulfonylamino)phenoxy]ethoxy}benzoic acid
2-[2-(4-phenylmethanesulfonylaminophenoxy)ethoxy]benzoic acid
2-{2-[4-(2,5-dimethoxybenzenesulfonylamino)phenoxy]ethoxy}benzoic acid
2-{2-[4-(2-fluorobenzenesulfonylamino)phenoxy]ethoxy}benzoic acid
2-{2-[4-(2,4-difluorobenzenesulfonylamino)phenoxy]ethoxy}benzoic acid
2-{2-[4-(2-trifluoromethylbenzenesulfonylamino)phenoxy]ethoxy}benzoic acid
2-{2-[4-(4-fluorobenzenesulfonylamino)phenoxy]ethoxy}benzoic acid
2-{2-[4-(biphenyl-4-sulfonylamino)phenoxy]ethoxy}benzoic acid
2-{2-[4-(4-acetylbenzenesulfonylamino)phenoxy]ethoxy}benzoic acid
2-[2-(4-ethanesulfonylaminophenoxy)ethoxy]benzoic acid
2-{2-[4-(butane-1-sulfonylamino)phenoxy]ethoxy}benzoic acid
2-{2-[4-(4-methoxy-2,3,6-trimethylbenzenesulfonylamino)phenoxy]ethoxy}-benzoic acid
2-{2-[4-(naphthalene-2-sulfonylamino)phenoxy]ethoxy}benzoic acid
2-{2-[4-(2-acetylamino-4-methylthiazole-5-sulfonylamino)phenoxy]ethoxy}-benzoic acid
2-[2-(4-benzenesulfonylaminophenoxy)ethoxy]benzoic acid
2-{2-[4-(2,5-dichlorobenzenesulfonylamino)phenoxy]ethoxy}benzoic acid
2-{2-[4-(2,4,6-triisopropylbenzenesulfonylamino)phenoxy]ethoxy}benzoic acid
2-{2-[4-(2,4,6-trimethylbenzenesulfonylamino)phenoxy]ethoxy}benzoic acid
2-{2-[4-(4-tert-butylbenzenesulfonylamino)phenoxy]ethoxy}benzoic acid
2-{2-[4-((E)-2-phenylethenesulfonylamino)phenoxy]ethoxy}benzoic acid
2-{2-[4-(3,4-dimethoxybenzenesulfonylamino)phenoxy]ethoxy}benzoic acid
2-{2-[4-(4-trifluoromethoxybenzenesulfonylamino)phenoxy]ethoxy}benzoic acid
2-{2-[4-(thiophene-2-sulfonylamino)phenoxy]ethoxy}benzoic acid
2-{2-[4-(4-carboxybenzenesulfonylamino)phenoxy]ethoxy}benzoic acid
2-{2-[4-(2-trifluoromethoxybenzenesulfonylamino)phenoxy]ethoxy}benzoic acid
2-{2-[4-(4-butoxybenzenesulfonylamino)phenoxy]ethoxy}benzoic acid
2-{2-[4-(5-fluoro-2-methylbenzenesulfonylamino)phenoxy]ethoxy}benzoic acid
2-{2-[4-(4-butylbenzenesulfonylamino)phenoxy]ethoxy}benzoic acid
2-{2-[4-(3-methoxybenzenesulfonylamino)phenoxy]ethoxy}benzoic acid
2-[2-(4-pentamethylbenzenesulfonylaminophenoxy)ethoxy]benzoic acid
2-{2-[4-(3,5-bis-trifluoromethylbenzenesulfonylamino)phenoxy]ethoxy}benzoic acid
2-{2-[4-(4-propylbenzenesulfonylamino)phenoxy]ethoxy}benzoic acid
2-{2-[4-(4-isopropylbenzenesulfonylamino)phenoxy]ethoxy}benzoic acid
2-{2-[4-(3-fluorobenzenesulfonylamino)phenoxy]ethoxy}benzoic acid
2-{2-[4-(toluene-3-sulfonylamino)phenoxy]ethoxy}benzoic acid
2-{2-[4-(4-benzenesulfonylthiophene-2-sulfonylamino)phenoxy]ethoxy}benzoic acid
2-(2-{4-[4-(1,1-dimethylpropyl)benzenesulfonylamino]phenoxy}ethoxy)benzoic acid
2-{2-[4-(2-carboxybenzenesulfonylamino)phenoxy]ethoxy}benzoic acid
2-{2-[4-(2-cyanobenzenesulfonylamino)phenoxy]ethoxy}benzoic acid
2-{2-[4-(4-ethylbenzenesulfonylamino)phenoxy]ethoxy}benzoic acid
2-{2-[4-(4-trifluoromethylbenzenesulfonylamino)phenoxy]ethoxy}benzoic acid
2-{2-[4-(7,7-dimethyl-2-oxobicyclo[2.2.1]hept-1-yl-methanesulfonylamino)-phenoxy]ethoxy}benzoic acid
4-[2-(4-methanesulfonylaminophenoxy)ethoxy]benzoic acid
4-{2-[4-(4-methoxybenzenesulfonylamino)phenoxy]ethoxy}benzoic acid
4-{2-[4-(2-nitrobenzenesulfonylamino)phenoxy]ethoxy}benzoic acid
4-{2-[4-(toluene-4-sulfonylamino)phenoxy]ethoxy}benzoic acid
4-{2-[4-(3-trifluoromethylbenzenesulfonylamino)phenoxy]ethoxy}benzoic acid
4-{2-[4-(naphthalene-1-sulfonylamino)phenoxy]ethoxy}benzoic acid
4-[2-(4-phenylmethanesulfonylaminophenoxy)ethoxy]benzoic acid
4-{2-[4-(2,5-dimethoxybenzenesulfonylamino)phenoxy]ethoxy}benzoic acid
4-{2-[4-(2,4-dimethylbenzenesulfonylamino)phenoxy]ethoxy}benzoic acid
4-{2-[4-(2-fluorobenzenesulfonylamino)phenoxy]ethoxy}benzoic acid
4-{2-[4-(2,4-difluorobenzenesulfonylamino)phenoxy]ethoxy}benzoic acid
4-{2-[4-(2-trifluoromethylbenzenesulfonylamino)phenoxy]ethoxy}benzoic acid
4-{2-[4-(4-fluorobenzenesulfonylamino)phenoxy]ethoxy}benzoic acid
4-[2-(4-ethanesulfonylaminophenoxy)ethoxy]benzoic acid
4-{2-[4-(butane-1-sulfonylamino)phenoxy]ethoxy}benzoic acid
4-{2-[4-(4-methoxy-2,3,6-trimethylbenzenesulfonylamino)phenoxy]ethoxy}-benzoic acid
4-{2-[4-(5-dimethylaminonaphthalene-1-sulfonylamino)phenoxy]ethoxy}benzoic acid 4-{2-[4-(naphthalene-2-sulfonylamino)phenoxy]
  ethoxy}benzoic acid
4-[2-(4-benzenesulfonylaminophenoxy)ethoxy]benzoic acid
4-{2-[4-(2,5-dichlorobenzenesulfonylamino)phenoxy]
  ethoxy}benzoic acid
4-{2-[4-(2,4,6-triisopropylbenzenesulfonylamino)phenoxy]
  ethoxy}benzoic acid
4-{2-[4-(2,4,6-trimethylbenzenesulfonylamino)phenoxy]
  ethoxy}benzoic acid
4-{2-[4-(4-tert-butylbenzenesulfonylamino)phenoxy]
  ethoxy}benzoic acid
4-[2-(4-trifluoromethanesulfonylaminophenoxy)ethoxy]
  benzoic acid
4-{2-[4-((E)-2-phenylethenesulfonylamino)phenoxy]
  ethoxy}benzoic acid
4-{2-[4-(3,4-dimethoxybenzenesulfonylamino)phenoxy]
  ethoxy}benzoic acid
4-{2-[4-(thiophene-2-sulfonylamino)phenoxy]
  ethoxy}benzoic acid
4-{2-[4-(propane-2-sulfonylamino)phenoxy]
  ethoxy}benzoic acid
4-{2-[4-(2,2,2-trifluoroethanesulfonylamino)phenoxy]
  ethoxy}benzoic acid
4-{2-[4-(quinoline-8-sulfonylamino)phenoxy]
  ethoxy}benzoic acid
4-{2-[4-(5-benzenesulfonylthiophene-2-sulfonylamino)phe-
  noxy]ethoxy}benzoic acid
4-{2-[4-(2-trifluoromethoxybenzenesulfonylamino)phe-
  noxy]ethoxy}benzoic acid
4-{2-[4-(4-butoxybenzenesulfonylamino)phenoxy]
  ethoxy}benzoic acid
4-{2-[4-(5-fluoro-2-methylbenzenesulfonylamino)phe-
  noxy]ethoxy}benzoic acid
4-{2-[4-(2,6-difluorobenzenesulfonylamino)phenoxy]
  ethoxy}benzoic acid
4-{2-[4-(4-butylbenzenesulfonylamino)phenoxy]
  ethoxy}benzoic acid
4-{2-[4-(3-methoxybenzenesulfonylamino)phenoxy]
  ethoxy}benzoic acid
4-[2-(4-pentamethylbenzenesulfonylaminophenoxy)ethoxy]
  benzoic acid
4-{2-[4-(3,5-bis-trifluoromethylbenzenesulfonylamino)phe-
  noxy]ethoxy}benzoic acid
4-{2-[4-(4-propylbenzenesulfonylamino)phenoxy]
  ethoxy}benzoic acid
4-{2-[4-(4-isopropylbenzenesulfonylamino)phenoxy]
  ethoxy}benzoic acid
4-{2-[4-(3-fluorobenzenesulfonylamino)phenoxy]
  ethoxy}benzoic acid
4-{2-[4-(toluene-3-sulfonylamino)phenoxy]ethoxy}benzoic
  acid
4-{2-[4-(4-benzenesulfonylthiophene-2-sulfonylamino)phe-
  noxy]ethoxy}benzoic acid
4-(2-{4-[4-(1,1-dimethylpropyl)benzenesulfonylamino]
  phenoxy}ethoxy)benzoic acid
4-{2-[4-(2-cyanobenzenesulfonylamino)phenoxy]
  ethoxy}benzoic acid
4-{2-[4-(4-ethylbenzenesulfonylamino)phenoxy]
  ethoxy}benzoic acid
4-{2-[4-(3,5-dichloro-2-hydroxybenzenesulfonylamino)
  phenoxy]ethoxy}benzoic acid
4-{2-[4-(7,7-dimethyl-2-oxobicyclo[2.2.1]hept-1-yl-
  methanesulfonylamino)-phenoxy]ethoxy}benzoic acid
(2-{2-[4-(4-acetylaminobenzenesulfonylamino)phenoxy]
  ethoxy}phenyl)acetic acid
(2-{2-[4-(4-chlorobenzenesulfonylamino)phenoxy]
  ethoxy}phenyl)acetic acid
(2-{2-[4-(4-methoxybenzenesulfonylamino)phenoxy]
  ethoxy}phenyl)acetic acid
(2-{2-[4-(toluene-4-sulfonylamino)phenoxy]
  ethoxy}phenyl)acetic acid
(2-{2-[4-(3-trifluoromethylbenzenesulfonylamino)phe-
  noxy]ethoxy}phenyl)acetic acid
(2-{2-[4-(2,5-dimethoxybenzenesulfonylamino)phenoxy]
  ethoxy}phenyl)acetic acid
(2-{2-[4-(2,4-dimethylbenzenesulfonylamino)phenoxy]
  ethoxy}phenyl)acetic acid
(2-{2-[4-(2-trifluoromethylbenzenesulfonylamino)phe-
  noxy]ethoxy}phenyl)acetic acid
(2-{2-[4-(4-fluorobenzenesulfonylamino)phenoxy]
  ethoxy}phenyl)acetic acid
(2-{2-[4-(biphenyl-4-sulfonylamino)phenoxy]
  ethoxy}phenyl)acetic acid
(2-{2-[4-(4-acetylbenzenesulfonylamino)phenoxy]
  ethoxy}phenyl)acetic acid
{2-[2-(4-ethanesulfonylaminophenoxy)ethoxy]
  phenyl}acetic acid
(2-{2-[4-(butane-1-sulfonylamino)phenoxy]ethoxy}phenyl)
  acetic acid
(2-{2-[4-(4-methoxy-2,3,6-trimethylbenzenesulfony-
  lamino)phenoxy]ethoxy}-phenyl)acetic acid
(2-{2-[4-(5-dimethylaminonaphthalene-1-sulfonylamino)
  phenoxy]ethoxy}phenyl)-acetic acid
(2-{2-[4-(naphthalene-2-sulfonylamino)phenoxy]
  ethoxy}phenyl)acetic acid
(2-{2-[4-(2-acetylamino-4-methylthiazole-5-sulfony-
  lamino)phenoxy]ethoxy}-phenyl)acetic acid
{2-[2-(4-benzenesulfonylaminophenoxy)ethoxy]
  phenyl}acetic acid
(2-{2-[4-(2,5-dichlorobenzenesulfonylamino)phenoxy]
  ethoxy}phenyl)acetic acid
(2-{2-[4-(2,4,6-triisopropylbenzenesulfonylamino)phe-
  noxy]ethoxy}phenyl)acetic acid
(2-{2-[4-(2,4,6-trimethylbenzenesulfonylamino)phenoxy]
  ethoxy}phenyl)acetic acid
(2-{2-[4-(4-tert-butylbenzenesulfonylamino)phenoxy]
  ethoxy}phenyl)acetic acid
(2-{2-[4-((E)-2-phenylethenesulfonylamino)phenoxy]
  ethoxy}phenyl)acetic acid
(2-{2-[4-(3,4-dimethoxybenzenesulfonylamino)phenoxy]
  ethoxy}phenyl)acetic acid
(2-{2-[4-(4-trifluoromethoxybenzenesulfonylamino)phe-
  noxy]ethoxy}phenyl)-acetic acid
(2-{2-[4-(thiophene-2-sulfonylamino)phenoxy]
  ethoxy}phenyl)acetic acid
4-{4-[2-(2-carboxymethylphenoxy)ethoxy]
  phenylsulfamoyl}benzoic acid
(2-{2-[4-(quinoline-8-sulfonylamino)phenoxy]
  ethoxy}phenyl)acetic acid
(2-{2-[4-(5-benzenesulfonylthiophene-2-sulfonylamino)
  phenoxy]ethoxy}phenyl)-acetic acid
(2-{2-[4-(2-trifluoromethoxybenzenesulfonylamino)phe-
  noxy]ethoxy}phenyl)-acetic acid
(2-{2-[4-(5-fluoro-2-methylbenzenesulfonylamino)phe-
  noxy]ethoxy}phenyl)acetic acid
(2-{2-[4-(2,6-difluorobenzenesulfonylamino)phenoxy]
  ethoxy}phenyl)acetic acid 1000
(2-{2-[4-(4-butylbenzenesulfonylamino)phenoxy]
  ethoxy}phenyl)acetic acid
(2-{2-[4-(3-methoxybenzenesulfonylamino)phenoxy]
  ethoxy}phenyl)acetic acid
{2-[2-(4-pentamethylbenzenesulfonylaminophenoxy)
  ethoxy]phenyl}acetic acid (2-{2-[4-(3,5-bis-trifluoromethylbenzenesulfonylamino)
  phenoxy]ethoxy}phenyl)-acetic acid
(2-{2-[4-(4-propylbenzenesulfonylamino)phenoxy]
  ethoxy}phenyl)acetic acid
(2-{2-[4-(4-isopropylbenzenesulfonylamino)phenoxy]
  ethoxy}phenyl)acetic acid
(2-{2-[4-(3-fluorobenzenesulfonylamino)phenoxy]
  ethoxy}phenyl)acetic acid
(2-{2-[4-(toluene-3-sulfonylamino)phenoxy]
  ethoxy}phenyl)acetic acid
(2-{2-[4-(4-benzenesulfonylthiophene-2-sulfonylamino)
  phenoxy]ethoxy}phenyl)-acetic acid
[2-(2-{4-[4-(1,1-dimethylpropyl)benzenesulfonylamino]
  phenoxy}ethoxy)phenyl]-acetic acid
methyl 2-{4-[2-(2-carboxymethylphenoxy)ethoxy]
  phenylsulfamoyl}benzoate
(2-{2-[4-(2-cyanobenzenesulfonylamino)phenoxy]
  ethoxy}phenyl)acetic acid
(2-{2-[4-(4-ethylbenzenesulfonylamino)phenoxy]
  ethoxy}phenyl)acetic acid
(2-{2-[4-(4-trifluoromethylbenzenesulfonylamino)phe-
  noxy]ethoxy}phenyl)acetic acid
(2-{2-[4-(2-nitrobenzenesulfonylamino)phenoxy]
  ethoxy}phenyl)acetic acid
3-(2-{2-[4-(4-acetylaminobenzenesulfonylamino)phenoxy]
  ethoxy}phenyl)-propionic acid
3-(2-{2-[4-(4-chlorobenzenesulfonylamino)phenoxy]
  ethoxy}phenyl)propionic acid
3-{2-[2-(4-methanesulfonylaminophenoxy)ethoxy]
  phenyl}propionic acid
3-(2-{2-[4-(4-methoxybenzenesulfonylamino)phenoxy]
  ethoxy}phenyl)propionic acid
3-(2-{2-[4-(toluene-4-sulfonylamino)phenoxy]
  ethoxy}phenyl)propionic acid
3-(2-{2-[4-(3-trifluoromethylbenzenesulfonylamino)phe-
  noxy]ethoxy}phenyl)-propionic acid
3-(2-{2-[4-(naphthalene-1-sulfonylamino)phenoxy]
  ethoxy}phenyl)propionic acid
3-(2-{2-[4-(2,5-dimethoxybenzenesulfonylamino)phenoxy]
  ethoxy}phenyl)-propionic acid
3-(2-{2-[4-(2,4-dimethylbenzenesulfonylamino)phenoxy]
  ethoxy}phenyl)propionic acid
3-(2-{2-[4-(2-fluorobenzenesulfonylamino)phenoxy]
  ethoxy}phenyl)propionic acid
3-(2-{2-[4-(2,4-difluorobenzenesulfonylamino)phenoxy]
  ethoxy}phenyl)propionic acid
3-(2-{2-[4-(2-trifluoromethylbenzenesulfonylamino)phe-
  noxy]ethoxy}phenyl)-propionic acid
3-(2-{2-[4-(4-fluorobenzenesulfonylamino)phenoxy]
  ethoxy}phenyl)propionic acid
3-(2-{2-[4-(biphenyl-4-sulfonylamino)phenoxy]
  ethoxy}phenyl)propionic acid
3-(2-{2-[4-(4-acetylbenzenesulfonylamino)phenoxy]
  ethoxy}phenyl)propionic acid
3-{2-[2-(4-ethanesulfonylaminophenoxy)ethoxy]
  phenyl}propionic acid
3-(2-{2-[4-(butane-1-sulfonylamino)phenoxy]
  ethoxy}phenyl)propionic acid
3-(2-{2-[4-(4-methoxy-2,3,6-trimethylbenzenesulfony-
  lamino)phenoxy]ethoxy}-phenyl)propionic acid
3-(2-{2-[4-(5-dimethylaminonaphthalene-1-sulfonylamino)
  phenoxy]ethoxy}-phenyl)propionic acid
3-(2-{2-[4-(naphthalene-2-sulfonylamino)phenoxy]
  ethoxy}phenyl)propionic acid
3-(2-{2-[4-(2-acetylamino-4-methylthiazole-5-sulfony-
  lamino)phenoxy]ethoxy}-phenyl)propionic acid
3-{2-[2-(4-benzenesulfonylaminophenoxy)ethoxy]
  phenyl}propionic acid
3-(2-{2-[4-(2,4,6-trimethylbenzenesulfonylamino)phenoxy]
  ethoxy}phenyl)-propionic acid
3-(2-(2-[4-(4-tert-butylbenzenesulfonylamino)phenoxy]
  ethoxyphenyl)propionic acid
3-(2-{2-[4-((E)-2-phenylethenesulfonylamino)phenoxy]
  ethoxy}phenyl)propionic acid
3-(2-{2-[4-(3,4-dimethoxybenzenesulfonylamino)phenoxy]
  ethoxy}phenyl)-propionic acid
3-(2-{2-[4-(4-trifluoromethoxybenzenesulfonylamino)phe-
  noxy]ethoxy}phenyl)-propionic acid
3-(2-{2-[4-(5-benzenesulfonylthiophene-2-sulfonylamino)
  phenoxy]ethoxy}-phenyl)propionic acid
3-(2-{2-[4-(2-trifluoromethoxybenzenesulfonylamino)phe-
  noxy]ethoxy}phenyl)-propionic acid
3-(2-{2-[4-(4-butoxybenzenesulfonylamino)phenoxy]
  ethoxy}phenyl)propionic acid
3-(2-{2-[4-(5-fluoro-2-methylbenzenesulfonylamino)phe-
  noxy]ethoxy}phenyl)-propionic acid
3-(2-{2-[4-(2,6-difluorobenzenesulfonylamino)phenoxy]
  ethoxy}phenyl)propionic acid
3-(2-{2-[4-(4-butylbenzenesulfonylamino)phenoxy]
  ethoxy}phenyl)propionic acid
3-(2-{2-[4-(3-methoxybenzenesulfonylamino)phenoxy]
  ethoxy}phenyl)propionic acid
3-{2-[2-(4-pentamethylbenzenesulfonylaminophenoxy)
  ethoxy]phenyl}propionic acid
3-(2-{2-[4-(3,5-bis-trifluoromethylbenzenesulfonylamino)
  phenoxy]ethoxy}-phenyl)propionic acid
3-(2-{2-[4-(4-propylbenzenesulfonylamino)phenoxy]
  ethoxy}phenyl)propionic acid
3-(2-{2-[4-(4-isopropylbenzenesulfonylamino)phenoxy]
  ethoxy}phenyl)propionic acid
3-(2-{2-[4-(3-fluorobenzenesulfonylamino)phenoxy]
  ethoxy}phenyl)propionic acid
3-(2-{2-[4-(toluene-3-sulfonylamino)phenoxy]
  ethoxy}phenyl)propionic acid methyl 2-(4-{2-[2-(2-car-
  boxy-ethyl)phenoxy]ethoxy}phenylsulfamoyl)benzoate
3-(2-{2-[4-(4-ethylbenzenesulfonylamino)phenoxy]
  ethoxy}phenyl)propionic acid
3-(2-{2-[4-(4-trifluoromethylbenzenesulfonylamino)phe-
  noxy]ethoxy}phenyl)-propionic acid
3-(2-{2-[4-(7,7-dimethyl-2-oxobicyclo[2.2.1]hept-1-yl-
  methanesulfonylamino)-phenoxy]ethoxy}phenyl)propi-
  onic acid
3-(2-{2-[4-(2-nitrobenzenesulfonylamino)phenoxy]
  ethoxy}phenyl)propionic acid
4-{2-[2-(2-hydroxybenzoylamino)phenoxy]ethoxy}benzoic
  acid
4-{2-[2-(3-methoxybenzoylamino)phenoxy]
  ethoxy}benzoic acid
4-{2-[2-(4-tert-butylbenzoylamino)phenoxy]
  ethoxy}benzoic acid
4-{2-[2-(3-carboxypropionylamino)phenoxy]
  ethoxy}benzoic acid
4-(2-{2-[2-(4-chlorophenyl)acetylamino]phenoxy}ethoxy)
  benzoic acid
4-{2-[2-(4-chlorobenzoylamino)phenoxy]ethoxy}benzoic
  acid
4-(2-{2-[(E)-(3-phenylacryloyl)amino]phenoxy}ethoxy)
  benzoic acid
4-[2-(2-hexanoylaminophenoxy)ethoxy]benzoic acid
4-[2-(2-decanoylaminophenoxy)ethoxy]benzoic acid
4-{2-[2-(2-fluorobenzoylamino)phenoxy]ethoxy}benzoic
  acid 4-{2-[2-(3-methylbutyrylamino)phenoxy]ethoxy}benzoic acid
4-[2-(2-pentanoylaminophenoxy)ethoxy]benzoic acid
4-{2-[2-(2-phenoxyacetylamino)phenoxy]ethoxy}benzoic acid
4-[2-(2-phenylacetylaminophenoxy)ethoxy]benzoic acid
4-{2-[2-(2,2-dimethylpropionylamino)phenoxy]ethoxy}benzoic acid
4-{2-[2-(2-methylbenzoylamino)phenoxy]ethoxy}benzoic acid
4-{2-[2-(4-methylbenzoylamino)phenoxy]ethoxy}benzoic acid
4-[2-(2-nonanoylaminophenoxy)ethoxy]benzoic acid
4-{2-[2-(3,5-difluorobenzoylamino)phenoxy]ethoxy}benzoic acid
4-{2-[2-(2-methoxybenzoylamino)phenoxy]ethoxy}benzoic acid
4-(2-{2-[(furan-2-carbonyl)amino]phenoxy}ethoxy)benzoic acid
4-{2-[2-(2-ethylhexanoylamino)phenoxy]ethoxy}benzoic acid
4-{2-[2-(4-ethylbenzoylamino)phenoxy]ethoxy}benzoic acid
4-(2-{2-[(thiophene-2-carbonyl)amino]phenoxy}ethoxy)benzoic acid
4-{2-[2-(3-methylbut-2-enoylamino)phenoxy]ethoxy}benzoic acid
4-{2-[2-(2-benzyloxyacetylamino)phenoxy]ethoxy}benzoic acid
4-{2-[2-(2-methoxyacetylamino)phenoxy]ethoxy}benzoic acid
4-{2-[2-(4-methoxybenzoylamino)phenoxy]ethoxy}benzoic acid
4-[2-(2-benzoylaminophenoxy)ethoxy]benzoic acid
4-{2-[2-(3,3-dimethylbutyrylamino)phenoxy]ethoxy}benzoic acid
4-{2-[2-(2-chlorobenzoylamino)phenoxy]ethoxy}benzoic acid
4-{2-[2-(3-cyclopentylpropionylamino)phenoxy]ethoxy}benzoic acid
4-{2-[2-(cyclohexanecarbonylamino)phenoxy]ethoxy}benzoic acid
4-{2-[2-(3-fluorobenzoylamino)phenoxy]ethoxy}benzoic acid
4-{2-[2-(3-bromobenzoylamino)phenoxy]ethoxy}benzoic acid
4-[2-(2-butyrylaminophenoxy)ethoxy]benzoic acid
4-{2-[2-(cyclopentanecarbonylamino)phenoxy]ethoxy}benzoic acid
4-(2-{2-[((1S,4R)-4,7,7-trimethyl-3-oxo-2-oxabicyclo[2.2.1]heptane-1-carbonyl)-amino]phenoxy}ethoxy)benzoic acid and also the tautomeric forms, enantiomers, diastereoisomers and epimers, and the pharmaceutically acceptable salts.

More preferably, the compounds of the formula (1) according to the invention may be chosen from:
2-{5-[2-(5-dimethylaminonaphthalene-1-sulfonylamino)phenyl]pentyl}benzoic acid
2-{5-[2-(2,4,6-trimethylbenzenesulfonylamino)phenyl]pentyl}benzoic acid
2-{5-[2-(quinoline-8-sulfonylamino)phenyl]pentyl}benzoic acid
2-[5-(2-ethanesulfonylaminophenyl)pentyl]benzoic acid
2-{5-[2-(2-fluorobenzenesulfonylamino)phenyl]pentyl}benzoic acid
2-{5-[2-(4-methoxybenzenesulfonylamino)phenyl]pentyl}benzoic acid
2-{5-[2-(2,4-dimethylbenzenesulfonylamino)phenyl]pentyl}benzoic acid
2-{5-[2-(4-methoxy-2,3,6-trimethylbenzenesulfonylamino)phenyl]pentyl}benzoic acid
2-{5-[2-(4-isopropylbenzenesulfonylamino)phenyl]pentyl}benzoic acid
2-{3-[2-(2,4,6-trimethylbenzenesulfonylamino)phenyl]propyl}benzoic acid
2-{3-[2-(naphthalene-2-sulfonylamino)phenyl]propyl}benzoic acid
2-{3-[2-(2,4-dimethylbenzenesulfonylamino)phenyl]propyl}benzoic acid
2-{2-[4-(4-chlorobenzenesulfonylamino)phenyl]ethyl}benzoic acid
4-{2-[3-(4-butylbenzenesulfonylamino)phenyl]ethyl}benzoic acid and also the tautomeric forms, enantiomers, diastereoisomers and epimers, and the pharmaceutically acceptable salts.

According to the present invention, the alkyl radicals represent saturated hydrocarbon-based radicals, in a straight or branched chain of 1 to 20 carbon atoms and preferably of 1 to 8 carbon atoms.

If they are linear, mention may be made especially of methyl, ethyl, propyl, butyl, pentyl, hexyl, octyl, nonyl, decyl, dodecyl, hexadecyl and octadecyl radicals.

If they are branched or substituted by one or more alkyl radicals, mention may be made especially of isopropyl, tert-butyl, 2-ethylhexyl, 2-methylbutyl, 2-methylpentyl, 1-methylpentyl and 3-methylheptyl radicals.

The alkoxy radicals according to the present invention are radicals of the formula —O-alkyl, the alkyl being as defined above.

Among the Halogen atoms that are more particularly mentioned are fluorine, chlorine, bromine and iodine atoms, preferably fluorine.

The alkenyl radicals represent hydrocarbon-based radicals in a straight or linear chain, and comprise one or more ethylenic unsaturations. Among the alkenyl radicals that may especially be mentioned are allyl or vinyl radicals.

The alkynyl radicals represent hydrocarbon-based radicals, in a straight or linear chain, and comprise one or more acetylenic unsaturations. Among the alkynyl radicals, mention may be made especially of acetylene.

The cycloalkyl radical is a saturated or partially unsaturated, non-aromatic mono-, bi- or tricyclic hydrocarbon-based group of 3 to 8 carbon atoms, especially, such as cyclopropyl, cyclopentyl, cyclohexyl or adamantyl, and also the corresponding rings containing one or more unsaturations.

Aryl denotes a monocyclic or bicyclic hydrocarbon-based aromatic system of 6 to 14 carbon atoms.

Among the aryl radicals that may especially be mentioned are phenyl and naphthyl radicals, more particularly substituted by at least one halogen atom.

Among the -alkylaryl radicals, mention may be made especially of benzyl and phenethyl radicals.

The heteroaryl radicals denote monocyclic or bicyclic aromatic systems of 5 to 13 carbon atoms, comprising one or more hetero atoms chosen from nitrogen, oxygen and sulfur. Among the heteroaryl radicals that may be mentioned are pyrazinyl, thienyl, oxazolyl, furazanyl, pyrrolyl, 1,2,4-thiadiazolyl, naphthyridinyl, pyridazinyl, quinoxalinyl, phthalazinyl, imidazo[1,2-a]pyridine, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzazaindole, 1,2,4-triazinyl, benzothiazolyl, furanyl, imidazolyl, indolyl, triazolyl, tetrazolyl, indolizinyl, isoxazolyl, isoquinolinyl, isothiazolyl, oxadiazolyl, pyrazinyl, pyridazinyl, pyrazolyl, pyridyl, pyrimidinyl, purinyl, quinazolinyl, quinolinyl, isoquinolyl, 1,3,4-thiadiazolyl, thiazolyl, triazinyl, isothiazolyl and carbazolyl, and also the corresponding groups derived from their fusion or from fusion with the phenyl nucleus. The preferred heteroaryl groups comprise thienyl, quinoxalinyl, furanyl, quinolinyl and thiazolyl, and groups derived from fusion with a phenyl nucleus, and more particularly benzothienyl.

The heterocyclic radicals denote saturated monocyclic or bicyclic systems of 3 to 8 carbon atoms, comprising one or more hetero atoms chosen from N, O and S. Among the heterocyclic groups, mention may be made especially of epoxyethyl, oxiranyl, aziridinyl, tetrahydrofuranyl, dioxolanyl, pyrrolidinyl, pyrazolidinyl, imidazolidinyl, tetrahydrothiophenyl, dithiolanyl, thiazolidinyl, tetrahydropyranyl, dioxanyl, morpholinyl, piperidyl, piperazinyl, tetrahydrothiopyranyl, dithianyl, thiomorpholinyl, dihydrofuranyl, 2-imidazolinyl, 2,3-pyrrolinyl, pyrazolinyl, dihydrothiophenyl, dihydropyranyl, pyranyl, tetrahydropyridyl, dihydropyridyl, tetrahydropyrimidinyl and dihydrothiopyranyl, and the corresponding groups derived from fusion with a phenyl nucleus.

The expression "pharmaceutically acceptable salts" refers to the relatively non-toxic mineral and organic acid-addition salts, and the base-addition salts, of the compounds of the present invention. These salts may be prepared in situ during the final isolation and purification of the compounds. In particular, the acid-addition salts may be prepared by separately reacting the purified compound in its purified form with an organic or mineral acid and isolating the salt thus formed. Among the examples of acid-addition salts are the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, sulfamates, malonates, salicylates, propionates, methylenebis-b-hydroxynaphthoates, gentisic acid, isethionates, di-p-toluoyl-tartrates, methanesulfonates, ethanesulfonates, benzenesulfonates, p-toluenesulfonates, cyclohexyl sulfamates and quinates-laurylsulfonate, and analogues. (See for example S. M. Berge et al. "Pharmaceutical Salts" *J. Pharm. Sci,* 66: pp. 1-19 (1977) which is incorporated herein by reference). The acid-addition salts may also be prepared by separately reacting the purified compound in its acid form with an organic or mineral base and isolating the salt thus formed. The acid-addition salts include amine salts and metal salts. The suitable metal salts include the sodium, potassium, calcium, barium, zinc, magnesium and aluminium salts. The sodium and potassium salts are preferred. The suitable mineral base-addition salts are prepared from metallic bases including sodium hydride, sodium hydroxide, potassium hydroxide, calcium hydroxide, aluminium hydroxide, lithium hydroxide, magnesium hydroxide and zinc hydroxide. The suitable amine base-addition salts are prepared from amines whose basicity is sufficient to form a stable salt, and preferably include amines that are often used in medicinal chemistry on account of their low toxicity and their acceptability for medical use: ammonia, ethylenediamine, N-methylglucamine, lysine, arginine, ornithine, choline, N,N'-dibenzylethylenediamine, chloroprocaine, diethanolamine, procaine, N-benzyl-phenethylamine, diethylamine, piperazine, tris(hydroxymethyl)aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, for example lysine and arginine, and dicyclohexylamine, and analogues.

The invention also relates to the tautomeric forms, enantiomers, diastereoisomers, epimers and organic or mineral salts of the compounds of the general formula (1).

The compounds of the invention of the formula (1) as defined above containing a sufficiently acidic function or a sufficiently basic function, or both, may include the corresponding pharmaceutically acceptable salts of an organic or mineral acid or of an organic or mineral base.

The compounds of the general formula (1) may be prepared by application or adaptation of any method known per se and/or within the capacity of a person skilled in the art, especially those described by Larock in *Comprehensive Organic Transformations,* VCH Pub., 1989, or by application or adaptation of the processes described in the procedures that follow.

The present invention thus also relates to the process for the preparation of the compounds of the formula (1) described above, comprising the step consisting in reacting a compound of the formula (A):

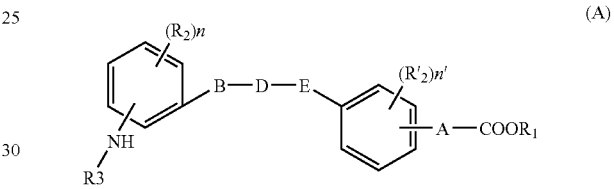

in which A, R1, R2, R'2', n, n', B, D and R3 are defined as in formula (1), with a compound of the formula (B) or (B'), according to the nature of the desired compound of the formula (1):

in which R4 is defined as in formula (1) and Hal represents a halogen atom, preferably chlorine. Preferentially, this reaction is performed in a suitable solvent, for example acetonitrile, at a temperature of between 0° C. and the boiling point of the solvent, and preferably at room temperature, for a time necessary to obtain a satisfactory degree of progress of the reaction, generally for 1 hour to 2 days.

Preferably, the product of the formula (B) is used if, in formula (1), R4 represents

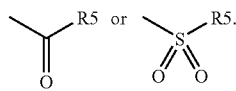

If R4 represents

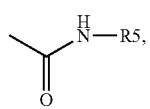

a product of the formula (B') is used.

Generally, the above reaction is performed using the ester (R1 other than H). If the acid is desired (R1=H), the reaction then also includes the step consisting in hydrolysing the ester to the acid.

This reaction is preferably performed in basic medium, especially in the presence of sodium hydrogen carbonate, potassium carbonate or an organic base, such as triethylamine or diisopropylethylamine, or alternatively sodium hydroxide or potassium hydroxide, or any other suitable base, in a suitable solvent, for example acetonitrile, at a temperature of between 0° C. and the boiling point of the solvent, preferably at room temperature, for a time required to obtain a satisfactory degree of progress of the reaction, generally for 1 hour to 2 days.

Preferably, the compound of the formula (B) corresponds to the following formulae:

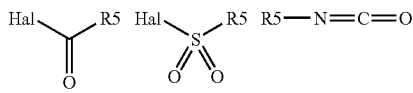

in which R5 is defined as in formula (1) and Hal is defined as above.

If, in formula (1), R3 is other than H, the process for the preparation of the corresponding compounds also includes the step of preparing the compounds of the formula (A) in which R3 is other than H by reductive amination of the corresponding compounds of the formula (A) in which R3=H. This reaction may be performed by application or adaptation of any reductive amination method known per se. The process may especially be performed by means of a compound of aldehyde type corresponding to the desired compound of the formula (1), in the presence of sodium triacetoxyborohydride in a suitable solvent, such as dichloroethane, at a temperature of between 0° C. and the boiling point of the solvent, preferably at room temperature, for a time that is necessary to obtain a satisfactory degree of progress of the reaction, generally for 1 hour to 24 hours.

More specifically, the compounds of the general formula (1) as described above may be prepared according to the following representative methods (1), (2), (2a), (3) and (4).

In the following reaction schemes, A, R1, R2, R'2', n, n', B, D, R4 and R5 are defined as in formula (1) and Hal and Hal' represent a halogen atom, such as Cl or Br.

The following schemes are given for representative purposes, and solely for the purpose of facilitating the representation. They have been represented for compounds containing given B, D and E. Needless to say, depending on the nature of the compounds of the formula (1) to be obtained, the methodologies presented may be adapted by a person skilled in the art by selecting the appropriate starting materials, in which the nature of the substituents B, D and E may be modified, especially as a function of the nature and length of the desired chain.

General Method 1:

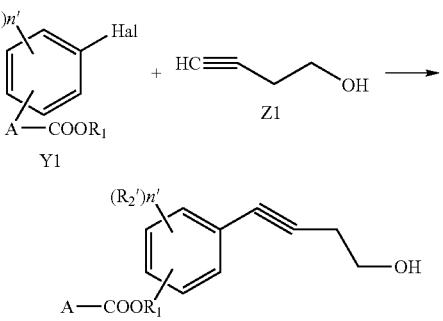

Compound A1

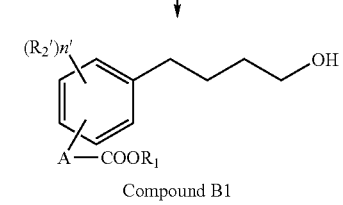

Compound B1

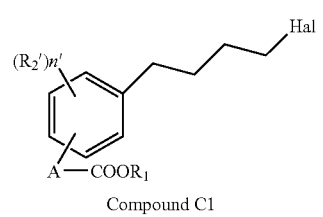

Compound C1

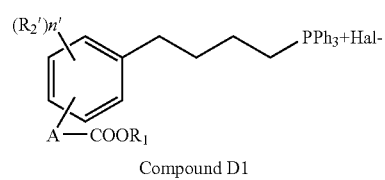

Compound D1

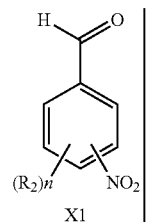

X1

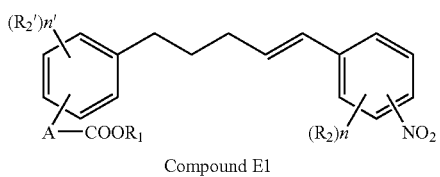

Compound E1

-continued

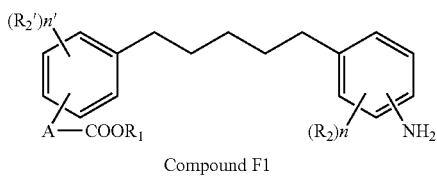
Compound F1

Production of the Sulfonyl Derivatives

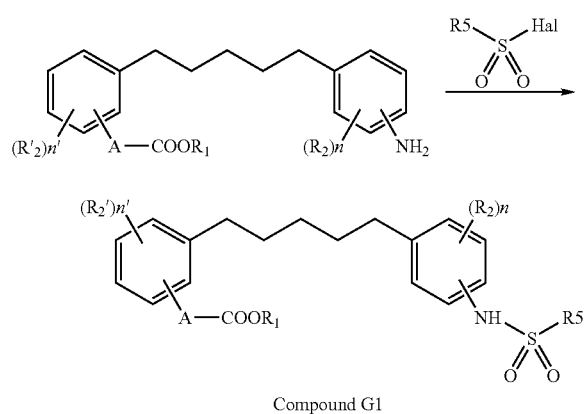
Compound G1

Production of the Acyl and Aminocarbonyl Derivatives

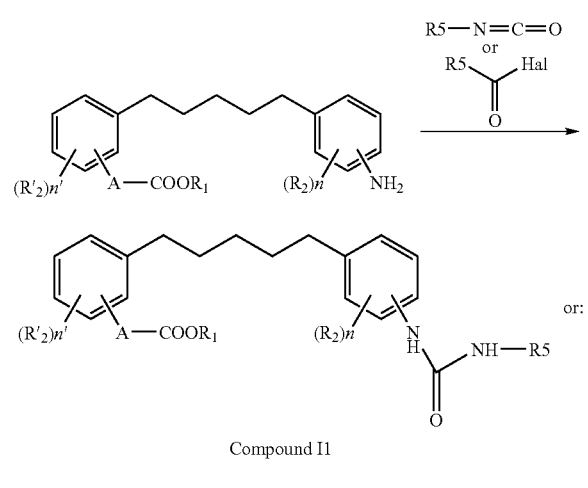
Compound I1

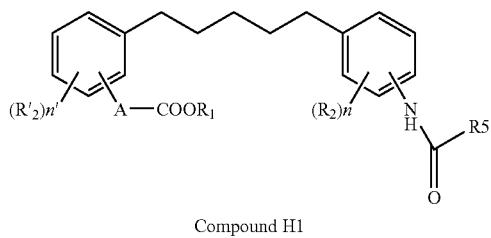
Compound H1

The synthesis of compound A1 may be performed via the action of a halide, such as phenyl bromide Y1 substituted onto a compound containing a triple bond Z1, in a solvent, such as triethylamine, in the presence of palladium chloride and triphenylphosphine. The triple bond of this intermediate is then reduced by hydrogenation in the presence of a catalyst, such as palladium-on-charcoal in a suitable solvent, such as methanol, dioxane or THF, at a temperature of between 25 and 90° C.

Compound B1 is then halogenated, for example via the action of $PHal_3$, such as $PBr_3$ in a suitable solvent, such as toluene, to give compound C1. The phosphonium halide (compound D1) is then obtained via the action of triphenylphosphine in a suitable solvent, such as acetonitrile. Compound E1 may be obtained via the action of a nitrobenzaldehyde X1 on compound D1 in water, at a temperature of between 50 and 100° C., in the presence of $K_2CO_3$. Compound F1 is then obtained by simultaneous hydrogenation of the double bond and of the nitro group in the presence of a catalyst, such as palladium-on-charcoal at a pressure of between 5 and 20 bar.

The sulfonyl derivatives G1 may be obtained via the action of a suitably selected sulfonyl halide, on compound F1, in the presence of a mineral base, for example sodium hydrogen carbonate, or an organic base, such as triethylamine or pyridine, in a solvent, such as acetonitrile, at a temperature of between 0° C. and the boiling point of the chosen solvent, the reaction time possibly ranging from 1 to 24 hours.

The ester, whether or not it is isolated, will be treated with, for example, aqueous sodium hydroxide solution to give the corresponding acid, in a temperature range of from 0° C. to 80° C. and preferably in a temperature range of from 0° C. to 50° C., the reaction time possibly ranging from 1 hour to 24 hours. A cosolvent, such as THF can be used to do this.

The derivatives of acyl type H1 may be obtained via a method similar to that described for the production of the derivatives of sulfonyl type. To this end, a suitable acyl halide will be reacted with compound F1.

Similarly, the ester obtained may or may not be isolated to saponify it via a method similar to that described above.

The compounds of aminocarbonyl type I1 may be obtained via the action of an isocyanate, for example, on compound F1. The reaction may be performed in a solvent chosen so as not to interfere with the reaction: dichloromethane, acetonitrile or toluene may especially be used, at a temperature of between 0° C. and the boiling point of the selected solvent, the reaction time possibly ranging from 1 to 24 hours.

The ester will be saponified in situ or after isolation, to give the acid. To this end, it is possible to use an aqueous sodium hydroxide solution in a temperature range of from 0° C. to 80° C., preferably hydroxide in a temperature range of from 0° C. to 50° C., the reaction time possibly ranging from 1 hour to 24 hours.

General Method 2:
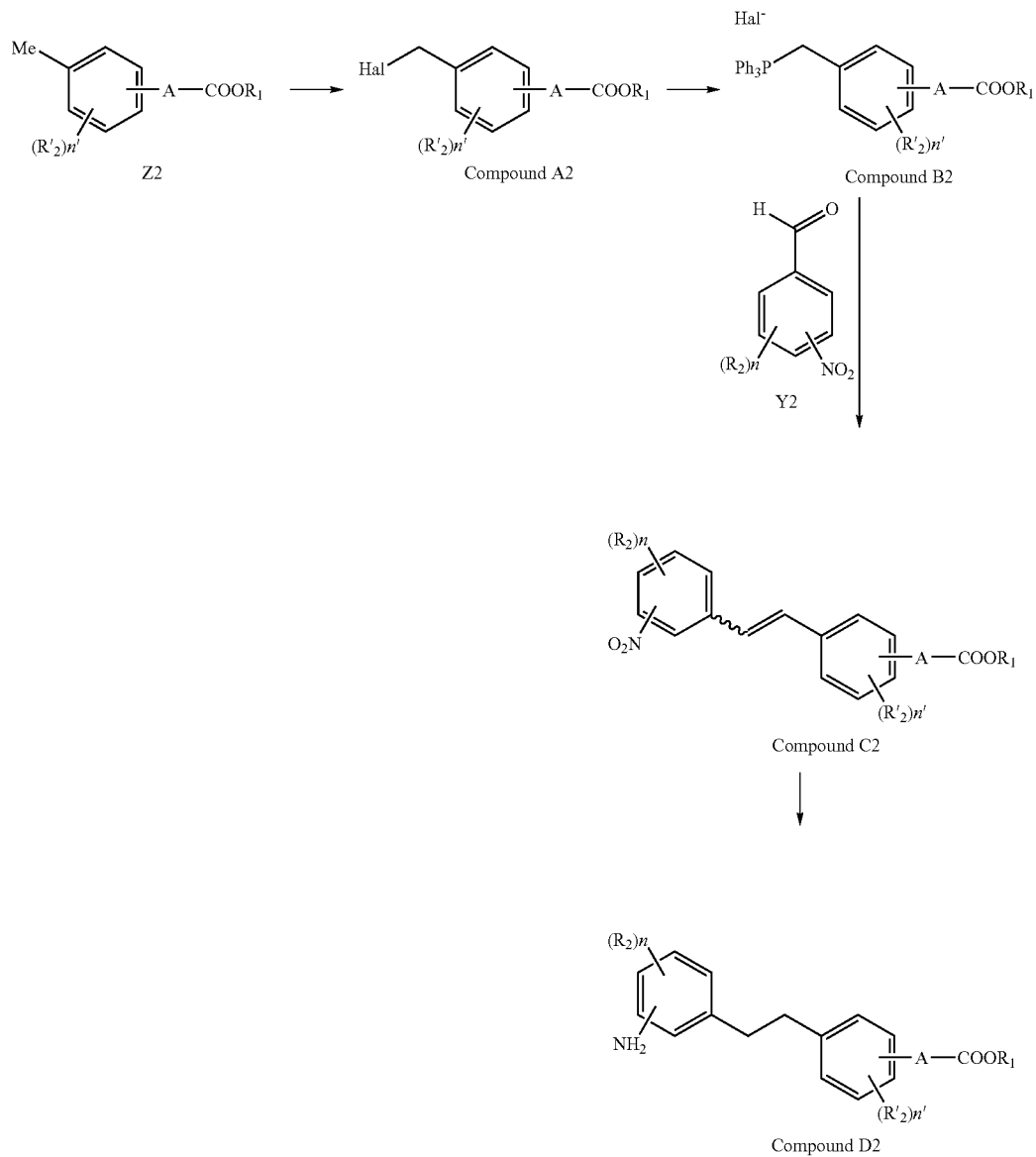
Production of the Sulfonyl Derivatives
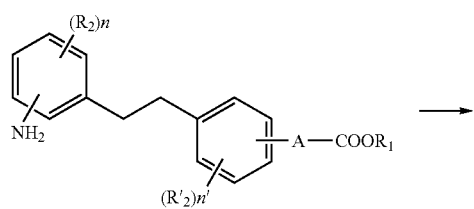
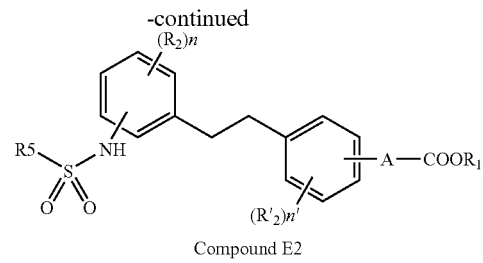

Production of the Acyl and Aminocarbonyl Derivatives

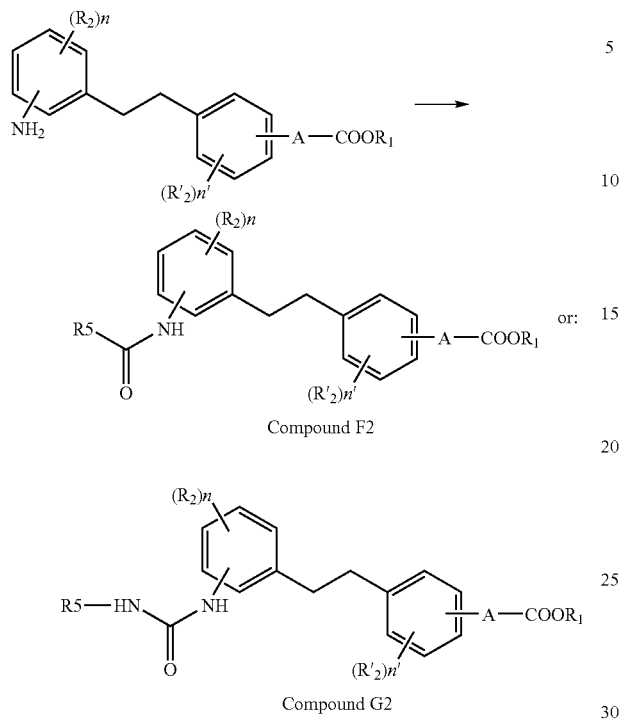

The synthesis of compound A2 may be performed starting with the corresponding compound Z2 via the action of a halogenating agent, preferably a brominating agent, for instance N-bromosuccinimide, in a suitable solvent, such as carbon tetrachloride, in the presence of a catalyst, for example benzoyl peroxide.

The corresponding phosphonium halide may be obtained by reacting the halogenated compound A2 with triphenylphosphine in refluxing acetonitrile.

Compound C2 may be obtained by reacting the phosphonium halide obtained via method 2 (compound 82) with a benzaldehyde substituted by a nitro group Y2 so as to obtain the desired intermediate, in a suitable solvent, such as THF or acetonitrile, in the presence of a strong base, for example sodium amide. Finally, the double bond and the nitro group may be reduced in a single step via catalytic hydrogenation in a suitable solvent, such as THF, methanol or a mixture thereof, in the presence, for example, of palladium-on-charcoal, to give compound D2.

The sulfonyl, acyl and aminocarbonyl derivatives may be obtained in the same manner as that indicated for method 1.

General Method 3:

Production of Sulfonyl Derivatives

Production of Acyl and Aminocarbonyl Derivatives

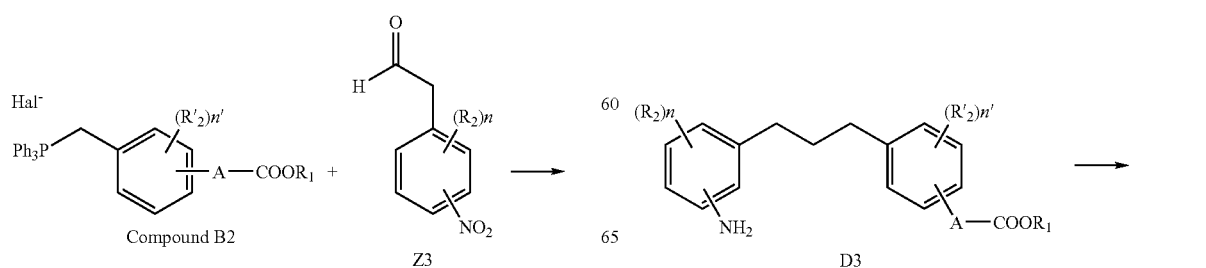

Production of the Sulfonyl Derivatives

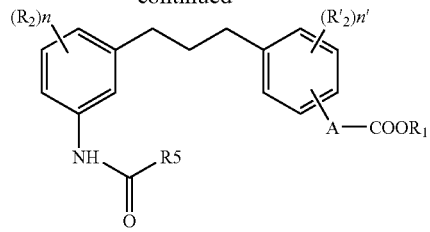

B4

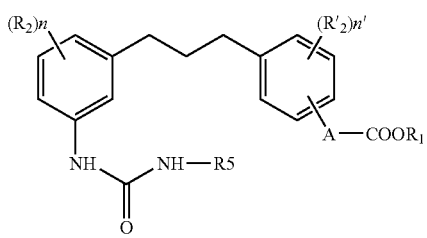

Compound C4

Compound C3 may be obtained by reacting the phosphonium halide obtained via method 2 (compound B2) with, for example, a corresponding phenylacetaldehyde substituted by a nitro group Z3 so as to obtain the desired intermediate C3, in a suitable solvent, such as an ether, such as dioxane or tetrahydrofuran, in the presence of a strong base for, for example sodium amide. Finally, the double bond and the nitro group may be reduced in a single step via catalytic hydrogenation in a suitable solvent of alcohol type, for example ethanol or methanol, in the presence of palladium-on-charcoal, at a pressure of between 1 and 20 bar, to give compound D3.

The sulfonyl, acyl and aminocarbonyl derivatives may be obtained in the same manner as that indicated for method 1.

General Method 4:

Production of the Acyl and Aminocarbonyl Derivatives

-continued

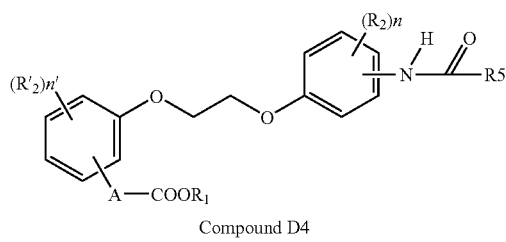

Compound D4

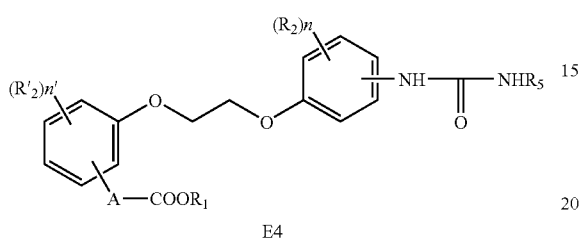

E4

Compound A4 may be obtained by reacting a compound of phenoxyalkyl halide (for example bromide) type bearing a nitro group, Y4, with a phenol bearing an acid function Z4 of the benzoic, acetic, propanoic, etc. type. The nitro group of the compound of the formula A4 may then be reduced via catalytic hydrogenation in the presence of a metal, for example palladium-on-charcoal, at a temperature of between room temperature and 80° C., in a solvent, such as an alcohol, for example methanol or ethanol, or an ether, such as tetrahydrofuran or dioxane, at a pressure of between 1 and 5 bar.

The compound of the general formula C4 will be obtained by reacting a suitably substituted sulfonyl halide with the compound of the general formula B4 in a suitable solvent, for example and in a non-limiting manner, DMF or acetonitrile at a temperature of between 20 and 80° C.

The sulfonyl, acyl and aminocarbonyl derivatives may be obtained as in method 1 or 2.

General Method 1, 2, 3, 4:

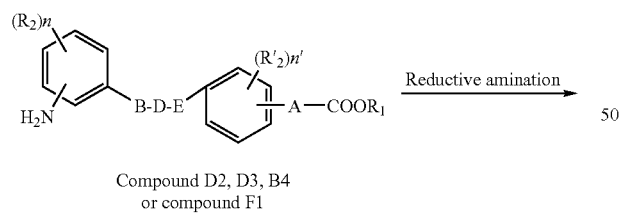

Compound D2, D3, B4
or compound F1

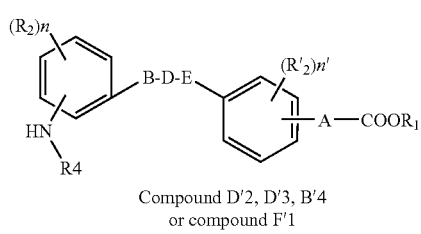

Compound D'2, D'3, B'4
or compound F'1

Production of the Sulfonyl Derivatives

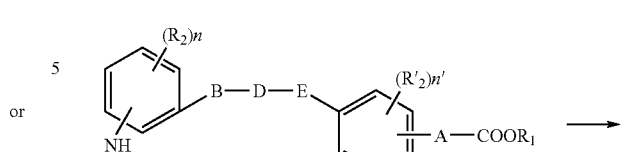

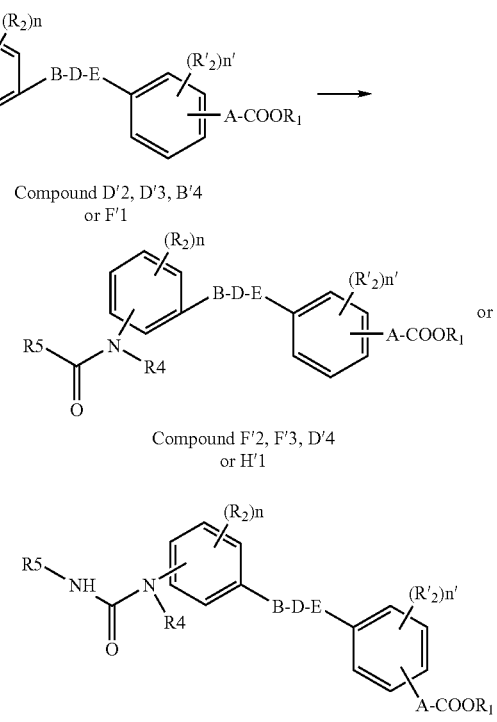

Production of the Acyl and Aminocarbonyl Derivatives

The reductive amination reaction may be performed by application or adaptation of any reductive amination method known per se. The process may especially be performed using a compound of aldehyde type corresponding to the desired compound of the formula (1), in the presence of sodium triacetoxyborohydride in a suitable solvent, such as dichloroethane, at a temperature of between 0° C. and the boiling point of the solvent, preferably at room temperature, for a time required to obtain a satisfactory degree of progress of the reaction, generally from 1 hour to 24 hours.

The sulfonyl, acyl and aminocarbonyl derivatives may be obtained as in method 1.

The compounds of the formula (1) in which R1=H may be obtained from the corresponding compounds G1, H1, I1, E2, F2, G2, E3, F3, G3, C4, D4, E4, E'2, E'3, C'4, G'1, F'2, F'3, D'4, H'1, G'2, G'3, E'4 and I'1 in which R1 is other than H, via hydrolysis according to methods that are known per se.

Optionally, the said process may also include the step consisting in isolating the product obtained.

In the reactions described hereinbelow, it may be necessary to protect reactive functional groups, for example the hydroxyl, amino, imino, thio or carboxyl groups, if they are desired in the final product, to avoid their unwanted participation in the reactions. The conventional protecting groups can be used in accordance with the standard practice; for examples, see T. W. Green and P. G. M. Wuts in *Protective Groups in Organic Chemistry*, John Wiley and Sons, 1991; J. F. W. McOmie in *Protective Groups in Organic Chemistry*, Plenum Press, 1973.

The compound thus prepared may be recovered from the reaction mixture via the conventional means. For example, the compounds may be recovered by distilling the solvent from the reaction mixture or, if necessary, after distilling off the solvent from the mixture of the solution, pouring the remainder into water, followed by extraction with a water-immiscible organic solvent, and distilling the solvent from the extract. In addition, the product may also be purified, if so desired, by various techniques, such as recrystallisation, reprecipitation or various chromatographic techniques, especially column chromatography or preparative thin-layer chromatography.

It will be appreciated that the compounds that are useful according to the present invention may contain asymmetric centres. These asymmetric centres may be, independently, of R or S configuration. It will be apparent to a person skilled in the art that certain compounds that are useful according to the invention may also exhibit geometrical isomerism. It should be understood that the present invention includes individual geometrical isomers and stereoisomers, and mixtures thereof, including racemic mixtures, of compounds of the formula (1) above. Isomers of this type may be separated from their mixtures by application or adaptation of known processes, for example chromatography techniques or recrystallisation techniques, or they are prepared separately from suitable isomers of their intermediates.

For the purposes of the present text, it is understood that the tautomeric forms are included in the citation of a given group, for example thio/mercapto or oxo/hydroxyl.

The acid-addition salts are formed with the compounds that are useful according to the invention in which a basic function, such as an amino, alkylamino or dialkylamino group is present. The pharmaceutically acceptable, i.e. non-toxic, acid-addition salts are preferred. The selected salts are optimally chosen so as to be compatible with the usual pharmaceutical vehicles and suitable for oral or parenteral administration. The acid-addition salts of the compounds that are useful according to the present invention may be prepared by reacting the free base with the appropriate acid, by application or adaptation of known processes. For example, the acid-addition salts of the compounds that are useful according to the present invention may be prepared either by dissolving the free base in water or in a basified aqueous solution or suitable solvents containing the appropriate acid, and isolating the solvent by evaporating the solution, or by reacting the free base and the acid in an organic solvent, in which case the salt separates out directly or may be obtained by concentrating the solution. Among the acids that are suitable for use in the preparation of these salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic acid, malic acid, methanesulfonic acid, toluenesulfonic acid, fatty acids, adipate, alginate, ascorbate, aspartate, benzenesulfonate, benzoate, cyclopentanepropionate, digluconate, dodecyl sulfate, bisulfate, butyrate, lactate, laurate, lauryl sulfate, malate, hydriodide, 2-hydroxyethanesulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonate, hexanoate, camphorate, camphorsulfonate and the like.

The acid-addition salts of the compounds that are useful according to the present invention may be regenerated from the salts by application or adaptation of known processes. For example, the parent compounds that are useful according to the invention may be regenerated from their acid-addition salts by treatment with an alkali, for example aqueous sodium bicarbonate solution or aqueous ammonia solution.

The compounds that are useful according to the present invention may be regenerated from their base-addition salts by application or adaptation of known processes. For example, the parent compounds that are useful according to the invention may be regenerated from their base-addition salts by treatment with an acid, for example hydrochloric acid.

The base-addition salts may be formed if the compound that is useful according to the invention contains a carboxyl group, or a sufficiently acidic bioisostere. The bases that can be used to prepare the base-addition salts preferably include those that produce, if they are combined with a free acid, pharmaceutically acceptable salts, i.e. salts whose cations are not toxic to the patient in the pharmaceutical doses of the salts, such that the beneficial inhibitory effects intrinsic to the free base are not negated by the side effects attributable to the cations. The pharmaceutically acceptable salts, including those derived from alkaline-earth metal salts, within the scope of the present invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, tetramethylammonium hydroxide and the like.

The compounds that are useful according to the present invention may be readily prepared, or formed during the process of the invention, in the form of solvates (for example hydrates). The hydrates of the compounds that are useful according to the present invention may be readily prepared by recrystallisation of an aqueous/organic solvent mixture, using organic solvents, such as dioxane, tetrahydrofuran or methanol.

The basic products or the reagents used are commercially available and/or may be prepared by application or adaptation of known processes, for example processes as described in the Reference Examples or obvious chemical equivalents thereof.

According to the present invention, the compounds of the formula (1) show hypoglycaemiant activity. They can reduce hyperglycaemia and more particularly the hyperglycaemia of non-insulin-dependent diabetes.

Insulin resistance is characterised by a reduction in the action of insulin (cf. Presse Médicale, 1997, 26 (No. 14), 671-677) and is involved in a large number of pathological conditions, such as diabetes and more particularly non-insulin-dependent diabetes (type II diabetes or NIDDM), dyslipidaemia, obesity and also certain microvascular and macrovascular complications, for instance arterial hypertension, atherosclerosis, inflammatory processes, macroangiopathy, microangiopathy, retinopathy and neuropathy.

In this respect, reference may be made, for example, to Diabetes, Vol. 37, 1988, 1595-1607; *Journal of Diabetes And Its Complications,* 1998, 12, 110-119 or Horm. Res., 1992, 38, 28-32.

The compounds of the invention especially show antihyperglycaemic activity.

The compounds of the formula (1) are thus useful in the treatment of pathologies associated with hyperglycaemia.

The present invention also relates to pharmaceutical compositions comprising a compound according to the invention with a pharmaceutically acceptable excipient.

Preferably, the said composition comprises an effective amount of the compound according to the invention.

The present invention also relates to the use of compounds of the general formula (1) for the preparation of pharmaceutical compositions for the prevention and/or treatment of pathologies associated with hyperglycaemia, more particularly diabetes.

Preferably, the said composition is administered to a patient in need thereof.

The pharmaceutical compositions according to the invention may be presented in forms intended for parenteral, oral, rectal, permucous or percutaneous administration.

They will thus be presented in the form of injectable solutions or suspensions or multi-dose bottles, in the form of plain or coated tablets, sugar-coated tablets, wafer capsules, gel capsules, pills, sachets, powders, suppositories or rectal capsules, solutions or suspensions, for percutaneous use in a polar solvent, or for permucous use.

The excipients that are suitable for such administrations are cellulose or microcrystalline cellulose derivatives, alkaline-earth metal carbonates, magnesium phosphate, starches, modified starches and lactose for solid forms.

For rectal use, cocoa butter or polyethylene glycol stearates are the preferred excipients.

For parenteral use, water, aqueous solutions, physiological saline and isotonic solutions are the vehicles most appropriately used.

The dosage may vary within wide ranges (0.5 mg to 1000 mg) depending on the therapeutic indication and the route of administration, and also on the age and weight of the patient.

The examples that follow illustrate the invention without, however, limiting it. The starting materials used are known products or products prepared according to known procedures.

The percentages are expressed on a weight basis, unless otherwise mentioned.

The compounds were characterised especially via the following analytical techniques:

The NMR spectra were acquired using a Brüker Advanced DPX200 MHz NMR spectrometer.

The masses were determined by HPLC coupled to an Agilent Series 1100 mass detector; the masses obtained were found in accordance with the theoretical masses.

The melting points (m.p.) were measured on a Leica VMHB Köfler block. The masses of the products obtained were in accordance with the theoretical values.

EXAMPLE 1

Methyl 2-bromomethylbenzoate 50 g of methyl 2-methylbenzoate (0.33 M), 60.4 g of N-bromosuccinimide (0.340 M) and 4 g of benzoyl peroxide are added to a 2000 ml reactor containing 1500 ml of carbon tetrachloride. The reaction mixture is refluxed for 2 hours. After cooling to room temperature, the reaction medium is concentrated under vacuum. The oil obtained is purified by chromatography on silica (eluent: $CH_2Cl_2$). 74.5 g of a colourless oil are obtained (98% yield).

TLC: diisopropyl ether/petroleum ether (50/50).
NMR (δ in ppm, DMSO, 200 MHz): 4.12 (s, 3H); 5.27 (s, 2H); 7.39 (d, 3H); 7.70 (d, 1H).
IR ($cm^{-1}$): 1720, 1577, 1269, 1294.

EXAMPLE 2

2-Nitrophenylacetaldehyde 45 g of 2-nitrophenylpyruvic acid (2.15 M), 20.6 g of morpholine (2.37 M) and 1 g of para-toluenesulfonic acid are added to 270 ml of toluene in a 1000 ml reactor equipped with Dean-Stark apparatus. The reaction medium is refluxed until all of the water formed during the reaction has been removed. At 20° C., 12 ml of 3 M HCl are then added and stirring is continued for one hour. The organic phase is then washed, dried over $Na_2SO_4$ and then concentrated under vacuum. The red oil obtained is purified by chromatography on silica (eluent: 80/20 $CH_2Cl_2$/heptane). 29.7 g of a red oil are obtained (84% yield).

TLC: dichloromethane
NMR (δ in ppm, $CDCl_3$, 200 MHz): 4.06 (s, 2H), 7.44 (dd, 1H), 7.68 (dd, 1H), 7.7 (d, 1H), 8.25 (d, 1H), 9.78 (t, 1H).
IR ($cm^{-1}$): 1726; 1526; 1348.

EXAMPLE 3

2-Methoxycarbonylbenzyltriphenylphosphonium bromide 74.2 g of triphenylphosphine (0.28 M) in 200 ml of acetonitrile are added to a solution of 74.5 g of methyl 2-bromomethylbenzoate (0.32 M) in 170 ml of acetonitrile in a 2000 ml reactor. The reaction mixture is refluxed with stirring for one hour and then cooled. 1000 ml of diethyl ether are then added slowly. Stirring is continued for 2 hours. A white precipitate forms. The solid is filtered off and washed with acetone. After drying, 112.6 g of a white powder are obtained (81% yield).

m.p. (Köfler): 258° C.
NMR (δ in ppm, $CDCl_3$, 200 MHz): 3.54 (s, 3H); 5.73 (d, 2H); 7.49 (d, 1H); 7.64 (m, 2H); 7.67 (m, 3H); 7.73 (m, 2H); 7.84 (m, 5H); 7.97 (m, 1H); 8.01 (m, 5H)
IR ($cm^{-1}$): 1697; 1431; 1267; 1111; 1075.

EXAMPLE 4

Methyl 2-[3-(2-nitrophenyl)-1-propenyl]benzoate 67.6 g of the phosphonium salt obtained in Example 3 (0.14 M) and then 5.7 g of sodium amide (0.146 M) are added to 120 ml of tetrahydrofuran in a 500 ml reactor under an inert atmosphere (N$_2$). The reaction medium is then stirred at room temperature for one hour. Next, 23.8 g of nitrophenylacetaldehyde (0.145 M) as a solution in 48 ml of tetrahydrofuran are added. The reaction medium is then refluxed for 5 minutes.

50 ml of 3M HCl are added and the mixture is extracted with ethyl acetate. The phases are separated by settling and the organic phase is dried over Na$_2$SO$_4$. The resulting solution is concentrated under vacuum. A red oil is obtained, which is purified by chromatography on silica (eluent: 95/5 CH$_2$Cl$_2$/acetone). 32.9 g of a red oil are obtained (80% yield).

TLC: dichloromethane.

NMR (δ in ppm, CDCl$_3$, 200 MHz): 3.81 (s, 3H), 4.05 (dd, 2H), 6.99 (d, 1H), 7.19 (d, 1H), 7.50 (m, 6H), 7.90 (m, 2H), IR (cm$^{-1}$): 1720; 1608; 1526; 1570.

EXAMPLE 5

Methyl 2-[3-(2-aminophenyl)propyl]benzoate 31 g of methyl 2-[3-(2-nitrophenyl)-1-propenyl]benzoate obtained in Example 4 (0.1 M) are added to 255 ml of methanol and 3.1 g of wet 10% palladium-on-charcoal in a 1 litre stainless-steel reactor. The solution obtained is then stirred for 30 minutes at 20° C. under a hydrogen pressure of 10 bar. 200 ml of tetrahydrofuran are then added and the mixture is filtered through Celite. After evaporation, 27.3 g of a red oil that crystallises are obtained (yield: 98%).

m.p. (Köfler): 48-50° C.

TLC: dichloromethane.

NMR (δ in ppm, CDCl$_3$, 200 MHz): 1.93 (m, 2H), 2.61 (t, 2H), 3.07 (t, 2H), 3.70 (multiplet, 2H), 3.95 (s, 3H), 6.74 (q, 2H), 7.34 (m, 4H), 7.50 (m, 1H), 7.92 (d, 1H).

IR (cm$^{-1}$): 1710, 1452, 1432, 1254.

EXAMPLE 6

Methyl 2-[3-{2-[(4-methylphenyl)sulfonylamino]phenyl}propyl]benzoate 1 g of methyl 2-[3-(2-aminophenyl)propyl]benzoate obtained in Example 5 (3.7 mM), 0.71 g of 4-methylphenylsulfonyl chloride (3.7 mM) and 34 mg of NaHCO$_3$ (4.1 mM) are added to 15 ml of acetonitrile in a 50 ml reactor. The reaction medium is stirred at 20° C. for 20 hours. 5 ml of 1M HCl are then added and the mixture is extracted with ethyl acetate. The organic phase is separated out after settling of the phases, washed and then dried over Na$_2$SO$_4$. After evaporation under vacuum, an oil is obtained, which is precipitated from ethyl ether. The solid is filtered off and washed with ether. 0.42 g of a grey-white solid is obtained (yield: 27%).

m.p. (Köfler): 98-100° C.

NMR (δ in ppm, CDCl$_3$, 200 MHz): 2.21 (s, 1H); 2.42 (t, 4H); 2.69 (m, 2H); 3.72 (s, 3H); 6.84 (m; 2H); 7.20 (m, 1H); 7.24 (m, 2H); 7.44 (m, 5H); 7.69 (m, 2H); 9.43 (s, 1H).

IR (cm$^{-1}$): 3282; 1718; 1254; 1160.

EXAMPLE 7

2-[3-{2-[(4-Methylphenyl)sulfonylamino]phenyl}propyl]benzoic acid

Methyl 2-[3-{2-[(4-methylphenyl)sulfonylamino]phenyl}propyl]benzoate (0.84 mM) obtained in Example 6 and 4.5 ml of aqueous 1M NaOH (4.5 mM) are added to 3 ml of acetonitrile in a 50 ml reactor. The reaction medium is then heated at 50° C. for 2 hours with stirring. The resulting mixture is cooled to room temperature, 2.5 ml of 3M HCl are then added and the mixture is stirred for 20 hours. The solid that precipitates is then filtered off and washed with water. 0.33 g of a pink solid is obtained (100% yield).

m.p. (Köfler): 142-144° C.

NMR (δ in ppm, CDCl$_3$, 200 MHz): 2.4 (s, 3H); 2.6 (m, 4H); 2.8 (d, 2H); 3.7 (lump, 1H); 1.5 (multiplet, 12H); 9.6 (s, 1H).

IR (cm$^{-1}$): 3280; 1690; 1670; 1490; 1406; 1330; 1162.

By way of example, the following compounds are prepared according to the procedures described in Example 7:

| R5 | M | No. |
|---|---|---|
| (4-methylphenyl-acetamido) | 452.5 | 1 |
| (4-chlorophenyl) | 429.9 | 2 |
| (4-methylphenyl, H$_3$C—) | 333.4 | 3 |
| (4-methoxyphenyl) | 425.5 | 4 |
| (2-nitrophenyl) | 440.4 | 5 |
| (4-methylphenyl) | 409.5 | 6 |
| (3-trifluoromethylphenyl) | 463.4 | 7 |
| (naphthyl) | 445.5 | 8 |
| (phenyl-ethyl) | 409.5 | 9 |

-continued
| R5 | M | No. |
|---|---|---|
| 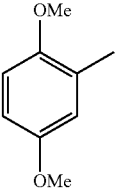 | 455.53 | 10 |
| 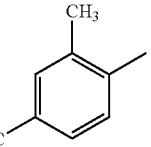 | 423.54 | 11 |
| 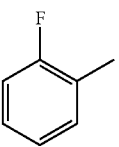 | 413.47 | 12 |
| 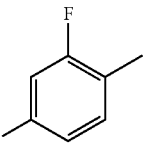 | 431.46 | 13 |
| 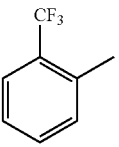 | 463.48 | 14 |
| 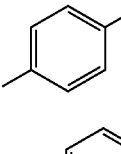 | 413.47 | 15 |
| 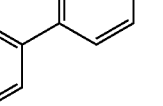 | 471.58 | 16 |
| 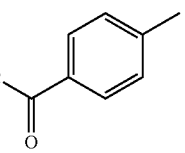 | 437.52 | 17 |
| 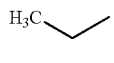 | 347.44 | 18 |
| 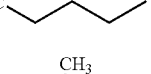 | 375.49 | 19 |
| 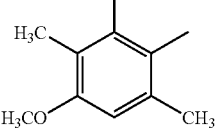 | 467.59 | 20 |
-continued
| R5 | M | No. |
|---|---|---|
| 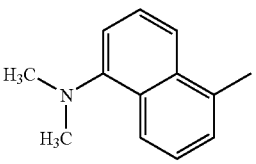 | 488.61 | 21 |
| 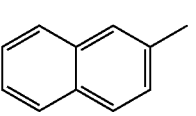 | 445.54 | 22 |
| 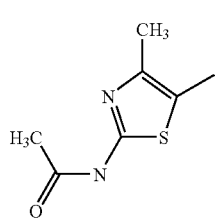 | 473.57 | 23 |
| 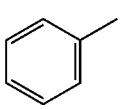 | 395.48 | 24 |
| 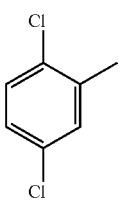 | 464.37 | 25 |
| 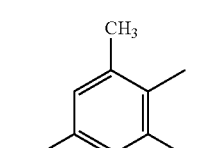 | 437.56 | 26 |
| 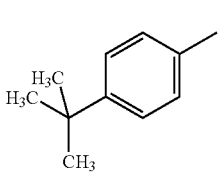 | 451.59 | 27 |
| 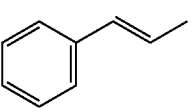 | 421.52 | 28 |
| 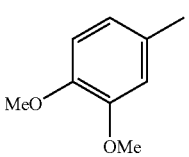 | 455.53 | 29 |
| 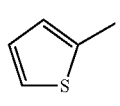 | 401.51 | 30 |

-continued
| R5 | M | No. |
|---|---|---|
|  | 361.46 | 31 |
| 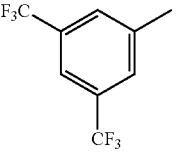 | 541.67 | 32 |
| 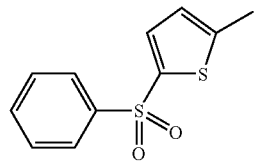 | 479.48 | 33 |
| 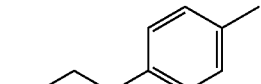 | 467.59 | 34 |
| 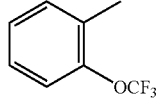 | 427.50 | 35 |
| 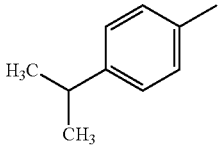 | 479.48 | 36 |
| 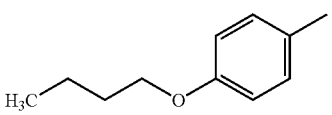 | 431.46 | 37 |
| 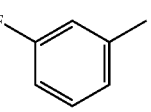 | 451.59 | 38 |
| 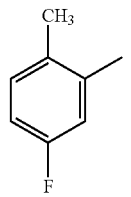 | 425.51 | 39 |
| 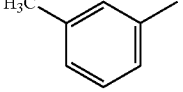 | 465.62 | 40 |
-continued
| R5 | M | No. |
|---|---|---|
| 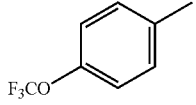 | 531.48 | 41 |
| 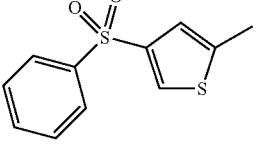 | 437.56 | 42 |
| 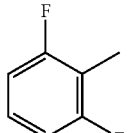 | 437.56 | 43 |
| 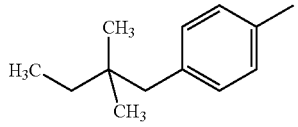 | 413.47 | 44 |
| 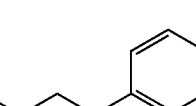 | 409.51 | 45 |
| 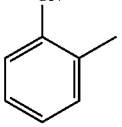 | 541.67 | 46 |
| 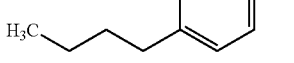 | 465.62 | 47 |
| 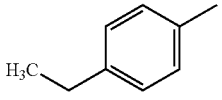 | 420.49 | 48 |
| 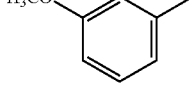 | 423.54 | 49 |
| 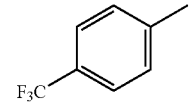 | 463.48 | 50 |
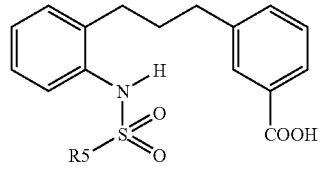

-continued

| R5 | M | No. |
|---|---|---|
| 4-acetamidophenyl (H3C-C(O)-NH-C6H4-) | 452.53 | 51 |
| 4-chlorophenyl | 429.93 | 52 |
| H3C— | 333.41 | 53 |
| 4-methoxyphenyl | 425.51 | 54 |
| 2-nitrophenyl | 440.48 | 55 |
| 4-methylphenyl | 409.51 | 56 |
| 3-(trifluoromethyl)phenyl | 463.48 | 57 |
| 1-naphthyl | 445.54 | 58 |
| benzyl/phenethyl | 409.51 | 59 |
| 2,5-dimethoxyphenyl | 455.53 | 60 |
| 2,4-dimethylphenyl | 423.54 | 61 |

-continued

| R5 | M | No. |
|---|---|---|
| 2-fluorophenyl | 413.47 | 62 |
| 2,4-difluorophenyl | 431.46 | 63 |
| 2-(trifluoromethyl)phenyl | 463.48 | 64 |
| 4-fluorophenyl | 413.47 | 65 |
| 4-biphenyl | 471.58 | 66 |
| 4-acetylphenyl | 437.52 | 67 |
| H3C— (ethyl) | 347.44 | 68 |
| H3C— (pentyl) | 375.49 | 69 |
| 4-methoxy-2,3,5-trimethylphenyl | 467.59 | 70 |
| 5-(dimethylamino)-1-naphthyl | 488.61 | 71 |
| 2-naphthyl | 445.54 | 72 |

| R5 | M | No. |
|---|---|---|
| 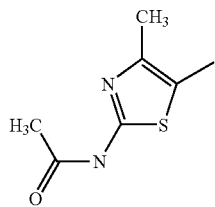 | 473.57 | 73 |
| 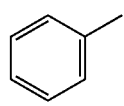 | 395.48 | 74 |
| 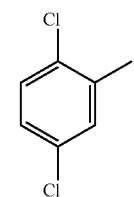 | 464.37 | 75 |
| 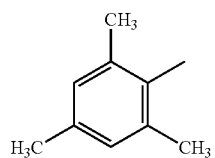 | 437.56 | 76 |
| 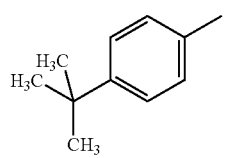 | 451.59 | 77 |
| 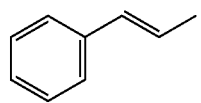 | 421.52 | 78 |
| 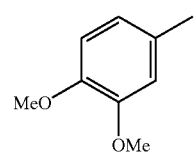 | 455.53 | 79 |
| 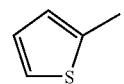 | 401.51 | 80 |
| 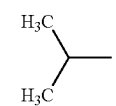 | 361.46 | 81 |
| 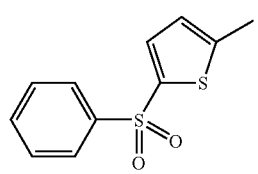 | 541.67 | 82 |
| R5 | M | No. |
|---|---|---|
| 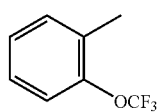 | 479.48 | 83 |
| 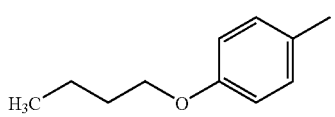 | 467.59 | 84 |
| 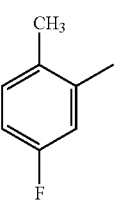 | 427.50 | 85 |
| 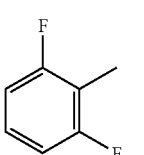 | 431.46 | 86 |
| 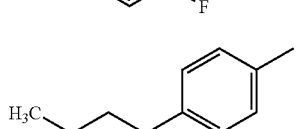 | 451.59 | 87 |
| 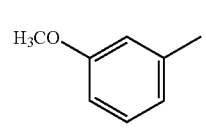 | 425.51 | 88 |
| 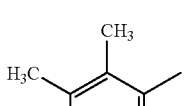 | 465.62 | 89 |
| 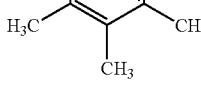 | 531.48 | 90 |
| 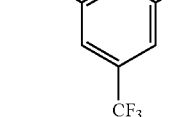 | 437.56 | 91 |
| 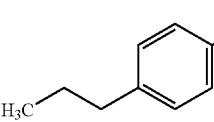 | 437.56 | 92 |

-continued

| R5 | M | No. |
|---|---|---|
| 3-fluorophenyl | 413.47 | 93 |
| 3-methylphenyl | 409.51 | 94 |
| 5-(phenylsulfonyl)thiophen-3-yl | 541.67 | 95 |
| 4-(2,2-dimethylbutyl)phenyl | 465.62 | 96 |
| 2-cyanophenyl | 420.49 | 97 |
| 4-ethylphenyl | 423.54 | 98 |
| 4-(trifluoromethyl)phenyl | 463.48 | 99 |
| camphor-derived | 469.60 | 100 |

Structure:

Ar-CH2-CH2-CH2-Ar'-NH-SO2-R5 (where Ar bears COOH)

| R5 | M | No. |
|---|---|---|
| 4-acetamidophenyl | 452.53 | 101 |
| 4-chlorophenyl | 429.93 | 102 |

-continued

| R5 | M | No. |
|---|---|---|
| 4-methoxyphenyl | 425.51 | 103 |
| 2-nitrophenyl | 440.48 | 104 |
| 4-methylphenyl | 409.51 | 105 |
| 3-(trifluoromethyl)phenyl | 463.48 | 106 |
| naphthalen-1-yl | 445.54 | 107 |
| 2,5-dimethoxyphenyl | 455.53 | 108 |
| 2,4-dimethylphenyl | 423.54 | 109 |
| 2-fluorophenyl | 413.47 | 110 |
| 2,4-difluorophenyl | 431.46 | 111 |
| 2-(trifluoromethyl)phenyl | 463.48 | 112 |

-continued
| R5 | M | No. |
|---|---|---|
| 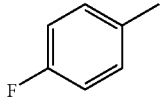 | 413.47 | 113 |
| 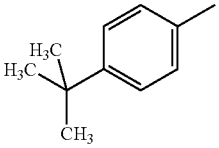 | 471.58 | 114 |
| 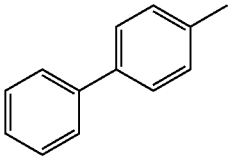 | 437.52 | 115 |
| 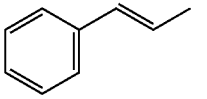 | 488.61 | 116 |
| 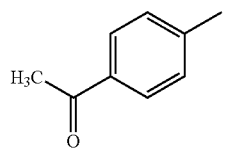 | 445.54 | 117 |
| 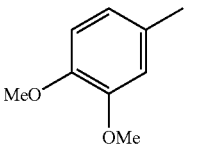 | 473.57 | 118 |
| 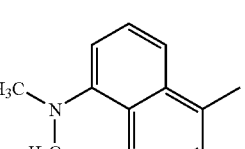 | 395.48 | 119 |
| 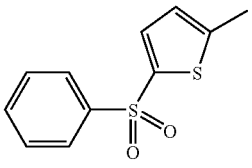 | 464.37 | 120 |
| 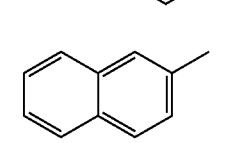 | 437.56 | 121 |
-continued
| R5 | M | No. |
|---|---|---|
| 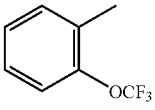 | 451.59 | 122 |
| 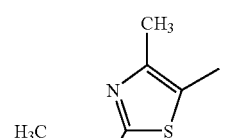 | 421.52 | 123 |
| 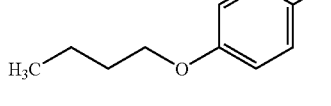 | 455.53 | 124 |
| 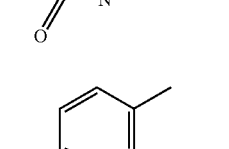 | 541.67 | 125 |
| 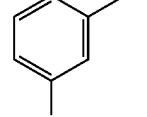 | 479.48 | 126 |
| 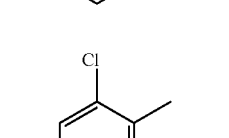 | 467.59 | 127 |
| 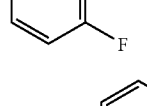 | 427.50 | 128 |
| 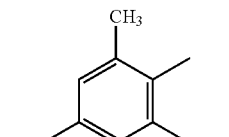 | 479.48 | 129 |
| 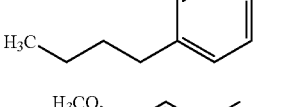 | 431.46 | 130 |
| 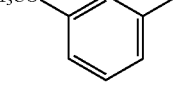 | 451.59 | 131 |
|  | 425.51 | 132 |

| R5 | M | No. |
|---|---|---|
| 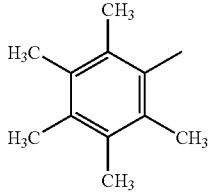 | 465.62 | 133 |
| 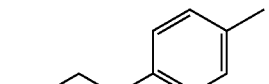 | 437.56 | 134 |
| 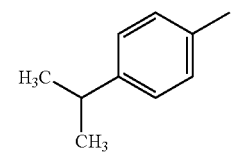 | 437.56 | 135 |
| 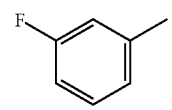 | 413.47 | 136 |
| 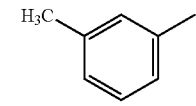 | 409.51 | 137 |
| 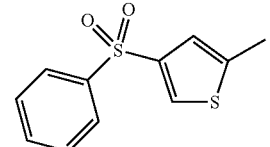 | 541.67 | 138 |
| 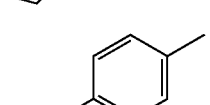 | 439.49 | 139 |
| 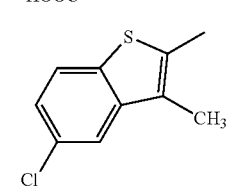 | 500.04 | 140 |

EXAMPLE 8

Methyl 2-(4-hydroxybut-1-ynyl)benzoate 50 ml (0.36 M) of methyl 2-bromobenzoate, 930 mg (3.56 mM) of triphenylphosphine and 316 mg (1.78 mM) of PdCl$_2$ are added to 1200 ml of diethylamine in a 2000 ml reactor. After stirring at room temperature for 5 minutes, 27 ml (0.36 M) of 3-butyn-1-ol and 680 mg (3.56 mM) of CuI (1) are added. The reaction medium is then stirred at 20° C. for 120 hours, the solvent is then evaporated off and the residue obtained is then purified by chromatography on silica, using dichloromethane as eluent. After evaporation, 46.7 g of a brown oil are thus obtained (64% yield).

NMR (δ in ppm, DMSO, 200 MHz): 2.85 (t, 2H); 3.88 (q, 2H); 4.08 (s, 3H); 7.77 (multiplet, 3H); 8.04 (d, 1H).

EXAMPLE 9

Methyl 2-(4-hydroxybutyl)benzoate 46.6 g (0.023 M) of methyl 2-(4-hydroxybut-1-ynyl)benzoate and 5 g of wet 10% palladium-on-charcoal are added to 900 ml of methanol in a 2000 ml stainless-steel autoclave. The reaction medium is then stirred under hydrogen pressure (10 bar) at 70° C. for 16 hours.

The reaction medium is then filtered through Celite and concentrated under vacuum to give 46.5 g of a pale yellow oil (98% yield).

NMR (δ in ppm, DMSO, 200 MHz): 1.64 (multiplet, 4H); 3.1 (t, 2H); 3.55 (m, 2H); 3.98 (s, 3H); 7.49 (m, 2H); 7.64 (m, 1H); 7.90 (d, 1H).

EXAMPLE 10

Methyl 2-(4-bromobutyl)benzoate 46.5 g (0.22 M) of methyl 2-(4-hydroxybutyl)benzoate are added to 120 ml of toluene predried over molecular sieves, in a 1000 ml reactor. 7 ml (0.073 M) of PBr$_3$ are then added and the reaction medium is stirred for 72 hours at room temperature.

The reaction medium is then added slowly to 800 ml of demineralised water.

The mixture is then extracted with ethyl acetate and the organic phase is separated out after settling of the phases, washed with demineralised water and then dried over sodium sulfate and finally concentrated under vacuum.

42.5 g of an oil are thus obtained, and are used as obtained, without further purification (71% yield).

NMR (δ in ppm, DMSO, 200 MHz): 1.59 (m, 2H); 1.78 (m, 2H); 2.86 (t, 2H); 3.49 (t, 2H); 3.79 (s, 3H); 7.31 (m, 2H); 7.46 (m, 1H); 7.75 (d, 1H).

EXAMPLE 11

Methyl 2-(4-bromobutyltriphenylphosphonium)benzoate 41 g (0.16 M) of triphenylphosphine and 42.4 g (0.16 M) of methyl 2-(4-bromobutyl)benzoate are added to 160 ml of acetonitrile predried over molecular sieves, in a 1000 ml reactor, and the mixture is then refluxed with stirring for 20 hours. The reaction medium is then concentrated under vacuum and the residue obtained is taken up in a mixture of 100 ml of dichloromethane and 700 ml of diisopropyl ether.

The crystalline solid is filtered off and washed and then dried under vacuum to give 76.1 g of a white solid (91% yield).

NMR (δ in ppm, DMSO, 200 MHz): 1.63 (m, 2H); 1.78 (m, 2H); 2.95 (t, 2H); 3.71 (m, 2H); 3.83 (s, 3H); 7.37 (m, 1H); 7.52 (m, 2H); 7.83 (multiplet, 16H).

EXAMPLE 12

Methyl 2-[5-(2-nitrophenyl)pent-4-enyl]benzoate 75 g (0.14 M) of methyl 2-(4-bromobutylphosphonium) benzoate obtained in Example 12, 7 g (0.17 M) of 2-nitrobenzaldehyde and 23.3 g (0.25 M) of K₂CO₃ are added to a mixture of 140 ml of dioxane and 4.5 ml of water in a 500 ml reactor, and the reaction medium is then maintained at 95° C. with stirring for 1 hour. The resulting mixture is filtered and the solution obtained is concentrated under vacuum. The residue obtained is then purified by chromatography on silica, using dichloromethane as eluent. 36.1 g of a thick oil are thus obtained (98% yield).

NMR (δ in ppm, DMSO, 200 MHz): 1.58 (m, 2H); 2.01 (m, 2H); 2.71 (t, 2H); 3.69 (s, 3H); 5.78 (m, 1H); 6.51 (m, 1H); 7.5 (multiplet, 8H).

EXAMPLE 13

Methyl 2-[5-(2-aminophenyl)pentyl]benzoate 36 g (0.11 M) of methyl 2-[5-(2-nitrophenyl)pentyl]benzoate and 4 g of palladium-on-charcoal are added to 400 ml of methanol in a 1000 ml stainless-steel autoclave. The reaction medium is then stirred under hydrogen pressure (10 bar) at 70° C. for 3 hours.

The reaction medium is then filtered through Celite and concentrated under vacuum.

The residue obtained is then purified by chromatography on silica, using dichloromethane as eluent. 28.2 g of an orange-coloured oil are thus obtained (86% yield).

NMR (δ in ppm, DMSO, 200 MHz): 1.59 (m, 2H); 1.73 (m, 4H); 2.61 (m, 2H); 3.07 (t, 2H); 4.01 (s, 3H); 4.96 (s, 2H); 6.67 (t, 1H); 6.82 (d, 1H); 7.07 (m, 3H); 7.5 (m, 2H); 7.97 (d, 1H).

EXAMPLE 14

2-{5-[2-(2,4,6-Trimethylphenylsulfonylamino)phenyl)pentyl}benzoic acid 19.8 g (0.066 M) of methyl 2-[5-(2-aminophenyl)pentyl]benzoate, 6.15 g (0.073 M) of sodium hydrogen carbonate and 14.6 g (0.066 M) of 2,4,6-trimethylbenzenesulfonyl chloride are added to 280 ml of acetonitrile in a 1000 ml reactor. The reaction medium is then stirred at 20° C. for 20 hours.

The intermediate ester is not isolated: 330 ml of aqueous 1N sodium hydroxide solution are added to the reaction medium and the mixture is stirred at 50° C. for 2 hours. The reaction medium is then washed with ethyl acetate and with diethyl ether in order to remove the impurities. The aqueous phase is then acidified with 3N hydrochloric acid, precipitation is observed, and stirring is continued for 16 hours. The precipitate is filtered off and washed thoroughly with water to give, after drying at 70° C. under vacuum, 21.1 g of a white solid (yield: 81%).

m.p. (Köfler): 119-121° C.

NMR (δ in ppm, DMSO, 200 MHz): 1.24 (m, 4H); 1.48 (m, 2H); 2.22 (s, 3H); 2.37 (m, 8H); 2.94 (t, 2H); 7.3 (multiplet, 10H); 9.48 (s, 1H); 12.87 (s, 1H).

By way of example, the following compounds are prepared according to the procedure described in Example 14:

| R5 | MW | No. |
|---|---|---|
| 4-methylphenyl-NHC(O)CH₃ (acetamido-p-tolyl) | 480.59 | 141 |
| 4-chlorophenyl | 457.98 | 142 |
| methyl (H₃C—) | 361.46 | 143 |
| 4-methoxyphenyl | 453.56 | 144 |
| 2-nitrophenyl | 468.53 | 145 |
| 4-methylphenyl | 437.56 | 146 |
| 3-trifluoromethylphenyl | 491.53 | 147 |
| 1-naphthyl | 473.60 | 148 |
| phenyl | 437.56 | 149 |
| 2,5-dimethoxyphenyl | 483.59 | 150 |

| | | | | | | |
|---|---|---|---|---|---|---|
| 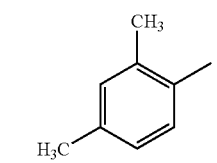 | 451.59 | 151 | | 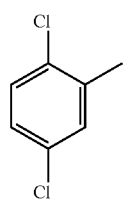 | 492.43 | 162 |
|  | 441.53 | 152 | | 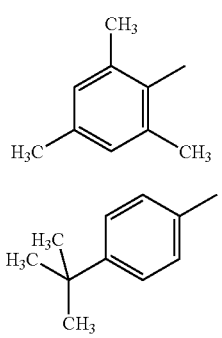 | 465.62 | 163 |
|  | 459.52 | 153 | | 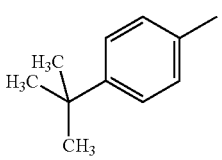 | 479.64 | 164 |
| 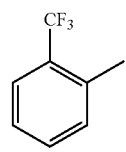 | 491.53 | 154 | | 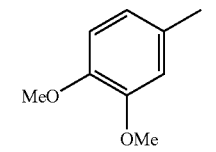 | 483.59 | 165 |
| 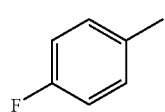 | 441.53 | 155 | | 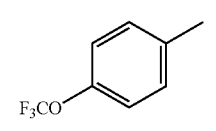 | 507.53 | 166 |
| 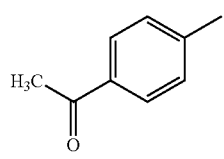 | 465.57 | 156 | | 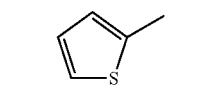 | 429.56 | 167 |
| 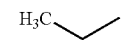 | 375.49 | 157 | | 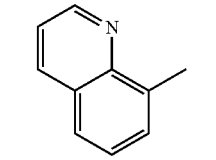 | 474.58 | 168 |
| 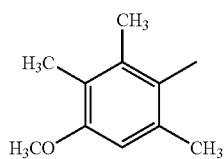 | 495.64 | 158 | | 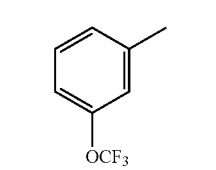 | 507.53 | 169 |
| 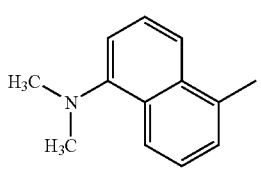 | 516.66 | 159 | | 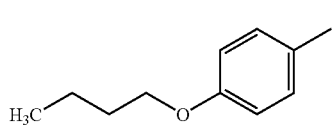 | 495.64 | 170 |
| 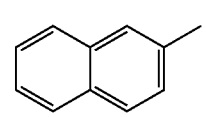 | 473.60 | 160 | | 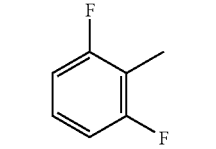 | 459.52 | 171 |
| 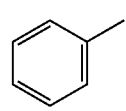 | 423.54 | 161 | | 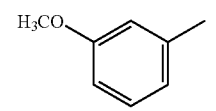 | 453.56 | 172 |

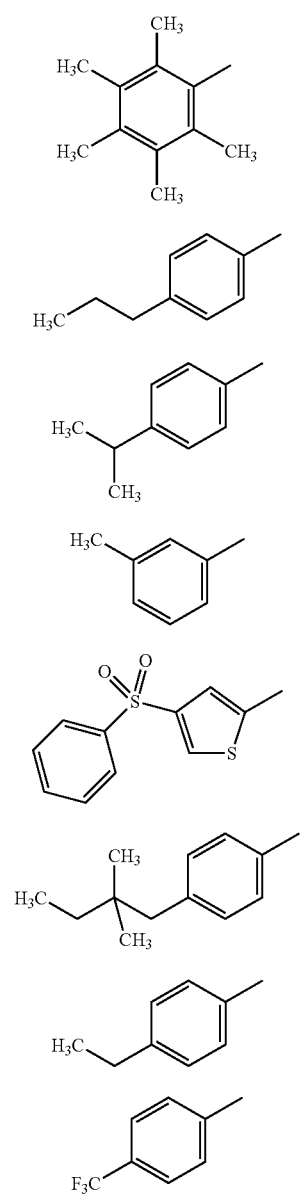

| | MW | No. |
|---|---|---|
| | 493.67 | 173 |
| | 465.62 | 174 |
| | 465.62 | 175 |
| | 437.56 | 176 |
| | 569.72 | 177 |
| | 493.67 | 178 |
| | 451.59 | 179 |
| | 491.53 | 180 |

EXAMPLE 15

2-{5-[2-(benzoylamino)phenyl]pentyl}benzoic acid 100 mg (0.34 mM) of 2-{5-[2-aminophenyl]pentyl}benzoic acid, 39.5 ml (0.34 mM) of benzoyl chloride and 47 mg (0.34 mM) of $K_2CO_3$ are added to 1.5 ml of acetonitrile predried over molecular sieves, in a 15 ml reactor, and the reaction medium is then stirred at 20° C. for 20 hours. 1 ml of methanol and 2 ml of aqueous 1N sodium hydroxide solution are then added and the mixture is maintained at 50° C. with stirring for 2 hours.

3 ml of 1N hydrochloric acid are added and the mixture is stirred at 20° C. for 20 hours. The precipitated solid is filtered off, washed and dried under vacuum to give 55 mg of a white solid.

(Yield: 54%)

NMR (δ in ppm, DMSO, 200 MHz): 1.5 (m, 2H); 1.75 (m, 4H); 2.85 (t, 2H); 3.05 (t, 2H); 7.7 (multiplet, 13H); 10.1 (s, 1H); 13 (s, 1H).

By way of example, the following compounds are prepared according to the procedure described in Example 15:

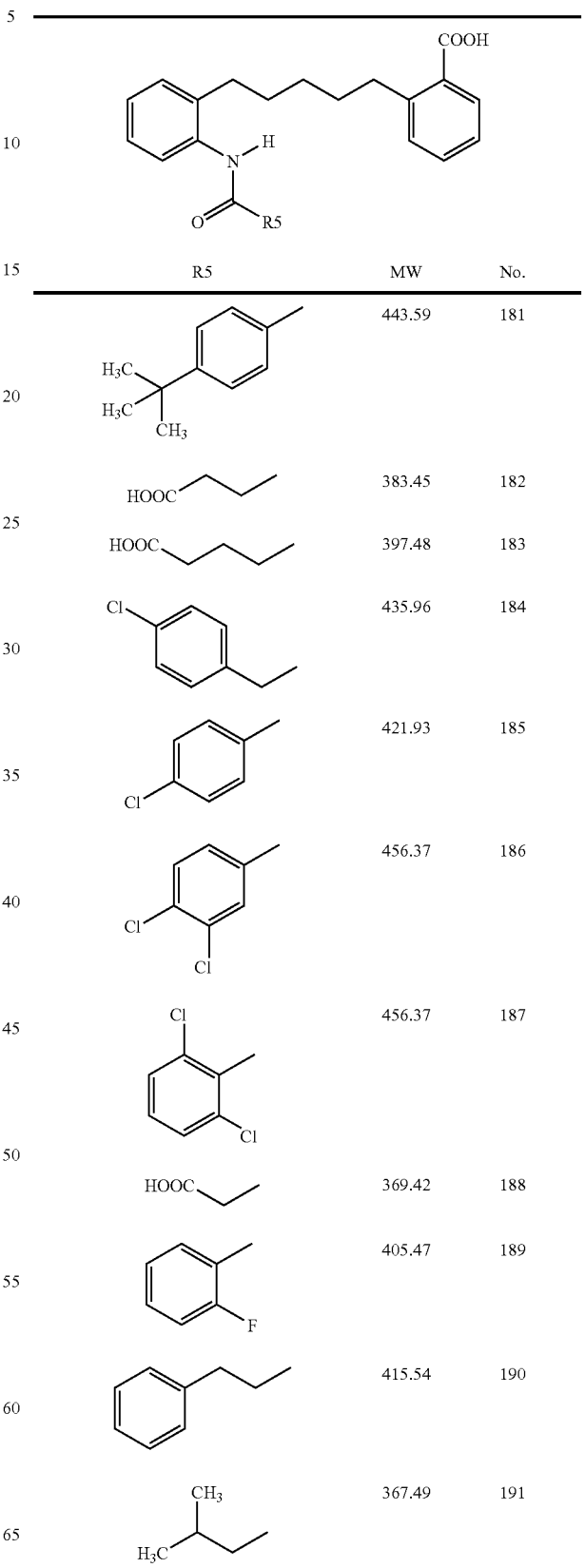

| R5 | MW | No. |
|---|---|---|
| | 443.59 | 181 |
| | 383.45 | 182 |
| | 397.48 | 183 |
| | 435.96 | 184 |
| | 421.93 | 185 |
| | 456.37 | 186 |
| | 456.37 | 187 |
| | 369.42 | 188 |
| | 405.47 | 189 |
| | 415.54 | 190 |
| | 367.49 | 191 |

-continued

Structure: 2-[5-(2-aminophenyl)pentyl]benzoic acid with N-C(=O)-R5 acyl group on the aniline nitrogen.

| R5 | MW | No. |
|---|---|---|
| phenoxymethyl (PhO-CH2-) | 417.51 | 192 |
| benzyl (Ph-CH2-) | 401.51 | 193 |
| tert-butyl ((CH3)3C-) | 367.49 | 194 |
| 2-methylphenyl (o-tolyl) | 401.51 | 195 |
| 4-methylphenyl (p-tolyl) | 401.51 | 196 |
| 3,5-difluorophenyl | 423.46 | 197 |
| trans-2-phenylcyclopropyl | 427.55 | 198 |
| 2-ethylhexyl (branched) | 409.57 | 199 |
| 4-ethylphenyl | 415.54 | 200 |
| 3,5-dichlorophenyl | 456.37 | 201 |

-continued

| R5 | MW | No. |
|---|---|---|
| 2-naphthyl | 437.54 | 202 |
| benzyloxymethyl (PhCH2-O-CH2-) | 431.54 | 203 |
| methoxymethyl (CH3-O-CH2-) | 355.44 | 204 |
| cyclohexyl | 393.53 | 205 |
| n-propyl | 353.47 | 206 |
| cyclopentyl | 379.50 | 207 |
| isopropyl | 353.47 | 208 |
| 2-hydroxyethyl (HO-CH2-) | 341.41 | 209 |
| 1-phenylpropyl | 429.56 | 210 |
| ethyl | 339.44 | 211 |
| 4-fluorobenzyl | 419.50 | 212 |
| (R)-1-hydroxyethyl | 355.44 | 213 |
| 4-methoxybenzyl | 431.54 | 214 |

-continued

| R5 | MW | No. |
|---|---|---|
| (CH3CH2CH(CH3)CH2-, isopentyl branched) | 381.52 | 215 |
| (isobutyl-CH2-) | 381.52 | 216 |
| (cyclopentyl-CH2CH2-) | 407.56 | 217 |
| (isobutyl) | 367.49 | 218 |
| (quinoxalin-2-yl-methyl) | 439.52 | 219 |
| (2,3-difluorophenyl-methyl) | 423.4 | 220 |
| (2-fluoro-4-trifluoromethylphenyl-methyl) | 473.4 | 221 |
| (3-chlorophenyl-methyl) | 421.9 | 222 |
| (4-methoxyphenyl-methyl) | 417.5 | 223 |
| (phenyl-methyl) | 387.4 | 224 |

-continued

| R5 | MW | No. |
|---|---|---|
| (tert-amyl / 2-methylbutan-2-yl) | 381.5 | 225 |
| (2-chlorophenyl-methyl) | 421.9 | 226 |
| (4-fluorophenyl-methyl) | 405.4 | 227 |
| (naphth-1-yl-methyl) | 437.5 | 228 |
| (4-acetamidophenyl-methyl) | | 229 |

EXAMPLE 16

4-Methoxycarbonylbenzyltriphenylphosphonium bromide

This compound is prepared via a method similar to that described in Example 3 for obtaining 2-methoxycarbonyl-benzyltriphenylphosphonium. The desired compound is thus obtained in a yield of 77%.

NMR (δ in ppm, DMSO, 200 MHz): 3.84 (s, 3H); 5.42 (d, 2H); 7.2 (d, 2H); 0.8 (multiplet, 17H).

EXAMPLE 17

Methyl 4-[2-(3-nitrophenyl)vinyl]benzoate 71.2 g of 4-methoxycarbonylbenzyltriphenylphosphonium bromide and 23 g (0.15 M) of 3-nitrobenzaldehyde are added to 360 ml of acetonitrile in a 1000 ml reactor. 19 ml (0.15 M) of 1,5-diazobicyclo[4.3.0]non-5-ene (DBN) are then added and the reaction medium is then refluxed with stirring for 1 hour. The solvent is then evaporated off and the residue obtained is then purified by chromatography on silica, using dichloromethane as eluent. After evaporation, 41.6 g of a white solid are obtained (yield: 95%).

NMR (δ in ppm, DMSO, 200 MHz): 3.86 (s, 3H); 7.8 (multiplet, 10H).

EXAMPLE 18

Methyl 4-[2-(3-aminophenyl)ethyl]benzoate 28.8 g (0.14 M) of methyl 4-[2-(3-nitrophenyl)vinyl]benzoate obtained in Example 16 and 4 g of wet 10% palladium-on-charcoal are added to 400 ml of methanol and 100 ml of tetrahydrofuran in a 1000 ml autoclave. The reaction medium is then stirred for 30 hours at 90° C. under a hydrogen pressure of 30 bar.

After filtration through Celite, the reaction medium is concentrated under vacuum and then purified by chromatography on silica, using dichloromethane as eluent. After evaporating off the solvent under vacuum, 24 g of a pink solid are thus obtained (yield: 68%).

NMR (δ in ppm, DMSO, 200 MHz): 2.96 (m, 2H); 3.11 (m, 2H); 4.05 (s, 3H); 5.16 (s, 2H); 6.60 (m, 3H); 7.12 (t, 1H); 7.59 (d, 2H); 8.10 (d, 2H).

EXAMPLE 19

4-{2-[3-(4-Butylphenylsulfonylamino)phenyl)ethyl}benzoic acid 17.9 g (0.07 M) of methyl 4-{2-[3-(phenylsulfonylamino)phenyl]ethyl}benzoate and 13 g (0.15 M) of sodium hydrogen carbonate are added to 250 ml of acetonitrile in a 500 ml reactor. 16.3 g (0.07 M) of 4-butylphenylsulfonyl chloride are then added, and the reaction medium is then stirred at 20° C. for 72 hours.

350 ml of aqueous sodium hydroxide solution are then added and the reaction medium is maintained at 50° C. for 2 hours, then acidified with 3 N hydrochloric acid, and the precipitated solid is filtered off, washed with water and then dried under vacuum to give 28.8 g of a white solid (yield: 94%).

m.p. (Köfler): 164-166° C.

NMR (δ in ppm, DMSO, 200 MHz): 1 (s, 3H); 1.4 (t, 2H); 1.6 (t, 2H); 2.7 (m, 2H); 3 (m, 4H); 7.4 (multiplet, 12H); 10.30 (s, 1H).

By way of example, the following compounds are prepared according to the procedures described in Examples 18 and 19

| R5 | MW | No. |
|---|---|---|
| 4-Cl-C6H4 | 415.90 | 230 |
| H3C— | 319.38 | 231 |
| 4-MeO-C6H4 | 411.48 | 232 |
| phenylethyl | 395.48 | 233 |
| H3C-butyl | 361.46 | 234 |
| camphor-type | 455.58 | 235 |
| phenyl | 381.45 | 236 |
| 4-(N-acetyl-N-methyl)amino-phenyl | 438.51 | 237 |
| 4-methylphenyl | 395.48 | 238 |
| 3-CF3-phenyl | 449.45 | 239 |
| 1-naphthyl | 431.51 | 260 |
| 2,5-dimethoxyphenyl | 441.51 | 261 |
| 2,4-dimethylphenyl | 409.51 | 262 |
| 2-fluorophenyl | 399.44 | 263 |

-continued
| R5 | MW | No. |
|---|---|---|
| 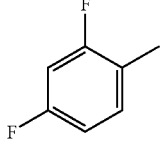 | 417.43 | 264 |
| 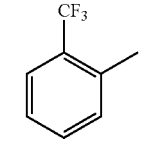 | 449.45 | 265 |
| 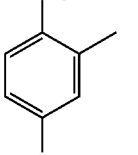 | 399.44 | 266 |
| 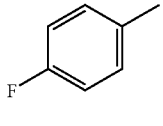 | 423.49 | 267 |
| 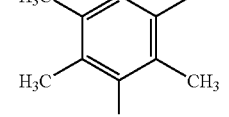 | 474.58 | 268 |
| 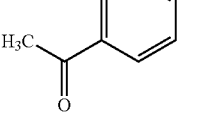 | 333.41 | 269 |
| 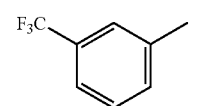 | 450.34 | 289 |
| 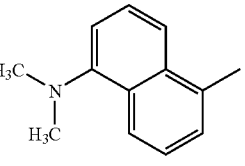 | 407.49 | 290 |
| 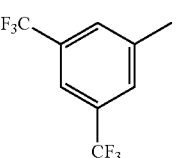 | 465.45 | 291 |
| 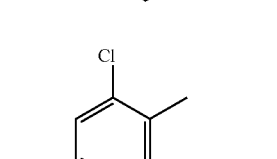 | 465.45 | 292 |
-continued
| R5 | MW | No. |
|---|---|---|
| 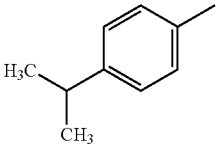 | 413.47 | 293 |
|  | 37.56 | 294 |
| 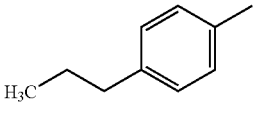 | 451.59 | 295 |
|  | 517.45 | 296 |
| 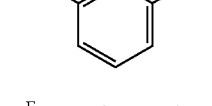 | 423.54 | 297 |
| 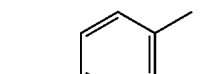 | 423.54 | 298 |
| 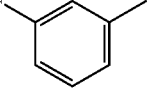 | 395.48 | 318 |
|  | 399.44 | 319 |
| 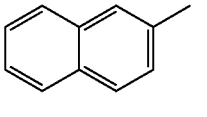 | 431.51 | 320 |
| 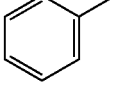 | 459.55 | 321 |

| R5 | MW | No. |
|---|---|---|
| 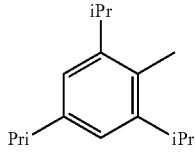 | 507.70 | 322 |
| 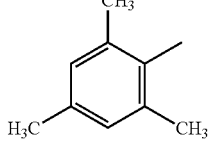 | 423.54 | 323 |
| 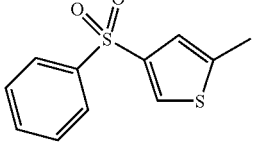 | 437.56 | 324 |
| 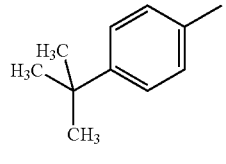 | 441.51 | 325 |
| 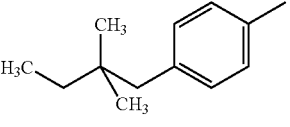 | 387.48 | 326 |
| 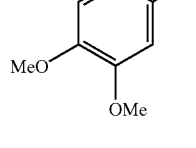 | 347.44 | 327 |
| 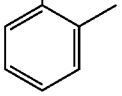 | 527.64 | 348 |
| 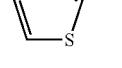 | 453.56 | 349 |
| 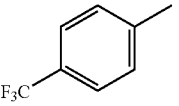 | 417.43 | 350 |
|  | 411.48 | 351 |
| R5 | MW | No. |
|---|---|---|
| 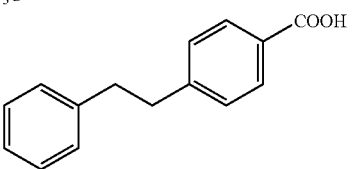 | 527.64 | 352 |
| 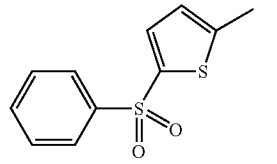 | 451.59 | 353 |
| 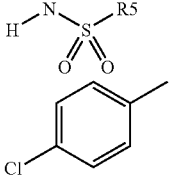 | 406.46 | 354 |
| 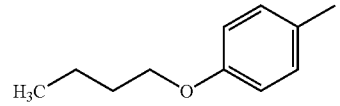 | 449.45 | 355 |
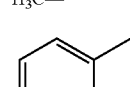
| R5 | MW | No. |
|---|---|---|
| 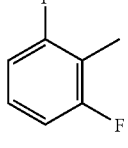 | 415.90 | 240 |
| H₃C— | 319.38 | 241 |
| 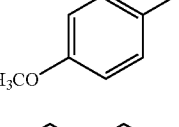 | 411.48 | 242 |
| 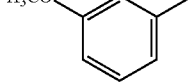 | 395.48 | 243 |
| 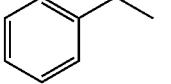 | 361.46 | 244 |
| 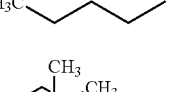 | 455.58 | 245 |
| 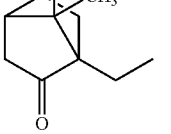 | 381.45 | 246 |

-continued
| R5 | MW | No. |
|---|---|---|
| 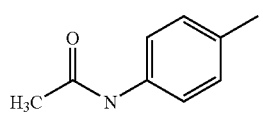 | 438.51 | 247 |
| 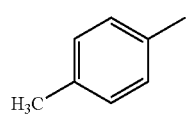 | 395.48 | 248 |
| 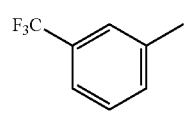 | 449.45 | 249 |
| 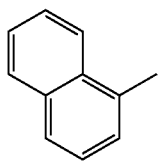 | 431.51 | 270 |
| 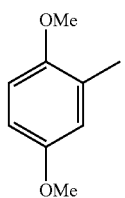 | 441.51 | 271 |
| 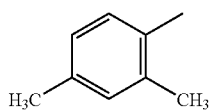 | 409.51 | 272 |
| 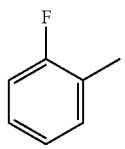 | 399.44 | 273 |
| 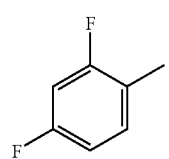 | 417.43 | 274 |
| 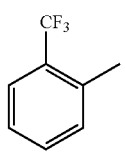 | 449.45 | 275 |
| 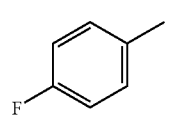 | 399.44 | 276 |
-continued
| R5 | MW | No. |
|---|---|---|
| 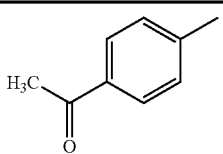 | 423.49 | 277 |
| 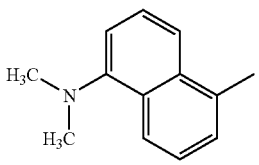 | 474.58 | 278 |
| 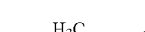 | 333.41 | 279 |
| 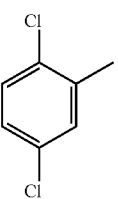 | 450.34 | 299 |
| 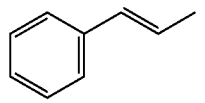 | 407.49 | 300 |
| 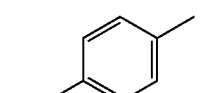 | 465.45 | 301 |
| 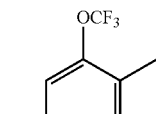 | 465.45 | 302 |
| 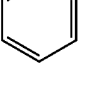 | 413.47 | 303 |
| 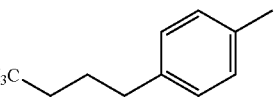 | 37.56 | 304 |
| 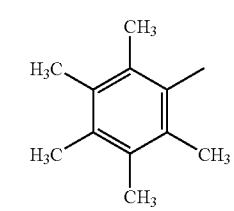 | 451.59 | 305 |

-continued
| R5 | MW | No. |
|---|---|---|
|  | 517.45 | 306 |
| 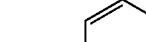 | 423.54 | 307 |
|  | 423.54 | |
| 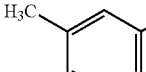 | 395.48 | 328 |
| 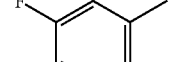 | 399.44 | 329 |
| 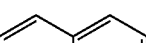 | 431.51 | 330 |
|  | 459.55 | 331 |
| 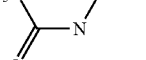 | 507.70 | 332 |
| 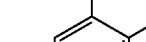 | 423.54 | 333 |
|  | 437.56 | 334 |
-continued
| R5 | MW | No. |
|---|---|---|
|  | 441.51 | 335 |
| 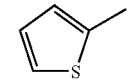 | 387.48 | 336 |
| 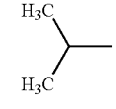 | 347.44 | 337 |
| 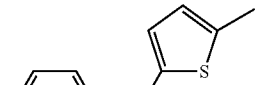 | 527.64 | 356 |
| 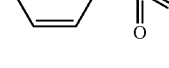 | 453.56 | 357 |
| 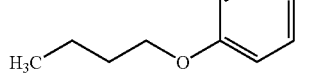 | 417.43 | 358 |
| 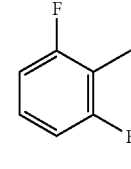 | 411.48 | 359 |
| 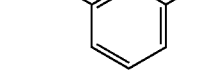 | 527.64 | 360 |
| 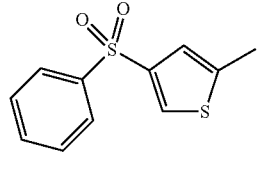 | 451.59 | 361 |
| 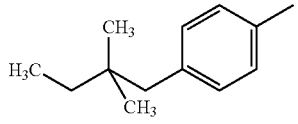 | 406.46 | 362 |
| 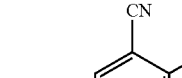 | 449.45 | 363 |

-continued
| R5 | MW | No. |
|---|---|---|
| 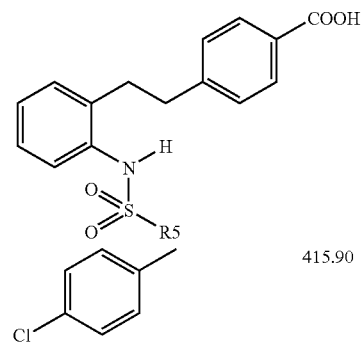 | | |
| 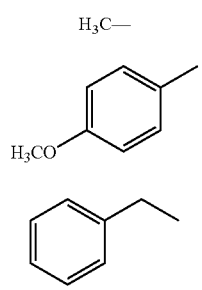 | 415.90 | 250 |
| H₃C— | 319.38 | 251 |
| 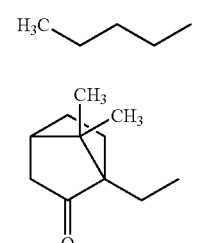 | 411.48 | 252 |
| 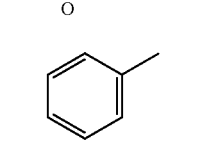 | 395.48 | 253 |
| H₃C— (pentyl) | 361.46 | 254 |
| 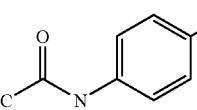 | 455.58 | 255 |
| 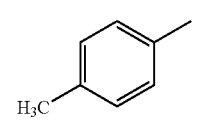 | 381.45 | 256 |
| 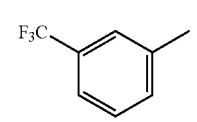 | 438.51 | 257 |
| 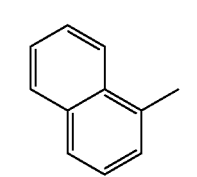 | 395.48 | 258 |
| 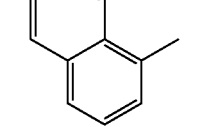 | 449.45 | 259 |
| 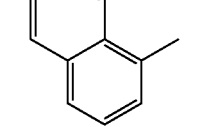 | 431.51 | 280 |
-continued
| R5 | MW | No. |
|---|---|---|
| 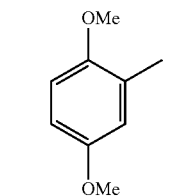 | 441.51 | 281 |
| 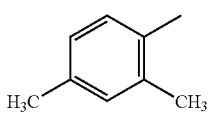 | 409.51 | 282 |
| 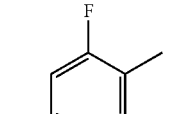 | 399.44 | 283 |
| 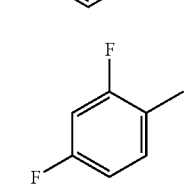 | 417.43 | 284 |
| 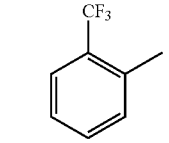 | 449.45 | 285 |
| 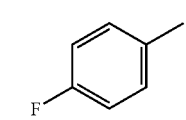 | 399.44 | 286 |
| 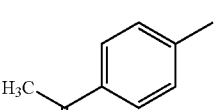 | 423.49 | 287 |
| 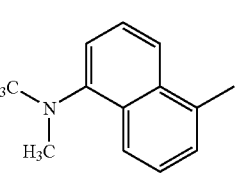 | 474.58 | 288 |
| 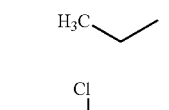 | 333.41 | |
| 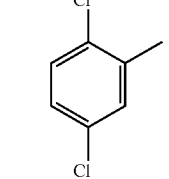 | 450.34 | 308 |

| R5 | MW | No. |
|---|---|---|
| 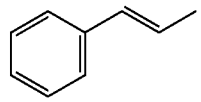 | 407.49 | 309 |
| 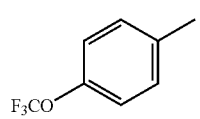 | 465.45 | 310 |
| 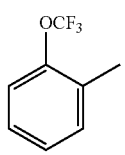 | 465.45 | 311 |
| 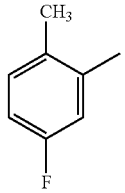 | 413.47 | 312 |
| 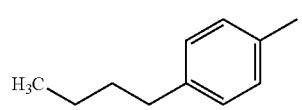 | 37.56 | 313 |
| 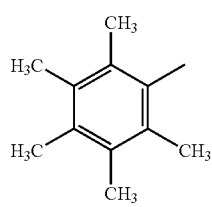 | 451.59 | 314 |
| 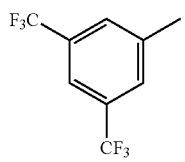 | 517.45 | 315 |
| 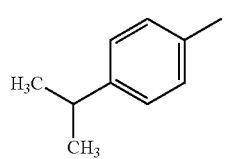 | 423.54 | 316 |
| 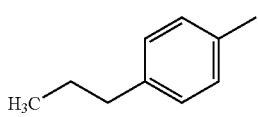 | 423.54 | 317 |
| 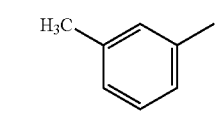 | 395.48 | 338 |
| R5 | MW | No. |
|---|---|---|
| 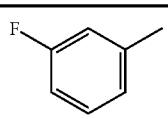 | 399.44 | 339 |
| 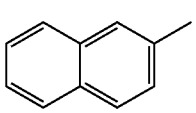 | 431.51 | 340 |
| 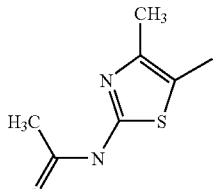 | 459.55 | 341 |
| 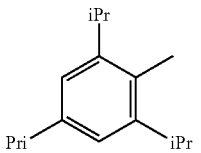 | 507.70 | 342 |
| 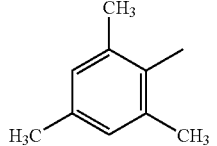 | 423.54 | 343 |
| 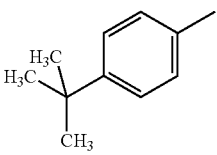 | 437.56 | 344 |
| 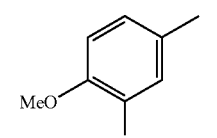 | 441.51 | 345 |
|  | 387.48 | 346 |
|  | | |
| 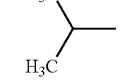 | 347.44 | 347 |
| 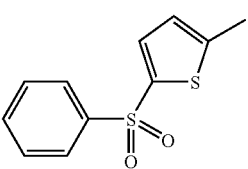 | 527.64 | 364 |

-continued
| R5 | MW | No. |
|---|---|---|
| 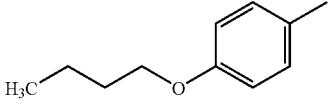 | 453.56 | 365 |
| 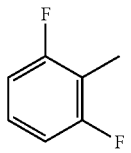 | 417.43 | 366 |
| 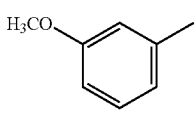 | 411.48 | 367 |
| 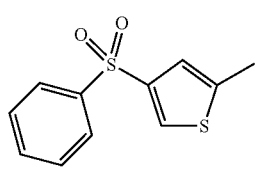 | 527.64 | 368 |
| 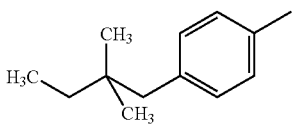 | 451.59 | 369 |
| 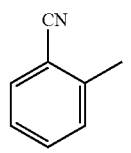 | 406.46 | 370 |
| 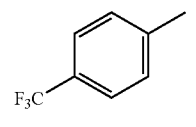 | 449.45 | 371 |
| 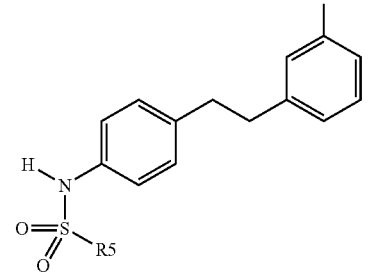 | | |
| 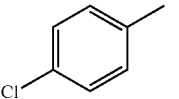 | 415.90 | 372 |
| H$_3$C— | 319.38 | 373 |
| 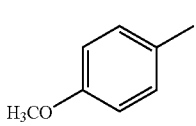 | 411.48 | 374 |
-continued
| R5 | MW | No. |
|---|---|---|
| 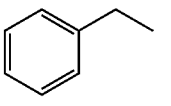 | 395.48 | 375 |
| 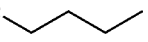 | 361.46 | 376 |
| 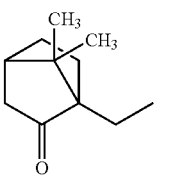 | 455.58 | 377 |
| 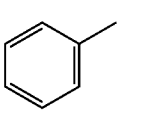 | 381.45 | 378 |
| 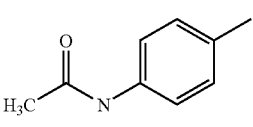 | 438.51 | 379 |
| 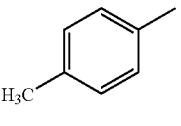 | 395.48 | 380 |
| 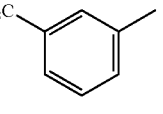 | 449.45 | 381 |
| 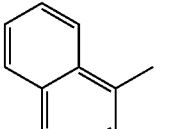 | 431.51 | 402 |
| 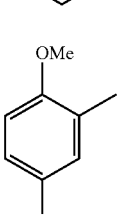 | 441.51 | 403 |
| 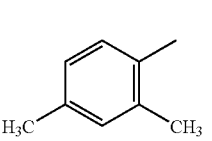 | 409.51 | 404 |
| 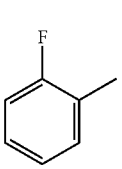 | 399.44 | 405 |

-continued
| R5 | MW | No. |
|---|---|---|
| 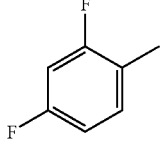 | 417.43 | 406 |
| 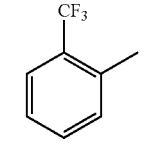 | 449.45 | 407 |
| 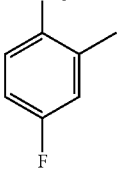 | 399.44 | 408 |
| 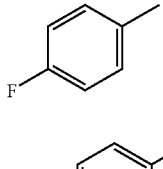 | 423.49 | 409 |
| 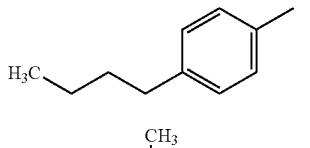 H₃C | 333.41 | 410 |
| 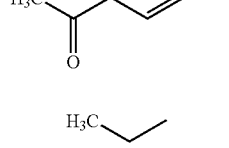 | 474.58 | 411 |
| 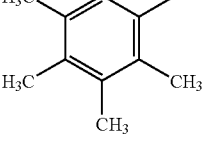 | 450.34 | 432 |
| 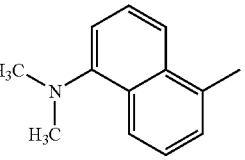 | 407.49 | 433 |
| 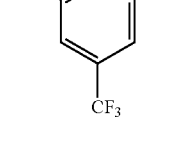 | 465.45 | 434 |
| 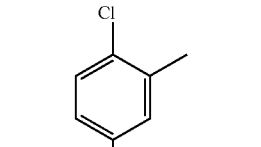 | 465.45 | 435 |
-continued
| R5 | MW | No. |
|---|---|---|
| 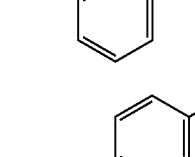 | 413.47 | 436 |
| 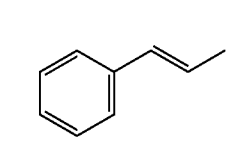 | 7.56 | 437 |
| 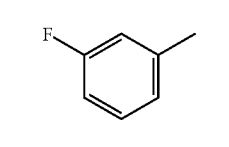 | 451.59 | 438 |
| 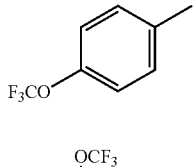 | 517.45 | 439 |
| 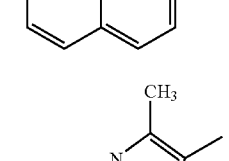 | 395.48 | 440 |
| 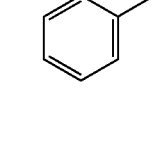 | 423.54 | 441 |
| 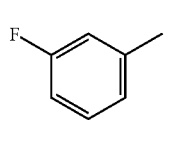 | 399.44 | 461 |
|  | 431.51 | 462 |
| 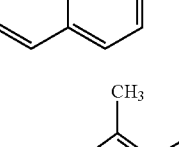 | 459.55 | 463 |
| 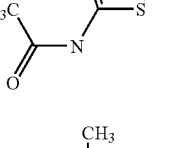 | 423.54 | 464 |

-continued

| R5 | MW | No. |
|---|---|---|
| 4-tert-butylphenyl | 437.56 | 465 |
| 3,4-dimethoxyphenyl | 441.51 | 466 |
| 2-thienyl | 387.48 | 467 |
| isobutyl | 347.44 | 468 |
| 5-(phenylsulfonyl)-2-thienyl | 527.64 | 469 |
| 4-isopropylphenyl | 423.54 | 470 |
| 4-butoxyphenyl | 453.56 | 490 |
| 2,6-difluorophenyl | 417.43 | 491 |
| 3-methoxyphenyl | 411.48 | 492 |
| 5-(phenylsulfonyl)-3-thienyl | 527.64 | 493 |
| 4-(2,2-dimethylbutyl)phenyl | 451.59 | 494 |

-continued

| R5 | MW | No. |
|---|---|---|
| 2-cyanophenyl | 406.46 | 495 |
| 4-(trifluoromethyl)phenyl | 449.45 | 496 | structure with R5-SO2-NH on para-substituted phenyl ethyl linked to 3-carboxyphenyl

| R5 | MW | No. |
|---|---|---|
| (see structure above) | 425.46 | 497 |
| 5-chloro-2,3-dimethylbenzothiophene | 486.01 | 498 |
| 8-quinolinyl | 432.50 | 499 |
| 4-biphenyl | | | structure with R5-SO2-NH on meta-substituted phenyl ethyl linked to 3-carboxyphenyl

| R5 | MW | No. |
|---|---|---|
| 4-chlorophenyl | 415.90 | 382 |
| CH3 | 319.38 | 383 |
| 4-methoxyphenyl | 411.48 | 384 |

-continued
| R5 | MW | No. |
|---|---|---|
| 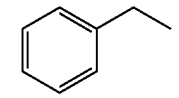 | 395.48 | 385 |
| 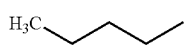 | 361.46 | 386 |
| 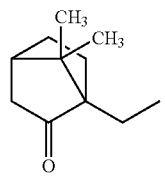 | 455.58 | 387 |
| 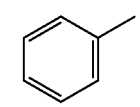 | 381.45 | 388 |
| 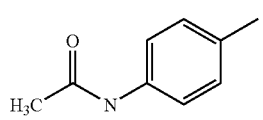 | 438.51 | 389 |
| 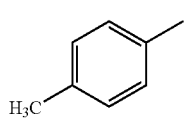 | 395.48 | 390 |
| 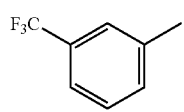 | 449.45 | 391 |
| 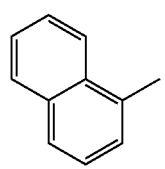 | 431.51 | 412 |
| 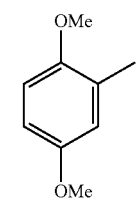 | 441.51 | 413 |
| 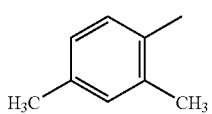 | 409.51 | 414 |
|  | 399.44 | 415 |
-continued
| R5 | MW | No. |
|---|---|---|
| 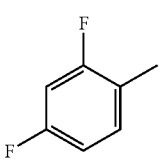 | 417.43 | 416 |
| 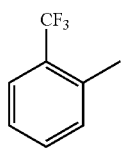 | 449.45 | 417 |
| 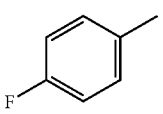 | 399.44 | 418 |
| 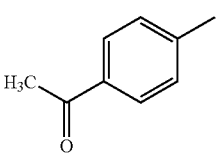 | 423.49 | 419 |
| 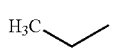 | 333.41 | 420 |
| 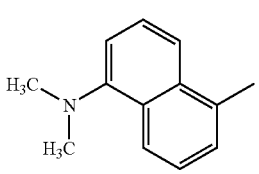 | 474.58 | 421 |
| 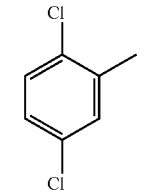 | 450.34 | 442 |
| 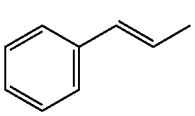 | 407.49 | 443 |
| 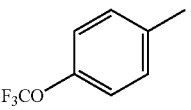 | 465.45 | 444 |
| 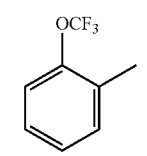 | 465.45 | 445 |

-continued
| R5 | MW | No. |
|---|---|---|
| 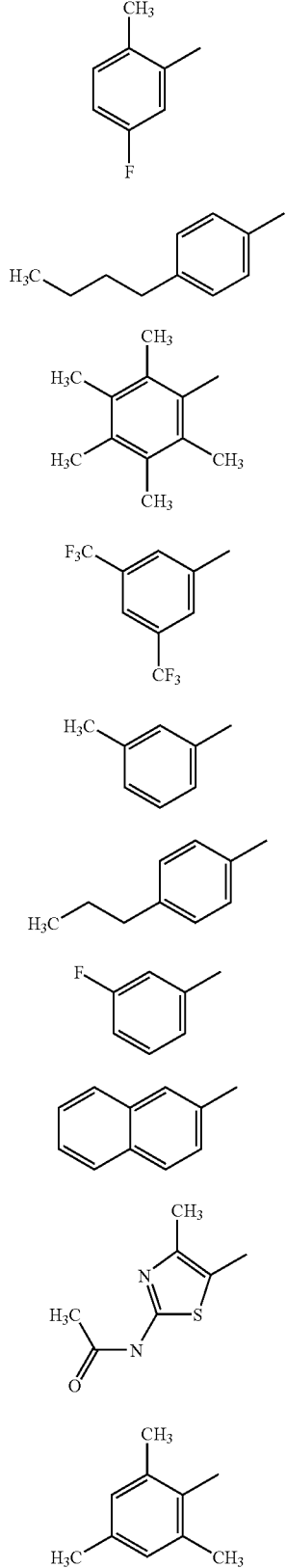 | 413.47 | 446 |
| | 7.56 | 447 |
| | 451.59 | 448 |
| | 517.45 | 449 |
| | 395.48 | 450 |
| | 423.54 | |
| | 399.44 | 471 |
| | 431.51 | 472 |
| | 459.55 | 473 |
| | 423.54 | 474 |
-continued
| R5 | MW | No. |
|---|---|---|
| 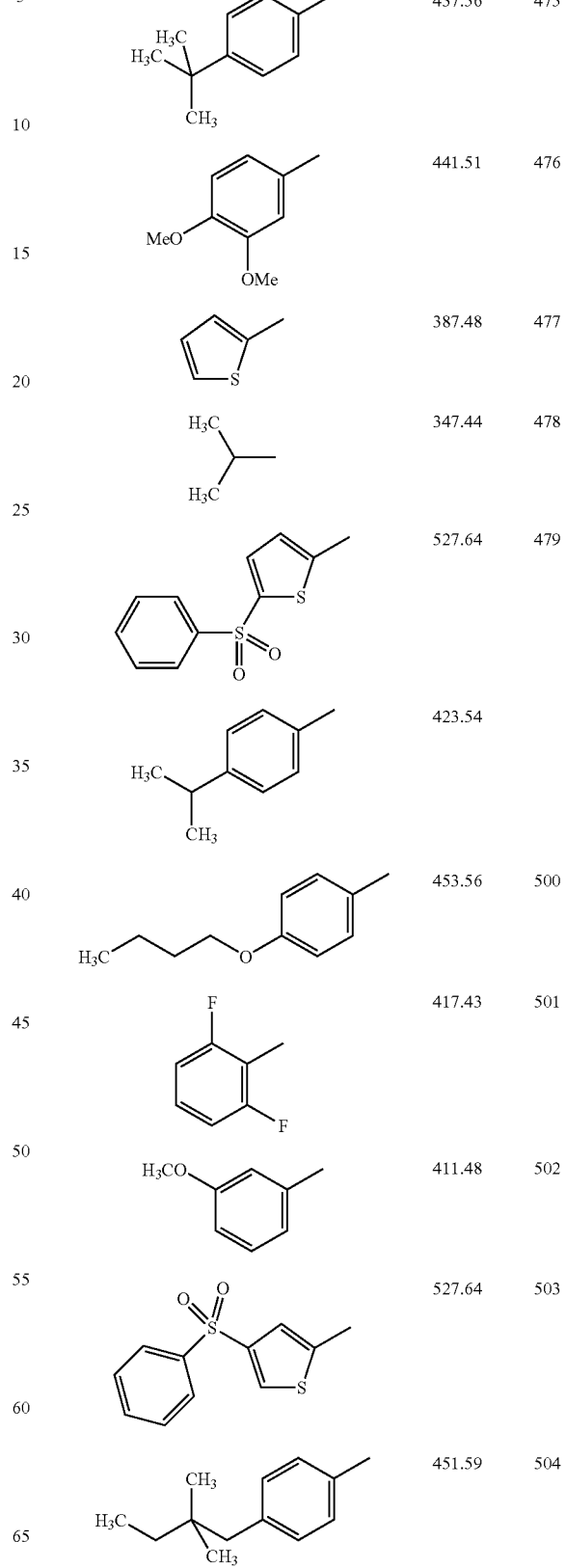 | 437.56 | 475 |
| | 441.51 | 476 |
| | 387.48 | 477 |
| | 347.44 | 478 |
| | 527.64 | 479 |
| | 423.54 | |
| | 453.56 | 500 |
| | 417.43 | 501 |
| | 411.48 | 502 |
| | 527.64 | 503 |
| | 451.59 | 504 |

| R5 | MW | No. |
|---|---|---|
|  | 406.46 | 505 |
|  | 449.45 | 506 |
|  | 425.46 | 507 |
|  | 486.01 | 508 |
|  | 432.50 | 509 |
|  | | 510 |
| R5 | MW | No. |
|---|---|---|
| 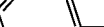 | 415.90 | 392 |
| H₃C— | 319.38 | 393 |
|  | 411.48 | 394 |
|  | 395.48 | 395 |
| R5 | MW | No. |
|---|---|---|
| H₃C~~~~ | 361.46 | 396 |
| camphor-like structure | 455.58 | 397 |
| phenyl | 381.45 | 398 |
| acetanilide-4-methyl | 438.51 | 399 |
| 4-methylphenyl (p-tolyl) | 395.48 | 400 |
| 3-CF₃-phenyl | 449.45 | 401 |
| 1-naphthyl | 431.51 | 422 |
| 2,5-dimethoxyphenyl | 441.51 | 423 |
| 2,4-dimethylphenyl | 409.51 | 424 |
| 2-fluorophenyl | 399.44 | 425 |
| 2,4-difluorophenyl | 417.43 | 426 |

-continued

| R5 | MW | No. |
|---|---|---|
| 2-(trifluoromethyl)phenyl | 449.45 | 427 |
| 4-fluorophenyl | 399.44 | 428 |
| 4-acetylphenyl | 423.49 | 429 |
| propyl | 333.41 | 430 |
| 5-(dimethylamino)naphthalen-1-yl | 474.58 | 431 |
| 2,4-dichlorophenyl | 450.34 | 451 |
| styryl | 407.49 | 452 |
| 4-(trifluoromethoxy)phenyl | 465.45 | 453 |
| 2-(trifluoromethoxy)phenyl | 465.45 | 454 |
| 4-fluoro-2-methylphenyl | 413.47 | 455 |
| 4-butylphenyl | 7.56 | 456 |

-continued

| R5 | MW | No. |
|---|---|---|
| pentamethylphenyl | 451.59 | 457 |
| 3,5-bis(trifluoromethyl)phenyl | 517.45 | 458 |
| 3,5-dimethylphenyl | 395.48 | 459 |
| 4-propylphenyl | 423.54 | 460 |
| 3-fluorophenyl | 399.44 | 480 |
| naphthalen-2-yl | 431.51 | 481 |
| N-(4,5-dimethylthiazol-2-yl)acetamide | 459.55 | 482 |
| 2,4,6-trimethylphenyl | 423.54 | 483 |
| 4-tert-butylphenyl | 437.56 | 484 |
| 3,4-dimethoxyphenyl | 441.51 | 485 |

-continued

| R5 | MW | No. |
|---|---|---|
| 2-methylthiophene | 387.48 | 486 |
| isobutyl | 347.44 | 487 |
| 5-(phenylsulfonyl)thiophen-2-yl | 527.64 | 488 |
| 4-isopropylphenyl | 423.54 | 489 |
| 4-butoxyphenyl | 453.56 | 511 |
| 2,6-difluorophenyl | 417.43 | 512 |
| 3-methoxyphenyl | 411.48 | 513 |
| 5-(phenylsulfonyl)thiophen-3-yl | 527.64 | 514 |
| 4-(2,2-dimethylbutyl)phenyl | 451.59 | 515 |
| 2-cyanophenyl | 406.46 | 516 |
| 4-(trifluoromethyl)phenyl | 449.45 | 517 |

-continued

| R5 | MW | No. |
|---|---|---|
| 4-carboxyphenyl | 425.46 | 518 |
| 5-chloro-3-methylbenzothiophen-2-yl | 486.01 | 519 |
| quinolin-8-yl | 432.50 | 520 |
| biphenyl-4-yl | | 521 |

Structure: R5-S(O)2-NH-C6H4-CH2CH2-C6H4-COOH

| R5 | MW | No. |
|---|---|---|
| 4-chlorophenyl | 415.90 | 522 |
| methyl | 319.38 | 523 |
| 4-methoxyphenyl | 411.48 | 524 |
| phenyl | 395.48 | 525 |
| pentyl | 361.46 | 526 |
| camphor-type | 455.58 | 527 |
| cyclohexyl | 381.45 | 528 |

-continued
| R5 | MW | No. |
|---|---|---|
| 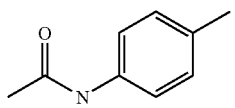 | 438.51 | 529 |
| 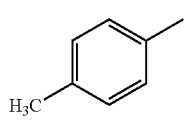 | 395.48 | 530 |
| 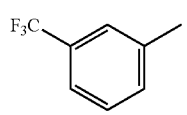 | 449.45 | 531 |
| 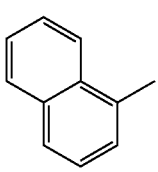 | 431.51 | 541 |
| 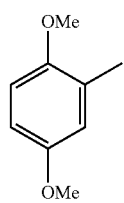 | 441.51 | 542 |
| 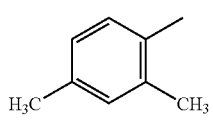 | 409.51 | 543 |
| 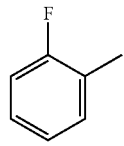 | 399.44 | 544 |
| 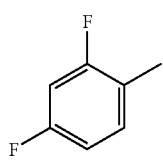 | 417.43 | 545 |
| 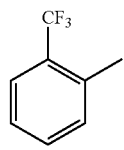 | 449.45 | 546 |
| 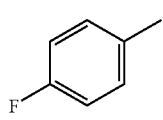 | 399.44 | 547 |
-continued
| R5 | MW | No. |
|---|---|---|
| 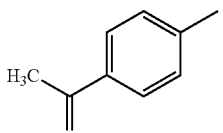 | 423.49 | 548 |
| 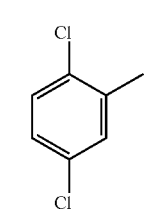 | 450.34 | 549 |
| 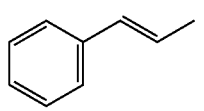 | 407.49 | 550 |
| 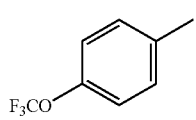 | 465.45 | 561 |
| 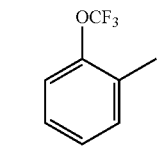 | 465.45 | 562 |
| 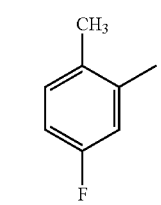 | 413.47 | 563 |
| 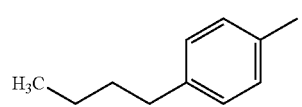 | 437.56 | 564 |
| 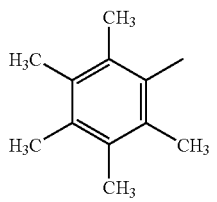 | 451.59 | 565 |
| 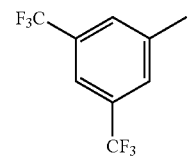 | 517.45 | 566 |
| 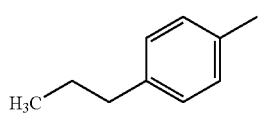 | 423.54 | 567 |

-continued
| R5 | MW | No. |
|---|---|---|
| 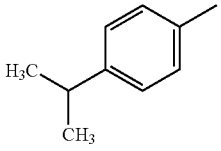 | 423.54 | 568 |
| 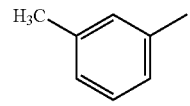 | 395.48 | 569 |
| 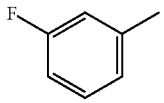 | 399.44 | 570 |
| 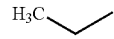 | 333.41 | 571 |
| 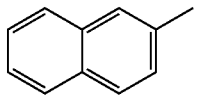 | 431.51 | 582 |
| 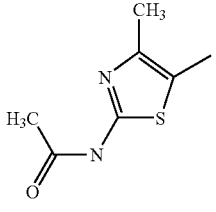 | 459.55 | 583 |
| 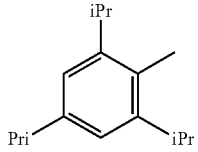 | 507.70 | 584 |
| 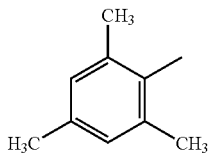 | 423.54 | 585 |
| 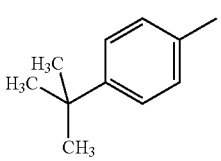 | 437.56 | 586 |
| 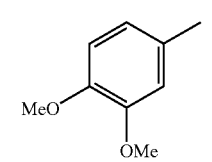 | 441.51 | 587 |
| 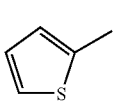 | 387.48 | 588 |
-continued
| R5 | MW | No. |
|---|---|---|
| 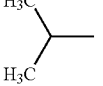 | 347.44 | 589 |
| 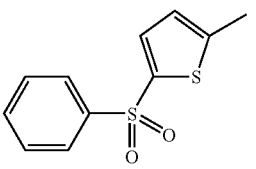 | 527.64 | 590 |
| 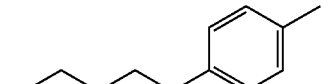 | 453.56 | 591 |
| 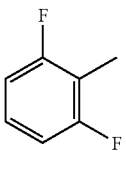 | 417.43 | 602 |
| 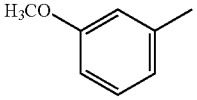 | 411.48 | 603 |
| 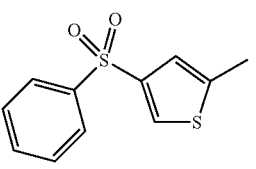 | 527.64 | 604 |
| 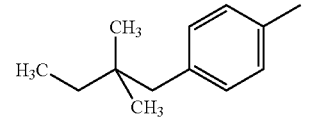 | 451.59 | 605 |
| 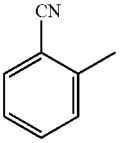 | 406.46 | 606 |
| 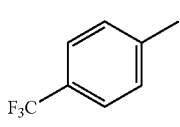 | 449.45 | 607 |
| 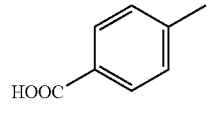 | 425.46 | 608 |
| 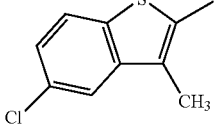 | 486.01 | 609 |

| R5 | MW | No. |
|---|---|---|
| 4-ethylphenyl | 409.51 | 610 |
| 4-biphenyl | 457.55 | 611 |

R5-SO2-NH- attached to 3-[2-(2-carboxyphenyl)ethyl]phenyl

| R5 | MW | No. |
|---|---|---|
| 4-chlorophenyl | 415.90 | 532 |
| H3C— | 319.38 | 533 |
| 4-methoxyphenyl | 411.48 | 534 |
| benzyl | 395.48 | 535 |
| H3C-pentyl | 361.46 | 536 |
| camphor-like | 455.58 | 537 |
| phenyl | 381.45 | 538 |
| 4-acetamidophenyl | 438.51 | 539 |
| 2,4-dimethylphenyl | 395.48 | 540 |

| R5 | MW | No. |
|---|---|---|
| 3-(trifluoromethyl)phenyl | 449.45 | |
| 1-naphthyl | 431.51 | 551 |
| 2,5-dimethoxyphenyl | 441.51 | 552 |
| 2,4-dimethylphenyl | 409.51 | 553 |
| 2-fluorophenyl | 399.44 | 554 |
| 2,4-difluorophenyl | 417.43 | 555 |
| 2-(trifluoromethyl)phenyl | 449.45 | 556 |
| 4-fluorophenyl | 399.44 | 557 |
| 4-acetylphenyl | 423.49 | 558 |
| 2,5-dichlorophenyl | 450.34 | 559 |

-continued
| R5 | MW | No. |
|---|---|---|
| 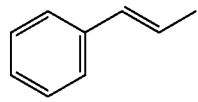 | 407.49 | 560 |
| 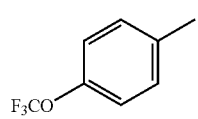 | 465.45 | 572 |
| 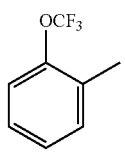 | 465.45 | 573 |
| 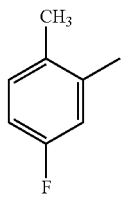 | 413.47 | 574 |
| 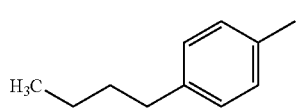 | 437.56 | 575 |
| 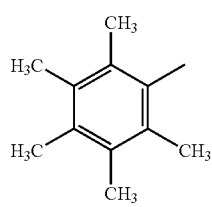 | 451.59 | 576 |
| 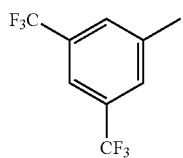 | 517.45 | 577 |
| 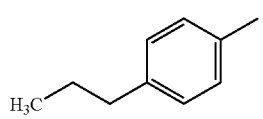 | 423.54 | 578 |
| 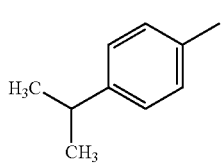 | 423.54 | 579 |
| 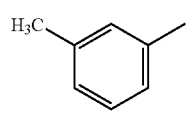 | 395.48 | 580 |
-continued
| R5 | MW | No. |
|---|---|---|
| 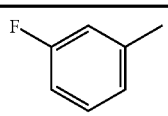 | 399.44 | 581 |
| H$_3$C— | 333.41 | |
| 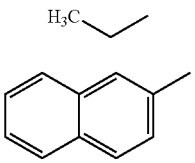 | 431.51 | 592 |
| 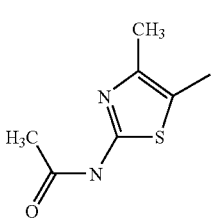 | 459.55 | 593 |
| 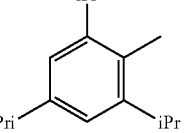 | 507.70 | 594 |
| 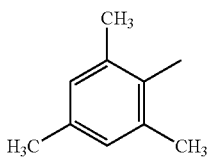 | 423.54 | 595 |
| 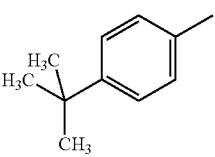 | 437.56 | 596 |
| 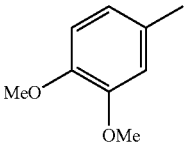 | 441.51 | 597 |
| 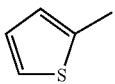 | 387.48 | 598 |
| 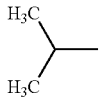 | 347.44 | 599 |
| 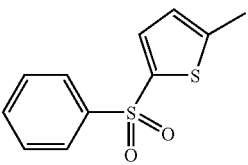 | 527.64 | 600 |

| R5 | MW | No. |
|---|---|---|
| 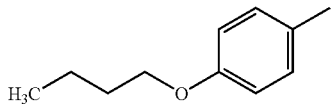 | 453.56 | 601 |
| 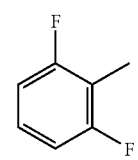 | 417.43 | 612 |
| 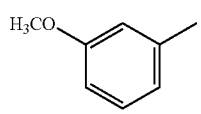 | 411.48 | 613 |
| 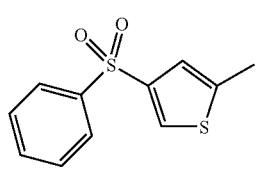 | 527.64 | 614 |
| 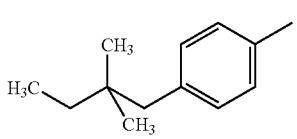 | 451.59 | 615 |
| 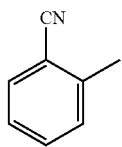 | 406.46 | 616 |
| 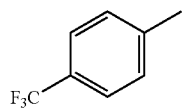 | 449.45 | 617 |
| 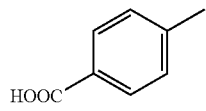 | 425.46 | 618 |
| 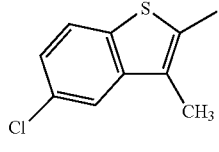 | 486.01 | 619 |
| 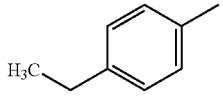 | 409.51 | 620 |
| 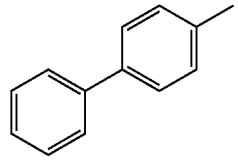 | 457.55 | |
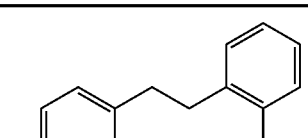
| R5 | MW | No. |
|---|---|---|
| 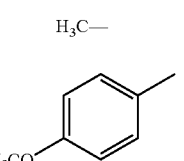 | 415.90 | 621 |
| H₃C— | 319.38 | 622 |
| 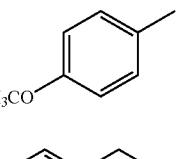 | 411.48 | 623 |
| 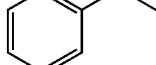 | 395.48 | 624 |
| H₃C⁓⁓⁓ | 361.46 | 625 |
| 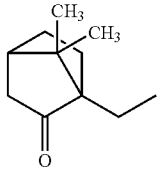 | 455.58 | 626 |
| 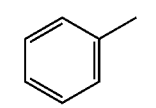 | 381.45 | 627 |
| 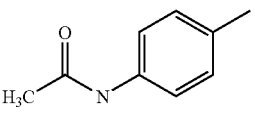 | 438.51 | 628 |
| 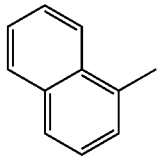 | 431.51 | 629 |
| 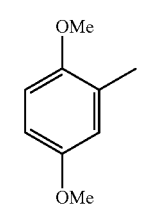 | 441.51 | 630 |

-continued
| R5 | MW | No. |
|---|---|---|
| 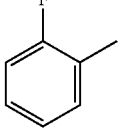 | 399.44 | 631 |
| 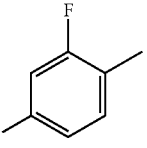 | 417.43 | 632 |
| 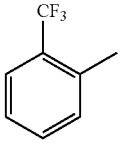 | 449.45 | 633 |
| 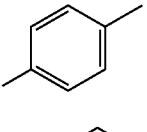 | 399.44 | 634 |
| 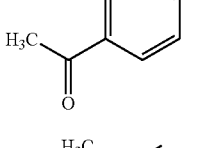 | 423.49 | 635 |
| 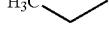 | 333.41 | 636 |
| 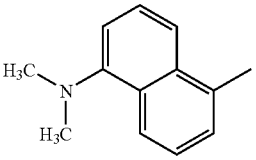 | 474.58 | 637 |
| 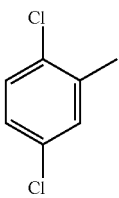 | 450.34 | 638 |
| 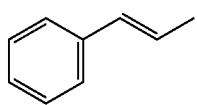 | 407.49 | 639 |
| 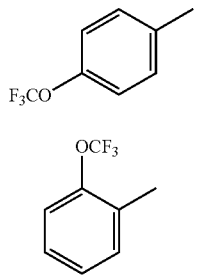 | 465.45 | 640 |
| 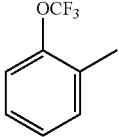 | 465.45 | 641 |
-continued
| R5 | MW | No. |
|---|---|---|
| 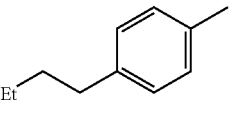 | 423.54 | 642 |
| 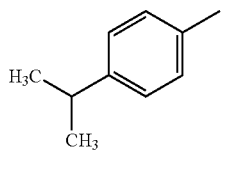 | 423.54 | 643 |
| 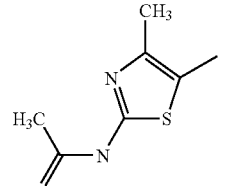 | 459.55 | 644 |
| 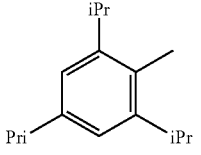 | 507.70 | 645 |
| 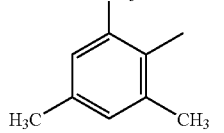 | 423.54 | 646 |
| 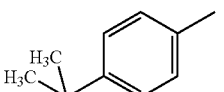 | 437.56 | 647 |
| 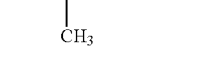 | 387.48 | 648 |
| 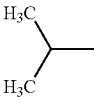 | 347.44 | 649 |
| 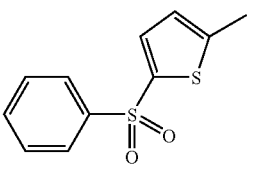 | 527.64 | 650 |
| 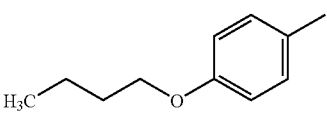 | 453.56 | 651 |

-continued

| R5 | MW | No. |
|---|---|---|
| 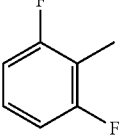 | 417.43 | 652 |
| 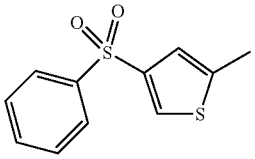 | 527.64 | 653 |
| 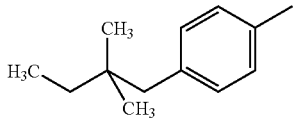 | 451.59 | 654 |
| 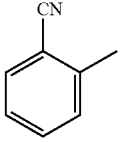 | 406.46 | 655 |
| 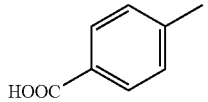 | 425.46 | 656 |
| 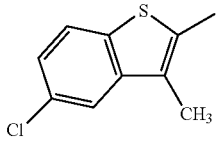 | 486.01 | 657 |
| 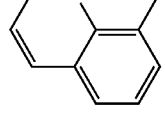 | 432.50 | 658 |
| 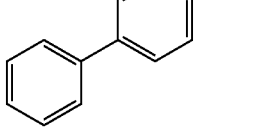 | 457.55 | 659 |
| 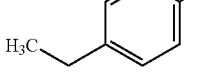 | 409.51 | 660 |

EXAMPLE 20

Methyl 4-[2-(2-butylaminophenyl)ethyl]benzoate 20 g (0.078 M) of 4-[2-(2-phenyl)ethyl]benzoic acid, 6.3 g (0.072 M) of butyraldehyde and 22.6 g (0.107 M) of sodium triacetoxyborohydride are added to 80 ml of 1,2-dichloroethane in a 500 ml reactor, and the mixture is then stirred at 20° C. for 20 hours.

Water is then added to the reaction medium and the resulting mixture is extracted with dichloromethane. The organic phase is separated out by settling of the phases, washed with water and then dried and evaporated under vacuum. The residue obtained is then purified by chromatography on silica, using a dichloromethane/heptane mixture (70/30) as eluent. After evaporation, 11 g of the desired compound are obtained in the form of an oil (yield: 45%).

NMR (δ in ppm, DMSO, 200 MHz): 1.1 (t, 3H); 1.6 (m, 4H); 2.8 (m, 2H); 3.0 (m, 2H); 3.1 (m, 2H); 4.1 (s, 3H); 5.1 (s, 1H); 7.5 (multiplet, 8H).

EXAMPLE 21

Compound 680

4-{2-[2-([3,5-Bis trifluoromethyl]phenylsulfonylbutylamino)phenyl]-ethyl}benzoic acid 120 mg (0.38 mM) of methyl 4-[2-(2-butylaminophenyl)ethyl]benzoate obtained in Example 20 and 50 mg (0.38 mM) of diisopropylethylamine are added to 4 ml of acetonitrile predried over molecular sieves, in a 15 ml reactor. 120 mg (0.96 mM) of 3,5-bis(trifluoro)benzenesulfonyl chloride are then added and the reaction medium is stirred at 20° C. for 20 hours.

1.9 ml of aqueous 1N sodium hydroxide solution are then added and the reaction medium is maintained at 50° C. for 2 hours. 1 ml of 3N hydrochloric acid are then added and, after stirring for 1 hour, the precipitate formed is filtered off. After drying under vacuum, 43 mg of solid are obtained (yield: 20%).

NMR (δ in ppm, DMSO, 200 MHz): 1.0 (t, 3H); 1.4 (m, 4H); 3.2 (m, 4H); 3.6 (m, 4H); 7.8 (multiplet, 11H).

By way of example, the following compounds are prepared according to the procedures described in Example 21:

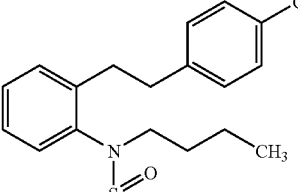

| R5 | MW | No. |
|---|---|---|
| 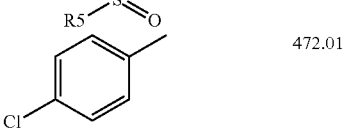 | 472.01 | 661 |
| 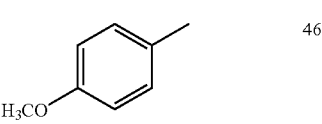 | 467.59 | 662 |
|  | 437.56 | 663 |

| R5 | MW | No. |
|---|---|---|
| 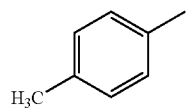 | 451.59 | 664 |
| 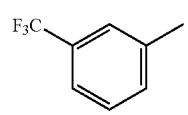 | 505.56 | 665 |
| 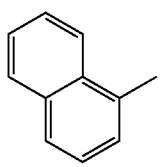 | 487.62 | 666 |
| 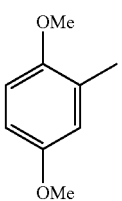 | 497.62 | 667 |
| 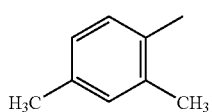 | 465.62 | 668 |
| 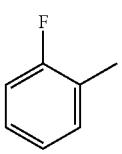 | 455.55 | 669 |
|  | 473.54 | 670 |
| 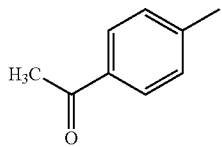 | 479.60 | 671 |
| 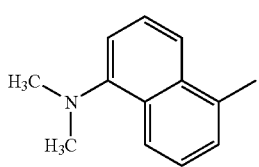 | 530.69 | 672 |
| R5 | MW | No. |
|---|---|---|
| 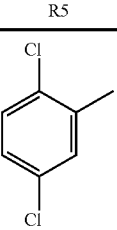 | 506.45 | 673 |
| 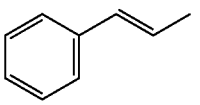 | 463.60 | 674 |
| 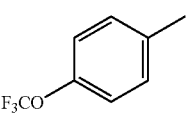 | 521.56 | 675 |
| 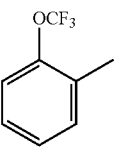 | 521.56 | 676 |
| 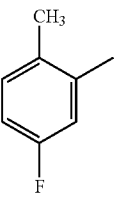 | 469.58 | 677 |
| 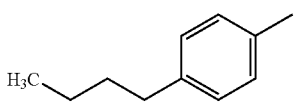 | 493.67 | 678 |
| 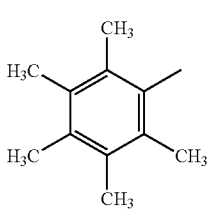 | 507.70 | 679 |
| 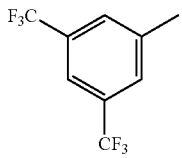 | 573.56 | 680 |
| 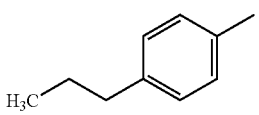 | 479.64 | 681 |
| 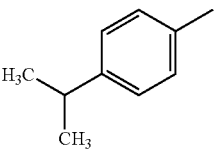 | 479.64 | 682 |

| R5 | MW | No. |
|---|---|---|
| 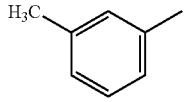 | 451.59 | 683 |
| 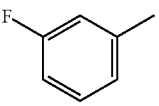 | 455.55 | 684 |
| 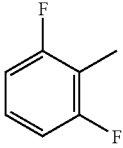 | 487.62 | 685 |
| 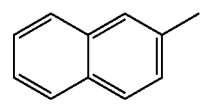 | 515.65 | 686 |
| 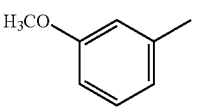 | 479.64 | 687 |
| 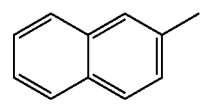 | 493.67 | 688 |
| 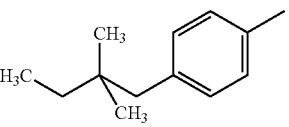 | 497.62 | 689 |
| 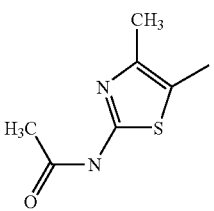 | 443.59 | 690 |
| 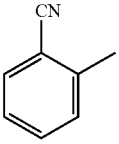 | 583.75 | 691 |
| 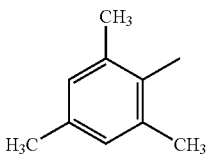 | 509.67 | 692 |
| R5 | MW | No. |
|---|---|---|
| 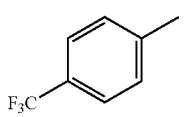 | 473.54 | 693 |
| 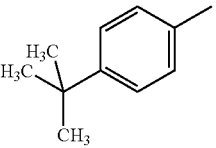 | 467.59 | 694 |
| 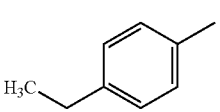 | 507.70 | 695 |
| 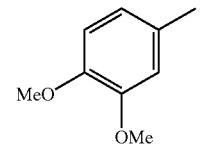 | 462.57 | 696 |
| 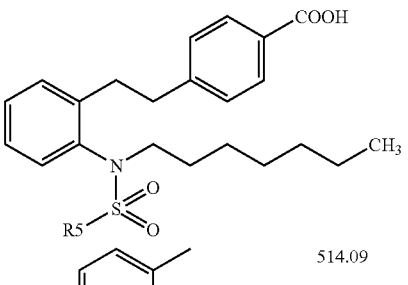 | 505.56 | 697 |
| 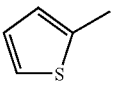 | 465.62 | 698 |
| 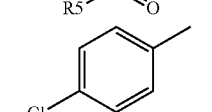 | | |
| 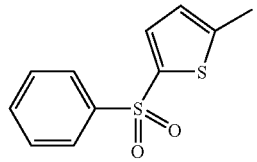 | 514.09 | 699 |
| 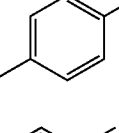 | 479.64 | 700 |
| 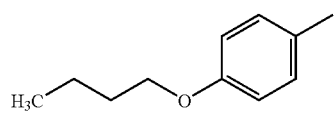 | 493.67 | 701 |
| 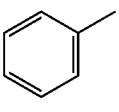 | 547.64 | 702 |

-continued
| R5 | MW | No. |
|---|---|---|
| 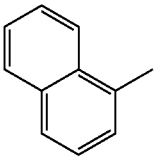 | 529.70 | 703 |
| 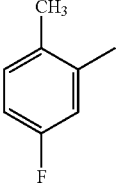 | 539.70 | 704 |
| 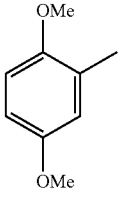 | 507.70 | 705 |
| 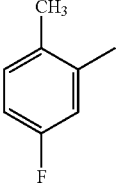 | 497.63 | 706 |
| 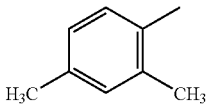 | 515.62 | 707 |
| 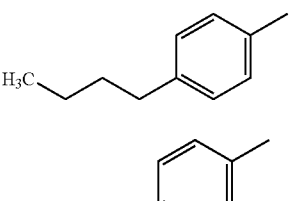 | 547.64 | 708 |
| 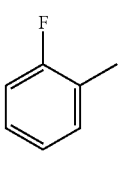 | 497.63 | 709 |
| 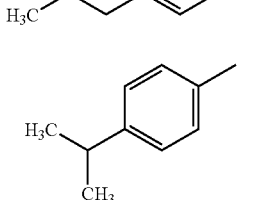 | 521.68 | 710 |
| 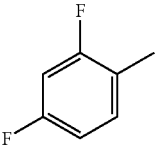 | 505.68 | 711 |
| 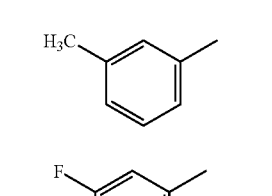 | 563.64 | 712 |
-continued
| R5 | MW | No. |
|---|---|---|
| 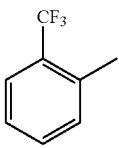 | 511.66 | 713 |
| 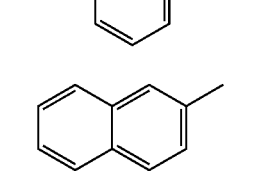 | 535.75 | 714 |
| 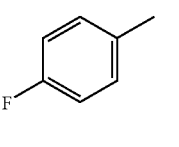 | 521.72 | 715 |
| 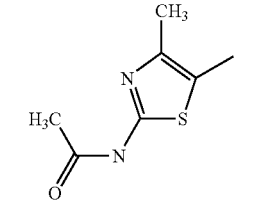 | 521.72 | 716 |
| 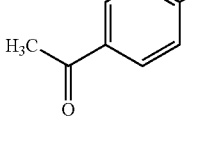 | 493.67 | 717 |
| 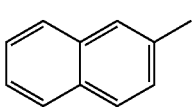 | 497.63 | 718 |
| 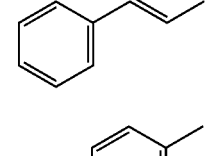 | 529.7 | 719 |
| 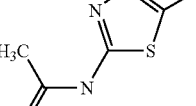 | 557.7 | 720 |
| 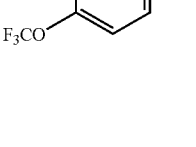 | 539.7 | 721 |
| 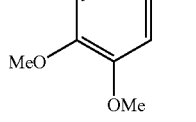 | 515.6 | 722 |

-continued

| R5 | MW | No. |
|---|---|---|
| 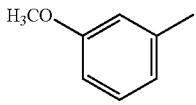 H₃CO— | 509.6 | 723 |
| 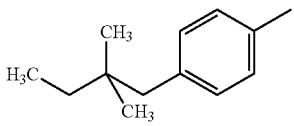 H₃C—C(CH₃)(CH₃)—CH₂— | 549.7 | 724 |
| 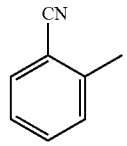 CN | 504.6 | 725 |
| 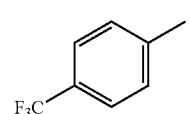 F₃C— | 547.6 | 726 |
| 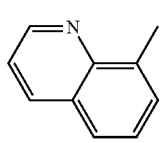 8-methylquinoline | | 727 |

EXAMPLE 22

Methyl 4-[2-(4-nitrophenoxy)ethoxy]benzoate 73.7 g (0.3 M) of (4-nitrophenoxy)-1-bromoethyl [lacuna] and then 45.6 g (0.3 M) of methyl 4-hydroxybenzoate and 138.2 g (0.6 M) of K₂CO₃ are added to 300 ml of methyl isobutyl ketone in a 1000 ml reactor. The reaction medium is then refluxed with stirring 20 hours.

The reaction medium is then taken up in water and extracted with ethyl acetate. The organic phase is separated out by settling of the phases and then washed with aqueous 1N sodium hydroxide solution, and then with saturated aqueous sodium chloride solution.

After evaporation of the organic phase under vacuum, the residue obtained is purified by chromatography on silica, with dichloromethane as eluent.

After concentrating, 68.5 g of a beige-coloured solid are obtained (yield: 72%).

NMR (δ in ppm, DMSO, 200 MHz): 3.97 (s, 3H); 4.65 (m, 4H); 7.24 (d, 2H); 7.39 (d, 2H); 8.10 (d, 2H); 8.35 (d, 2H).

EXAMPLE 23

Methyl 4-[2-(4-aminophenoxy)ethoxy]benzoate 68.4 g (0.22 M) of methyl 4-[2-(4-nitrophenoxy)ethoxy] benzoate and 1.3 g of palladium-on-charcoal are added to a mixture of 800 ml of methanol and 200 ml of tetrahydrofuran in a 2000 ml reactor, and the mixture is then maintained under ambient pressure of hydrogen at 60° C. with vigorous stirring for 6 hours.

After filtration through Celite, the solution obtained is evaporated under vacuum and the residue is taken up while hot in 100 ml of THF, and a solid crystallises. The solid is isolated and purified by chromatography on silica, with dichloromethane as eluent. After concentrating, 19.6 g of a beige-coloured solid are obtained (yield: 77%).

NMR (δ in ppm, DMSO, 200 MHz): 3.9 (s, 3H); 4.3 (m, 4H); 7 (multiplet, 6H); 8 (m, 2H).

EXAMPLE 24

4-{2-[4-(4-Fluorophenylsulfonylamino)phenoxy)ethoxy}benzoic acid 100 mg (0.35 M) of methyl 4-[2-(4-aminophenoxy) ethoxy]benzoate, 0.029 g (0.35 mM) of sodium hydrogen carbonate and 66.3 mg (0.35 mM) of 4-fluorobenzenesulfonyl chloride are added to 1 ml of acetonitrile predried over molecular sieves, in a 15 ml reactor.

The reaction medium is then stirred at 20° C. for 16 hours. The intermediate ester is not isolated: 1.6 ml of aqueous 1N sodium hydroxide solution are added and the mixture is maintained at 50° C. with stirring for 1 hour. After cooling to 20° C., the reaction medium is acidified with 2 ml of 1N hydrochloric acid and, after stirring at 20° C. for 30 minutes, the precipitate formed is filtered off. The solid obtained is then washed with water, and then dried under vacuum to give 80 mg of 4-{2-[4-(4-fluorophenylamino)phenoxy) ethoxy}benzoic acid (51% yield).

NMR (δ in ppm, DMSO, 200 MHz): 4.1 (m, 4H); 6.8 (m, 6H); 7.2 (m, 2H); 7.55 (m, 2H); 7.7 (m, 2H); 9.75 (s, 1H).

By way of example, the following compounds are prepared according to the procedures described in Example 24:

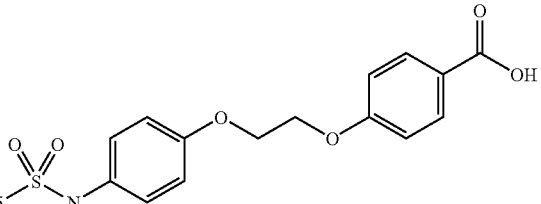

| R5 | MW | No. |
|---|---|---|
| H₃C— | 351.38 | 728 |
| 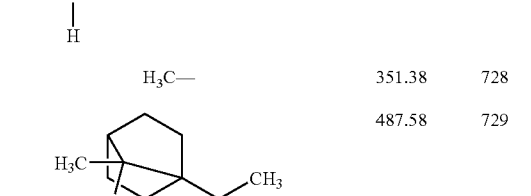 camphor-like | 487.58 | 729 |
| 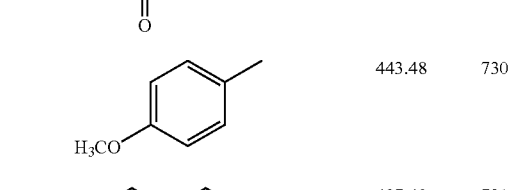 H₃CO— | 443.48 | 730 |
| 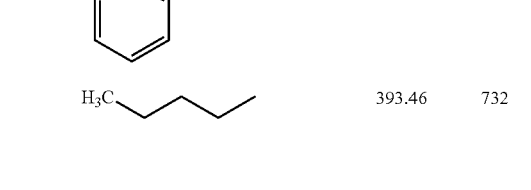 ethylphenyl | 427.48 | 731 |
|  H₃C—butyl | 393.46 | 732 |

-continued

| R5 | MW | No. |
|---|---|---|
| phenyl | 413.45 | 733 |
| 4-methylphenyl | 427.48 | 734 |
| 3-(trifluoromethyl)phenyl | 481.45 | 735 |
| 1-naphthyl | 463.51 | 736 |
| 2,5-dimethoxyphenyl | 473.51 | 737 |
| 2,4-dimethylphenyl | 441.51 | 738 |
| 2-fluorophenyl | 431.44 | 739 |
| 2,4-difluorophenyl | 449.43 | 740 |
| 2-(trifluoromethyl)phenyl | 481.45 | 741 |
| 4-fluorophenyl | 431.44 | 742 |
| ethyl | 365.41 | 743 |

-continued

| R5 | MW | No. |
|---|---|---|
| 5-(dimethylamino)naphthalen-1-yl | 506.58 | 744 |
| 2,5-dichlorophenyl | 482.34 | 745 |
| (E)-prop-1-en-1-yl-phenyl | 439.49 | 746 |
| 2-(trifluoromethoxy)phenyl | 497.45 | 747 |
| 4-fluoro-2-methylphenyl | 445.47 | 748 |
| 4-butylphenyl | 469.56 | 749 |
| 3-methoxy-2,4,5-trimethylphenyl | 485.56 | 750 |
| pentamethylphenyl | 483.59 | 751 |
| 3,5-bis(trifluoromethyl)phenyl | 549.45 | 752 |

| R5 | MW | No. |
|---|---|---|
| 4-propylphenyl | 455.53 | 753 |
| 4-isopropylphenyl | 455.53 | 754 |
| 3-methylphenyl | 427.48 | 755 |
| 3-fluorophenyl | 431.44 | 756 |
| naphthalen-2-yl | 463.51 | 757 |
| 2,4,6-triisopropylphenyl | 539.70 | 758 |
| 2,4,6-trimethylphenyl | 455.53 | 759 |
| 4-tert-butylphenyl | 469.56 | 760 |
| 2,2,2-trifluoroethyl | 405.35 | 761 |
| 2,2,2-trifluoropropyl (CF3CH2CH-) | 419.38 | 762 |
| 3,4-dimethoxyphenyl | 473.51 | 763 |
| thiophen-2-yl | 419.48 | 764 |

| R5 | MW | No. |
|---|---|---|
| isobutyl | 379.44 | 765 |
| 5-(phenylsulfonyl)thiophen-2-yl | 559.64 | 766 |
| 4-butoxyphenyl | 485.56 | 767 |
| 2,6-difluorophenyl | 449.4 | 768 |
| 3-methoxyphenyl | 443.4 | 769 |
| 3,5-dichloro-2-hydroxyphenyl | 431.4 | 770 |
| 4-(phenylsulfonyl)thiophen-2-yl | 559.6 | 771 |
| 4-(2,2-dimethylbutyl)phenyl | 483.5 | 772 |
| 2-cyanophenyl | 438.4 | 773 |
| 4-ethylphenyl | 441.5 | 774 |

-continued
| R5 | MW | No. |
|---|---|---|
| 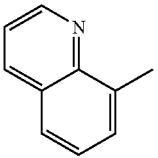 | 464.5 | 775 |
| 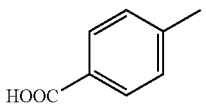 |  | 776 |
| 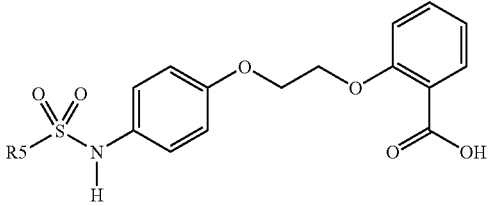 | 447.90 | 777 |
| H₃C— | 351.38 | 778 |
| 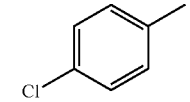 | 487.58 | 779 |
|  | 443.48 | 780 |
| 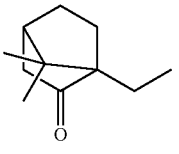 | 427.48 | 781 |
| H₃C⁀⁀ | 393.46 | 782 |
| 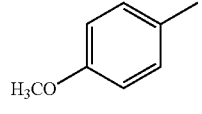 | 413.45 | 783 |
| 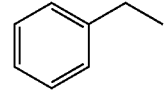 | 427.48 | 784 |
| 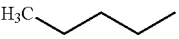 | 473.51 | 785 |
Structure for 776:
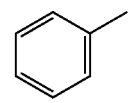
-continued
| R5 | MW | No. |
|---|---|---|
| 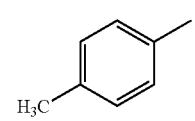 | 431.44 | 786 |
| 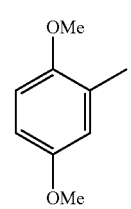 | 449.43 | 787 |
| 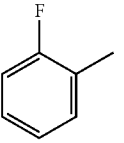 | 481.45 | 788 |
| 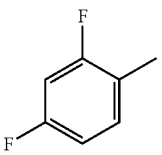 | 431.44 | 789 |
| 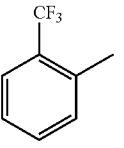 | 455.49 | 790 |
| H₃C⁀ | 365.41 | 791 |
| 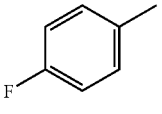 | 482.34 | 792 |
| 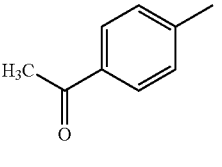 | 439.49 | 793 |
|  | 497.45 | 794 |
| 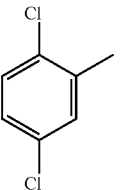 | 497.45 | 795 |

-continued
| R5 | MW | No. |
|---|---|---|
| 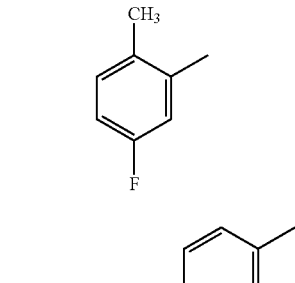 | 445.47 | 796 |
|  | 469.56 | 797 |
| 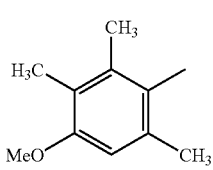 | 485.56 | 798 |
| 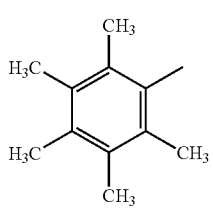 | 483.59 | 799 |
| 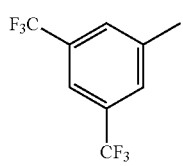 | 549.45 | 800 |
| 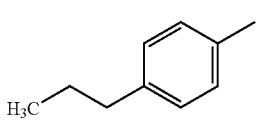 | 455.53 | 801 |
| 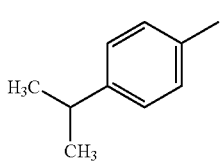 | 455.53 | 802 |
| 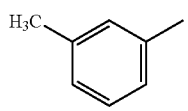 | 427.48 | 803 |
| 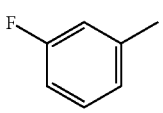 | 431.44 | 804 |
| 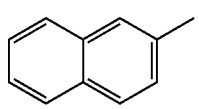 | 463.51 | 805 |
-continued
| R5 | MW | No. |
|---|---|---|
| 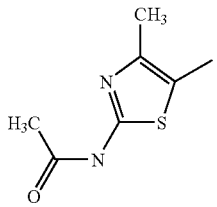 | 491.55 | 806 |
| 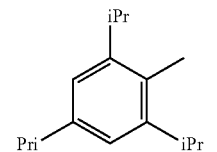 | 539.70 | 807 |
| 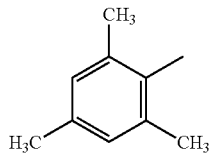 | 455.53 | 808 |
| 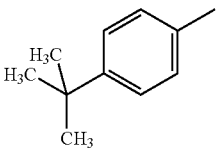 | 469.56 | 809 |
| 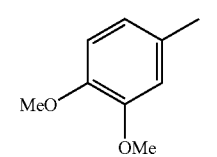 | 473.51 | 810 |
| 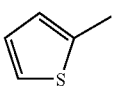 | 419.48 | 811 |
| 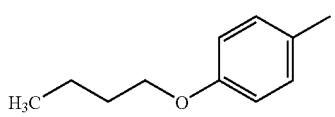 | 485.56 | 812 |
| 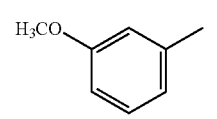 | 443.48 | 813 |
| 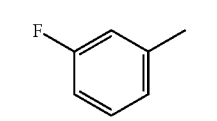 | 431.44 | 814 |
| 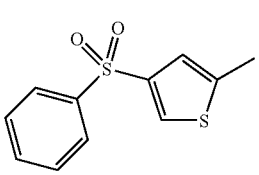 | 559.64 | 815 |

-continued
| R5 | MW | No. |
|---|---|---|
| 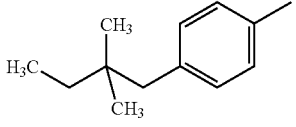 | 483.59 | 816 |
| 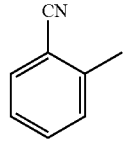 | 438.46 | 817 |
| 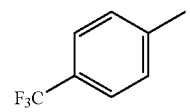 | 481.45 | 818 |
| 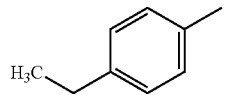 | 441.51 | 819 |
| 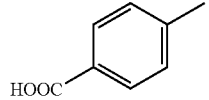 | 457.46 | 820 |
| 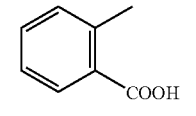 | 457.46 | 821 |
| 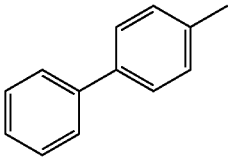 | 489.55 | 822 |
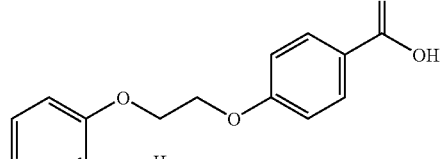
| R5 | MW | No. |
|---|---|---|
| 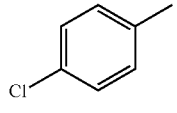 | 447.90 | 823 |
| H$_3$C— | 351.38 | 824 |
| 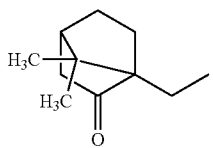 | 487.58 | 825 |
-continued
| R5 | MW | No. |
|---|---|---|
| 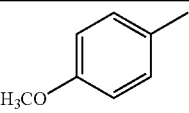 | 443.48 | 826 |
| 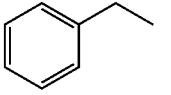 | 427.48 | 827 |
| 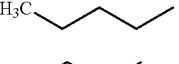 | 393.46 | 828 |
| 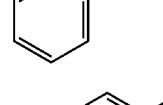 | 413.45 | 829 |
| 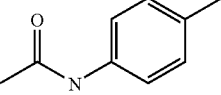 | 470.50 | 830 |
| 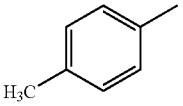 | 427.48 | 831 |
| 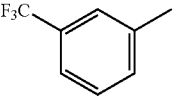 | 481.45 | 832 |
| 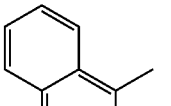 | 463.51 | 833 |
| 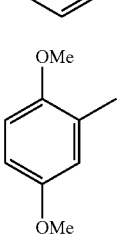 | 473.51 | 834 |
| 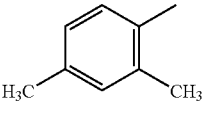 | 441.51 | 835 |
| 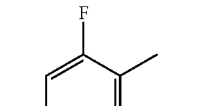 | 431.44 | 836 |
| 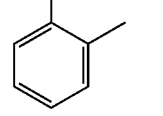 | 449.43 | 837 |

| R5 | MW | No. |
|---|---|---|
| 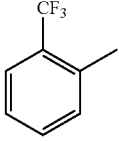 | 481.45 | 838 |
| 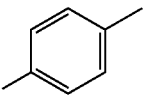 | 431.44 | 839 |
| 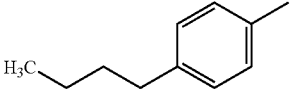 | 455.49 | 840 |
| 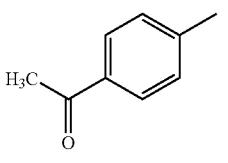 | 365.41 | 841 |
| 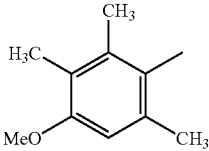 | 506.58 | 842 |
| 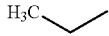 | 482.34 | 843 |
| 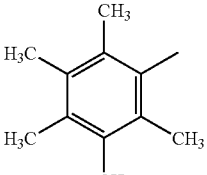 | 439.49 | 844 |
| 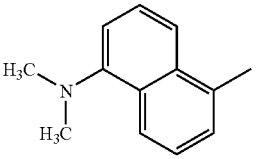 | 497.45 | 845 |
| 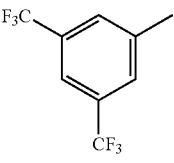 | 497.45 | 846 |
| 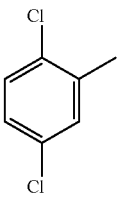 | 445.47 | 847 |
| R5 | MW | No. |
|---|---|---|
| 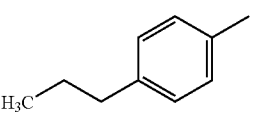 | 469.56 | 848 |
| 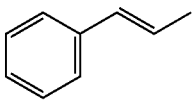 | 485.56 | 849 |
| 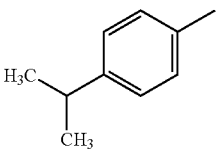 | 483.59 | 850 |
| 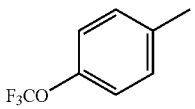 | 549.45 | 851 |
| 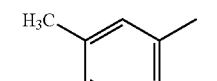 | 455.53 | 852 |
| 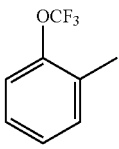 | 455.53 | 853 |
| 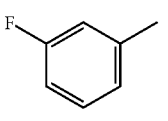 | 427.48 | 854 |
| 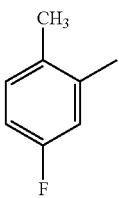 | 431.44 | 855 |
| 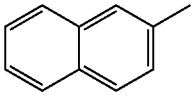 | 463.51 | 856 |
| 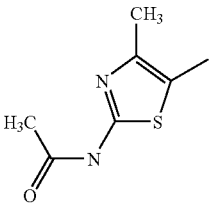 | 491.55 | 857 |

-continued

| R5 | MW | No. |
|---|---|---|
| 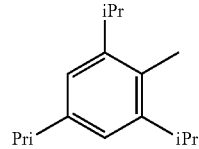 | 539.70 | 858 |
| 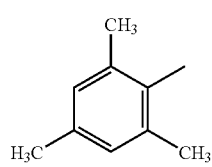 | 455.53 | 859 |
| 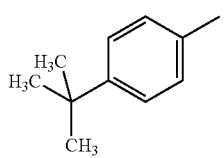 | 469.56 | 860 |
| 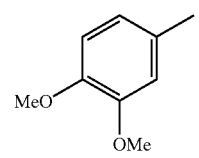 | 473.51 | 861 |
| 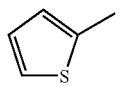 | 419.48 | 862 |
| 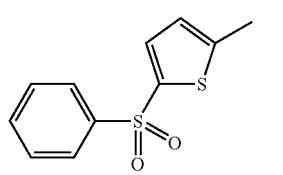 | 559.64 | 863 |
| 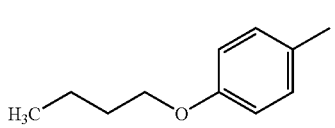 | 485.56 | 864 |
| 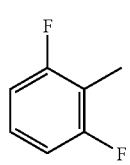 | 449.43 | 865 |
| 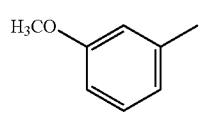 | 443.48 | 866 |
| 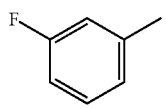 | 431.44 | 867 |

-continued

| R5 | MW | No. |
|---|---|---|
| 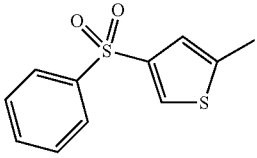 | 559.64 | 868 |
| 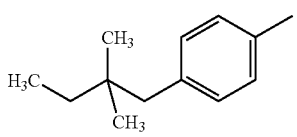 | 483.59 | 869 |
| 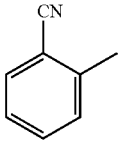 | 438.46 | 870 |
| 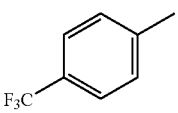 | 481.4 | 871 |
| 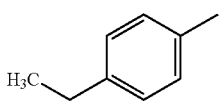 | 441.5 | 872 |
| 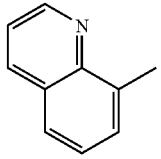 | 464.5 | 873 |
| 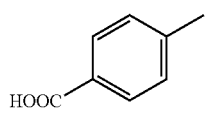 | 457.4 | 874 |
| 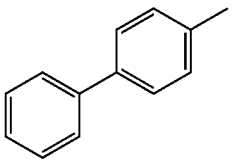 | 489.5 | 875 |

EXAMPLE 25

2-{2-[(4-Nitrophenoxy)ethoxy]}phenylacetic acid 18.5 g (0.12 M) of 2-hydroxyphenylacetic acid and 13.7 g (0.12 M) of potassium hydroxide are added to 120 ml of methanol in a 500 ml reactor. After stirring for 10 minutes, 30 g (0.12 M) of -(4-nitrophenoxy)ethyl bromide are added and the reaction medium is then refluxed for 24 hours with stirring. The methanol is evaporated off and the residue is taken up in water. The aqueous phase obtained is first washed with ethyl acetate and then acidified with dilute aqueous hydrochloric acid and extracted with ethyl acetate.

The organic phase is evaporated under vacuum and the residue obtained is purified by chromatography on silica, with a dichloromethane/acetone mixture (95/5) as eluent. After concentrating, 9 g of a beige-coloured solid are obtained (yield: 23%).

NMR (δ in ppm, DMSO, 200 MHz): 3.7 (s, 2H); 4.53 (s, 2H); 4.64 (s, 2H); 7.09 (m, 2H); 7.24 (m, 2H); 7.40 (m, 2H); 8.41 (m, 2H); 12.29 (s, 1H).

EXAMPLE 26

2-{2-(4-Aminophenoxy)ethoxy]}phenylacetic acid 9 g (0.028 M) of 2-{2-[(4-nitrophenoxy)ethoxy]}phenylacetic acid and 0.9 g of wet 10% palladium-on-charcoal are added to 60 ml of tetrahydrofuran in a 500 ml reactor. The reaction medium is then stirred vigorously for 3 hours under ambient pressure of hydrogen: exothermicity is observed and the temperature of the reaction medium rises to 40° C.

The reaction medium is then filtered through Celite and concentrated under vacuum to give a residue, which is taken up in diethyl ether. 6.5 g of a light brown solid are thus obtained (80% yield).

NMR (δ in ppm, DMSO, 200 MHz): 3.74 (s, 2H); 4.33 (t, 2H); 4.42 (t, 2H); 7.2 (multiplet, 8H).

EXAMPLE 27

2-{2-[4-(4-[2-Methylethyl)phenyl]sulfonylamino)phenoxy-ethoxy}phenylacetic acid 100 mg (0.348 mM) of 2-[2-(4-aminophenoxy)ethoxy]phenylacetic acid, 0.056 ml (0.694 mM) of pyridine and 61.5 mg (0.348 mM) of 4-(2-methylethyl)benzenesulfonyl chloride are added to 0.3 ml of dimethylformamide in a 15 ml reactor.

The reaction medium is then stirred for 24 hours at room temperature, and then acidified with 3 ml of 3N hydrochloric acid. The mixture is extracted with ethyl acetate to give, after evaporation, 29.7 mg of 2-{2-[4-(4-(2-methylethyl)-phenylsulfonylamino)phenoxy]ethoxy}phenylacetic acid (yield: 18.5%).

NMR (δ in ppm, DMSO, 200 MHz): 1.3 (d, 6H); 3.05 (m, 1H); 3.63 (s, 2H); 4.35 (m, 4H); 7.4 (multiplet, 12H); 10.05 (s, 1H); 12.25 (s, 1H).

By way of example, the following compounds are prepared according to the procedures described in Example 27:

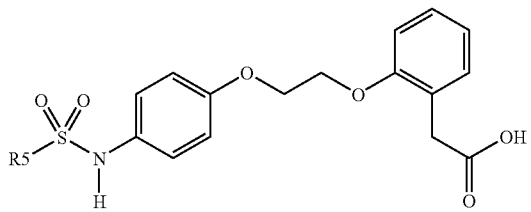

| R5 | MW | No. |
|---|---|---|
| 4-Cl-C6H4- | 461.92 | 876 |
| 4-MeO-C6H4- | 457.51 | 877 |
| n-Bu- | 407.49 | 878 |
| C6H5- | 427.48 | 879 |
| 4-(CH3CONH)-C6H4- | 484.53 | 880 |
| 4-CH3-C6H4- | 441.51 | 881 |
| 3-CF3-C6H4- | 495.48 | 882 |
| 2,4-(MeO)2-C6H3- | 487.53 | 883 |
| 2,4-(CH3)2-C6H3- | 455.53 | 884 |
| 2,4-F2-C6H3- | | 885 |
| 2-CF3-C6H4- | 495.4 | 886 |

-continued

| R5 | MW | No. |
|---|---|---|
| 4-fluorophenyl | 445.4 | 887 |
| 4-acetylphenyl | 469.5 | 888 |
| propyl | 379.4 | 889 |
| 5-(dimethylamino)naphthalen-1-yl | 520.6 | 890 |
| 2,4-dichlorophenyl | 496.3 | 891 |
| (E)-styryl | 453.5 | 892 |
| 4-(trifluoromethoxy)phenyl | 511.4 | 893 |
| 2-(trifluoromethoxy)phenyl | 511.48 | 894 |
| 4-fluoro-2-methylphenyl | 459.50 | 895 |

-continued

| R5 | MW | No. |
|---|---|---|
| 4-butylphenyl | 483.59 | 896 |
| 3-methoxy-2,4,6-trimethylphenyl | 499.59 | 897 |
| pentamethylphenyl | 497.62 | 898 |
| 3,5-bis(trifluoromethyl)phenyl | 563.48 | 899 |
| 4-propylphenyl | 469.56 | 900 |
| 4-isopropylphenyl | 469.56 | 901 |
| 3-methylphenyl | 441.51 | 902 |
| 3-fluorophenyl | 445.47 | 903 |
| naphthalen-2-yl | 477.54 | 904 |

-continued

| R5 | MW | No. |
|---|---|---|
| 4,5-dimethyl-2-(acetylamino)thiazole | 505.57 | 905 |
| 2,4,6-triisopropylphenyl (iPr, iPr, iPr) | 553.72 | 906 |
| 2,4,6-trimethylphenyl | 469.56 | 907 |
| 4-tert-butylphenyl | 483.59 | 908 |
| 3,4-dimethoxyphenyl | 487.53 | 909 |
| 2-thienyl | 433.51 | 910 |
| 5-(phenylsulfonyl)-2-thienyl | 573.67 | 911 |
| 2,6-difluorophenyl | 463.46 | 912 |

-continued

| R5 | MW | No. |
|---|---|---|
| 3-methoxyphenyl (H₃CO) | 457.51 | 913 |
| 3-fluorophenyl | 445.47 | 914 |
| 4-(phenylsulfonyl)-5-methyl-thienyl | 573.67 | 915 |
| 4-(2,2-dimethylbutyl)phenyl | 497.62 | 916 |
| 2-cyanophenyl | 452.49 | 917 |
| 4-(trifluoromethyl)phenyl | 495.48 | 918 |
| 4-ethylphenyl | 455.53 | 919 |
| 8-quinolinyl | 478.53 | 920 |
| 4-carboxyphenyl | 471.49 | 921 |

-continued

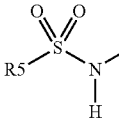

| R5 | MW | No. |
|---|---|---|
| 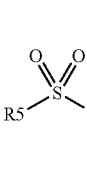 | 503.58 | 922 |

EXAMPLE 28

2-[2-(4-Nitrophenoxy)ethoxy]phenylpropanoic acid 25 g (0.15 M) of 2-hydroxyphenylpropanoic acid and 16.9 g (0.12 M) of potassium hydroxide are added to a mixture of 150 ml of methanol and 20 ml of dimethylformamide in a 1000 ml reactor. After stirring for 10 minutes, 30 g (0.15 M) of 2-(4-nitrophenoxy)ethyl bromide are added and the reaction medium is then refluxed for 24 hours with stirring. The methanol is evaporated off and the residue is taken up in water. The aqueous phase obtained is first washed with ethyl acetate and then acidified with dilute aqueous hydrochloric acid and extracted with ethyl acetate.

The organic phase is evaporated under vacuum and the residue obtained is purified by chromatography on silica, with a dichloromethane/methanol mixture (95/5) as eluent. After concentrating, 9 g of a beige-coloured solid are obtained (yield: 23%).

NMR (δ in ppm, DMSO, 200 MHz): 2.33 (t, 2H); 2.58 (t, 2H); 4.20 (s, 2H); 4.35 (s, 2H); 6.8 (multiplet, 6H); 8.06 (d, 2H).

EXAMPLE 29

2-[2-(4-Aminophenoxy)ethoxy]phenylpropanoic acid 8.4 g (0.025 M) of 2-[2-(4-nitrophenoxy)ethoxy]phenylpropanoic acid and 0.9 g of wet 10% palladium-on-charcoal are added to 60 ml of tetrahydrofuran in a 500 ml reactor. The reaction medium is then stirred vigorously for 3 hours under ambient pressure of hydrogen: exothermicity is observed and the temperature of the reaction medium rises to 40° C.

The reaction medium is then filtered through Celite and concentrated under vacuum to give a residue, which is taken up in diethyl ether. 6.5 g of a light brown solid are thus obtained (80% yield).

NMR (δ in ppm, DMSO, 200 MHz): 2.55 (t, 2H); 2.8 (t, 2H); 4.25 (m, 4H); 6.85 (multiplet, 8H).

EXAMPLE 30

2-{2-[4-(Methylsulfonylamino)phenoxy]ethoxy}phenylpropanoic acid 38 mg (0.332 mM) of methanesulfonyl chloride are added to a mixture of 0.25 ml of dimethylformamide and 1.5 ml of tetrahydrofuran in a 15 ml reactor. 100 mg (0.332 mM) of 2-{2-(4-aminophenoxy)ethoxy}phenylpropanoic acid are then added, followed by addition of 0.060 ml (0.74 mM) of pyridine. The reaction medium is then stirred for 48 hours at room temperature. After extraction with ethyl acetate, 20 mg of 2-{2-[4-(methylsulfonylamino)phenoxy]ethoxy}phenylpropanoic acid are obtained (yield: 16%).

NMR (δ in ppm, DMSO, 200 MHz): 2.8 (t, 2H); 3.05 (t, 2H); 4.6 (m, 4H); 7.3 (multiplet, 8H).

By way of example, the following compounds are prepared according to the procedures described in Example 30.

In particular, the corresponding compounds of the type —NH—CO(R5) (Examples 966 to 1004) may be prepared from the corresponding compounds so of the type —NH₂ according to the method described in Example 15.

| R5 | MW | No. |
|---|---|---|
| 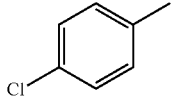 | | |
| 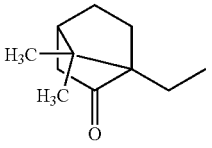 | 475.95 | 923 |
| 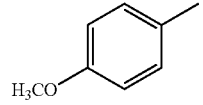 | 379.44 | 924 |
| | 515.63 | 925 |
| 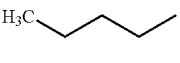 | 471.53 | 926 |
| | 421.52 | 927 |
| 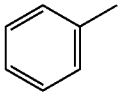 | 441.51 | 928 |
| 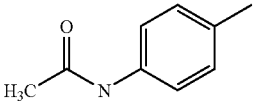 | 498.56 | 929 |

-continued
| R5 | MW | No. |
|---|---|---|
| 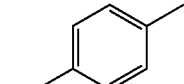 | 455.53 | 930 |
| 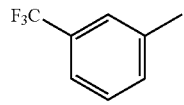 | 509.51 | 931 |
| 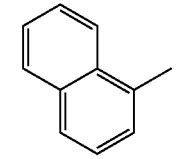 | 491.57 | 932 |
| 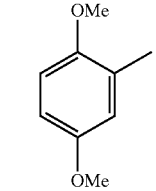 | 501.56 | 933 |
| 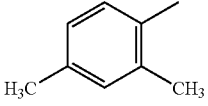 | 469.56 | 934 |
| 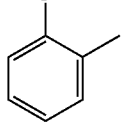 | 459.50 | 935 |
| 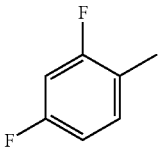 | 477.49 | 936 |
| 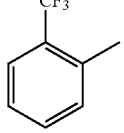 | 509.51 | 937 |
| 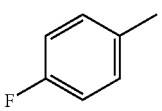 | 459.50 | 938 |
| 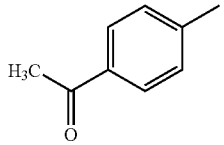 | 483.54 | 939 |
|  | 393.46 | 940 |
-continued
| R5 | MW | No. |
|---|---|---|
| 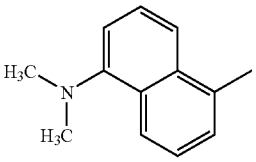 | 534.64 | 941 |
| 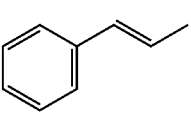 | 467.55 | 942 |
| 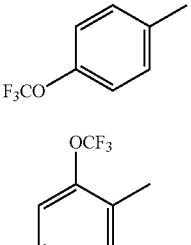 | 525.50 | 943 |
| 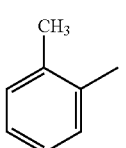 | 525.50 | 944 |
| 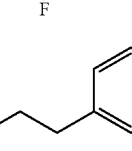 | 473.52 | 945 |
| 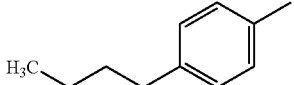 | 497.62 | 946 |
| 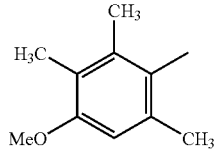 | 513.61 | 947 |
| 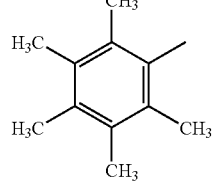 | 511.64 | 948 |
| 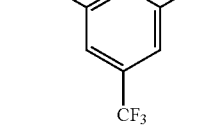 | 577.5 | 949 |
| 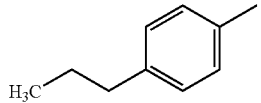 | 483.5 | 950 |

-continued

| R5 | MW | No. |
|---|---|---|
| 4-isopropylphenyl | 483.5 | 951 |
| 3-methylphenyl | 455.5 | 952 |
| 3-fluorophenyl | 459.5 | 953 |
| 2-naphthyl | 491.5 | 954 |
| N-(4,5-dimethylthiazol-2-yl)acetamido | 519.6 | 955 |
| 2,4,6-trimethylphenyl (mesityl) | 483.5 | 956 |
| 4-tert-butylphenyl | 497.6 | 957 |
| 3,4-dimethoxyphenyl | 501.56 | 958 |
| 5-(phenylsulfonyl)thiophen-2-yl | 587.69 | 959 |
| 4-butoxyphenyl | 513.61 | 960 |

-continued

| R5 | MW | No. |
|---|---|---|
| 2,6-difluorophenyl | 477.49 | 961 |
| 3-methoxyphenyl | 471.53 | 962 |
| 4-(trifluoromethyl)phenyl | 509.51 | 963 |
| 4-ethylphenyl | 469.56 | 964 |
| biphenyl-4-yl | 517.61 | 965 |

Structure:

[benzene ring]-O-CH$_2$CH$_2$-O-[benzene ring]-COOH
with NH-C(=O)-R5 substituent

| R5 | MW | No. |
|---|---|---|
| 3-methoxyphenyl | 407.43 | 966 |
| 4-tert-butylphenyl | 433.51 | 967 |
| 3-carboxypropyl (HOOC-CH$_2$CH$_2$-) | 373.37 | 968 |
| 4-chlorophenethyl | 425.87 | 969 |
| 4-chlorophenyl | 411.85 | 970 |
| 2-fluorophenyl | 395.39 | 971 |

-continued
| R5 | MW | No. |
|---|---|---|
| 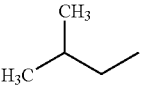 | 357.41 | 972 |
| 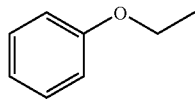 | 407.43 | 973 |
| 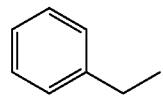 | 391.43 | 974 |
| 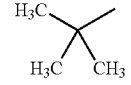 | 357.41 | 975 |
| 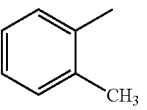 | 391.43 | 976 |
| 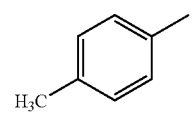 | 391.43 | 977 |
| 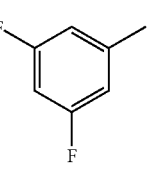 | 413.38 | 978 |
| 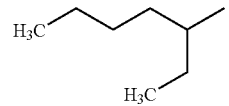 | 399.49 | 979 |
| 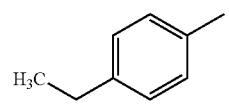 | 405.45 | 980 |
| 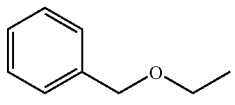 | 421.45 | 981 |
| 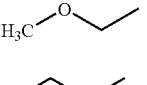 | 345.36 | 982 |
| 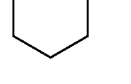 | 383.45 | 983 |
| 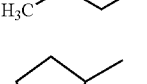 | 343.38 | 984 |
| 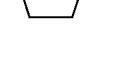 | 369.42 | 985 |
-continued
| R5 | MW | No. |
|---|---|---|
| 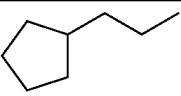 | 397.48 | 986 |
| 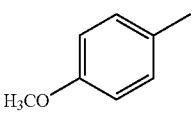 | 407.43 | 987 |
| 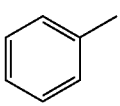 | 377.40 | 988 |
| 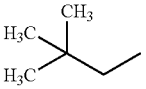 | 371.44 | 989 |
| 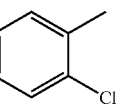 | 411.85 | 990 |
| 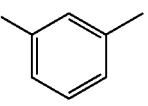 | 395.39 | 991 |
| 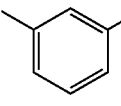 | 456.30 | 992 |
| 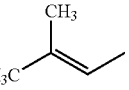 | 355.39 | 993 |
|  | 383.43 | 994 |
| 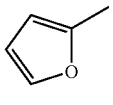 | 367.36 | 995 |
| 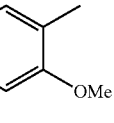 | 407.43 | 996 |
| 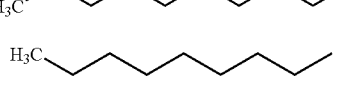 | 427.55 | 997 |
| 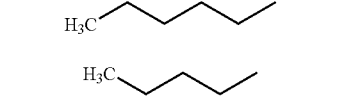 | 413.52 | 998 |
| 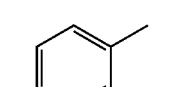 | 371.44 | 999 |
|  | 357.41 | 1000 |
|  | 391.43 | 1001 |

-continued
| R5 | MW | No. |
|---|---|---|
| 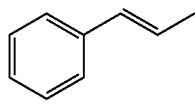 | 403.44 | 1002 |
| 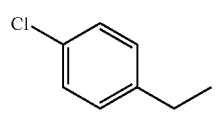 | 425.87 | 1003 |
-continued
| R5 | MW | No. |
|---|---|---|
| 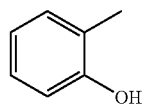 | 393.40 | 1004 |
Examples of Biological Activity:
Insulin Secretion Test on INS-1 Cells
According to the method described in Endocrinology, 1992 vol. 130 (1) pp. 167-178
| Structure | Number | INS-1 Test concentration $10^{-5}$ M % |
|---|---|---|
| 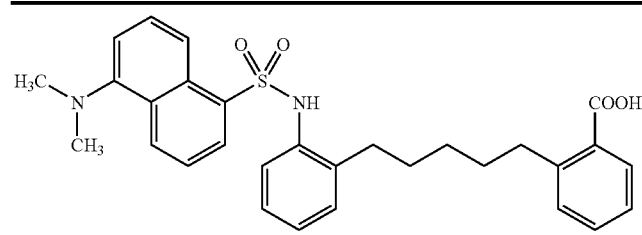 | 159 | 269 |
| 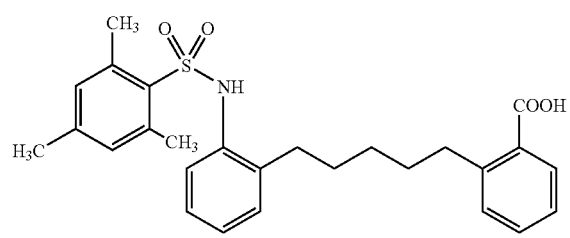 | 163 | 259 |
| 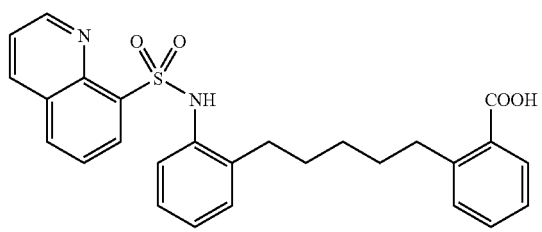 | 168 | 256 |
| 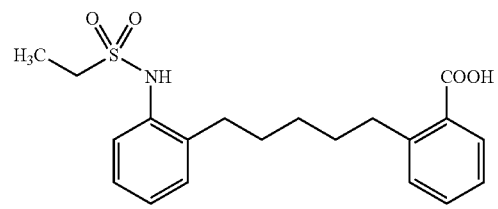 | 157 | 203 |
| 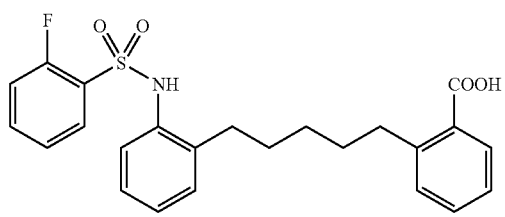 | 152 | 202 |

-continued

| Structure | Number | INS-1 Test concentration $10^{-5}$ M % |
|---|---|---|
| 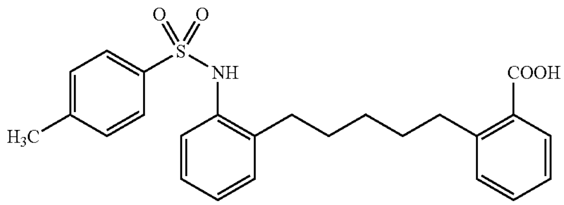 | 144 | 191 |
| 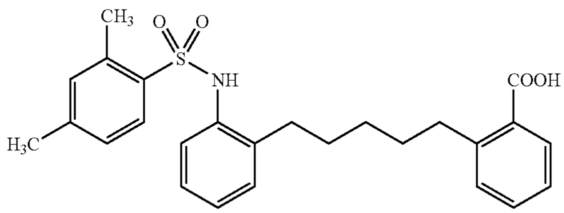 | 151 | 190 |
| 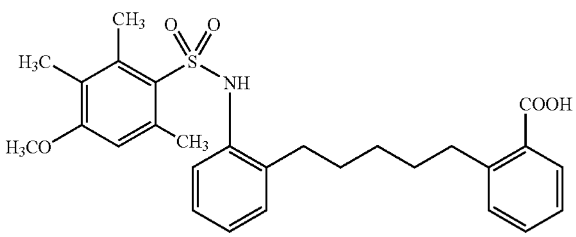 | 158 | 182 |
| 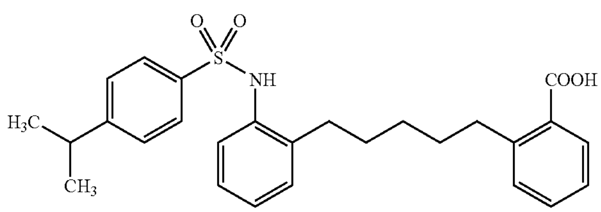 | 164 | 180 |
| 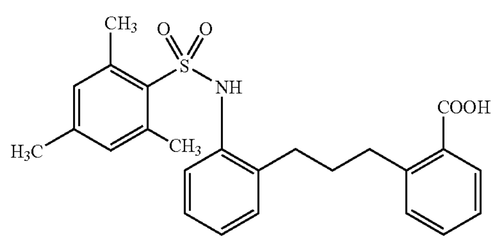 | 121 | 184 |
| 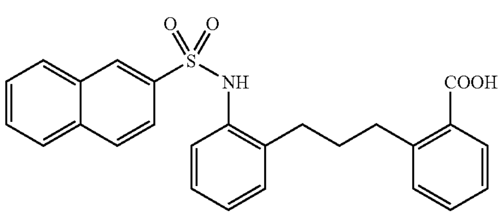 | 117 | 175 |
| 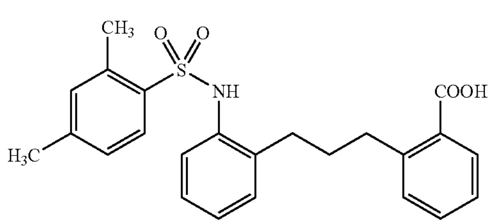 | 109 | 162 |

-continued

| Structure | Number | INS-1 Test concentration $10^{-5}$ M % |
|---|---|---|
| (structure) | 654 | 148 |
| (structure) | 655 | 147 |
| (structure) | 639 | 144 |
| (structure) | 642 | 140 |
| (structure) | 650 | 139 |

Sec INS corresponds to the percentage of insulin secretion.

C corresponds to the concentration of test compound according to the invention.

Insulin Secretion Test on Islets Isolated from Rats

The effect of the compounds on insulin secretion as a function of the glucose concentration was tested, in vitro, in isolated islets of Langerhans in static incubation.

The islets Langerhans obtained by digestion of exocrine pancreatic tissue with collagenase, followed by purification on a Ficoll gradient, are incubated for 90 minutes in the presence of two concentrations of glucose (2.8 mM or 8 mM), in the presence or absence of the chemical compound. The insulin secretion is assayed by RIA in the incubation medium.

The potential of the various chemical compounds to stimulate insulin secretion is estimated by calculating the stimulation factor*.

A compound stimulates insulin secretion if this factor is greater than or equal to 130% for a given dose of glucose.

$$*NB : \text{Stimulation factor} = \frac{(G + P) * 100}{G}$$

In which:

G=insulin secretion (pmol/min. islet) in the presence of glucose alone

G+P=insulin secretion (pmol/min. islet) in the presence of the same concentration of glucose and of the test compound.

| Structure | Number | Isolated islets $10^{-5}$ M | Isolated islets $10^{-7}$ M |
|---|---|---|---|
| [structure: 3,4-dimethyl-5-methoxy benzenesulfonamide with 2,6-dimethyl, linked via NH to phenyl-(CH2)4-phenyl-COOH] | 158 | +166% | +135% |
| [structure: 2-methyl-4-methoxy benzenesulfonamide with 6-methyl, linked via NH to phenyl-(CH2)4-phenyl-COOH] | 163 | +223% | +160% |
| [structure: quinoline-8-sulfonamide linked via NH to phenyl-(CH2)4-phenyl-COOH] | 168 | +236% | +169% |

In Vivo Test

Objective:

To evaluate the effect of 2-{2-[4-(4-chlorobenzenesulfonylamino)phenyl]-ethyl}benzoic acid (compound 522) on the glucose tolerance of n0-STZ/sucrose rats, after a daily treatment for 7 days.

Animals and Treatment:

Rats Wistar (origin: Charles River, France), which received an injection of streptozotocin (100 mg/kg i.v.) on the day of birth. On their arrival at the Research Centre, at seven weeks old:

9 rats were placed on a standard diet (A04, SAFE).

19 rats were placed on a sucrose-rich diet (58% sucrose, SAFE).

After 2 months on the diet, the rats on the sucrose diet were divided randomly into 2 subgroups (control diabetic, treated diabetic).

The three groups were then treated daily for 7 days, with excipient (0.5% methylcellulose solution) for the control group (healthy animals) and the diabetic control group, or with product (compound 522, 100 mg/kg/day) for the third group.

Glucose Tolerance Test (OGTT):

After treatment for 7 days, the animals were fasted for 3 hours before the start of the test. Samples were taken from the tail of the conscious rats. The first blood sample was taken 10 minutes before the administration of glucose (2 g/$kg_{body\ weight}$/oral route). Blood was then taken 10, 20, 30, 45, 60, 90 and 120 minutes after the administration of glucose.

The glucose tolerance was evaluated by means of the $\Delta_{AUC}$ glc, which represents the cumulative increase in glycaemia above the basal value over the 120 minutes of the test.

The insulin response to glucose was estimated by means of the ΔAUC Ins, which represents the cumulative increase in insulinaemia above the basal value over the 120 minutes of the test.

Results:

Figure 1:
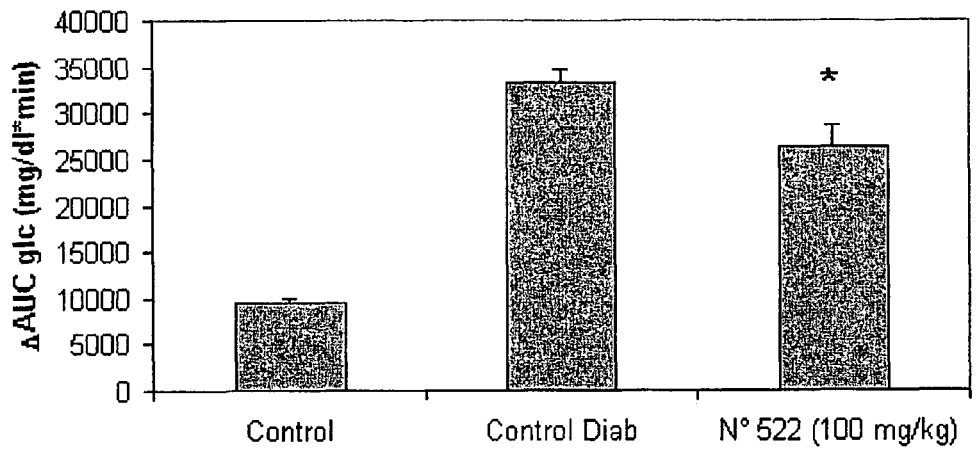
FIG. 1 represents the $\Delta_{AUC}$ glucose, which is down by 21% (significant: p<0.05) on the treated rats (26438+/−2255) compared with the diabetic controls (33306+/−1403 mg/dl·min).
Figure 2:
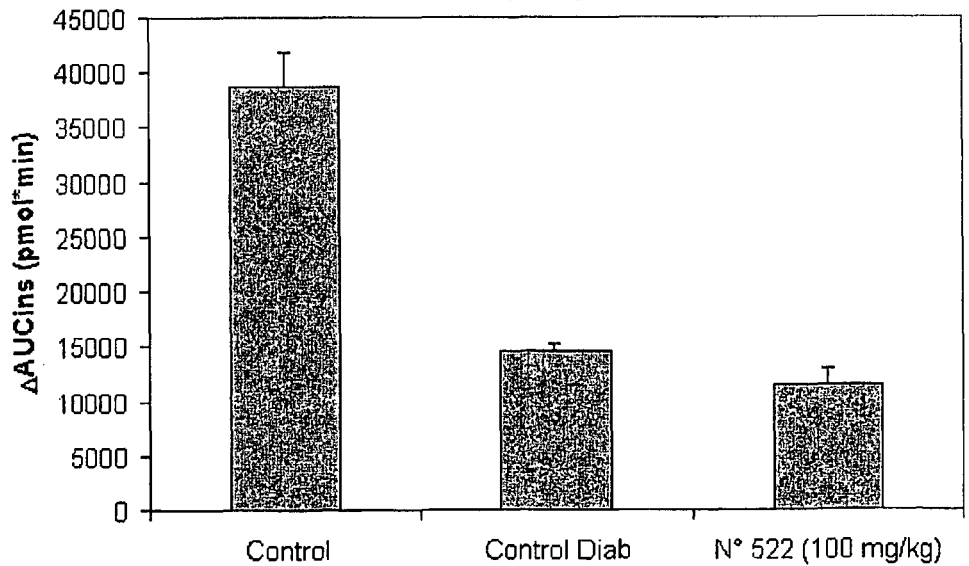
FIG. 2 represents the unchanged $\Delta_{AUC}$ insulin (Treated: 14494+/−665, Diabetic Controls: 11417+/−1440 pmol·min).

The invention claimed is:

1. A compound of the formula (1):

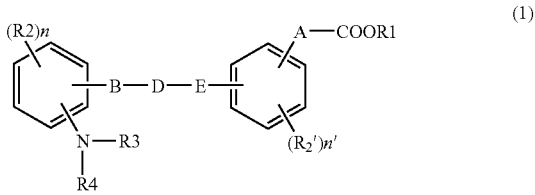

(1)

wherein:
B and E are both each a —CH$_2$— group or are both each an oxygen atom;
R1 is:
H, or ($C_1$-$C_8$)alkyl which is optionally substituted by one or more groups chosen independently from halogen, ($C_1$-$C_5$)alkyl, ($C_1$-$C_5$)alkoxy, ($C_3$-$C_8$)cycloalkyl and ($C_6$-$C_{14}$)aryl R2 and R2' are each:
H;

R3 is:
H, or
($C_1$-$C_{20}$)alkyl;

R4 is:

R5 is Z;
D is a single bond or a ($C_1$-$C_6$)alkyl group;
A is a single bond;
Z is in each case:
($C_1$-$C_{20}$)alkyl which is optionally substituted by one or more groups X;
($C_2$-$C_{20}$)alkene which is optionally substituted by one or more groups X;
($C_2$-$C_{20}$)alkyne which is optionally substituted by one or more groups X;
($C_6$-$C_{14}$)aryl, ($C_6$-$C_{14}$)aryl($C_1$-$C_5$)alkoxy, ($C_6$-$C_{14}$)aryloxy or ($C_6$-$C_{14}$)aryloxy($C_1$-$C_5$)alkoxy, the aryl group of each of these groups being optionally substituted by one or more groups X;
—($C_3$-$C_8$)cycloalkyl which is optionally substituted by one or more groups X;
($C_3$-$C_8$)heterocycle comprising one or more hetero atoms chosen from N, O and S and which is optionally substituted by one or more groups X;
($C_6$-$C_{14}$)aryl($C_1$-$C_{20}$)alkyl, ($C_6$-$C_{14}$)aryl($C_2$-$C_{20}$)alkene or ($C_6$-$C_{14}$)aryl-($C_2$-$C_{20}$)alkyne, the aryl group of each of these groups being optionally substituted by one or more groups X;
($C_5$-$C_{13}$)heteroaryl and ($C_5$-$C_{13}$)heteroaryl($C_1$-$C_{20}$)alkyl comprising one or more hetero atoms chosen from N, O and S, the heteroaryl group of each of these groups being optionally substituted by one or more groups X;
($C_3$-$C_8$)cycloalkyl($C_1$-$C_{20}$)alkyl, ($C_3$-$C_8$)cycloalkyl($C_2$-$C_{20}$)alkene or ($C_3$-$C_8$)cycloalkyl($C_2$-$C_{20}$)alkyne, the cycloalkyl group of each of these groups being optionally substituted by one or more groups X;
X is in each case amino, hydroxyl, thio, halogen, cyano, nitro, trifluoromethoxy, trifluoromethyl, carboxyl, carboxymethyl or carboxyethyl, ($C_1$-$C_8$)alkyl, ($C_1$-$C_8$)alkoxy, ($C_1$-$C_8$)alkylthio, ($C_1$-$C_8$)alkylamino, ($C_6$-$C_{14}$)aryl, ($C_6$-$C_{14}$)arykl($C_1$-$C_8$)-sulfonylalkyl, ($C_6$-$C_{14}$)aryloxy, ($C_6$-$C_{14}$)aryl($C_1$-$C_8$)alkoxy, —NHCO($C_1$-$C_8$)alkyl, —N—($C_1$-$C_8$)alkylCO($C_1$-$C_8$)alkyl, —CO($C_1$-$C_8$)alkyl, —SO$_2$($C_6$-$C_{14}$)aryl, di($C_1$-$C_8$)alkylamino, ($C_3$-$C_8$)cycloalkyl or a ketone function;
n and n' are each independently 1, 2 or 3,
or a tautomeric form, enantiomer, diastereoisomer or epimer thereof, or a pharmaceutically acceptable salt thereof.

2. A compound according to claim 1, wherein B and E are each a —CH$_2$— group.

3. A compound according to claim 1, wherein R1 is a hydrogen atom.

4. A compound according to claim 1, wherein X is in each case hydroxyl, halogen, cyano, nitro, trifluoromethoxy, trifluoromethyl, carboxyl, ($C_1$-$C_8$)alkyl, —SO$_2$($C_6$-$C_{14}$)aryl, ($C_1$-$C_8$)alkoxy, di($C_1$-$C_8$)alkylamino, —NHCO($C_1$-$C_8$)alkyl, —N—($C_1$-$C_8$)alkylCO($C_1$-$C_8$)alkyl, —CO($C_1$-$C_8$)alkyl or ($C_6$-$C_{14}$)aryl($C_1$-$C_8$)alkoxy or a ketone function.

5. A compound according to claim 1, wherein Z is ($C_1$-$C_{20}$)alkyl, ($C_6$-$C_{14}$)aryl, ($C_3$-$C_8$)cycloalkyl, ($C_6$-$C_{14}$)aryl($C_1$-$C_{20}$)alkyl or ($C_1$-$C_{13}$)heteroaryl, which in each case is optionally substituted by one or more groups.

6. A compound according to claim 1, wherein R3 is H or ($C_1$-$C_8$)alkyl.

7. A compound according to claim 1, wherein R5 is ($C_1$-$C_{20}$)alkyl, ($C_6$-$C_{14}$)aryl, ($C_3$-$C_8$)cycloalkyl, ($C_3$-$C_8$)cycloalkyl($C_1$-$C_{20}$)alkyl, ($C_6$-$C_{14}$)aryl($C_1$-$C_{20}$)alkyl or ($C_1$-$C_{13}$)heteroaryl, which in each case is optionally substituted by one or more groups.

8. A compound according to claim 1, wherein said compound is of formula (2) or (2') in which the group -A-COOR1 is in an ortho or meta position on the ring relative to E:

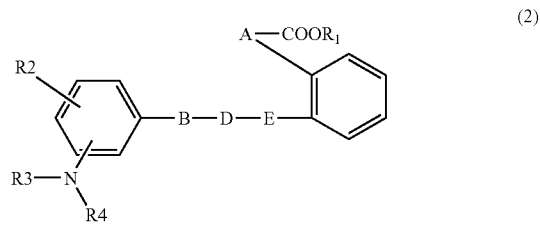

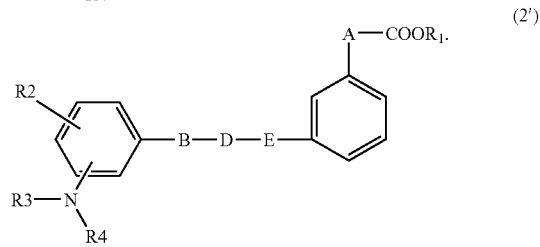

9. A compound according to claim 1, wherein if -ACOOR1 is in the para position, then —NR3R4 is in the para or meta position relative to the chain B-D-E.

10. A compound according to claim 1, wherein if -ACOOR1 is in the para position, then —NR3R4 is in an ortho position relative to the chain B-D-E, and R2 is H.

11. A compound according to claim 1, wherein said compound is of such that they have a general formula (3) which the function NR3R4 is in a meta position on the ring relative to B:

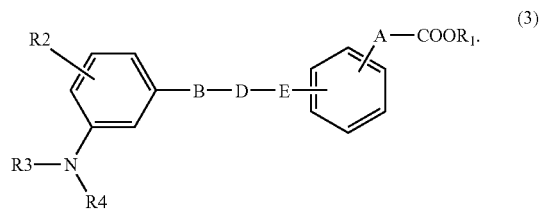

12. A compound according to claim 1, wherein said compound is of formula (4) in which the function NR3R4 is in the para position on the ring relative to B:

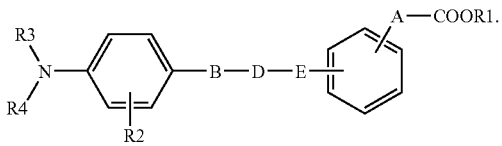

(4)

13. A compound according to claim 1, wherein B and E are each a —CH$_2$— group and D is a single bond or a —CH$_2$ group.

14. A compound according to claim 1, wherein B and E are each an oxygen atom and D is a —C$_2$H$_4$ group.

15. A compound according to claim 1, wherein B and E are each a —CH$_2$— group, D is a chain containing 3 carbon atoms.

16. A compound selected from:
- 4-{2-[2-(4-chlorobenzenesulfonylamino)phenyl]ethyl}benzoic acid
- 4-[2-(2-methanesulfonylaminophenyl)ethyl]benzoic acid
- 4-{2-[2-(4-methoxybenzenesulfonylamino)phenyl]ethyl}benzoic acid
- 4-[2-(2-phenylmethanesulfonylaminophenyl)ethyl]benzoic acid
- 4-{2-[2-(butane-1-sulfonylamino)phenyl]ethyl}benzoic acid
- 4-[2-(2-benzenesulfonylaminophenyl)ethyl]benzoic acid
- 4-{2-[2-(4-acetylaminobenzenesulfonylamino)phenyl]ethyl}benzoic acid
- 4-{2-[2-(2-nitrobenzenesulfonylamino)phenyl]ethyl}benzoic acid
- 4-{2-[2-(4-methylbenzenesulfonylamino)phenyl]ethyl}benzoic acid
- 4-{2-[2-(3-trifluoromethylbenzenesulfonylamino)phenyl]ethyl}benzoic acid
- 4-{2-[2-(naphthalene-1-sulfonylamino)phenyl]ethyl}benzoic acid
- 4-{2-[2-(2,5-dimethoxybenzenesulfonylamino)phenyl]ethyl}benzoic acid
- 4-{2-[2-(2,4-dimethylbenzenesulfonylamino)phenyl]ethyl}benzoic acid
- 4-{2-[2-(2-fluorobenzenesulfonylamino)phenyl]ethyl}benzoic acid
- 4-{2-[2-(2,4-difluorobenzenesulfonylamino)phenyl]ethyl}benzoic acid
- 4-{2-[2-(2-trifluoromethylbenzenesulfonylamino)phenyl]ethyl}benzoic acid
- 4-{2-[2-(4-fluoromethylbenzenesulfonylamino)phenyl]ethyl}benzoic acid
- 4-{2-[2-(5-chloro-3-methylbenzo[b]thiophene-2-sulfonylamino)phenyl]ethyl}benzoic acid
- 4-{2-[2-(4-acetylbenzenesulfonylamino)phenyl]ethyl}benzoic acid
- 4-{2-[2-(4-methoxy-2,5,6-trimethylbenzenesulfonylamino)phenyl]ethyl}benzoic acid
- 4-{2-[2-(naphthalene-2-sulfonylamino)phenyl]ethyl}benzoic acid
- 4-{2-[2-(2,5-dichlorobenzenesulfonylamino)phenyl]ethyl}benzoic acid
- 4-{2-[2-(2,4,6-triisopropylbenzenesulfonylamino)phenyl]ethyl}benzoic acid
- 4-{2-[2-(2,4,6-trimethylbenzenesulfonylamino)phenyl]ethyl}benzoic acid
- 4-{2-[2-(4-isopropylbenzenesulfonylamino)phenyl]ethyl}benzoic acid
- 4-{2-[2-(2-phenylethenesulfonylamino)phenyl]ethyl}benzoic acid
- 4-{2-[2-(3,4-dimethoxybenzenesulfonylamino)phenyl]ethyl}benzoic acid
- 4-{2-[2-(4-trifluoromethoxybenzenesulfonylamino)phenyl]ethyl}benzoic acid
- 4-{2-[2-(thiophene-2-sulfonylamino)phenyl]ethyl}benzoic acid
- 4-{2-[2-(propane-2-sulfonylamino)phenyl]ethyl}benzoic acid
- 4-{2-[2-(hexadecane-1-sulfonylamino)phenyl]ethyl}benzoic acid
- 4-{2-[2-(5-benzenesulfonylthiophene-2-sulfonylamino)phenyl]ethyl}benzoic acid
- 4-{2-[2-(2-trifluoromethoxybenzenesulfonylamino)phenyl]ethyl}benzoic acid
- 4-{2-[2-(4-butoxybenzenesulfonylamino)phenyl]ethyl}benzoic acid
- 4-{2-[2-(3-fluoro-6-methylbenzenesulfonylamino)phenyl]ethyl}benzoic acid
- 4-{2-[2-(2,6-difluorobenzenesulfonylamino)phenyl]ethyl}benzoic acid
- 4-{2-[2-(4-butylbenzenesulfonylamino)phenyl]ethyl}benzoic acid
- 4-{2-[2-(3-methoxybenzenesulfonylamino)phenyl]ethyl}benzoic acid
- 4-{2-[2-(2,3,4,5,6-pentamethylbenzenesulfonylamino)phenyl]ethyl}benzoic acid
- 4-{2-[2-(3,5-bis-trifluoromethylbenzenesulfonylamino)phenyl]ethyl}benzoic acid
- 4-{2-[2-(4-propylbenzenesulfonylamino)phenyl]ethyl}benzoic acid
- 4-{2-[2-(4-isopropylbenzenesulfonylamino)phenyl]ethyl}benzoic acid
- 4-{2-[2-(3-fluorobenzenesulfonylamino)phenyl]ethyl}benzoic acid
- 4-{2-[2-(3-methylbenzenesulfonylamino)phenyl]ethyl}benzoic acid
- 4-{2-[2-(4-benzenesulfonylthiophene-2-sulfonylamino)phenyl]ethyl}benzoic acid
- 4-(2-{2-[4-(1,1-dimethylpropyl)benzenesulfonylamino]phenyl}ethyl)benzoic acid
- 4-{2-[2-(4-ethylbenzenesulfonylamino)phenyl]ethyl}benzoic acid
- 4-{2-[2-(4-trifluoromethylbenzenesulfonylamino)phenyl]ethyl}benzoic acid
- 4-{2-[2-(5-dimethylaminonaphthalene-1-sulfonylamino)phenyl]ethyl}benzoic acid
- 4-{2-[2-(2-acetylamino-4-methylthiazole-5-sulfonylamino)phenyl]ethyl}benzoic acid
- 4-{2-[2-(2-cyanobenzenesulfonylamino)phenyl]ethyl}benzoic acid
- 4-{2-[2-(7,7-dimethyl-2-oxobicyclo[2.2.1]hept-1-yl-methanesulfonylamino)phenyl]ethyl}benzoic acid
- 4-(2-{2-[(4-acetylaminobenzenesulfonyl)butylamino]phenyl}ethyl)benzoic acid
- 4-(2-{2-[butyl(4-chlorobenzenesulfonyl)amino]phenyl}ethyl)benzoic acid
- 4-(2-{2-[butyl(4-methoxybenzenesulfonyl)amino]phenyl}ethyl)benzoic acid
- 4-(2-{2-[butyl(2-nitrobenzenesulfonyl)amino]phenyl}ethyl)benzoic acid
- 4-(2-{2-[butyl(toluene-4-sulfonyl)amino]phenyl}ethyl)benzoic acid 4-(2-{2-[butyl(3-trifluoromethylbenzenesulfonyl)amino]phenyl}ethyl)benzoic acid
4-(2-{2-[butyl(naphthalene-1-sulfonyl)amino]phenyl}ethyl)benzoic acid
4-(2-{2-[butyl(2,5-dimethoxybenzenesulfonyl)amino]phenyl}ethyl)benzoic acid
4-(2-{2-[butyl(2,4-dimethylbenzenesulfonyl)amino]phenyl}ethyl)benzoic acid
4-(2-{2-[butyl(2-fluorobenzenesulfonyl)amino]phenyl}ethyl)benzoic acid
4-(2-{2-[butyl(2,4-difluorobenzenesulfonyl)amino]phenyl}ethyl)benzoic acid
4-(2-{2-[(4-acetylbenzenesulfonyl)butylamino]phenyl}ethyl)benzoic acid
4-(2-{2-[butyl(4-methoxy-2,3,6-trimethylbenzenesulfonyl)amino]phenyl}ethyl)benzoic acid
4-(2-{2-[butyl(5-dimethylaminonaphthalene-1-sulfonyl)amino]phenyl}ethyl)benzoic acid
4-(2-{2-[butyl(naphthalene-2-sulfonyl)amino]phenyl}ethyl)benzoic acid
4-(2-{2-[(2-acetylamino-4-methylthiazole-5-sulfonyl)butylamino]phenyl}ethyl)benzoic acid
4-{2-[2-(benzenesulfonylbutylamino)phenyl]ethyl}benzoic acid
4-(2-{2-[butyl(2,5-dichlorobenzenesulfonyl)amino]phenyl}ethyl)benzoic acid
4-(2-{2-[butyl(2,4,6-trimethylbenzenesulfonyl)amino]phenyl}ethyl)benzoic acid
4-(2-{2-[butyl(4-tert-butylbenzenesulfonyl)amino]phenyl}ethyl)benzoic acid
4-(2-{2-[butyl((E)-2-phenylethenesulfonyl)amino]phenyl}ethyl)benzoic acid
4-(2-{2-[butyl(3,4-dimethoxybenzenesulfonyl)amino]phenyl}ethyl)benzoic acid
4-(2-{2-[butyl(4-trifluoromethoxybenzenesulfonyl)amino]phenyl}ethyl)benzoic acid
4-(2-{2-[butyl(thiophene-2-sulfonyl)amino]phenyl}ethyl)benzoic acid
4-(2-{2-[(5-benzenesulfonylthiophene-2-sulfonyl)butylamino]phenyl}ethyl)benzoic acid
4-(2-{2-[butyl(2-trifluoromethoxybenzenesulfonyl)amino]phenyl}ethyl)benzoic acid
4-(2-{2-[(4-butoxybenzenesulfonyl)butylamino]phenyl}ethyl)benzoic acid
4-(2-{2-[butyl(5-fluoro-2-methylbenzenesulfonyl)amino]phenyl}ethyl)benzoic acid
4-(2-{2-[butyl(2,6-difluorobenzenesulfonyl)amino]phenyl}ethyl)benzoic acid
4-(2-{2-[butyl(4-butylbenzenesulfonyl)amino]phenyl}ethyl)benzoic acid
4-(2-{2-[butyl(3-methoxybenzenesulfonyl)amino]phenyl}ethyl)benzoic acid
4-{2-[2-(butylpentamethylbenzenesulfonylamino)phenyl]ethyl}benzoic acid
4-(2-{2-[(3,5-bis-trifluoromethylbenzenesulfonyl)butylamino]phenyl}ethyl)benzoic acid
4-(2-{2-[butyl(4-propylbenzenesulfonyl)amino]phenyl}ethyl)benzoic acid
4-(2-{2-[butyl(4-isopropylbenzenesulfonyl)amino]phenyl}ethyl)benzoic acid
4-(2-{2-[butyl(3-fluorobenzenesulfonyl)amino]phenyl}ethyl)benzoic acid
4-(2-{2-[butyl(toluene-3-sulfonyl)amino]phenyl}ethyl)benzoic acid
4-[2-(2-{butyl-[4-(1,1-dimethylpropyl)benzenesulfonyl]amino}phenyl)ethyl]benzoic acid
4-(2-{2-[butyl(2-cyanobenzenesulfonyl)amino]phenyl}ethyl)benzoic acid
4-(2-{2-[butyl(4-ethylbenzenesulfonyl)amino]phenyl}ethyl)benzoic acid
4-(2-{2-[butyl(4-trifluoromethylbenzenesulfonyl)amino]phenyl}ethyl)benzoic acid
4-(2-{2-[(4-chlorobenzenesulfonyl)heptylamino]phenyl}ethyl)benzoic acid
4-(2-{2-[heptyl(toluene-4-sulfonyl)amino]phenyl}ethyl)benzoic acid
4-(2-{2-[heptyl(3-trifluoromethylbenzenesulfonyl)amino]phenyl}ethyl)benzoic acid
4-(2-{2-[heptyl(naphthalene-1-sulfonyl)amino]phenyl}ethyl)benzoic acid
4-(2-{2-[(2,5-dimethoxybenzenesulfonyl)heptylamino]phenyl}ethyl)benzoic acid
4-(2-{2-[(2,4-dimethylbenzenesulfonyl)heptylamino]phenyl}ethyl)benzoic acid
4-(2-{2-[(2-fluorobenzenesulfonyl)heptylamino]phenyl}ethyl)benzoic acid
4-(2-{2-[(2,4-difluorobenzenesulfonyl)heptylamino]phenyl}ethyl)benzoic acid
4-(2-{2-[heptyl(2-trifluoromethylbenzenesulfonyl)amino]phenyl}ethyl)benzoic acid
4-(2-{2-[(4-fluorobenzenesulfonyl)heptylamino]phenyl}ethyl)benzoic acid
4-(2-{2-[(4-acetylbenzenesulfonyl)heptylamino]phenyl}ethyl)benzoic acid
4-(2-{2-[heptyl(4-methoxy-2,3,6-trimethylbenzenesulfonyl)amino]phenyl}ethyl)benzoic acid
4-(2-{2-[heptyl(naphthalene-2-sulfonyl)amino]phenyl}ethyl)benzoic acid
4-(2-{2-[(2-acetylamino-4-methylthiazole-5-sulfonyl)heptylamino]phenyl}ethyl)benzoic acid
4-{2-[2-(benzenesulfonylheptylamino)phenyl]ethyl}benzoic acid
4-(2-{2-[heptyl((E)-2-phenylethenesulfonyl)amino]phenyl}ethyl)benzoic acid
4-(2-{2-[(3,4-dimethoxybenzenesulfonyl)heptylamino]phenyl}ethyl)benzoic acid
4-(2-{2-[heptyl(4-trifluoromethoxybenzenesulfonyl)amino]phenyl}ethyl)benzoic acid
4-(2-{2-[heptyl(quinoline-8-sulfonyl)amino]phenyl}ethyl)benzoic acid
4-(2-{2-[(5-fluoro-2-methylbenzenesulfonyl)heptylamino]phenyl}ethyl)benzoic acid
4-(2-{2-[(2,6-difluorobenzenesulfonyl)heptylamino]phenyl}ethyl)benzoic acid
4-(2-{2-[(4-butylbenzenesulfonyl)heptylamino]phenyl}ethyl)benzoic acid
4-(2-{2-[heptyl(3-methoxybenzenesulfonyl)amino]phenyl}ethyl)benzoic acid
4-(2-{2-[heptyl(4-propylbenzenesulfonyl)amino]phenyl}ethyl)benzoic acid
4-(2-{2-[heptyl(4-isopropylbenzenesulfonyl)amino]phenyl}ethyl)benzoic acid
4-(2-{2-[(3-fluorobenzenesulfonyl)heptylamino]phenyl}ethyl)benzoic acid
4-(2-{2-[heptyl(toluene-3-sulfonyl)amino]phenyl}ethyl)benzoic acid
4-[2-(2-{[4-(1,1-dimethylpropyl)benzenesulfonyl]heptylamino}phenyl)ethyl]benzoic acid
4-(2-{2-[(2-cyanobenzenesulfonyl)heptylamino]phenyl}ethyl)benzoic acid
4-(2-{2-[heptyl(4-trifluoromethylbenzenesulfonyl)amino]phenyl}ethyl)benzoic acid 4-{2-[3-(4-chlorobenzenesulfonylamino)phenyl]ethyl}benzoic acid
4-[2-(3-methanesulfonylaminophenyl)ethyl]benzoic acid
4-{2-[3-(4-methoxybenzenesulfonylamino)phenyl]ethyl}benzoic acid
4-[2-(3-phenylmethanesulfonylaminophenyl)ethyl]benzoic acid
4-{2-[3-(butane-1-sulfonylamino)phenyl]ethyl}benzoic acid
4-[2-(3-benzenesulfonylaminophenyl)ethyl]benzoic acid
4-{2-[3-(4-acetylaminobenzenesulfonylamino)phenyl]ethyl}benzoic acid
4-{2-[3-(2-nitrobenzenesulfonylamino)phenyl]ethyl}benzoic acid
4-{2-[3-(4-methylbenzenesulfonylamino)phenyl]ethyl}benzoic acid
4-{2-[3-(2-fluorobenzenesulfonylamino)phenyl]ethyl}benzoic acid
4-{2-[3-(2,4-difluorobenzenesulfonylamino)phenyl]ethyl}benzoic acid
4-{2-[3-(2-trifluoro-methylbenzenesulfonylamino)phenyl]ethyl}benzoic acid
4-{2-[3-(4-fluorobenzenesulfonylamino)phenyl]ethyl}benzoic acid
4-{2-[3-(4-acetylbenzenesulfonylamino)phenyl]ethyl}benzoic acid
4-{2-[3-(ethanesulfonylamino)phenyl]ethyl}benzoic acid
4-{2-[3-(naphthalene-2-sulfonylamino)phenyl]ethyl}benzoic acid
4-(2-{3-[4-(1,1-dimethylethyl)benzenesulfonylamino]phenyl}ethyl)benzoic acid
4-{2-[3-(thiophene-2-sulfonylamino)phenyl]ethyl}benzoic acid
4-{2-[3-(2-trifluoromethoxybenzenesulfonylamino)phenyl]ethyl}benzoic acid
4-{2-[3-(2,6-difluorobenzenesulfonylamino)phenyl]ethyl}benzoic acid
4-{2-[3-(4-butylbenzenesulfonylamino)phenyl]ethyl}benzoic acid
4-{2-[3-(4-trifluoromethoxybenzenesulfonylamino)phenyl]ethyl}benzoic acid
4-{2-[3-(3-trifluoromethylbenzenesulfonylamino)phenyl]ethyl}benzoic acid
4-{2-[3-(naphthalene-1-sulfonylamino)phenyl]ethyl}benzoic acid
4-{2-[3-(2,5-dimethoxybenzenesulfonylamino)phenyl]ethyl}benzoic acid
4-{2-[3-(2,4-dimethylbenzenesulfonylamino)phenyl]ethyl}benzoic acid
4-{2-[3-(biphenyl-4-sulfonylamino)phenyl]ethyl}benzoic acid
4-{2-[3-(4-methoxy-2,3,6-trimethylbenzenesulfonylamino)phenyl]ethyl}benzoic acid
4-{2-[3-(5-dimethylaminonaphthalene-1-sulfonylamino)phenyl]ethyl}benzoic acid
4-{2-[3-(2-acetylamino-4-methylthiazole-5-sulfonylamino)phenyl]ethyl}benzoic acid
4-{2-[3-(2,5-dichlorobenzenesulfonylamino)phenyl]ethyl]benzoic acid
4-{2-[3-(2,4,6-triisopropylbenzenesulfonylamino)phenyl]ethyl}benzoic acid
4-{2-[3-(2,4,6-trimethylbenzenesulfonylamino)phenyl]ethyl}benzoic acid
4-{2-[3-((E)-2-phenylethenesulfonylamino)phenyl]ethyl}benzoic acid
4-{2-[3-(3,4-dimethoxybenzenesulfonylamino)phenyl]ethyl}benzoic acid
4-{2-[3-(4-trifluoromethoxybenzenesulfonylamino)phenyl]ethyl}benzoic acid
4-{2-[3-(4-carboxybenzenesulfonylamino)phenyl]ethyl}benzoic acid
4-{2-[3-(propane-2-sulfonylamino)phenyl]ethyl}benzoic acid
4-{2-[3-(5-benzenesulfonylthiophene-2-sulfonylamino)phenyl]ethyl}benzoic acid
4-{2-[3-(4-butoxybenzenesulfonylamino)phenyl]ethyl}benzoic acid
4-{2-[3-(5-fluoro-2-methylbenzenesulfonylamino)phenyl]ethyl}benzoic acid
4-{2-[3-(3-methoxybenzenesulfonylamino)phenyl]ethyl}benzoic acid
4-[2-(3-pentamethylbenzenesulfonylaminophenyl)ethyl]benzoic acid
4-{2-[3-(3,5-bis-trifluoromethylbenzenesulfonylamino)phenyl]ethyl}benzoic acid
4-{2-[3-(4-isopropylbenzenesulfonylamino)phenyl]ethyl}benzoic acid
4-{2-[3-(3-fluorobenzenesulfonylamino)phenyl]ethyl}benzoic acid
4-{2-[3-(toluene-3-sulfonylamino)phenyl]ethyl}benzoic acid
4-{2-[3-(4-benzenesulfonylthiophene-2-sulfonylamino)phenyl]ethyl}benzoic acid
4-(2-{3-[4-(1,1-dimethylpropyl)benzenesulfonylamino]phenyl}ethyl)benzoic acid
4-{2-[3-(2-cyanobenzenesulfonylamino)phenyl]ethyl}benzoic acid
4-{2-[3-(4-ethylbenzenesulfonylamino)phenyl]ethyl}benzoic acid
4-{2-[3-(7,7-dimethyl-2-oxobicyclo[2.2.1]hept-1-yl-methanesulfonylamino)phenyl]ethyl}benzoic acid
4-{2-[4-(4-chlorobenzenesulfonylamino)phenyl]ethyl}benzoic acid
4-[2-(4-methanesulfonylaminophenyl)ethyl]benzoic acid
4-{2-[4-(4-methoxybenzenesulfonylamino)phenyl]ethyl}benzoic acid
4-[2-(4-phenylmethanesulfonylaminophenyl)ethyl]benzoic acid
4-{2-[4-(butane-1-sulfonylamino)phenyl]ethyl}benzoic acid
4-[2-(4-benzenesulfonylaminophenyl)ethyl]benzoic acid
4-{2-[4-(4-acetylaminobenzenesulfonylamino)phenyl]ethyl}benzoic acid
4-{2-[4-(7,7-dimethyl-2-oxobicyclo[2.2.1]hept-1-yl-methanesulfonylamino)phenyl]ethyl}benzoic acid
4-{2-[4-(4-methylbenzenesulfonylamino)phenyl]ethyl}benzoic acid
4-{2-[4-(3-trifluoromethylbenzenesulfonylamino)phenyl]ethyl}benzoic acid
4-{2-[4-(naphthalene-1-sulfonylamino)phenyl]ethyl}benzoic acid
4-{2-[4-(2,5-dimethoxybenzenesulfonylamino)phenyl]ethyl}benzoic acid
4-{2-[4-(2,4-dimethylbenzenesulfonylamino)phenyl]ethyl}benzoic acid
4-{2-[4-(2,4-difluorobenzenesulfonylamino)phenyl]ethyl}benzoic acid
4-{2-[4-(2-trifluoromethylbenzenesulfonylamino)phenyl]ethyl}benzoic acid
4-{2-[4-(4-fluorobenzenesulfonylamino)phenyl]ethyl}benzoic acid
4-{2-[4-(4-acetylbenzenesulfonylamino)phenyl]ethyl}benzoic acid
4-{2-[4-(ethanesulfonylamino)phenyl]ethyl}benzoic acid 4-{2-[4-(5-dimethylaminonaphthalene-1-sulfonylamino)phenyl]ethyl}benzoic acid
4-{2-[4-(2,5-dichlorobenzenesulfonylamino)phenyl]ethyl}benzoic acid
4-{2-[4-(2-phenylethenesulfonylamino)phenyl]ethyl}benzoic acid
4-{2-[4-(4-trifluoromethoxybenzenesulfonylamino)phenyl]ethyl}benzoic acid
4-{2-[4-(2-trifluoromethoxybenzenesulfonylamino)phenyl]ethyl}benzoic acid
4-{2-[4-(5-fluoro-2-methylbenzenesulfonylamino)phenyl]ethyl}benzoic acid
4-{2-[4-(4-butylbenzenesulfonylamino)phenyl]ethyl}benzoic acid
4-{2-[4-(2,3,4,5,6-pentamethylbenzenesulfonylamino)phenyl]ethyl}benzoic acid
4-{2-[4-(3,5-bis-trifluoromethylbenzenesulfonylamino)phenyl]ethyl}benzoic acid
4-{2-[4-(4-propylbenzenesulfonylamino)phenyl]ethyl}benzoic acid
4-{2-[4-(4-isopropylbenzenesulfonylamino)phenyl]ethyl}benzoic acid
4-{2-[4-(3-methylbenzenesulfonylamino)phenyl]ethyl}benzoic acid
4-{2-[4-(2-fluorobenzenesulfonylamino)phenyl]ethyl}benzoic acid
4-{2-[4-(naphthalene-2-sulfonylamino)phenyl]ethyl}benzoic acid
4-{2-[4-(2-acetylamino-4-methylthiazole-5-sulfonylamino)phenyl]ethyl}benzoic acid
4-{2-[4-(2,4,6-triisopropylbenzenesulfonylamino)phenyl]ethyl}benzoic acid
4-{2-[4-(2,4,6-trimethylbenzenesulfonylamino)phenyl]ethyl}benzoic acid
4-{2-[4-(4-tert-butylbenzenesulfonylamino)phenyl]ethyl}benzoic acid
4-{2-[4-(3,4-dimethoxybenzenesulfonylamino)phenyl]ethyl}benzoic acid
4-{2-[4-(thiophene-2-sulfonylamino)phenyl]ethyl}benzoic acid
4-{2-[4-(propane-2-sulfonylamino)phenyl]ethyl}benzoic acid
4-{2-[4-(5-benzenesulfonylthiophene-2-sulfonylamino)phenyl]ethyl]benzoic acid
4-{2-[4-(4-butoxybenzenesulfonylamino)phenyl}ethyl]benzoic acid
4-{2-[4-(2,6-difluorobenzenesulfonylamino)phenyl}ethyl]benzoic acid
4-{2-[4-(3-methoxybenzenesulfonylamino)phenyl}ethyl]benzoic acid
4-{2-[4-(3-fluorobenzenesulfonylamino)phenyl}ethyl]benzoic acid
4-{2-[4-(4-benzenesulfonylthiophene-2-sulfonylamino)phenyl}ethyl]benzoic acid
4-(2-{4-[4-(1,1-dimethylpropyl)benzenesulfonylamino]phenyl}ethyl)benzoic acid
4-{2-[4-(2-cyanobenzenesulfonylamino)phenyl}ethyl]benzoic acid
4-{2-[4-(4-trifluoromethylbenzenesulfonylamino)phenyl}ethyl]benzoic acid
3-{2-[2-(4-chlorobenzenesulfonylamino)phenyl]ethyl}benzoic acid
3-[2-(2-methanesulfonylaminophenyl)ethyl]benzoic acid
3-{2-[2-(4-methoxybenzenesulfonylamino)phenyl}ethyl]benzoic acid
3-[2-(2-phenylmethanesulfonylaminophenyl)ethyl]benzoic acid
3-{2-[2-(butane-1-sulfonylamino)phenyl]ethyl}benzoic acid
3-[2-(2-benzenesulfonylaminophenyl)ethyl]benzoic acid
3-{2-[2-(4-acetylaminobenzenesulfonylamino)phenyl]ethyl}benzoic acid
3-{2-[2-(2-nitrobenzenesulfonylamino)phenyl]ethyl}benzoic acid
3-{2-[2-(toluene-4-sulfonylamino)phenyl]ethyl}benzoic acid
3-{2-[2-(3-trifluoromethylbenzenesulfonylamino)phenyl]ethyl]benzoic acid
3-{2-[2-(naphthalene-1-sulfonylamino)phenyl}ethyl]benzoic acid
3-{2-[2-(2,5-dimethoxybenzenesulfonylamino)phenyl}ethyl]benzoic acid
3-{2-[2-(2,4-dimethylbenzenesulfonylamino)phenyl]ethyl}benzoic acid
3-{2-[2-(2,4-difluorobenzenesulfonylamino)phenyl}ethyl]benzoic acid
3-{2-[2-(2-trifluoromethylbenzenesulfonylamino)phenyl}ethyl]benzoic acid
3-{2-[2-(4-fluorobenzenesulfonylamino)phenyl}ethyl]benzoic acid
3-{2-[2-(5-chloro-3-methylbenzo[b]thiophene-2-sulfonylamino)phenyl}ethyl]benzoic acid
3-{2-[2-(biphenyl-4-sulfonylamino)phenyl]ethyl}benzoic acid
3-{2-[2-(4-acetylbenzenesulfonylamino)phenyl}ethyl]benzoic acid
3-[2-(2-ethanesulfonylaminophenyl)ethyl]benzoic acid
3-{2-[2-(5-dimethylaminonaphthalene-1-sulfonylamino)phenyl]ethyl}benzoic acid
3-{2-[2-(naphthalene-2-sulfonylamino)phenyl]ethyl}benzoic acid
3-{2-[2-(2-acetylamino-4-methylthiazole-5-sulfonylamino)phenyl]ethyl}benzoic acid
3-{2-[2-(2,5-dichlorobenzenesulfonylamino)phenyl]ethyl}benzoic acid
3-{2-[2-(2,4,6-trimethylbenzenesulfonylamino)phenyl]ethyl}benzoic acid
3-{2-[2-(4-tert-butylbenzenesulfonylamino)phenyl]ethyl}benzoic acid
3-{2-[2-(E)-2-phenylethenesulfonylamino)phenyl]ethyl}benzoic acid
3-{2-[2-(3,4-dimethoxybenzenesulfonylamino)phenyl]ethyl}benzoic acid
3-{2-[2-(4-trifluoromethoxybenzenesulfonylamino)phenyl]ethyl}benzoic acid
3-{2-[2-(thiophene-2-sulfonylamino)phenyl]ethyl}benzoic acid
3-{2-[2-(4-carboxybenzenesulfonylamino)phenyl]ethyl}benzoic acid
3-{2-[2-(propane-2-sulfonylamino)phenyl]ethyl}benzoic acid
3-{2-[2-(hexadecane-1-sulfonylamino)phenyl]ethyl}benzoic acid
3-{2-[2-(quinoline-8-sulfonylamino)phenyl]ethyl}benzoic acid
3-{2-[2-(5-benzenesulfonylthiophene-2-sulfonylamino)phenyl]ethyl}benzoic acid
3-{2-[2-(2-trifluoromethoxybenzenesulfonylamino)phenyl]ethyl}benzoic acid
3-{2-[2-(4-butoxybenzenesulfonylamino)phenyl]ethyl}benzoic acid
3-{2-[2-(5-fluoro-2-methylbenzenesulfonylamino)phenyl]ethyl}benzoic acid 3-{2-[2-(2,6-difluorobenzenesulfonylamino)phenyl]ethyl}benzoic acid
3-{2-[2-(4-butylbenzenesulfonylamino)phenyl]ethyl}benzoic acid
3-{2-[2-(3-methoxybenzenesulfonylamino)phenyl]ethyl}benzoic acid
3-[2-(2-pentamethylbenzenesulfonylaminophenyl)ethyl]benzoic acid
3-{2-[2-(3,5-bis-trifluoromethylbenzenesulfonylamino)phenyl]ethyl}benzoic acid
3-{2-[2-(3-fluorobenzenesulfonylamino)phenyl]ethyl}benzoic acid
3-{2-[2-(toluene-3-sulfonylamino)phenyl]ethyl}benzoic acid
3-{2-[2-(4-benzenesulfonylthiophene-2-sulfonylamino)phenyl]ethyl}benzoic acid
3-(2-{2-[4-(1,1-dimethylpropyl)benzenesulfonylamino]phenyl}ethyl)benzoic acid
3-{2-[2-(4-ethylbenzenesulfonylamino)phenyl]ethyl}benzoic acid
3-{2-[2-(4-trifluoromethylbenzenesulfonylamino)phenyl]ethyl}benzoic acid
3-{2-[2-(7,7-dimethyl-2-oxobicyclo[2.2.1]hept-1-yl-methanesulfonylamino)phenyl]ethyl})benzoic acid
3-{2-[2-(2-fluorobenzenesulfonylamino)phenyl]ethyl}benzoic acid
3-{2-[2-(4-propylbenzenesulfonylamino)phenyl]ethyl}benzoic acid
3-{2-[2-(4-isopropylbenzenesulfonylamino)phenyl]ethyl}benzoic acid
3-{2-[2-(2-cyanobenzenesulfonylamino)phenyl]ethyl}benzoic acid
3-{2-[3-(4-chlorobenzenesulfonylamino)phenyl]ethyl}benzoic acid
3-[2-(3-methanesulfonylaminophenyl)ethyl]benzoic acid
3-{2-[3-(4-methoxybenzenesulfonylamino)phenyl]ethyl}benzoic acid
3-[2-(3-phenylmethanesulfonylaminophenyl)ethyl]benzoic acid
3-{2-[3-(butane-1-sulfonylamino)phenyl]ethyl}benzoic acid
3-[2-(3-benzenesulfonylaminophenyl)ethyl]benzoic acid
3-{2-[3-(4-acetylaminobenzenesulfonylamino)phenyl]ethyl}benzoic acid
3-{2-[3-(2-nitrobenzenesulfonylamino)phenyl]ethyl}benzoic acid
3-{2-[3-(toluene-4-sulfonylamino)phenyl]ethyl}benzoic acid
3-{2-[3-(3-trifluoromethylbenzenesulfonylamino)phenyl]ethyl}benzoic acid
3-{2-[3-(naphthalene-1-sulfonylamino)phenyl]ethyl}benzoic acid
3-{2-[3-(2,5-dimethoxybenzenesulfonylamino)phenyl]ethyl}benzoic acid
3-{2-[3-(2,4-dimethylbenzenesulfonylamino)phenyl]ethyl}benzoic acid
3-{2-[3-(2-fluorobenzenesulfonylamino)phenyl]ethyl}benzoic acid
3-{2-[3-(2,4-difluorobenzenesulfonylamino)phenyl]ethyl}benzoic acid
3-{2-[3-(2-trifluoromethylbenzenesulfonylamino)phenyl]ethyl}benzoic acid
3-{2-[3-(4-fluorobenzenesulfonylamino)phenyl]ethyl}benzoic acid
3-{2-[3-(5-chloro-3-methylbenzo[b]thiophene-2-sulfonylamino)phenyl]ethyl}benzoic acid
3-{2-[3-(biphenyl-4-sulfonylamino)phenyl]ethyl}benzoic acid
3-{2-[3-(4-acetylbenzenesulfonylamino)phenyl}ethyl]benzoic acid
3-[2-(3-ethanesulfonylaminophenyl)ethyl]benzoic acid
3-{2-[3-(5-dimethylaminonaphthalene-1-sulfonylamino)phenyl]ethyl]benzoic acid
3-{2-[3-(naphthalene-2-sulfonylamino)phenyl}ethyl]benzoic acid
3-{2-[3-(2-acetylamino-4-methylthiazole-5-sulfonylamino)phenyl}ethyl]benzoic acid
3-{2-[3-(2,5-dichlorobenzenesulfonylamino)phenyl}ethyl]benzoic acid
3-{2-[3-(2,4,6-triisopropylbenzenesulfonylamino)phenyl}ethyl]benzoic acid
3-{2-[3-(2,4,6-trimethylbenzenesulfonylamino)phenyl}ethyl]benzoic acid
3-{2-[3-(4-tert-butylbenzenesulfonylamino)phenyl]ethyl}benzoic acid
3-{2-[3-((E)-2-phenylethenesulfonylamino)phenyl]ethyl}benzoic acid
3-{2-[3-(3,4-dimethoxybenzenesulfonylamino)phenyl}ethyl]benzoic acid
3-{2-[3-(4-trifluoromethoxybenzenesulfonylamino)phenyl]ethyl}benzoic acid
3-{2-[3-(thiophene-2-sulfonylamino)phenyl]ethyl}benzoic acid
3-{2-[3-(4-carboxybenzenesulfonylamino)phenyl]ethyl}benzoic acid
3-{2-[3-(propane-2-sulfonylamino)phenyl}ethyl]benzoic acid
3-{2-[3-(2,2,2-trifluoroethanesulfonylamino)phenyl}ethyl]benzoic acid
3-{2-[3-(quinoline-8-sulfonylamino)phenyl}ethyl]benzoic acid
3-{2-[3-(5-benzenesulfonylthiophene-2-sulfonylamino)phenyl}ethyl]benzoic acid
3-{2-[3-(2-trifluoromethoxybenzenesulfonylamino)phenyl]ethyl}benzoic acid
3-{2-[3-(4-butoxybenzenesulfonylamino)phenyl}ethyl]benzoic acid
3-{2-[3-(5-fluoro-2-methylbenzenesulfonylamino)phenyl}ethyl]benzoic acid
3-{2-[3-(2,6-difluorobenzenesulfonylamino)phenyl}ethyl]benzoic acid
3-{2-[3-(4-butylbenzenesulfonylamino)phenyl}ethyl]benzoic acid
3-{2-[3-(3-methoxybenzenesulfonylamino)phenyl}ethyl]benzoic acid
3-[2-(3-pentamethylbenzenesulfonylaminophenyl)ethyl]benzoic acid
3-{2-[3-(3,5-bis-trifluoromethylbenzenesulfonylamino)phenyl}ethyl]benzoic acid
3-{2-[3-(3-fluorobenzenesulfonylamino)phenyl}ethyl]benzoic acid
3-{2-[3-(toluene-3-sulfonylamino)phenyl]ethyl}benzoic acid
3-{2-[3-(4-benzenesulfonylthiophene-2-sulfonylamino)phenyl}ethyl]benzoic acid
3-(2-{3-[4-(1,1-dimethylpropyl)benzenesulfonylamino]phenyl}ethyl)benzoic acid
3-{2-[3-(2-cyanobenzenesulfonylamino)phenyl}ethyl]benzoic acid
3-{2-[3-(4-ethylbenzenesulfonylamino)phenyl}ethyl]benzoic acid
3-{2-[3-(4-trifluoromethylbenzenesulfonylamino)phenyl}ethyl]benzoic acid 3-{2-[3-(7,7-dimethyl-2-oxobicyclo[2.2.1]hept-1-yl-methanesulfonylamino)phenyl]ethyl}benzoic acid
3-{2-[4-(4-chlorobenzenesulfonylamino)phenyl]ethyl}benzoic acid
3-[2-(4-methanesulfonylaminophenyl)ethyl]benzoic acid
3-{2-[4-(4-methoxybenzenesulfonylamino)phenyl]ethyl}benzoic acid
3-[2-(4-phenylmethanesulfonylaminophenyl)ethyl]benzoic acid
3-{2-[4-(butane-1-sulfonylamino)phenyl]ethyl}benzoic acid
3-[2-(4-benzenesulfonylaminophenyl)ethyl]benzoic acid
3-{2-[4-(4-acetylaminobenzenesulfonyl amino)phenyl]ethyl}benzoic acid
3-{2-[4-(2-nitrobenzenesulfonylamino)phenyl]ethyl}benzoic acid
3-{2-[4-(toluene-4-sulfonylamino)phenyl]ethyl}benzoic acid
3-{2-[4-(3-trifluoromethylbenzenesulfonylamino)phenyl]ethyl}benzoic acid
3-{2-[4-(2,5-dimethoxybenzenesulfonylamino)phenyl]ethyl}benzoic acid
3-{2-[4-(2,4-dimethylbenzenesulfonylamino)phenyl]ethyl}benzoic acid
3-{2-[4-(2-fluorobenzenesulfonylamino)phenyl]ethyl}benzoic acid
3-{2-[4-(2,4-difluorobenzenesulfonylamino)phenyl]ethyl}benzoic acid
3-{2-[4-(2-trifluoromethylbenzenesulfonylamino)phenyl]ethyl}benzoic acid
3-{2-[4-(4-fluorobenzenesulfonylamino)phenyl]ethyl}benzoic acid
3-{2-[4-(5-chloro-3-methylbenzo[b]thiophene-2-sulfonylamino)phenyl]ethyl}benzoic acid
3-{2-[4-(4-acetylbenzenesulfonylamino)phenyl]ethyl}benzoic acid
3-[2-(4-ethanesulfonylaminophenyl)ethyl]benzoic acid
3-{2-[4-(5-dimethylaminonaphthalene-1-sulfonylamino)phenyl]ethyl}benzoic acid
3-{2-[4-(naphthalene-2-sulfonylamino)phenyl]ethyl}benzoic acid
3-{2-[4-(2-acetylamino-4-methylthiazole-5-sulfonylamino)phenyl]ethyl}benzoic acid
3-{2-[4-(2,5-dichlorobenzenesulfonylamino)phenyl]ethyl}benzoic acid
3-{2-[4-(2,4,6-trimethylbenzenesulfonylamino)phenyl]ethyl}benzoic acid
3-{2-[4-(4-tert-butylbenzenesulfonylamino)phenyl]ethyl}benzoic acid
3-{2-[4-((E)-2-phenylethenesulfonylamino)phenyl]ethyl}benzoic acid
3-{2-[4-(3,4-dimethoxybenzenesulfonylamino)phenyl]ethyl}benzoic acid
3-{2-[4-(4-trifluoromethoxybenzenesulfonylamino)phenyl]ethyl}benzoic acid
3-{2-[4-(thiophene-2-sulfonylamino)phenyl]ethyl}benzoic acid
3-{2-[4-(4-carboxybenzenesulfonylamino)phenyl]ethyl}benzoic acid
3-{2-[4-(propane-2-sulfonylamino)phenyl]ethyl}benzoic acid
3-{2-[4-(quinoline-8-sulfonylamino)phenyl]ethyl}benzoic acid
3-{2-[4-(5-benzenesulfonylthiophene-2-sulfonylamino)phenyl]ethyl}benzoic acid
3-{2-[4-(2-trifluoromethoxybenzenesulfonylamino)phenyl]ethyl}benzoic acid
3-{2-[4-(4-butoxybenzenesulfonylamino)phenyl]ethyl}benzoic acid
3-{2-[4-(5-fluoro-2-methylbenzenesulfonylamino)phenyl]ethyl}benzoic acid
3-{2-[4-(2,6-difluorobenzenesulfonylamino)phenyl]ethyl}benzoic acid
3-{2-[4-(4-butylbenzenesulfonylamino)phenyl]ethyl}benzoic acid
3-{2-[4-(3-methoxybenzenesulfonylamino)phenyl]ethyl}benzoic acid
3-{2-[4-(3,5-bis-trifluoromethylbenzenesulfonylamino)phenyl]ethyl}benzoic acid
3-{2-[4-(3-fluorobenzenesulfonylamino)phenyl]ethyl}benzoic acid
3-{2-[4-(toluene-3-sulfonylamino)phenyl]ethyl}benzoic acid
3-{2-[4-(4-benzenesulfonylthiophene-2-sulfonylamino)phenyl]ethyl}benzoic acid
3-(2-{4-[4-(1,1-dimethylpropyl)benzenesulfonylamino]phenyl}ethyl)benzoic acid
3-{2-[4-(2-cyanobenzenesulfonylamino)phenyl]ethyl}benzoic acid
3-{2-[4-(4-ethylbenzenesulfonylamino)phenyl]ethyl}benzoic acid
3-{2-[4-(4-trifluoromethylbenzenesulfonylamino)phenyl]ethyl}benzoic acid
3-{2-[4-(7,7-dimethyl-2-oxobicyclo[2.2.1]hept-1-yl-methanesulfonylamino)phenyl]ethyl}benzoic acid
3-{2-[4-(naphthalene-1-sulfonylamino)phenyl]ethyl}benzoic acid
3-[2-(4-pentamethylbenzenesulfonylaminophenyl)ethyl]benzoic acid
3-{2-[4-(4-propylbenzenesulfonylamino)phenyl]ethyl}benzoic acid
3-{2-[4-(4-isopropylbenzenesulfonylamino)phenyl]ethyl}benzoic acid
2-{2-[2-(2-nitrobenzenesulfonylamino)phenyl]ethyl}benzoic acid
2-{2-[2-(2,5-dimethoxybenzenesulfonylamino)phenyl]ethyl}benzoic acid
2-{2-[2-(2-fluorobenzenesulfonylamino)phenyl]ethyl}benzoic acid
2-{2-[2-(4-fluorobenzenesulfonylamino)phenyl]ethyl}benzoic acid
2-{2-[2-(5-chloro-3-methylbenzo[b]thiophene-2-sulfonylamino)phenyl]ethyl}benzoic acid
2-{2-[2-(biphenyl-4-sulfonylamino)phenyl]ethyl}benzoic acid
2-{2-[2-(4-acetylbenzenesulfonylamino)phenyl]ethyl}benzoic acid
2-[2-(2-ethanesulfonylaminophenyl)ethyl]benzoic acid
2-{2-[2-(2,4,6-trimethylbenzenesulfonylamino)phenyl]ethyl}benzoic acid
2-{2-[2-(4-tert-butylbenzenesulfonylamino)phenyl]ethyl}benzoic acid
2-{2-[2-(E)-2-phenylethenesulfonylamino)phenyl]ethyl}benzoic acid
2-{2-[2-(3,4-dimethoxybenzenesulfonylamino)phenyl]ethyl}benzoic acid
2-{2-[2-(4-trifluoromethoxybenzenesulfonylamino)phenyl]ethyl}benzoic acid
2-{2-[2-(thiophene-2-sulfonylamino)phenyl]ethyl}benzoic acid
2-{2-[2-(4-carboxybenzenesulfonylamino)phenyl]ethyl}benzoic acid
2-{2-[2-(propane-2-sulfonylamino)phenyl]ethyl}benzoic acid 2-{2-[2-(quinoline-8-sulfonylamino)phenyl]ethyl}benzoic acid
2-{2-[2-(5-benzenesulfonylthiophene-2-sulfonylamino)phenyl]ethyl}benzoic acid
2-{2-[2-(2-trifluoromethoxybenzenesulfonylamino)phenyl]ethyl}benzoic acid
2-{2-[2-(4-butoxybenzenesulfonylamino)phenyl]ethyl}benzoic acid
2-{2-[2-(5-fluoro-2-methylbenzenesulfonylamino)phenyl]ethyl}benzoic acid
2-{2-[2-(2,6-difluorobenzenesulfonylamino)phenyl]ethyl}benzoic acid
2-{2-[2-(4-butylbenzenesulfonylamino)phenyl]ethyl}benzoic acid
2-{2-[2-(3-methoxybenzenesulfonylamino)phenyl]ethyl}benzoic acid
2-[2-(2-pentamethylbenzenesulfonylaminophenyl)ethyl]benzoic acid
2-{2-[2-(3,5-bis-trifluoromethylbenzenesulfonylamino)phenyl]ethyl}benzoic acid
2-{2-[2-(3-fluorobenzenesulfonylamino)phenyl]ethyl}benzoic acid
2-{2-[2-(toluene-3-sulfonylamino)phenyl]ethyl}benzoic acid
2-{2-[2-(4-benzenesulfonylthiophene-2-sulfonylamino)phenyl]ethyl}benzoic acid
2-(2-{2-[4-(1,1-dimethylpropyl)benzenesulfonylamino]phenyl}ethyl)benzoic acid
2-{2-[2-(2-cyanobenzenesulfonylamino)phenyl]ethyl}benzoic acid
2-{2-[2-(4-ethylbenzenesulfonylamino)phenyl]ethyl}benzoic acid
2-{2-[2-(4-trifluoromethylbenzenesulfonylamino)phenyl]ethyl}benzoic acid
2-{2-[2-(4-chlorobenzenesulfonylamino)phenyl]ethyl}benzoic acid
2-[2-(2-methanesulfonylaminophenyl)ethyl]benzoic acid
2-{2-[2-(4-methoxybenzenesulfonylamino)phenyl]ethyl}benzoic acid
2-[2-(2-phenylmethanesulfonylaminophenyl)ethyl]benzoic acid
2-{2-[2-(butane-1-sulfonylamino)phenyl]ethyl}benzoic acid
2-[2-(2-benzenesulfonylaminophenyl)ethyl]benzoic acid
2-{2-[2-(4-acetylaminobenzenesulfonyl amino)phenyl]ethyl}benzoic acid
2-{2-[2-(2,4-difluorobenzenesulfonylamino)phenyl]ethyl}benzoic acid
2-{2-[2-(toluene-4-sulfonylamino)phenyl]ethyl}benzoic acid
2-{2-[2-(naphthalene-1-sulfonylamino)phenyl]ethyl}benzoic acid
2-{2-[2-(2-trifluoromethylbenzenesulfonylamino)phenyl]ethyl}benzoic acid
2-{2-[2-(5-dimethylaminonaphthalene-1-sulfonylamino)phenyl]ethyl}benzoic acid
2-{2-[2-(naphthalene-2-sulfonylamino)phenyl]ethyl}benzoic acid
2-{2-[2-(2-acetylamino-4-methylthiazole-5-sulfonylamino)phenyl]ethyl}benzoic acid
2-{2-[2-(2,5-dichlorobenzenesulfonylamino)phenyl]ethyl}benzoic acid
2-{2-[2-(2,4,6-triisopropylbenzenesulfonylamino)phenyl]ethyl}benzoic acid
2-{2-[2-(4-propylbenzenesulfonylamino)phenyl]ethyl}benzoic acid
2-{2-[2-(4-isopropylbenzenesulfonylamino)phenyl]ethyl}benzoic acid
2-{2-[2-(7,7-dimethyl-2-oxobicyclo[2.2.1]hept-1-yl-methanesulfonylamino)phenyl]ethyl}benzoic acid
2-{2-[3-(4-acetylaminobenzenesulfonylamino)phenyl]ethyl}benzoic acid
2-{2-[3-(toluene-4-sulfonylamino)phenyl]ethyl}benzoic acid
2-{2-[3-(naphthalene-1-sulfonylamino)phenyl]ethyl}benzoic acid
2-{2-[3-(2,5-dimethoxybenzenesulfonylamino)phenyl]ethyl}benzoic acid
2-{2-[3-(2,4-dimethylbenzenesulfonylamino)phenyl]ethyl}benzoic acid
2-{2-[3-(2-trifluoromethylbenzenesulfonylamino)phenyl]ethyl}benzoic acid
2-{2-[3-(5-chloro-3-methylbenzo[b]thiophene-2-sulfonylamino)phenyl]ethyl}benzoic acid
2-{2-[3-(naphthalene-2-sulfonylamino)phenyl]ethyl}benzoic acid
2-{2-[3-(2,5-dichlorobenzenesulfonylamino)phenyl]ethyl}benzoic acid
2-{2-[3-(2,4,6-trimethylbenzenesulfonylamino)phenyl]ethyl}benzoic acid
2-{2-[3-(4-tert-butylbenzenesulfonylamino)phenyl]ethyl}benzoic acid
2-{2-[3-(E)-2-phenylethenesulfonylamino)phenyl]ethyl}benzoic acid
2-{2-[3-(3,4-dimethoxybenzenesulfonylamino)phenyl]ethyl}benzoic acid
2-{2-[3-(4-trifluoromethoxybenzenesulfonylamino)phenyl]ethyl}benzoic acid
2-{2-[3-(thiophene-2-sulfonylamino)phenyl]ethyl}benzoic acid
2-{2-[3-(4-carboxybenzenesulfonylamino)phenyl]ethyl}benzoic acid
2-{2-[3-(propane-2-sulfonylamino)phenyl]ethyl}benzoic acid
2-{2-[3-(5-benzenesulfonylthiophene-2-sulfonylamino)phenyl]ethyl}benzoic acid
2-{2-[3-(2-trifluoromethoxybenzenesulfonylamino)phenyl]ethyl}benzoic acid
2-{2-[3-(4-butoxybenzenesulfonylamino)phenyl]ethyl}benzoic acid
2-{2-[3-(5-fluoro-2-methylbenzenesulfonylamino)phenyl]ethyl}benzoic acid
2-{2-[3-(2,6-difluorobenzenesulfonylamino)phenyl]ethyl}benzoic acid
2-{2-[3-(4-butylbenzenesulfonylamino)phenyl]ethyl}benzoic acid
2-{2-[3-(3-methoxybenzenesulfonylamino)phenyl]ethyl}benzoic acid
2-[2-(3-pentamethylbenzenesulfonylaminophenyl)ethyl]benzoic acid
2-{2-[3-(3,5-bis-trifluoromethylbenzenesulfonylamino)phenyl]ethyl}benzoic acid
2-{2-[3-(3-fluorobenzenesulfonylamino)phenyl]ethyl}benzoic acid
2-{2-[3-(toluene-3-sulfonylamino)phenyl]ethyl}benzoic acid
2-{2-[3-(4-benzenesulfonylthiophene-2-sulfonylamino)phenyl]ethyl}benzoic acid
2-(2-{3-[4-(1,1-dimethylpropyl)benzenesulfonylamino]phenyl}ethyl)benzoic acid
2-{2-[3-(4-ethylbenzenesulfonylamino)phenyl]ethyl}benzoic acid 2-{2-[3-(4-trifluoromethylbenzenesulfonylamino)phenyl]ethyl}benzoic acid
2-{2-[3-(4-chlorobenzenesulfonylamino)phenyl]ethyl}benzoic acid
2-[2-(3-methanesulfonylaminophenyl)ethyl]benzoic acid
2-{2-[3-(4-methoxybenzenesulfonylamino)phenyl]ethyl}benzoic acid
2-[2-(3-phenylmethanesulfonylaminophenyl)ethyl]benzoic acid
2-{2-[3-(butane-1-sulfonylamino)phenyl]ethyl}benzoic acid
2-[2-(3-benzenesulfonylaminophenyl)ethyl]benzoic acid
2-{2-[3-(2-nitrobenzenesulfonylamino)phenyl]ethyl}benzoic acid
2-{2-[3-(2-fluorobenzenesulfonylamino)phenyl]ethyl}benzoic acid
2-{2-[3-(2,4-difluorobenzenesulfonylamino)phenyl]ethyl}benzoic acid
2-{2-[3-(4-fluorobenzenesulfonylamino)phenyl]ethyl}benzoic acid
2-{2-[3-(4-acetylbenzenesulfonylamino)phenyl]ethyl}benzoic acid
2-{2-[3-(2-acetylamino-4-methylthiazole-5-sulfonylamino)phenyl]ethyl}benzoic acid
2-{2-[3-(2,4,6-triisopropylbenzenesulfonylamino)phenyl]ethyl}benzoic acid
2-{2-[3-(4-propylbenzenesulfonylamino)phenyl]ethyl}benzoic acid
2-{2-[3-(4-isopropylbenzenesulfonylamino)phenyl]ethyl}benzoic acid
2-{2-[3-(2-cyanobenzenesulfonylamino)phenyl]ethyl}benzoic acid
2-{2-[3-(7,7-dimethyl-2-oxobicyclo[2.2.1]hept-1-yl-methanesulfonylamino)phenyl]ethyl}benzoic acid
2-{2-[4-(4-acetylaminobenzenesulfonyl amino)phenyl]ethyl}benzoic acid
2-[2-[4-(toluene-4-sulfonylamino)phenyl]ethyl}benzoic acid
2-{2-[4-(3-trifluoromethylbenzenesulfonylamino)phenyl]ethyl}benzoic acid
2-{2-[4-(naphthalene-1-sulfonylamino)phenyl]ethyl}benzoic acid
2-{2-[4-(2,5-dimethoxybenzenesulfonylamino)phenyl]ethyl}benzoic acid
2-{2-[4-(2,4-dimethylbenzenesulfonylamino)phenyl]ethyl}benzoic acid
2-{2-[4-(2-fluorobenzenesulfonylamino)phenyl]ethyl}benzoic acid
2-{2-[4-(2,4-difluorobenzenesulfonylamino)phenyl]ethyl}benzoic acid
2-{2-[4-(2-trifluoromethylbenzenesulfonylamino)phenyl]ethyl}benzoic acid
2-{2-[4-(4-fluorobenzenesulfonylamino)phenyl]ethyl}benzoic acid
2-{2-[4-(5-chloro-3-methylbenzo[b]thiophene-2-sulfonylamino)phenyl]ethyl]benzoic acid
2-{2-[4-(biphenyl-4-sulfonylamino)phenyl]ethyl}benzoic acid
2-{2-[4-(4-acetylbenzenesulfonylamino)phenyl]ethyl}benzoic acid
2-[2-(4-ethanesulfonylaminophenyl)ethyl]benzoic acid
2-{2-[4-(naphthalene-2-sulfonylamino)phenyl]ethyl}benzoic acid
2-{2-[4-(2-acetylamino-4-methylthiazole-5-sulfonylamino)phenyl]ethyl}benzoic acid
2-{2-[4-(2,5-dichlorobenzenesulfonylamino)phenyl]ethyl}benzoic acid
2-{2-[4-(2,4,6-trimethylbenzenesulfonylamino)phenyl]ethyl}benzoic acid
2-{2-[4-(4-tert-butylbenzenesulfonylamino)phenyl]ethyl}benzoic acid
2-{2-[4-(E)-2-phenylethenesulfonylamino)phenyl]ethyl}benzoic acid
2-{2-[4-(3,4-dimethoxybenzenesulfonylamino)phenyl]ethyl}benzoic acid
2-{2-[4-(4-trifluoromethoxybenzenesulfonylamino)phenyl]ethyl}benzoic acid
2-{2-[4-(thiophene-2-sulfonylamino)phenyl]ethyl}benzoic acid
2-{2-[4-(4-carboxybenzenesulfonylamino)phenyl]ethyl}benzoic acid
2-{2-[4-(propane-2-sulfonylamino)phenyl]ethyl}benzoic acid
2-{2-[4-(5-benzenesulfonylthiophene-2-sulfonylamino)phenyl]ethyl}benzoic acid
2-{2-[4-(2-trifluoromethoxybenzenesulfonylamino)phenyl]ethyl}benzoic acid
2-{2-[4-(4-butoxybenzenesulfonylamino)phenyl]ethyl}benzoic acid
2-{2-[4-(5-fluoro-2-methylbenzenesulfonylamino)phenyl]ethyl}benzoic acid
2-{2-[4-(2,6-difluorobenzenesulfonylamino)phenyl]ethyl}benzoic acid
2-{2-[4-(4-butylbenzenesulfonylamino)phenyl]ethyl}benzoic acid
2-{2-[4-(3-methoxybenzenesulfonylamino)phenyl]ethyl}benzoic acid
2-[2-(4-pentamethylbenzenesulfonylaminophenyl)ethyl]benzoic acid
2-{2-[4-(3,5-bis-trifluoromethylbenzenesulfonylamino)phenyl]ethyl}benzoic acid
2-{2-[4-(3-fluorobenzenesulfonylamino)phenyl]ethyl}benzoic acid
2-{2-[4-(toluene-3-sulfonylamino)phenyl]ethyl}benzoic acid
2-{2-[4-(4-benzenesulfonylthiophene-2-sulfonylamino)phenyl]ethyl}benzoic acid
2-(2-{4-[4-(1,1-dimethylpropyl)benzenesulfonylamino]phenyl}ethyl)benzoic acid
2-{2-[4-(2-cyanobenzenesulfonylamino)phenyl]ethyl}benzoic acid
2-{2-[4-(4-ethylbenzenesulfonylamino)phenyl]ethyl}benzoic acid
2-{2-[4-(4-trifluoromethylbenzenesulfonylamino)phenyl]ethyl}benzoic acid
2-{2-[4-(4-chlorobenzenesulfonyl amino)phenyl]ethyl}benzoic acid
2-[2-(4-methanesulfonylaminophenyl)ethyl]benzoic acid
2-{2-[4-(4-methoxybenzenesulfonylamino)phenyl]ethyl}benzoic acid
2-[2-(4-phenylmethanesulfonylaminophenyl)ethyl]benzoic acid
2-{2-[4-(butane-1-sulfonylamino)phenyl]ethyl}benzoic acid
2-[2-(4-benzenesulfonylaminophenyl)ethyl]benzoic acid
2-{2-[4-(2-nitrobenzenesulfonyl amino)phenyl]ethyl}benzoic acid
2-{2-[4-(2,4,6-triisopropylbenzenesulfonylamino)phenyl]ethyl}benzoic acid
2-{2-[4(4-propylbenzenesulfonylamino)phenyl]ethyl}benzoic acid
2-{2-[4-(4-isopropylbenzenesulfonylamino)phenyl]ethyl}benzoic acid 2-{2-[4-(7,7-dimethyl-2-oxobicyclo[2.2.1]hept-1-yl-methanesulfonylamino)-phenyl]ethyl]benzoic acid
2-{3-[2-(4-acetylaminobenzenesulfonylamino)phenyl]propyl}benzoic acid
2-{3-[2-(4-chlorobenzenesulfonylamino)phenyl]propyl}benzoic acid
2-{3-[2-(4-methoxybenzenesulfonylamino)phenyl]propyl}benzoic acid
2-{3-[2-(2-nitrobenzenesulfonylamino)phenyl]propyl}benzoic acid
2-{3-[2-(toluene-4-sulfonylamino)phenyl]propyl}benzoic acid
2-{3-[2-(3-trifluoromethylbenzenesulfonylamino)phenyl]propyl}benzoic acid
2-{3-[2-(naphthalene-1-sulfonylamino)phenyl]propyl}benzoic acid
2-{3-[2-(2,5-dimethoxybenzenesulfonylamino)phenyl]propyl}benzoic acid
2-{3-[2-(2,4-dimethylbenzenesulfonylamino)phenyl]propyl}benzoic acid
2-{3-[2-(2-fluorobenzenesulfonylamino)phenyl]propyl}benzoic acid
2-{3-[2-(2,4-difluorobenzenesulfonylamino)phenyl]propyl}benzoic acid
2-{3-[2-(2-trifluoromethylbenzenesulfonylamino)phenyl]propyl}benzoic acid
2-{3-[2-(4-fluorobenzenesulfonylamino)phenyl]propyl}benzoic acid
2-{3-[2-(5-chloro-3-methylbenzo[b]thiophene-2-sulfonylamino)phenyl]propyl}benzoic acid
2-{3-[2-(biphenyl-4-sulfonylamino)phenyl]propyl}benzoic acid
2-{3-[2-(4-acetylbenzenesulfonylamino)phenyl]propyl}benzoic acid
2-{3-[2-(5-dimethylaminonaphthalene-1-sulfonylamino)phenyl]propyl}benzoic acid
2-{3-[2-(naphthalene-2-sulfonylamino)phenyl]propyl}benzoic acid
2-{3-[2-(2-acetylamino-4-methylthiazole-5-sulfonylamino)phenyl]propyl}benzoic acid
2-[3-(2-benzenesulfonylaminophenyl)propyl]benzoic acid
2-{3-[2-(2,5-dichlorobenzenesulfonylamino)phenyl]propyl}benzoic acid
2-{3-[2-(2,4,6-trimethylbenzenesulfonylamino)phenyl]propyl}benzoic acid
2-{3-[2-(4-isopropylbenzenesulfonylamino)phenyl]propyl}benzoic acid
2-{3-[2-((E)-2-phenylethenesulfonylamino)phenyl]propyl}benzoic acid
2-{3-[2-(3,4-dimethoxybenzenesulfonylamino)phenyl]propyl}benzoic acid
2-{3-[2-(4-trifluoromethoxybenzenesulfonylamino)phenyl]propyl}benzoic acid
2-{3-[2-(4-carboxybenzenesulfonylamino)phenyl]propyl}benzoic acid
2-{3-[2-(5-benzenesulfonylthiophene-2-sulfonylamino)phenyl]propyl}benzoic acid
2-{3-[2-(2-trifluoromethoxybenzenesulfonylamino)phenyl]propyl}benzoic acid
2-{3-[2-(4-butoxybenzenesulfonylamino)phenyl]propyl}benzoic acid
2-{3-[2-(5-fluoro-2-methylbenzenesulfonylamino)phenyl]propyl}benzoic acid
2-{3-[2-(2,6-difluorobenzenesulfonylamino)phenyl]propyl}benzoic acid
2-{3-[2-(4-butylbenzenesulfonylamino)phenyl]propyl}benzoic acid
2-{3-[2-(3-methoxybenzenesulfonylamino)phenyl]propyl}benzoic acid
2-[3-(2,3,4,5,6-pentamethylbenzenesulfonylaminophenyl)propyl]benzoic acid
2-{3-[2-(4-propylbenzenesulfonylamino)phenyl]propyl}benzoic acid
2-{3-[2-(4-isopropylbenzenesulfonylamino)phenyl]propyl}benzoic acid
2-{3-[2-(3-fluorobenzenesulfonylamino)phenyl]propyl}benzoic acid
2-{3-[2-(toluene-3-sulfonylamino)phenyl]propyl}benzoic acid
2-{3-[2-(4-benzenesulfonylthiophene-2-sulfonylamino)phenyl]propyl}benzoic acid
3-{3-[2-(4-acetylaminobenzenesulfonylamino)phenyl]propyl}benzoic acid
3-{3-[2-(4-chlorobenzenesulfonylamino)phenyl]propyl}benzoic acid
3-[3-(2-methanesulfonylaminophenyl)propyl]benzoic acid
3-{3-[2-(4-methoxybenzenesulfonylamino)phenyl]propyl}benzoic acid
3-{3-[2-(2-nitrobenzenesulfonylamino)phenyl]propyl}benzoic acid
3-{3-[2-(toluene-4-sulfonylamino)phenyl]propyl}benzoic acid
3-{3-[2-(3-trifluoromethylbenzenesulfonylamino)phenyl]propyl}benzoic acid
3-{3-[2-(naphthalene-1-sulfonylamino)phenyl]propyl}benzoic acid
3-[3-(2-phenylmethanesulfonylaminophenyl)propyl]benzoic acid
3-{3-[2-(2,5-dimethoxybenzenesulfonylamino)phenyl]propyl}benzoic acid
3-{3-[2-(2,4-dimethylbenzenesulfonylamino)phenyl]propyl}benzoic acid
3-{3-[2-(2-fluorobenzenesulfonylamino)phenyl]propyl}benzoic acid
3-{3-[2-(2,4-difluorobenzenesulfonylamino)phenyl]propyl}benzoic acid
3-{3-[2-(2-trifluoromethylbenzenesulfonylamino)phenyl]propyl}benzoic acid
3-{3-[2-(4-fluorobenzenesulfonylamino)phenyl]propyl}benzoic acid
3-{3-[2-(biphenyl-4-sulfonylamino)phenyl]propyl}benzoic acid
3-{3-[2-(4-acetylbenzenesulfonylamino)phenyl]propyl}benzoic acid
3-[3-(2-ethanesulfonyl aminophenyl)propyl]benzoic acid
3-{3-[2-(butane-1-sulfonylamino)phenyl]propyl}benzoic acid
3-{3-[2-(4-methoxy-2,3,6-trimethylbenzenesulfonylamino)phenyl]propyl}benzoic acid
3-{3-[2-(5-dimethylaminonaphthalene-1-sulfonylamino)phenyl]propyl}benzoic acid
3-{3-[2-(naphthalene-2-sulfonylamino)phenyl]propyl}benzoic acid
3-{3-[2-(2-acetylamino-4-methylthiazole-5-sulfonylamino)phenyl]propyl}benzoic acid
3-[3-(2-benzenesulfonylaminophenyl)propyl]benzoic acid
3-{3-[2-(2,5-dichlorobenzenesulfonylamino)phenyl]propyl}benzoic acid
3-{3-[2-(2,4,6-triisopropylbenzenesulfonylamino)phenyl]propyl}benzoic acid 3-{3-[2-(2,4,6-trimethylbenzenesulfonylamino)phenyl]
propyl}benzoic acid
3-{3-[2-(4-tert-butylbenzenesulfonylamino)phenyl]
propyl}benzoic acid
3-[3-(2-trifluoromethanesulfonylaminophenyl)propyl]
benzoic acid
3-{3-[2-((E)-2-phenylethenesulfonylamino)phenyl]
propyl}benzoic acid
3-{3-[2-(3,4-dimethoxybenzenesulfonylamino)phenyl]
propyl}benzoic acid
3-{3-[2-(thiophene-2-sulfonylamino)phenyl]
propyl}benzoic acid
3-{3-[2-(propane-2-sulfonylamino)phenyl]
propyl}benzoic acid
3-{3-[2-(5-benzenesulfonylthiophene-2-sulfonylamino)
phenyl]propyl}benzoic acid
3-{3-[2-(2-trifluoromethoxybenzenesulfonylamino)phe-
nyl]propyl}benzoic acid
3-{3-[2-(4-butoxybenzenesulfonylamino)phenyl]
propyl}benzoic acid
3-{3-[2-(5-fluoro-2-methylbenzenesulfonylamino)phe-
nyl]propyl}benzoic acid
3-{3-[2-(2,6-difluorobenzenesulfonylamino)phenyl]
propyl}benzoic acid
3-{3-[2-(4-butylbenzenesulfonylamino)phenyl]
propyl}benzoic acid
3-{3-[2-(3-methoxybenzenesulfonylamino)phenyl]
propyl}benzoic acid
3-[3-(2-pentamethylbenzenesulfonylaminophenyl)pro-
pyl]benzoic acid
3-{3-[2-(3,5-bis-trifluoromethylbenzenesulfonylamino)
phenyl]propyl}benzoic acid
3-{3-[2-(4-propylbenzenesulfonylamino)phenyl]
propyl}benzoic acid
3-{3-[2-(4-isopropylbenzenesulfonylamino)phenyl]
propyl}benzoic acid
3-{3-[2-(3-fluorobenzenesulfonylamino)phenyl]
propyl}benzoic acid
3-{3-[2-(toluene-3-sulfonylamino)phenyl]
propyl}benzoic acid
3-{3-[2-(4-benzenesulfonylthiophene-2-sulfonylamino)
phenyl]propyl}benzoic acid
3-(3-{2-[4-(1,1-dimethylpropyl)benzenesulfonylamino]
phenyl}propyl)benzoic acid
3-{3-[2-(2-cyanobenzenesulfonylamino)phenyl]
propyl}benzoic acid
3-{3-[2-(4-ethylbenzenesulfonylamino)phenyl]
propyl}benzoic acid
3-{3-[2-(4-trifluoromethylbenzenesulfonylamino)phenyl]
propyl}benzoic acid
3-{3-[2-(7,7-dimethyl-2-oxobicyclo[2.2.1]hept-1-yl-
methanesulfonylamino)phenyl]-propyl}benzoic acid
4-{3-[2-(4-acetylaminobenzenesulfonylamino)phenyl]
propyl}benzoic acid
4-{3-[2-(4-chlorobenzenesulfonylamino)phenyl]
propyl}benzoic acid
4-[3-(2-methanesulfonylaminophenyl)propyl]benzoic
acid
4-{3-[2-(4-methoxybenzenesulfonylamino)phenyl]
propyl}benzoic acid
4-{3-[2-(2-nitrobenzenesulfonyl amino)phenyl]
propyl}benzoic acid
4-{3-[2-(toluene-4-sulfonylamino)phenyl]
propyl}benzoic acid
4-{3-[2-(3-trifluoromethylbenzenesulfonylamino)phenyl]
propyl}benzoic acid
4-{3-[2-(naphthalene-1-sulfonylamino)phenyl]
propyl}benzoic acid
4-[3-(2-phenylmethanesulfonylaminophenyl)propyl]ben-
zoic acid
4-{3-[2-(2,5-dimethoxybenzenesulfonylamino)phenyl]
propyl}benzoic acid
4-{3-[2-(2,4-dimethylbenzenesulfonylamino)phenyl]
propyl}benzoic acid
4-{3-[2-(2-fluorobenzenesulfonylamino)phenyl]
propyl}benzoic acid
4-{3-[2-(2,4-difluorobenzenesulfonylamino)phenyl]
propyl}benzoic acid
4-{3-[2-(2-trifluoromethylbenzenesulfonylamino)phenyl]
propyl}benzoic acid
4-{3-[2-(4-fluorobenzenesulfonylamino)phenyl]
propyl}benzoic acid
4-{3-[2-(biphenyl-4-sulfonylamino)phenyl]
propyl}benzoic acid
4-{3-[2-(4-acetylbenzenesulfonylamino)phenyl]
propyl}benzoic acid
4-[3-(2-ethanesulfonylaminophenyl)propyl]benzoic acid
4-{3-[2-(butane-1-sulfonylamino)phenyl]propyl}benzoic
acid
4-{3-[2-(4-methoxy-2,3,6-trimethylbenzenesulfony-
lamino)phenyl]propyl}benzoic acid
4-{3-[2-(5-dimethylaminonaphthalene-1-sulfonylamino)
phenyl]propyl}benzoic acid
4-{3-[2-(naphthalene-2-sulfonylamino)phenyl]
propyl}benzoic acid
4-{3-[2-(2-acetylamino-4-methylthiazole-5-sulfony-
lamino)phenyl]propyl}benzoic acid
4-[3-(2-benzenesulfonylaminophenyl)propyl]benzoic
acid
4-{3-[2-(2,5-dichlorobenzenesulfonylamino)phenyl]
propyl}benzoic acid
4-{3-[2-(2,4,6-trimethylbenzenesulfonylamino)phenyl]
propyl}benzoic acid
4-{3-[2-(4-tert-butylbenzenesulfonylamino)phenyl]
propyl}benzoic acid
4-{3-[2-(E)-2-phenylethenesulfonylamino)phenyl]
propyl}benzoic acid
4-{3-[2-(3,4-dimethoxybenzenesulfonylamino)phenyl]
propyl}benzoic acid
4-{3-[2-(4-trifluoromethoxybenzenesulfonylamino)phe-
nyl]propyl}benzoic acid
4-{3-[2-(thiophene-2-sulfonylamino)phenyl]
propyl}benzoic acid
4-{3-[2-(propane-2-sulfonylamino)phenyl]
propyl}benzoic acid
4-{3-[2-(5-benzenesulfonylthiophene-2-sulfonylamino)
phenyl]propyl}benzoic acid
4-{3-[2-(2-trifluoromethoxybenzenesulfonylamino)phe-
nyl]propyl}benzoic acid
4-{3-[2-(4-butoxybenzenesulfonylamino)phenyl]
propyl}benzoic acid
4-{3-[2-(5-fluoro-2-methylbenzenesulfonylamino)phe-
nyl]propyl}benzoic acid
4-{3-[2-(2,6-difluorobenzenesulfonylamino)phenyl]
propyl}benzoic acid
4-{3-[2-(4-butylbenzenesulfonylamino)phenyl]
propyl}benzoic acid
4-{3-[2-(3-methoxybenzenesulfonylamino)phenyl]
propyl}benzoic acid
4-[3-(2,3,4,5,6-pentamethylbenzenesulfony-
laminophenyl)propyl]benzoic acid
4-{3-[2-(3,5-bis-trifluoromethylbenzenesulfonylamino)
phenyl]propyl}benzoic acid 4-{3-[2-(4-propylbenzenesulfonylamino)phenyl]propyl}benzoic acid
4-{3-[2-(4-isopropylbenzenesulfonylamino)phenyl]propyl}benzoic acid
4-{3-[2-(3-fluorobenzenesulfonylamino)phenyl]propyl}benzoic acid
4-{3-[2-(toluene-3-sulfonylamino)phenyl]propyl}benzoic acid
4-{3-[2-(4-benzenesulfonylthiophene-2-sulfonylamino)phenyl]propyl}benzoic acid
4-(3-{2-[4-(1,1-dimethylpropyl)benzenesulfonylamino]phenyl}propyl)benzoic acid
4-{3-[2-(2-cyanobenzenesulfonylamino)phenyl]propyl}benzoic acid
4-{3-[2-(4-ethylbenzenesulfonylamino)phenyl]propyl}benzoic acid
4-{3-[2-(4-trifluoromethylbenzenesulfonylamino)phenyl]propyl}benzoic acid
2-{5-[2-(4-acetylaminobenzenesulfonylamino)phenyl]pentyl}benzoic acid
2-{5-[2-(4-chlorobenzenesulfonylamino)phenyl]pentyl}benzoic acid
2-[5-(2-methanesulfonylaminophenyl)pentyl]benzoic acid
2-{5-[2-(4-methoxybenzenesulfonylamino)phenyl]pentyl}benzoic acid
2-{5-[2-(2-nitrobenzenesulfonylamino)phenyl]pentyl}benzoic acid
2-{5-[2-(toluene-4-sulfonylamino)phenyl]pentyl}benzoic acid
2-{5-[2-(3-trifluoromethylbenzenesulfonylamino)phenyl]pentyl}benzoic acid
2-{5-[2-(naphthalene-1-sulfonylamino)phenyl]pentyl}benzoic acid
2-[5-(2-phenylmethanesulfonylaminophenyl)pentyl]benzoic acid
2-{5-[2-(2,5-dimethoxybenzenesulfonylamino)phenyl]pentyl}benzoic acid
2-{5-[2-(2,4-dimethylbenzenesulfonylamino)phenyl]pentyl}benzoic acid
2-{5-[2-(2-fluorobenzenesulfonylamino)phenyl]pentyl}benzoic acid
2-{5-[2-(2,4-difluorobenzenesulfonylamino)phenyl]pentyl}benzoic acid
2-{5-[2-(2-trifluoromethylbenzenesulfonylamino)phenyl]pentyl}benzoic acid
2-{5-[2-(4-fluorobenzenesulfonylamino)phenyl]pentyl}benzoic acid
2-{5-[2-(4-acetylbenzenesulfonylamino)phenyl]pentyl}benzoic acid
2-[5-(2-ethanesulfonylaminophenyl)pentyl]benzoic acid
2-{5-[2-(4-methoxy-2,3,6-trimethylbenzenesulfonylamino)phenyl]pentyl}benzoic acid
2-{5-[2-(5-dimethylaminonaphthalene-1-sulfonylamino)phenyl]pentyl}benzoic acid
2-{5-[2-(naphthalene-2-sulfonylamino)phenyl]pentyl}benzoic acid
2-[5-(2-benzenesulfonylaminophenyl)pentyl]benzoic acid
2-{5-[2-(2,5-dichlorobenzenesulfonylamino)phenyl]pentyl}benzoic acid
2-{5-[2-(2,4,6-triisopropylbenzenesulfonylamino)phenyl]pentyl}benzoic acid
2-{5-[2-(2,4,6-trimethylbenzenesulfonylamino)phenyl]pentyl}benzoic acid
2-{5-[2-(4-tert-butylbenzenesulfonylamino)phenyl]pentyl}benzoic acid
2-{5-[2-(3,4-dimethoxybenzenesulfonylamino)phenyl]pentyl}benzoic acid
2-{5-[2-(4-trifluoromethoxybenzenesulfonylamino)phenyl]pentyl}benzoic acid
2-{5-[2-(thiophene-2-sulfonylamino)phenyl]pentyl}benzoic acid
2-{5-[2-(quinoline-8-sulfonylamino)phenyl]pentyl}benzoic acid
2-{5-[2-(2-trifluoromethoxybenzenesulfonylamino)phenyl]pentyl}benzoic acid
2-{5-[2-(4-butoxybenzenesulfonylamino)phenyl]pentyl}benzoic acid
2-{5-[2-(2,6-difluorobenzenesulfonylamino)phenyl]pentyl}benzoic acid
2-{5-[2-(3-methoxybenzenesulfonylamino)phenyl]pentyl}benzoic acid
2-[5-(2-pentamethylbenzenesulfonylaminophenyl)pentyl]benzoic acid
2-{5-[2-(4-propylbenzenesulfonylamino)phenyl]pentyl}benzoic acid
2-{5-[2-(4-isopropylbenzenesulfonylamino)phenyl]pentyl}benzoic acid
2-{5-[2-(toluene-3-sulfonylamino)phenyl]pentyl}benzoic acid
2-{5-[2-(4-benzenesulfonylthiophene-2-sulfonylamino)phenyl]pentyl}benzoic acid
2-(5-{2-[4-(1,1-dimethylpropyl)benzenesulfonylamino]phenyl}pentyl)benzoic acid
2-{5-[2-(2-carboxybenzenesulfonylamino)phenyl]pentyl}benzoic acid
2-{5-[2-(4-ethylbenzenesulfonylamino)phenyl]pentyl}benzoic acid
2-{5-[2-(4-trifluoromethylbenzenesulfonylamino)phenyl]pentyl}benzoic acid
2-{5-[2-(3-methoxybenzoylamino)phenyl]pentyl}benzoic acid
2-{5-[2-(4-tert-butylbenzoylamino)phenyl]pentyl}benzoic acid
2-{5-[2-(3-carboxypropionylamino)phenyl]pentyl}benzoic acid
2-{5-[2-(4-carboxybutyrylamino)phenyl]pentyl}benzoic acid
2-(5-{2-[2-(4-chlorophenyl)acetylamino]phenyl}pentyl)benzoic acid
2-{5-[2-(4-chlorobenzoylamino)phenyl]pentyl}benzoic acid
2-{5-[2-(3,4-dichlorobenzoylamino)phenyl]pentyl}benzoic acid
2-{5-[2-(2,6-dichlorobenzoylamino)phenyl]pentyl}benzoic acid
2-{5-[2-(2-carboxyacetylamino)phenyl]pentyl}benzoic acid
2-{5-[2-(2-fluorobenzoylamino)phenyl]pentyl}benzoic acid
2-{5-[2-(3-phenylpropionylamino)phenyl]pentyl}benzoic acid
2-{5-[2-(3-methylbutyrylamino)phenyl]pentyl}benzoic acid
2-{5-[2-(2-phenoxyacetylamino)phenyl]pentyl}benzoic acid
2-[5-(2-phenylacetylaminophenyl)pentyl]benzoic acid
2-{5-[2-(2,2-dimethylpropionylamino)phenyl]pentyl}benzoic acid
2-{5-[2-(2-methylbenzoylamino)phenyl]pentyl}benzoic acid
2-{5-[2-(4-methylbenzoylamino)phenyl]pentyl}benzoic acid 2-{5-[2-(3,5-difluorobenzoylamino)phenyl]pentyl}benzoic acid
2-(5-{2-[((1R,2R)-2-phenylcyclopropanecarbonyl)amino]phenyl}pentyl)benzoic acid
2-{5-[2-(2-ethylhexanoylamino)phenyl]pentyl}benzoic acid
2-{5-[2-(4-ethylbenzoylamino)phenyl]pentyl}benzoic acid
2-{5-[2-(3,5-dichlorobenzoylamino)phenyl]pentyl}benzoic acid
2-(5-{2-[(naphthalene-2-carbonyl)amino]phenyl}pentyl)benzoic acid
2-{5-[2-(2-benzyloxyacetylamino)phenyl]pentyl}benzoic acid
2-{5-[2-(2-methoxyacetylamino)phenyl]pentyl}benzoic acid
2-{5-[2-(cyclohexanecarbonylamino)phenyl]pentyl}benzoic acid
2-[5-(2-butyrylaminophenyl)pentyl]benzoic acid
2-{5-[2-(cyclopentanecarbonylamino)phenyl]pentyl}benzoic acid
2-[5-(2-isobutyrylaminophenyl)pentyl]benzoic acid
2-{5-[2-(2-hydroxyacetylamino)phenyl]pentyl}benzoic acid
2-{5-[2-(2-phenylbutyrylamino)phenyl]pentyl}benzoic acid
2-[5-(2-propionylaminophenyl)pentyl]benzoic acid
2-(5-{2-[2-(4-fluorophenyl)acetylamino]phenyl}pentyl)benzoic acid
2-{5-[2-((S)-2-hydroxypropionylamino)phenyl]pentyl}benzoic acid
2-(5-{2-[2-(4-methoxyphenyl)acetylamino]phenyl}pentyl)benzoic acid
2-{5-[2-(2-ethylbutyrylamino)phenyl]pentyl}benzoic acid
2-{5-[2-(2-methylpentanoylamino)phenyl]pentyl}benzoic acid
2-{5-[2-(3-cyclopentylpropionylamino)phenyl]pentyl}benzoic acid
2-{5-[2-(2-methylbutyrylamino)phenyl]pentyl}benzoic acid
2-(5-{2-[(quinoxaline-2-carbonyl)amino]phenyl}pentyl)benzoic acid
2-{5-[2-(2,3-difluorobenzoylamino)phenyl]pentyl}benzoic acid
2-{5-[2-(2-fluoro-4-trifluoromethylbenzoylamino)phenyl]pentyl}benzoic acid
2-{5-[2-(3-chlorobenzoylamino)phenyl]pentyl}benzoic acid
2-{5-[2-(4-methoxybenzoylamino)phenyl]pentyl}benzoic acid
2-[5-(2-benzoylaminophenyl)pentyl]benzoic acid
2-{5-[2-(3,3-dimethylbutyrylamino)phenyl]pentyl}benzoic acid
2-{5-[2-(2-chlorobenzoylamino)phenyl]pentyl}benzoic acid
2-{5-[2-(4-fluorobenzoylamino)phenyl]pentyl}benzoic acid
2-(5-{2-[(naphthalene-1-carbonyl)amino]phenyl}pentyl)benzoic acid
4-{2-[2-(4-acetylaminobenzenesulfonylamino)phenoxy]ethoxy}benzoic acid
4-{2-[2-(4-chlorobenzenesulfonylamino)phenoxy]ethoxy}benzoic acid
4-[2-(2-methanesulfonylaminophenoxy)ethoxy]benzoic acid
4-{2-[2-(4-methoxybenzenesulfonylamino)phenoxy]ethoxy}benzoic acid
4-{2-[2-(2-nitrobenzenesulfonylamino)phenoxy]ethoxy}benzoic acid
4-{2-[2-(toluene-4-sulfonylamino)phenoxy]ethoxy}benzoic acid
4-{2-[2-(3-trifluoromethylbenzenesulfonylamino)phenoxy]ethoxy}benzoic acid
4-{2-[2-(naphthalene-1-sulfonylamino)phenoxy]ethoxy}benzoic acid
4-[2-(2-phenylmethanesulfonylaminophenoxy)ethoxy]benzoic acid
4-{2-[2-(2,5-dimethoxybenzenesulfonylamino)phenoxy]ethoxy}benzoic acid
4-{2-[2-(2,4-dimethylbenzenesulfonylamino)phenoxy]ethoxy}benzoic acid
4-{2-[2-(2-fluorobenzenesulfonylamino)phenoxy]ethoxy}benzoic acid
4-{2-[2-(2,4-difluorobenzenesulfonylamino)phenoxy]ethoxy}benzoic acid
4-{2-[2-(2-trifluoromethylbenzenesulfonylamino)phenoxy]ethoxy}benzoic acid
4-{2-[2-(4-fluorobenzenesulfonylamino)phenoxy]ethoxy}benzoic acid
4-{2-[2-(biphenyl-4-sulfonylamino)phenoxy]ethoxy}benzoic acid
4-{2-[2-(4-acetylbenzenesulfonylamino)phenoxy]ethoxy}benzoic acid
4-[2-(2-ethanesulfonylaminophenoxy)ethoxy]benzoic acid
4-{2-[2-(butane-1-sulfonylamino)phenoxy]ethoxy}benzoic acid
4-{2-[2-(4-methoxy-2,3,6-trimethylbenzenesulfonylamino)phenoxy]ethoxy}benzoic acid
4-{2-[2-(5-dimethylaminonaphthalene-1-sulfonylamino)phenoxy]ethoxy}benzoic acid
4-{2-[2-(naphthalene-2-sulfonylamino)phenoxy]ethoxy}benzoic acid
4-{2-[2-(2-acetylamino-4-methylthiazole-5-sulfonylamino)phenoxy]ethoxy}benzoic acid
4-[2-(2-benzenesulfonylaminophenoxy)ethoxy]benzoic acid
4-{2-[2-(2,5-dichlorobenzenesulfonylamino)phenoxy]ethoxy}benzoic acid
4-{2-[2-(2,4,6-triisopropylbenzenesulfonylamino)phenoxy]ethoxy}benzoic acid
4-{2-[2-(2,4,6-trimethylbenzenesulfonylamino)phenoxy]ethoxy}benzoic acid
4-{2-[2-(4-tert-butylbenzenesulfonylamino)phenoxy]ethoxy}benzoic acid
4-{2-[2-(E)-2-phenylethenesulfonylamino)phenoxy]ethoxy}benzoic acid
4-{2-[2-(3,4-dimethoxybenzenesulfonylamino)phenoxy]ethoxy}benzoic acid
4-{2-[2-(4-trifluoromethoxybenzenesulfonylamino)phenoxy]ethoxy}benzoic acid
4-{2-[2-(thiophene-2-sulfonylamino)phenoxy]ethoxy}benzoic acid
4-{2-[2-(4-carboxybenzenesulfonylamino)phenoxy]ethoxy}benzoic acid
4-{2-[2-(quinoline-8-sulfonylamino)phenoxy]ethoxy}benzoic acid
4-{2-[2-(5-benzenesulfonylthiophene-2-sulfonylamino)phenoxy]ethoxy}benzoic acid
4-{2-[2-(2-trifluoromethoxybenzenesulfonylamino)phenoxy]ethoxy}benzoic acid 4-{2-[2-(4-butoxybenzenesulfonylamino)phenoxy]ethoxy}benzoic acid
4-{2-[2-(5-fluoro-2-methylbenzenesulfonylamino)phenoxy]ethoxy}benzoic acid
4-{2-[2-(2,6-difluorobenzenesulfonylamino)phenoxy]ethoxy}benzoic acid
4-{2-[2-(4-butylbenzenesulfonylamino)phenoxy]ethoxy}benzoic acid
4-{2-[2-(3-methoxybenzenesulfonylamino)phenoxy]ethoxy}benzoic acid
4-[2-(2-pentamethylbenzenesulfonylaminophenoxy)ethoxy]benzoic acid
4-{2-[2-(3,5-bis-trifluoromethylbenzenesulfonylamino)phenoxy]ethoxy}benzoic acid
4-{2-[2-(4-propylbenzenesulfonylamino)phenoxy]ethoxy}benzoic acid
4-{2-[2-(4-isopropylbenzenesulfonylamino)phenoxy]ethoxy}benzoic acid
4-{2-[2-(3-fluorobenzenesulfonylamino)phenoxy]ethoxy}benzoic acid
4-{2-[2-(toluene-3-sulfonylamino)phenoxy]ethoxy}benzoic acid
4-{2-[2-(4-benzenesulfonylthiophene-2-sulfonylamino)phenoxy]ethoxy}benzoic acid
4-(2-{2-[4-(1,1-dimethylpropyl)benzenesulfonylamino]phenoxy}ethoxy)benzoic acid
4-{2-[2-(2-carboxybenzenesulfonylamino)phenoxy]ethoxy}benzoic acid
4-{2-[2-(2-cyanobenzenesulfonylamino)phenoxy]ethoxy}benzoic acid
4-{2-[2-(4-ethylbenzenesulfonylamino)phenoxy]ethoxy}benzoic acid
4-{2-[2-(4-trifluoromethylbenzenesulfonylamino)phenoxy]ethoxy}benzoic acid
4-{2-[2-(7,7-dimethyl-2-oxobicyclo[2.2.1]hept-1-yl-methanesulfonylamino)phenoxy]ethoxy}benzoic acid
2-{2-[4-(4-chlorobenzenesulfonylamino)phenoxy]ethoxy}benzoic acid
2[2-(4-methanesulfonylaminophenoxy)ethoxy]benzoic acid
2-{2-[4-(4-methoxybenzenesulfonylamino)phenoxy]ethoxy}benzoic acid
2-{2-[4-(2-nitrobenzenesulfonylamino)phenoxy]ethoxy}benzoic acid
2-{2-[4-(toluene-4-sulfonylamino)phenoxy]ethoxy}benzoic acid
2-[2-(4-phenylmethanesulfonylaminophenoxy)ethoxy]benzoic acid
2-{2-[4-(2,5-dimethoxybenzenesulfonylamino)phenoxy]ethoxy}benzoic acid
2-{2-[4-(2-fluorobenzenesulfonylamino)phenoxy]ethoxy}benzoic acid
2-{2-[4-(2,4-difluorobenzenesulfonylamino)phenoxy]ethoxy}benzoic acid
2-{2-[4-(2-trifluoromethylbenzenesulfonylamino)phenoxy]ethoxy}benzoic acid
2-{2-[4-(4-fluorobenzenesulfonylamino)phenoxy]ethoxy}benzoic acid
2-{2-[4-(biphenyl-4-sulfonylamino)phenoxy]ethoxy}benzoic acid
2-{2-[4-(4-acetylbenzenesulfonylamino)phenoxy]ethoxy}benzoic acid
2-[2-(4-ethanesulfonylaminophenoxy)ethoxy]benzoic acid
2-{2-[4-(butane-1-sulfonylamino)phenoxy]ethoxy}benzoic acid
2-{2-[4-(4-methoxy-2,3,6-trimethylbenzenesulfonylamino)phenoxy]ethoxy}benzoic acid
2-{2-[4-(naphthalene-2-sulfonylamino)phenoxy]ethoxy}benzoic acid
2-{2-[4-(2-acetylamino-4-methylthiazole-5-sulfonylamino)phenoxy]ethoxy}benzoic acid
2-[2-(4-benzenesulfonylaminophenoxy)ethoxy]benzoic acid
2-{2-[4-(2,5-dichlorobenzenesulfonylamino)phenoxy]ethoxy}benzoic acid
2-{2-[4-(2,4,6-triisopropylbenzenesulfonylamino)phenoxy]ethoxy}benzoic acid
2-{2-[4-(2,4,6-trimethylbenzenesulfonylamino)phenoxy]ethoxy}benzoic acid
2-{2-[4-(4-tert-butylbenzenesulfonylamino)phenoxy]ethoxy}benzoic acid
2-{2-[4-(E)-2-phenylethenesulfonylamino)phenoxy]ethoxy}benzoic acid
2-{2-[4-(3,4-dimethoxybenzenesulfonylamino)phenoxy]ethoxy}benzoic acid
2-{2-[4-(4-trifluoromethoxybenzenesulfonylamino)phenoxy]ethoxy}benzoic acid
2-{2-[4-(thiophene-2-sulfonylamino)phenoxy]ethoxy}benzoic acid
2-{2-[4-(4-carboxybenzenesulfonylamino)phenoxy]ethoxy}benzoic acid
2-{2-[4-(2-trifluoromethoxybenzenesulfonylamino)phenoxy]ethoxy}benzoic acid
2-{2-[4-(4-butoxybenzenesulfonylamino)phenoxy]ethoxy}benzoic acid
2-{2-[4-(5-fluoro-2-methylbenzenesulfonylamino)phenoxy]ethoxy}benzoic acid
2-{2-[4-(4-butylbenzenesulfonylamino)phenoxy]ethoxy}benzoic acid
2-{2-[4-(3-methoxybenzenesulfonylamino)phenoxy]ethoxy}benzoic acid
2-[2-(4-pentamethylbenzenesulfonylaminophenoxy)ethoxy]benzoic acid
2-{2-[4-(3,5-bis-trifluoromethylbenzenesulfonylamino)phenoxy]ethoxy}benzoic acid
2-{2-[4-(4-propylbenzenesulfonylamino)phenoxy]ethoxy}benzoic acid
2-{2-[4-(4-isopropylbenzenesulfonylamino)phenoxy]ethoxy}benzoic acid
2-{2-[4-(3-fluorobenzenesulfonylamino)phenoxy]ethoxy}benzoic acid
2-{2-[4-(toluene-3-sulfonylamino)phenoxy]ethoxy}benzoic acid
2-{2-[4-(4-benzenesulfonylthiophene-2-sulfonylamino)phenoxy]ethoxy}benzoic acid
2-(2-{4-[4-(1,1-dimethylpropyl)benzenesulfonylamino]phenoxy}ethoxy)benzoic acid
2-{2-[4-(2-carboxybenzenesulfonylamino)phenoxy]ethoxy}benzoic acid
2-{2-[4-(2-cyanobenzenesulfonylamino)phenoxy]ethoxy}benzoic acid
2-{2-[4-(4-ethylbenzenesulfonylamino)phenoxy]ethoxy}benzoic acid
2-{2-[4-(4-trifluoromethylbenzenesulfonylamino)phenoxy]ethoxy}benzoic acid
2-{2-[4-(7,7-dimethyl-2-oxobicyclo[2.2.1]hept-1-yl-methanesulfonylamino)phenoxy]ethoxy}benzoic acid
4-[2-(4-methanesulfonylaminophenoxy)ethoxy]benzoic acid
4-{2-[4-(4-methoxybenzenesulfonylamino)phenoxy]ethoxy}benzoic acid 4-{2-[4-(2-nitrobenzenesulfonylamino)phenoxy]ethoxy}benzoic acid
4-{2-[4-(toluene-4-sulfonylamino)phenoxy]ethoxy}benzoic acid
4-{2-[4-(3-trifluoromethylbenzenesulfonylamino)phenoxy]ethoxy}benzoic acid
4-{2-[4-(naphthalene-1-sulfonylamino)phenoxy]ethoxy}benzoic acid
4-[2-(4-phenylmethanesulfonylaminophenoxy)ethoxy]benzoic acid
4-{2-[4-(2,5-dimethoxybenzenesulfonylamino)phenoxy]ethoxy}benzoic acid
4-{2-[4-(2,4-dimethylbenzenesulfonylamino)phenoxy]ethoxy}benzoic acid
4-{2-[4-(2-fluorobenzenesulfonylamino)phenoxy]ethoxy}benzoic acid
4-{2-[4-(2,4-difluorobenzenesulfonylamino)phenoxy]ethoxy}benzoic acid
4-{2-[4-(2-trifluoromethylbenzenesulfonylamino)phenoxy]ethoxy}benzoic acid
4-{2-[4-(4-fluorobenzenesulfonylamino)phenoxy]ethoxy}benzoic acid
4-[2-(4-ethanesulfonylaminophenoxy)ethoxy]benzoic acid
4-{2-[4-(butane-1-sulfonylamino)phenoxy]ethoxy}benzoic acid
4-{2-[4-(4-methoxy-2,3,6-trimethylbenzenesulfonylamino)phenoxy]ethoxy}benzoic acid
4-{2-[4-(5-dimethylaminonaphthalene-1-sulfonylamino)phenoxy]ethoxy}benzoic acid
4-{2-[4-(naphthalene-2-sulfonylamino)phenoxy]ethoxy}benzoic acid
4-[2-(4-benzenesulfonylaminophenoxy)ethoxy]benzoic acid
4-{2-[4-(2,5-dichlorobenzenesulfonylamino)phenoxy]ethoxy}benzoic acid
4-{2-[4-(2,4,6-triisopropylbenzenesulfonylamino)phenoxy]ethoxy}benzoic acid
4-{2-[4-(2,4,6-trimethylbenzenesulfonylamino)phenoxy]ethoxy}benzoic acid
4-{2-[4-(4-tert-butylbenzenesulfonylamino)phenoxy]ethoxy}benzoic acid
4-[2-(4-trifluoromethanesulfonylaminophenoxy)ethoxy]benzoic acid
4-{2-[4-(E)-2-phenylethenesulfonylamino)phenoxy]ethoxy}benzoic acid
4-{2-[4-(3,4-dimethoxybenzenesulfonylamino)phenoxy]ethoxy}benzoic acid
4-{2-[4-(thiophene-2-sulfonylamino)phenoxy]ethoxy}benzoic acid
4-{2-[4-(propane-2-sulfonylamino)phenoxy]ethoxy}benzoic acid
4-{2-[4-(2,2,2-trifluoroethanesulfonylamino)phenoxy]ethoxy}benzoic acid
4-{2-[4-(quinoline-8-sulfonylamino)phenoxy]ethoxy}benzoic acid
4-{2-[4-(5-benzenesulfonylthiophene-2-sulfonylamino)phenoxy]ethoxy}benzoic acid
4-{2-[4-(2-trifluoromethoxybenzenesulfonylamino)phenoxy]ethoxy}benzoic acid
4-{2-[4-(4-butoxybenzenesulfonylamino)phenoxy]ethoxy}benzoic acid
4-{2-[4-(5-fluoro-2-methylbenzenesulfonylamino)phenoxy]ethoxy}benzoic acid
4-{2-[4-(2,6-difluorobenzenesulfonylamino)phenoxy]ethoxy}benzoic acid
4-{2-[4-(4-butylbenzenesulfonylamino)phenoxy]ethoxy}benzoic acid
4-{2-[4-(3-methoxybenzenesulfonylamino)phenoxy]ethoxy}benzoic acid
4-[2-(4-pentamethylbenzenesulfonylaminophenoxy)ethoxy]benzoic acid
4-{2-[4-(3,5-bis-trifluoromethylbenzenesulfonylamino)phenoxy]ethoxy}benzoic acid
4-{2-[4-(4-propylbenzenesulfonylamino)phenoxy]ethoxy}benzoic acid
4-{2-[4-(4-isopropylbenzenesulfonylamino)phenoxy]ethoxy}benzoic acid
4-{2-[4-(3-fluorobenzenesulfonylamino)phenoxy]ethoxy}benzoic acid
4-{2-[4-(toluene-3-sulfonylamino)phenoxy]ethoxy}benzoic acid
4-{2-[4-(4-benzenesulfonylthiophene-2-sulfonylamino)phenoxy]ethoxy}benzoic acid
4-(2-{4-[4-(1,1-dimethylpropyl)benzenesulfonylamino]phenoxy}ethoxy)benzoic acid
4-{2-[4-(2-cyanobenzenesulfonylamino)phenoxy]ethoxy}benzoic acid
4-{2-[4-(4-ethylbenzenesulfonylamino)phenoxy]ethoxy}benzoic acid
4-{2-[4-(3,5-dichloro-2-hydroxybenzenesulfonylamino)phenoxy]ethoxy}benzoic acid
4-{2-[4-(7,7-dimethyl-2-oxobicyclo[2.2.1]hept-1-yl-methanesulfonylamino)phenoxy]ethoxy}benzoic acid
(2-{2-[4-(4-acetylaminobenzenesulfonylamino)phenoxy]ethoxy}phenyl)acetic acid
(2-{2-[4-(4-chlorobenzenesulfonylamino)phenoxy]ethoxy}phenyl)acetic acid
(2-{2-[4-(4-methoxybenzenesulfonylamino)phenoxy]ethoxy}phenyl)acetic acid
(2-{2-[4-(toluene-4-sulfonylamino)phenoxy]ethoxy}phenyl)acetic acid
(2-{2-[4-(3-trifluoromethylbenzenesulfonylamino)phenoxy]ethoxy}phenyl)acetic acid
(2-{2-[4-(2,5-dimethoxybenzenesulfonylamino)phenoxy]ethoxy}phenyl)acetic acid
(2-{2-[4-(2,4-dimethylbenzenesulfonylamino)phenoxy]ethoxy}phenyl)acetic acid
(2-{2-[4-(2-trifluoromethylbenzenesulfonylamino)phenoxy]ethoxy}phenyl)acetic acid
(2-{2-[4-(4-fluorobenzenesulfonylamino)phenoxy]ethoxy}phenyl)acetic acid
(2-{2-[4-(biphenyl-4-sulfonylamino)phenoxy]ethoxy}phenyl)acetic acid
(2-{2-[4-(4-acetylbenzenesulfonylamino)phenoxy]ethoxy}phenyl)acetic acid
{2-[2-(4-ethanesulfonylaminophenoxy)ethoxy]phenyl}acetic acid
(2-{2-[4-(butane-1-sulfonylamino)phenoxy]ethoxy}phenyl)acetic acid
(2-{2-[4-(4-methoxy-2,3,6-trimethylbenzenesulfonylamino)phenoxy]ethoxy}phenyl)acetic acid
(2-{2-[4-(5-dimethylaminonaphthalene-1-sulfonylamino)phenoxy]ethoxy}phenyl)acetic acid
(2-{2-[4-(naphthalene-2-sulfonylamino)phenoxy]ethoxy}phenyl)acetic acid
(2-{2-[4-(2-acetylamino-4-methylthiazole-5-sulfonylamino)phenoxy]ethoxy}phenyl)acetic acid
{2-[2-(4-benzenesulfonylaminophenoxy)ethoxy]phenyl}acetic acid
(2-{2-[4-2,5-dichlorobenzenesulfonylamino)phenoxy]ethoxy}phenyl)acetic acid (2-{2-[4-(2,4,6-triisopropylbenzenesulfonylamino)phenoxy]ethoxy}phenyl)acetic acid
(2-{2-[4-(2,4,6-trimethylbenzenesulfonylamino)phenoxy]ethoxy}phenyl)acetic acid
(2-{2-[4-(4-tert-butylbenzenesulfonylamino)phenoxy]ethoxy}phenyl)acetic acid
(2-{2-[4-((E)-2-phenylethenesulfonylamino)phenoxy]ethoxy}phenyl)acetic acid
(2-{2-[4-(3,4-dimethoxybenzenesulfonylamino)phenoxy]ethoxy}phenyl)acetic acid
(2-{2-[4-(4-trifluoromethoxybenzenesulfonylamino)phenoxy]ethoxy}phenyl)acetic acid
(2-{2-[4-(thiophene-2-sulfonylamino)phenoxy]ethoxy}phenyl)acetic acid
4-{4-[2-(2-carboxymethylphenoxy)ethoxy]phenylsulfamoyl}benzoic acid
(2-{2-[4-(quinoline-8-sulfonylamino)phenoxy]ethoxy}phenyl)acetic acid
(2-{2-[4-(5-benzenesulfonylthiophene-2-sulfonylamino)phenoxy]ethoxy}phenyl)acetic acid
(2-{2-[4-(2-trifluoromethoxybenzenesulfonylamino)phenoxy]ethoxy}phenyl)acetic acid
(2-{2-[4-(5-fluoro-2-methylbenzenesulfonylamino)phenoxy]ethoxy}phenyl)acetic acid
(2-{2-[4-(2,6-difluorobenzenesulfonylamino)phenoxy]ethoxy}phenyl)acetic acid
(2-{2-[4-(4-butylbenzenesulfonylamino)phenoxy]ethoxy}phenyl)acetic acid
(2-{2-[4-(3-methoxybenzenesulfonylamino)phenoxy]ethoxy}phenyl)acetic acid
{2-[2-(4-pentamethylbenzenesulfonylaminophenoxy)ethoxy]phenyl}acetic acid
(2-{2-[4-(3,5-bis-trifluoromethylbenzenesulfonylamino)phenoxy]ethoxy}phenyl)acetic acid
(2-{2-[4-(4-propylbenzenesulfonylamino)phenoxy]ethoxy}phenyl)acetic acid
(2-{2-[4-(4-isopropylbenzenesulfonylamino)phenoxy]ethoxy}phenyl)acetic acid
(2-{2-[4-(3-fluorobenzenesulfonylamino)phenoxy]ethoxy}phenyl)acetic acid
(2-{2-[4-(toluene-3-sulfonylamino)phenoxy]ethoxy}phenyl)acetic acid
(2-{2-[4-(4-benzenesulfonylthiophene-2-sulfonylamino)phenoxy]ethoxy}phenyl)acetic acid
[2-(2-{4-[4-(1,1-dimethylpropyl)benzenesulfonylamino]phenoxy}ethoxy)phenyl]acetic acid
methyl 2-{4-[2-(2-carboxymethylphenoxy)ethoxy]phenylsulfamoyl}benzoate
(2-{2-[4-(2-cyanobenzenesulfonylamino)phenoxy]ethoxy}phenyl)acetic acid
(2-{2-[4-(4-ethylbenzenesulfonylamino)phenoxy]ethoxy}phenyl)acetic acid
(2-{2-[4-(4-trifluoromethylbenzenesulfonylamino)phenoxy]ethoxy}phenyl)acetic acid
(2-{2-[4-(2-nitrobenzenesulfonylamino)phenoxy]ethoxy}phenyl)acetic acid
3-(2-{2-[4-(4-acetylaminobenzenesulfonylamino)phenoxy]ethoxy}phenyl)propionic acid
3-(2-{2-[4-(4-chlorobenzenesulfonylamino)phenoxy]ethoxy}phenyl)propionic acid
3-{2-[2-(4-methanesulfonylaminophenoxy)ethoxy]phenyl}propionic acid
3-(2-{2-[4-(4-methoxybenzenesulfonylamino)phenoxy]ethoxy}phenyl)propionic acid
3-(2-{2-[4-(toluene-4-sulfonylamino)phenoxy]ethoxy}phenyl)propionic acid
3-(2-{2-[4-(3-trifluoromethylbenzenesulfonylamino)phenoxy]ethoxy}phenyl)propionic acid
3-(2-{2-[4-(naphthalene-1-sulfonylamino)phenoxy]ethoxy}phenyl)propionic acid
3-(2-{2-[4-(2,5-dimethoxybenzenesulfonylamino)phenoxy]ethoxy}phenyl)propionic acid
3-(2-{2-[4-(2,4-dimethylbenzenesulfonylamino)phenoxy]ethoxy}phenyl)propionic acid
3-(2-{2-[4-(2-fluorobenzenesulfonylamino)phenoxy]ethoxy}phenyl)propionic acid
3-(2-{2-[4-(2,4-difluorobenzenesulfonylamino)phenoxy]ethoxy}phenyl)propionic acid
3-(2-{2-[4-(2-trifluoromethylbenzenesulfonylamino)phenoxy]ethoxy}phenyl)propionic acid
3-(2-{2-[4-(4-fluorobenzenesulfonylamino)phenoxy]ethoxy}phenyl)propionic acid
3-(2-{2-[4-(biphenyl-4-sulfonylamino)phenoxy]ethoxy}phenyl)propionic acid
3-(2-{2-[4-(4-acetylbenzenesulfonylamino)phenoxy]ethoxy}phenyl)propionic acid
3-{2-[2-(4-ethanesulfonylaminophenoxy)ethoxy]phenyl}propionic acid
3-(2-{2-[4-(butane-1-sulfonylamino)phenoxy]ethoxy}phenyl)propionic acid
3-(2-{2-[4-(4-methoxy-2,3,6-trimethylbenzenesulfonylamino)phenoxy]ethoxy}-phenyl)propionic acid
3-(2-{2-[4-(5-dimethylaminonaphthalene-1-sulfonylamino)phenoxy]ethoxy}phenyl)-propionic acid
3-(2-{2-[4-(naphthalene-2-sulfonylamino)phenoxy]ethoxy}phenyl)propionic acid
3-(2-{2-[4-(2-acetylamino-4-methylthiazole-5-sulfonylamino)phenoxy]-ethoxy}phenyl)propionic acid
3-{2-[2-(4-benzenesulfonylaminophenoxy)ethoxy]phenyl}propionic acid
3-(2-{2-[4-(2,4,6-trimethylbenzenesulfonylamino)phenoxy]ethoxy}phenyl)propionic acid
3-(2-{2-[4-(4-tert-butylbenzenesulfonylamino)phenoxy]ethoxy}phenyl)propionic acid
3-(2-{2-[4-((E)-2-phenylethenesulfonylamino)phenoxy]ethoxy}phenyl)propionic acid
3-(2-{2-[4-(3,4-dimethoxybenzenesulfonylamino)phenoxy]ethoxy}phenyl)propionic acid
3-(2-{2-[4-(4-trifluoromethoxybenzenesulfonylamino)phenoxy]ethoxy}phenyl)propionic acid
3-(2-{2-[4-(5-benzenesulfonylthiophene-2-sulfonylamino)phenoxy]ethoxy}phenyl)-propionic acid
3-(2-{2-[4-(2-trifluoromethoxybenzenesulfonylamino)phenoxy]ethoxy}phenyl)propionic acid
3-(2-{2-[4-(4-butoxybenzenesulfonylamino)phenoxy]ethoxy}phenyl)propionic acid
3-(2-{2-[4-(5-fluoro-2-methylbenzenesulfonylamino)phenoxy]ethoxy}phenyl)propionic acid
3-(2-{2-[4-(2,6-difluorobenzenesulfonylamino)phenoxy]ethoxy}phenyl)propionic acid
3-(2-{2-[4-(4-butylbenzenesulfonylamino)phenoxy]ethoxy}phenyl)propionic acid
3-(2-{2-[4-(3-methoxybenzenesulfonylamino)phenoxy]ethoxy}phenyl)propionic acid
3-{2-[2-(4-pentamethylbenzenesulfonylaminophenoxy)ethoxy]phenyl}propionic acid
3-(2-{2-[4-(3,5-bis-trifluoromethylbenzenesulfonylamino)phenoxy]ethoxy}-phenyl)propionic acid
3-(2-{2-[4-(4-propylbenzenesulfonylamino)phenoxy]ethoxy}phenyl)propionic acid
3-(2-{2-[4-(4-isopropylbenzenesulfonylamino)phenoxy]ethoxy}phenyl)propionic acid 3-(2-{2-[4-(3-fluorobenzenesulfonylamino)phenoxy]
ethoxy}phenyl)propionic acid
3-(2-{2-[4-(toluene-3-sulfonylamino)phenoxy]
ethoxy}phenyl)propionic acid methyl 2-(4-{2-[2-(2-carboxy-ethyl)phenoxy]ethoxy}phenylsulfamoyl)benzoate
3-(2-{2-[4-(4-ethylbenzenesulfonylamino)phenoxy]
ethoxy}phenyl)propionic acid
3-(2-{2-[4-(4-trifluoromethylbenzenesulfonylamino)phenoxy]ethoxy}phenyl)propionic acid
3-(2-{2-[4-(7,7-dimethyl-2-oxobicyclo[2.2.1]hept-1-yl-methanesulfonylamino)-phenoxy]ethoxy}phenyl)propionic acid
3-(2-{2-[4-(2-nitrobenzenesulfonylamino)phenoxy]
ethoxy}phenyl)propionic acid
4-{2-[2-(2-hydroxybenzoylamino)phenoxy]
ethoxy}benzoic acid
4-{2-[2-(3-methoxybenzoylamino)phenoxy]
ethoxy}benzoic acid
4-{2-[2-(4-tert-butylbenzoylamino)phenoxy]
ethoxy}benzoic acid
4-{2-[2-(3-carboxypropionylamino)phenoxy]
ethoxy}benzoic acid
4-(2-{2-[2-(4-chlorophenyl)acetylamino]
phenoxy}ethoxy)benzoic acid
4-{2-[2-(4-chlorobenzoylamino)phenoxy]
ethoxy}benzoic acid
4-(2-{2-[(E)-(3-phenylacryloyl)amino]phenoxy}ethoxy)
benzoic acid
4-[2-(2-hexanoylaminophenoxy)ethoxy]benzoic acid
4-[2-(2-decanoylaminophenoxy)ethoxy]benzoic acid
4-{2-[2-(2-fluorobenzoylamino)phenoxy]ethoxy}benzoic acid
4-{2-[2-(3-methylbutyrylamino)phenoxy]
ethoxy}benzoic acid
4-[2-(2-pentanoylaminophenoxy)ethoxy]benzoic acid
4-{2-[2-(2-phenoxyacetylamino)phenoxy]
ethoxy}benzoic acid
4-[2-(2-phenylacetylaminophenoxy)ethoxy]benzoic acid
4-{2-[2-(2,2-dimethylpropionylamino)phenoxy]
ethoxy}benzoic acid
4-{2-[2-(2-methylbenzoylamino)phenoxy]
ethoxy}benzoic acid
4-{2-[2-(4-methylbenzoylamino)phenoxy]
ethoxy}benzoic acid
4-[2-(2-nonanoylaminophenoxy)ethoxy]benzoic acid
4-{2-[2-(3,5-difluorobenzoylamino)phenoxy]
ethoxy}benzoic acid
4-{2-[2-(2-methoxybenzoylamino)phenoxy]
ethoxy}benzoic acid
4-(2-{2-[(furan-2-carbonyl)amino]phenoxy}ethoxy)benzoic acid
4-{2-[2-(2-ethylhexanoylamino)phenoxy]
ethoxy}benzoic acid
4-{2-[2-(4-ethylbenzoylamino)phenoxy]ethoxy}benzoic acid
4-(2-{2-[(thiophene-2-carbonyl)amino]phenoxy}ethoxy)
benzoic acid
4-{2-[2-(3-methylbut-2-enoylamino)phenoxy]
ethoxy}benzoic acid
4-{2-[2-(2-benzyloxyacetylamino)phenoxy]
ethoxy}benzoic acid
4-{2-[2-(2-methoxyacetylamino)phenoxy]
ethoxy}benzoic acid
4-{2-[2-(4-methoxybenzoylamino)phenoxy]
ethoxy}benzoic acid
4-[2-(2-benzoylaminophenoxy)ethoxy]benzoic acid
4-{2-[2-(3,3-dimethylbutyrylamino)phenoxy]
ethoxy}benzoic acid
4-{2-[2-(2-chlorobenzoylamino)phenoxy]
ethoxy}benzoic acid
4-{2-[2-(3-cyclopentylpropionylamino)phenoxy]
ethoxy}benzoic acid
4-{2-[2-(cyclohexanecarbonylamino)phenoxy]
ethoxy}benzoic acid
4-{2-[2-(3-fluorobenzoylamino)phenoxy]ethoxy}benzoic acid
4-{2-[2-(3-bromobenzoylamino)phenoxy]
ethoxy}benzoic acid
4-[2-(2-butyrylaminophenoxy)ethoxy]benzoic acid
4-{2-[2-(cyclopentanecarbonylamino)phenoxy]
ethoxy}benzoic acid, and
4-(2-{2-[((1S,4R)-4,7,7-Trimethyl-3-oxo-2-oxabicyclo
[2.2.1]heptane-1-carbonyl)amino]phenoxy}ethoxy)
benzoic acid; and
tautomeric forms, enantiomers, diastereoisomers, epimers, and pharmaceutically acceptable salts thereof.

17. A compound according to claim 1, wherein said compound is:
2-{5-[2-(5-dimethylaminonaphthalene-1-sulfonylamino)
phenyl]pentyl}benzoic acid
2-{5-[2-(2,4,6-trimethylbenzenesulfonylamino)phenyl]
pentyl}benzoic acid
2-{5-[2-(quinoline-8-sulfonylamino)phenyl]
pentyl}benzoic acid
2-[5-(2-ethanesulfonylaminophenyl)pentyl]benzoic acid
2-{5-[2-(2-fluorobenzenesulfonylamino)phenyl]
pentyl}benzoic acid
2-{5-[2-(4-methoxybenzenesulfonylamino)phenyl]
pentyl}benzoic acid
2-{5-[2-(2,4-dimethylbenzenesulfonylamino)phenyl]
pentyl}benzoic acid
2-{5-[2-(4-methoxy-2,3,6-trimethylbenzenesulfonylamino)phenyl]pentyl}benzoic acid
2-{5-[2-(4-isopropylbenzenesulfonylamino)phenyl]
pentyl}benzoic acid
2-{3-[2-(2,4,6-trimethylbenzenesulfonylamino)phenyl]
propyl}benzoic acid
2-{3-[2-(naphthalene-2-sulfonylamino)phenyl]
propyl}benzoic acid
2-{3-[2-(2,4-dimethylbenzenesulfonylamino)phenyl]
propyl}benzoic acid
2-{2-[4-(4-chlorobenzenesulfonylamino)phenyl]
ethyl}benzoic acid, or
4-{2-[3-(4-butylbenzenesulfonylamino)phenyl]
ethyl}benzoic acid;
or a tautomeric form, enantiomer, diastereoisomer or epimer thereof, or a pharmaceutically acceptable salt thereof.

18. A pharmaceutical composition comprising a compound according to claim 1 and a pharmaceutically acceptable excipient.

19. A compound according to claim 1, wherein the chain B-D-E is —CH$_2$—CH$_2$—.

20. A compound according to claim 1, wherein the chain B-D-E is —CH$_2$—CH$_2$—CH$_2$—.

21. A pharmaceutical composition comprising a compound according to claim 16 and a pharmaceutically acceptable excipient.

* * * * *

UNITED STATES PATENT AND TRADEMARK OFFICE
CERTIFICATE OF CORRECTION

PATENT NO. : 7,816,397 B2  Page 1 of 1
APPLICATION NO. : 11/630892
DATED : October 19, 2010
INVENTOR(S) : Moinet et al.

It is certified that error appears in the above-identified patent and that said Letters Patent is hereby corrected as shown below:

Column 169, Line 53 reads: "aryl, $(C_6\text{-}C_{14})$arykl$(C_1\text{-}C_8)$-sulfonylalkyl, $(C_6\text{-}C_{14})$" should read — aryl, $(C_6\text{-}C_{14})$aryl$(C_1\text{-}C_8)$-sulfonylalkyl, $(C_6\text{-}C_{14})$.

Signed and Sealed this
Twenty-eighth Day of February, 2012

David J. Kappos
*Director of the United States Patent and Trademark Office*